(12) United States Patent
Allgeier et al.

(10) Patent No.: US 7,655,666 B2
(45) Date of Patent: Feb. 2, 2010

(54) SUBSTITUTED 1H-QUINAZOLINE-2,4-DIONES USEFUL AS AMPA RECEPTOR LIGANDS

(75) Inventors: Hans Allgeier, Loerrach (DE); Yves Auberson, Allschwil (CH); David Carcache, Binningen (CH); Philipp Floersheim, Basel (CH); Christel Guibourdenche, Aesch (CH); Wolfgang Froestl, Basel (CH); Jörg Kallen, Basel (CH); Manuel Koller, Schliern (CH); Henri Mattes, Brunstatt (FR); Joachim Nozulak, Heitersheim (DE); David Orain, Hesingue (FR); Johanne Renaud, Basel (CH)

(73) Assignee: Novartis AG, Basel (CH)

( * ) Notice: Subject to any disclaimer, the term of this patent is extended or adjusted under 35 U.S.C. 154(b) by 47 days.

(21) Appl. No.: 11/911,040

(22) PCT Filed: Apr. 10, 2006

(86) PCT No.: PCT/EP2006/003251

§ 371 (c)(1),
(2), (4) Date: Oct. 9, 2007

(87) PCT Pub. No.: WO2006/108591

PCT Pub. Date: Oct. 19, 2006

(65) Prior Publication Data

US 2008/0153836 A1 Jun. 26, 2008

(30) Foreign Application Priority Data

Apr. 11, 2005 (GB) .................................. 0507298.8

(51) Int. Cl.
*A61K 31/517* (2006.01)

(52) U.S. Cl. .................. 514/266.2; 544/283; 546/268.1; 548/255; 548/373.1; 548/579; 549/429

(58) Field of Classification Search .............. 514/266.2; 544/283; 546/268.1; 548/255, 373.1, 579; 549/429

See application file for complete search history.

(56) References Cited

U.S. PATENT DOCUMENTS

| | | | |
|---|---|---|---|
| 6,562,839 | B1 | 5/2003 | Takano et al. |
| 2003/0153584 | A1 | 8/2003 | Weaver et al. |
| 2007/0208018 | A1 | 9/2007 | Allgeier et al. |

FOREIGN PATENT DOCUMENTS

| | | |
|---|---|---|
| WO | WO 95/19346 A1 | 7/1995 |
| WO | WO 1996/04288 | 2/1996 |
| WO | WO 97/07799 A1 | 3/1997 |
| WO | WO 98/11892 A1 | 3/1998 |
| WO | WO 98/50036 A1 | 11/1998 |
| WO | WO 2005/030217 A1 | 4/2005 |
| WO | WO 2005/033311 A2 | 4/2005 |
| WO | WO 2006/010591 A2 | 2/2006 |

OTHER PUBLICATIONS

Colotta et al., "3-Hydroxy-quinazoline-2,4-dioe as a useful scaffold to obtain selective Gly/NMDA and AMPA receptor antagonists", Bioorg. Med. Chem. Lett., XP-002389894, vol. 14 (2004), pp. 2345-2349.
Ohmori et al., "6-(1H-Imidazol-1-yl)-7-nitro-2,3(1H,4H)-quinoxalinedione hydrochloride (YM90K) and related compounds: structure-activity relationships for the AMPA-type non-NMDA receptor", J. Med. Chem., vol. 37 (1994), pp. 467-475
Takano et al., "Synthesis and AMPA Receptor Antagonistic Activity of a Novel Class of Quinoxalinecarboxylic Acid with a Substituted Phenyl Group at the C-7 Position", Bioorg. Med. Chem. Lett. vol. 13 (2003), pp. 3521-3525.
Jörg Striessnig, "Pathophysiology of migraine headache: Insight from pharmacology and genetics", Drug Discovery Today, vol. 2, No. 4 (2005), pp. 453-462.
Catarzi et al., "Synthesis and Biological Evaluation of Analogues of 7-Chloro-4,5-dihydro-4-oxo-8- (1,2,4-triazol-4-yl)-1,2,4-triazolo[1,5-a]quinoxaline-2-carboxylic Acid (TQX-173) as Novel Selective AMPA Receptor Antagonists", J. Med. Chem. vol. 47, No. 1 (2004), pp. 262-272.
Novartis AG, Office Action issued in Singapore Patent App. No. 200706385-2, Oct. 5, 2009, 8 pages.

*Primary Examiner*—James O Wilson
*Assistant Examiner*—Douglas M Willis
(74) *Attorney, Agent, or Firm*—Paul D. Strain; Fanelli, Strain & Haag, PLLC

(57) ABSTRACT

The present invention relates to 1H-Quinazoline-2,4-diones of formula (I)

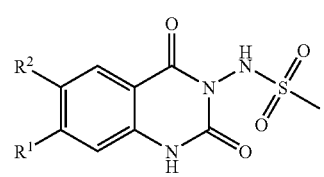

wherein $R^1$ and $R^2$ are as defined in the specification, their preparation, their use as pharmaceuticals, and pharmaceutical compositions containing them. Further, intermediates for the manufacture of compounds of formula (I) are and combinations comprising compounds of formula (I) are disclosed.

5 Claims, No Drawings

SUBSTITUTED 1H-QUINAZOLINE-2,4-DIONES USEFUL AS AMPA RECEPTOR LIGANDS

This application is the National Stage of Application No. PCT/EP2006/003251, filed on Apr. 10, 2006, which claims benefit under 35 U.S.C. § 119(e) of Great Britain Application No. 0507298.8, filed Apr. 11, 2005, the contents of which are incorporated herein by reference in their entirety.

SUMMARY

The present invention relates to 1H-Quinazoline-2,4-diones, their preparation, their use as pharmaceuticals, and pharmaceutical compositions containing them.

In particular, the present invention provides compounds of formula (I)

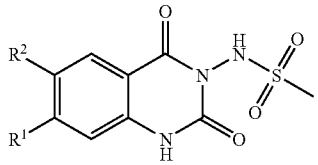

wherein
$R^1$ represents $CF_3$, $CHF_2$, $CH_2F$, $CH_3CHF$—, $CH_3CF_2$—, ethyl or iso-propyl and
$R^2$ represents alkyl substituted by one or more substituents, the substituents being selected from the group consisting of halogen, nitro, cyano, acyl, hydroxy, oxo (=O), alkoxy, cycloalkoxy, acyloxy, alkoxycarbonyloxy, amino, alkylamino, dialkylamino, formyl, acylamino, alkoxycarbonylamino or
$R^2$ represents heterocyclylakyl substituted by one or more substituents, the substituents being selected from the group consisting of halogen, nitro, cyano, hydroxy, alkoxy, alkylcarbonyloxy, alkoxycarbonyloxy, amino, alkylamino, dialkylamino, alkoxycarbonylamino, or
$R^2$ represents phenyl substituted by one or more substituents, the substituents being selected from the group consisting of cyano, hydroxy, alkanediyl, alkenediyl, alkoxy, hydroxyalkyl, formyl, alkylcarbonyl, alkoxycarbonyl, alkylcarbonyloxy, alkoxycarbonyloxy, amino, alkylamino, dialkylamino, aminoalkyl, alkylaminoalkyl, dialkylaminoalkyl, alkoxycarbonylamino, or
$R^2$ represents heterocyclyl optionally substituted by one or more substituents, the substituents being selected from the group consisting of halogen, hydroxy, amino, nitro, cyano, alkyl, hydroxyalkyl, alkoxyalkyl, aminoalkyl, alkylaminoalkyl, dialkylaminoalkyl, acyl, alkoxy, acyloxy, alkoxycarbonyloxy, amino, alkylamino, dialkylamino, acylamino, alkoxycarbonylamino and whereby the heterocycle is bound to the phenyl-ring by a carbon-atom;

and their salts.

DETAILED DESCRIPTION

In the present specification, the following definitions shall apply if no specific other definition is given:

"Alkyl" represents a straight-chain or branched-chain alkyl group, preferably represents a straight-chain or branched-chain $C_{1-12}$alkyl, particularly preferably represents a straight-chain or branched-chain $C_{1-6}$alkyl; for example, methyl, ethyl, n- or iso-propyl, n-, iso-, sec- or tert-butyl, n-pentyl, n-hexyl, n-heptyl, n-octyl, n-nonyl, n-decyl, n-undecyl, n-dodecyl, with particular preference given to methyl, ethyl, n-propyl, iso-propyl and tert-butyl.

"Alkanediyl" represents a straight-chain or branched-chain alkandiyl group bound by two different carbon atoms to the molecule, it preferably represents a straight-chain or branched-chain $C_{1-12}$ alkandiyl, particularly preferably represents a straight-chain or branched-chain $C_{1-6}$ alkanediyl; for example, methanediyl (—$CH_2$—), 1,2-ethanediyl (—$CH_2$—$CH_2$—), 1,1-ethanediyl ((—$CH(CH_3)$—), 1,1-, 1,2-, 1,3-propanediyl and 1,1-, 1,2-, 1,3-, 1,4-butanediyl, with particular preference given to methanediyl, 1,1-ethanediyl, 1,2-ethanediyl, 1,3-propanediyl, 1,4-butanediyl.

Each alkyl part of "alkoxy", "alkoxyalkyl", "alkoxycarbonyl", "alkoxycarbonylalkyl" and "halogenalkyl" shall have the same meaning as described in the above-mentioned definition of "alkyl".

"Alkenyl" represents a straight-chain or branched-chain alkenyl group, preferably $C_{2-6}$alkenyl, for example, vinyl, allyl, 1-propenyl, isopropenyl, 2-butenyl, 2-pentenyl, 2-hexenyl, etc. and preferably represents $C_{2-4}$ alkenyl.

"Alkenediyl" represents a straight-chain or branched-chain alkenediyl group bound by two different carbon atoms to the molecule, it preferably represents a straight-chain or branched-chain $C_{2-6}$ alkenediyl; for example, —CH=CH—, —CH=C($CH_3$)—, —CH=CH—$CH_2$—, —C($CH_3$)=CH—$CH_2$—, —CH=C($CH_3$)—$CH_2$—, —CH=CH—C($CH_3$)H—, —CH=CH—CH=CH—, —C($CH_3$)=CH—CH=CH—, —CH=C($CH_3$)—CH=CH—, with particular preference given to —CH=CH—$CH_2$—, —CH=CH—CH=CH—.

Acyl is alkylcarbonyl, arylcarbonyl or aralkylcarbonyl.

"Alkynyl" represents a straight-chain or branched-chain alkynyl group, preferably $C_{2-6}$alkynyl, for example, ethenyl, propargyl, 1-propynyl, isopropenyl, 1-(2- or 3) butynyl, 1-(2- or 3) pentenyl, 1-(2- or 3) hexenyl, etc., preferably represents $C_{2-4}$alkynyl and particularly preferably represents ethynyl.

"Aryl" represents an aromatic hydrocarbon group, preferably a $C_{6-10}$ aromatic hydrocarbon group; for example phenyl, naphthyl, especially phenyl.

"Aralkyl" denotes an "Aryl" bound to an "Alkyl" (both as defined above) an represents, for example benzyl, α-methylbenzyl, 2-phenylethyl, α,α-dimethylbenzyl, especially benzyl.

"Heterocycle" represents a saturated, partly saturated or aromatic ring system containing at least one hetero atom. Preferably, heterocycles consist of 3 to 11 ring atoms of which 1-3 ring atoms are hetero atoms. Heterocycles may be present as a single ring system or as bicyclic or tricyclic ring systems; preferably as single ring system or as benz-annelated ring system. Bicyclic or tricyclic ring systems may be formed by annelation of two or more rings, by a bridging atom, e.g. oxygen, sulfur, nitrogen or by a bridging group, e.g. alkanediyl or alkenediyl. A heterocycle may be substituted by one or more substituents selected from the group consisting of oxo (=O), halogen, nitro, cyano, alkyl, alkandiyl, alkenediyl, alkoxy, alkoxyalkyl, alkoxycarbonyl, alkoxycarbonylalkyl, halogenalkyl, aryl, aryloxy, arylalkyl. Examples of heterocyclic moieties are: pyrrole, pyrroline, pyrrolidine, pyrazole, pyrazoline, pyrazolidine, imidazole, imidazoline, imidazolidine, triazole, triazoline, triazolidine, tetrazole, furane, dihydrofurane, tetrahydrofurane, furazane (oxadiazole), dioxolane, thiophene, dihydrothiophene, tetrahydrothiophene, oxazole, oxazoline, oxazolidine, isoxazole, isoxazoline, isoxazolidine, thiazole, thiazoline, thiazolidine, isothiazole, isothiazoline, isothiazolidine, thiadiazole, thiadiazoline, thiadiazolidine, pyridine, piperidine, pyridazine, pyrazine, piperazine, triazine, pyrane, tetrahydropyrane, thiopyrane, tetrahydrothiopyrane, oxazine, thiazine, dioxine, morpholine, purine, pteridine, and the corresponding benzannelated heterocycles, e.g. indole, isoindole, coumarin, isoquinoline, quinoline and the like.

"Hetero atoms" are atoms other than carbon and hydrogen, preferably nitrogen (N), oxygen (O) or sulfur (S).

"Halogen" represents fluoro, chloro, bromo or iodo, preferably represents fluoro, chloro or bromo and particularly preferably represents chloro.

Compounds of formula (I) exist in free form, as a salt or as zwitterion. In this specification, unless otherwise indicated, language such as "compounds of formula (I)" is to be understood as embracing the compounds in any form, for example free base or acid addition salt form. Salts which are unsuitable for pharmaceutical uses but which can be employed, for example, for the isolation or purification of free compounds of formula (I), such as picrates or perchlorates, are also included. For therapeutic use, only pharmaceutically acceptable salts or free compounds are employed (where applicable in the form of pharmaceutical preparations), and are therefore preferred. Salts are preferably physiologically acceptable salts, formed, as applicable, by the addition of an acid or base.

Compounds of formula (I) may exist in the form of various tautomers. For example, the compounds of formula (I) may show keto-enol-tautomerism. In this specification, the drawing of one possible tautomer includes other possible tautomers as well. The tautomers of the compounds of formula (I) are also embraced by the invention.

Compounds of formula (I) may exist in the form of various zwitterions. For example, the compounds of formula (I) may show protonated amino-groups and deprotonated carboxy-groups. Further, the amino group of the sulfonamide sub-structure may be deprotonated. In this specification, the drawing of the compound in the free form includes other possible zwitterions as well. The zwitterions of the compounds of formula (I) are also embraced by the invention.

The compounds of formula (I) may exist in optically active form or in form of mixtures of optical isomers, e.g. in form of racemic mixtures or diastereomeric mixtures. In particular, asymmetrical carbon atom(s) may be present in the compounds of formula (I) and their salts. All optical isomers and their mixtures, including the racemic mixtures, are embraced by the invention.

The compounds of formula (I) may exist in optically active form or in form of mixtures of atropisomers, e.g. due to the hindered rotation on a single bond. In particular, the hindered rotation between $R^2$ and the core of the molecule may be a source of atropisomerism. All atropisomers and their mixtures, including the racemic mixtures, are embraced by the invention.

Preferred substituents, preferred ranges of numerical values or preferred ranges of the radicals present in the formula (I) and the corresponding intermediate compounds are defined below.

$R^1$ represents $CF_3$, $CHF_2$, $CF_2H$ or iso-propyl.

$R^1$ very preferably represents $CF_3$ or iso-Propyl.

$R^1$ very particularly preferably represents $CF_3$.

$R^1$ very particularly preferably represents iso-propyl.

$R^2$ preferably represents $(C_1-C_4)$alkyl substituted by one to three substituents, the substituents being selected from the group consisting of halogen, nitro, cyano, HCO, $(C_1-C_4)$alkylcarbonyl, hydroxy, $(C_1-C_4)$alkoxy, $(C_1-C_4)$alkylcarbonyloxy, $(C_1-C_4)$alkoxycarbonyloxy, amino, $(C_1-C_4)$alkylamino, di$(C_1-C_4)$alkylamino, acylamino, $(C_1-C_4)$alkoxycarbonylamino.

$R^2$ preferably represents heterocyclyl$(C_1-C_4)$alkyl substituted by one to three substituents, the substituents being selected from the group consisting of halogen, nitro, cyano, hydroxy, oxo, $(C_1-C_4)$alkoxy, $(C_3-C_7)$cycloalkoxy, $(C_1-C_4)$alkylcarbonyloxy, $(C_1-C_4)$alkoxycarbonyloxy, amino, $(C_1-C_4)$alkylamino, di$(C_1-C_4)$alkylamino, $(C_1-C_4)$alkoxycarbonylamino and the heterocyclyl consist of 3 to 11 ring atoms of which 1-3 ring atoms are hetero atoms.

$R^2$ preferably represents phenyl substituted by one to three substituents, the substituents being selected from the group consisting of cyano, hydroxy, hydroxy$(C_1-C_4)$alkyl, $(C_1-C_4)$alkanediyl, alkenediyl, $(C_1-C_4)$alkoxy, $(C_1-C_4)$alkylcarbonyloxy, $(C_1-C_4)$alkoxycarbonyloxy, $(C_1-C_4)$alkylcarbonyloxy, $(C_1-C_4)$alkoxycarbonyloxy, amino, $(C_1-C_4)$alkylamino, di$(C_1-C_4)$alkylamino, amino$(C_1-C_4)$alkyl, $(C_1-C_4)$alkylamino$(C_1-C_4)$alkyl, di$(C_1-C_4)$alkylamino $(C_1-C_4)$alkylamino, $(C_1-C_4)$alkoxycarbonylamino.

$R^2$ preferably represents heterocyclyl optionally substituted by one to three substituents, the substituents being selected from the group consisting of halogen, hydroxy, amino, nitro, cyano, $(C_1-C_4)$alkyl, hydroxy$(C_1-C_4)$alkyl, $(C_1-C_4)$alkoxyalkyl, amino$(C_1-C_4)$alkyl, $(C_1-C_4)$alkylamino$(C_1-C_4)$alkyl, di$(C_1-C_4)$alkylamino$(C_1-C_4)$alkyl, HCO, $(C_1-C_4)$alkylcarbonyl, $(C_1-C_4)$alkoxy, acyloxy, $(C_1-C_4)$alkoxycarbonyloxy, amino, $(C_1-C_4)$alkylamino, di$(C_1-C_4)$alkylamino, acylamino, $(C_1-C_4)$alkoxycarbonylamino; the heterocyclyl consist of 3 to 11 ring atoms of which 1-3 ring atoms are hetero atoms and whereby the heterocycle is bound to the phenyl-ring by a carbon-atom.

$R^2$ particularly preferably represents $(C_1-C_4)$alkyl substituted by one substituent, the substituent being selected from the group consisting of fluoro, chloro, bromo, nitro, cyano, HCO, methylcarbonyl, ethylcarbonyl, n-propylcarbonyl, i-propylcarbonyl, hydroxy, methoxy, ethoxy, n-propoxy, i-propoxy, HCONH, methylcarbonylamino, ethylcarbonylamino, n-propylcarbonylamino, i-propylcarbonylamino, methoxycarbonyloxy, ethoxycarbonyloxy, n-propoxycarbonyloxy, i-propoxycarbonyloxy, amino, methylamino, ethylamino, n-propylamino, i-propylamino, dimethylamino, diethylamino, di(n-propyl)amino, di(i-propyl) amino, methoxycarbonylamino, ethoxycarbonylamino, n-propoxycarbonylamino, i-propoxycarbonylamino.

$R^2$ particularly preferably represents heterocyclylmethyl substituted by one substituent, the substituent being selected from the group consisting of halogen, nitro, cyano, hydroxy, methoxy, ethoxy, n-propoxy, i-propoxy, methylcarbonyloxy, ethylcarbonyloxy, n-propylcarbonyloxy, i-propylcarbonyloxy, methoxycarbonyloxy, ethoxycarbonyloxy, n-propoxycarbonyloxy, i-propoxycarbonyloxy, amino, methylamino, ethylamino, n-propylamino, i-propylamino, dimethylamino, diethylamino, di(n-propyl) amino, di(i-propyl)amino, methoxycarbonylamino, ethoxycarbonylamino, n-propoxycarbonylamino, i-propoxycarbonylamino and the heterocyclyl being selected from the group consisting of pyrrole, pyrroline, pyrrolidine, pyrazole, pyrazoline, pyrazolidine, imidazole, imidazoline, imidazolidine, triazole, triazoline, triazolidine, tetrazole, furane, dihydrofurane, tetrahydrofurane, furazane (oxadiazole), dioxolane, thiophene, dihydrothiophene, tetrahydrothiophene, oxazole, oxazoline, oxazolidine, isoxazole, isoxazoline, isoxazolidine, thiazole, thiazoline, thiazolidine, isothiazole, isothiazoline, isothiazolidine, thiadiazole, thiadiazoline, thiadiazolidine, pyridine, piperidine, pyridazine, pyrazine, piperazine, triazine, pyrane, tetrahydropyrane, thiopyrane, tetrahydrothiopyrane, oxazine, thiazine, dioxine, morpholine, purine, pteridine, and the corresponding benz-annelated heterocycles, e.g. indole, isoindole, coumarin, isoquinoline, quinoline $R^2$ particularly preferably represents phenyl substituted by one to three substituents, the substituents being selected from the group consisting of cyano, hydroxy, alkanediyl, alkenediyl, methoxy, ethoxy, n-propoxy, i-propoxy, methylcarbonyloxy, ethylcarbonyloxy, n-propylcarbonyloxy, i-propylcarbonyloxy, methoxycarbonyloxy, ethoxycarbonyloxy, n-propoxycarbonyloxy, i-propoxycarbonyloxy, amino, methylamino, ethylamino, n-propylamino, i-propylamino, dimethylamino, diethylamino, di(n-propyl)amino, di(i-propyl)amino, aminomethyl, methylaminomethyl, ethylaminomethyl, n-propylaminomethyl, i-propylaminomethyl, dimethylaminomethyl, diethylaminomethyl, di(n-propyl)aminomethyl, di(i-propyl)aminomethyl, methoxycarbonylamino, ethoxycarbonylamino, n-propoxycarbonylamino, i-propoxycarbonylamino.

$R^2$ particularly preferably represents heterocyclyl optionally substituted by one or two substituents, the substituents being selected from the group consisting of halogen, hydroxy, amino, nitro, cyano, methyl, ethyl, n-propyl, i-propyl, hydroxymethyl, hydroxyethyl, hydroxy-n-propyl, hydroxy-i-propyl, methoxymethyl, methoxyethyl, methoxy-n-propyl, methoxy-i-propyl, aminomethyl, aminoethyl, amino-n-propyl, amino-i-propyl, methylaminomethyl, methylaminoethyl, methylamino-n-propyl, methylamino-i-propyl, dimethylaminomethyl, dimethylaminoethyl, dimethylamino-n-propyl, dimethylamino-i-propyl, HCO, methylcarbonyl, ethylcarbonyl, n-propylcarbonyl, i-propylcarbonyl, methoxy, ethoxy, n-propoxy, i-propoxy, HCONH, methylcarbonylamino, ethylcarbonylamino, n-propylcarbonylamino, i-propylcarbonylamino HCO, methylcarbonyl, ethylcarbonyl, n-propylcarbonyl, i-propylcarbonyl, methylcarbonyloxy, ethylcarbonyloxy, n-propylcarbonyloxy, i-propylcarbonyloxy, methoxycarbonylamino, ethoxycarbonylamino, n-propoxycarbonylamino, i-propoxycarbonylamino;

the heterocyclyl being selected from the group consisting of

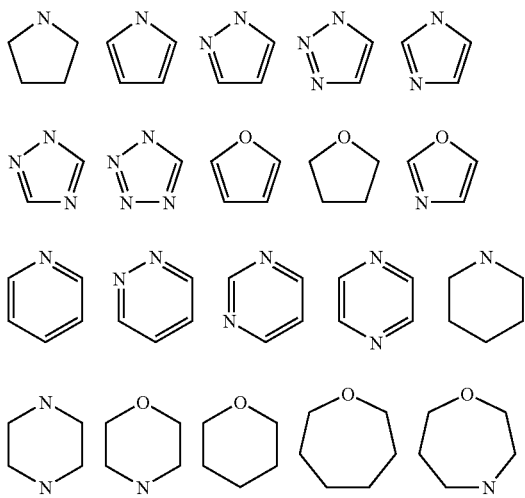

and whereby the heterocycle is bound to the phenyl-ring by a carbon-atom.

$R^2$ particularly preferably represents heterocyclyl optionally substituted by one or two substituents, the substituents being selected from the group consisting of halogen, hydroxy, amino, nitro, cyano, methyl, ethyl, n-propyl, i-propyl, the heterocyclyl being selected from the group consisting of

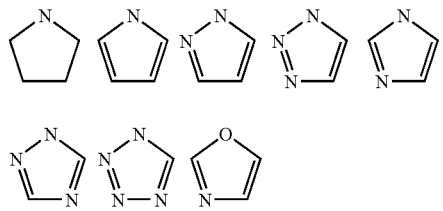

and whereby the heterocycle is bound to the phenyl-ring by a carbon-atom.

Further, compounds of formula (I) are preferred, wherein $R^2$ does not represent trifluoromethyl.

In a further embodiment, the invention relates to compounds of formula (I) wherein $R^1$ represents $CF_3$, $CHF_2$, $CF_2H$ or iso-propyl and $R^2$ represents alkyl substituted by one or more substituents, the substituents being selected from the group consisting of halogen, nitro, cyano, acyl, hydroxy, alkoxy, acyloxy, alkoxycarbonyloxy, amino, alkylamino, dialkylamino, formyl, acylamino, alkoxycarbonylamino, except trifluoromethyl or $R^2$ represents heterocyclylakyl substituted by one or more substituents, the substituents being selected from the group consisting of halogen, nitro, cyano, hydroxy, alkoxy, alkylcarbonyloxy, alkoxycarbonyloxy, amino, alkylamino, dialkylamino, alkoxycarbonylamino, or $R^2$ represents phenyl substituted by one or more substituents, the substituents being selected from the group consisting of cyano, hydroxy, alkanediyl, alkenediyl, alkoxy, alkylcarbonyloxy, alkoxycarbonyloxy, amino, alkylamino, dialkylamino, alkoxycarbonylamino, or $R^2$ represents heterocyclyl optionally substituted by one or more substituents, the substituents being selected from the group consisting of halogen, hydroxy, amino, nitro, cyano, alkyl, hydroxyalkyl, alkoxyalkyl, aminoalkyl, alkylaminoalkyl, dialkylaminoalkyl, acyl, alkoxy, acyloxy, alkoxycarbonyloxy, amino, alkylamino, dialkylamino, acylamino, alkoxycarbonylamino and whereby the heterocycle is bound to the phenyl-ring by a carbon-atom and their salts.

The definition of the substituents applies to the end-products as well as to the corresponding intermediates. The definitions of the substituents may be combined at will, i.e. preferred substituents $R^1$ and particularly preferred substituents $R^2$. Further, selected definitions may not apply.

In a further aspect, the present invention also provides processes for the production of compounds of the invention. Compounds of formula (I) are obtainable according to Process 1 which is summarized by the following scheme.

In this process, step 1.1, substituent $R^1$ may be transformed into another substituent $R^1$ according to conventional procedures.

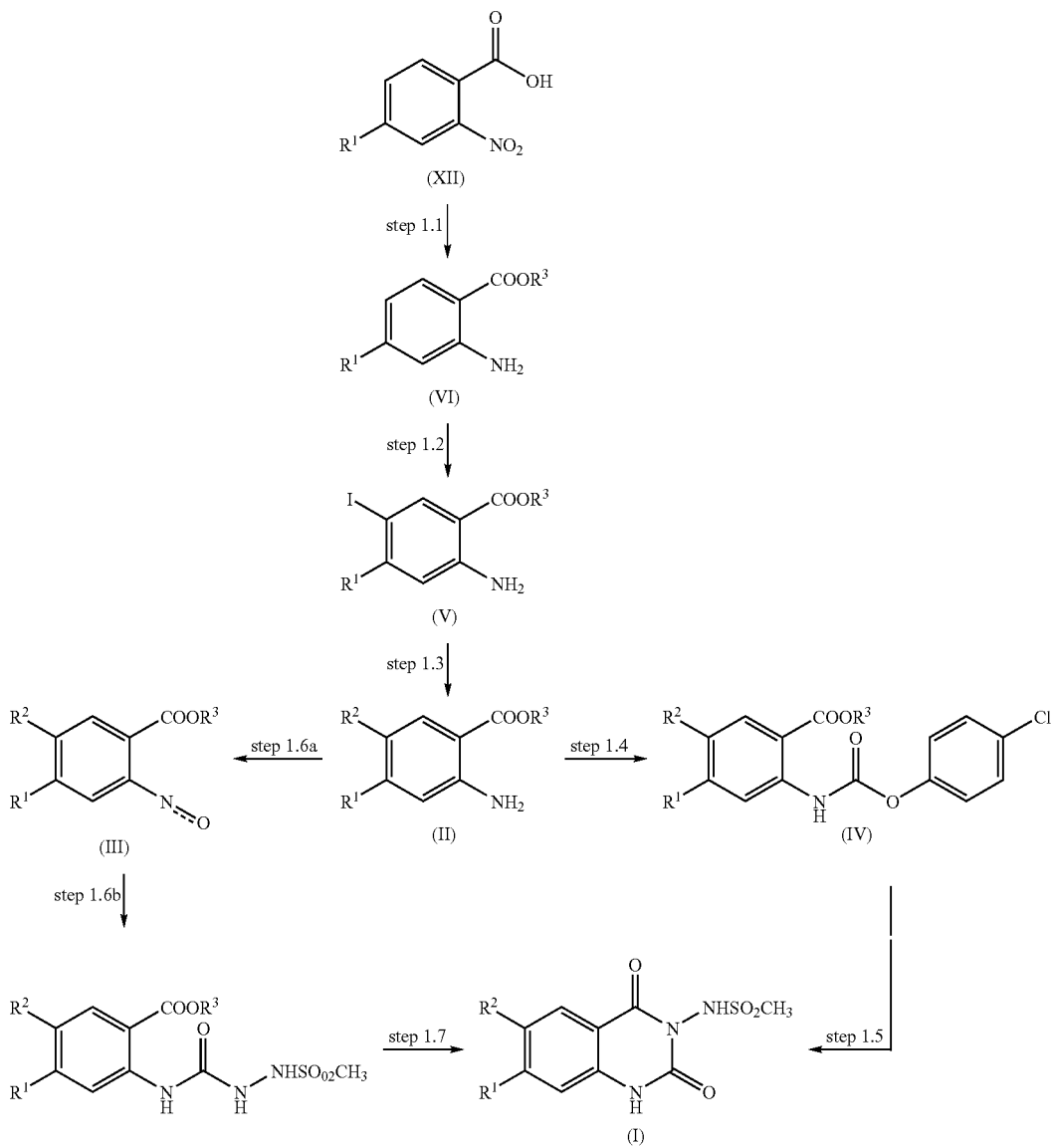
Further, compounds of formula (I) are obtainable according to Process 2 which is summarized by the following scheme.
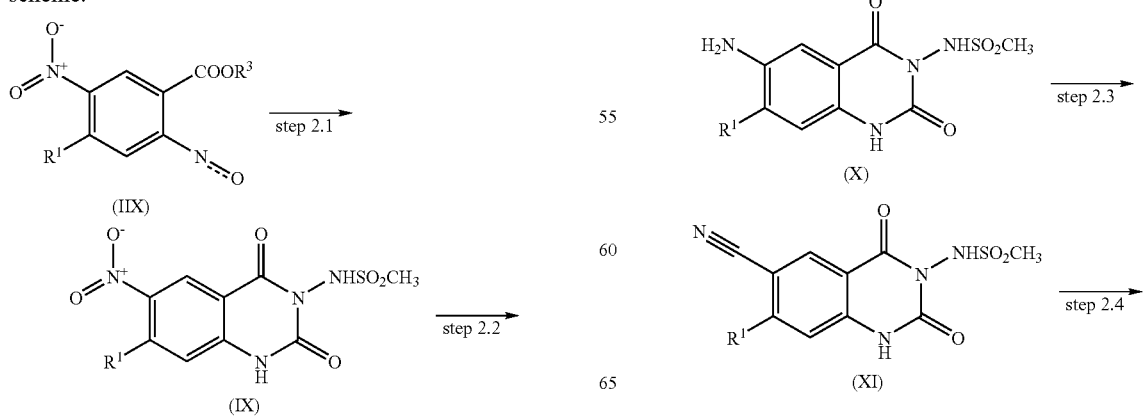

-continued

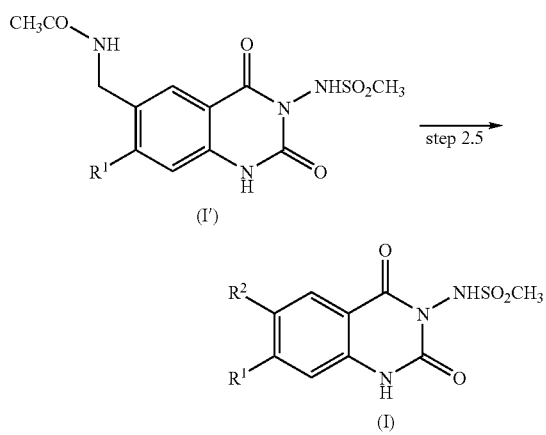

Depending on the substitution pattern, either of the processes 1 or 2 may be preferred. The starting material of formula (IIX) is obtainable according to Process 3 which is summarized by the following scheme.

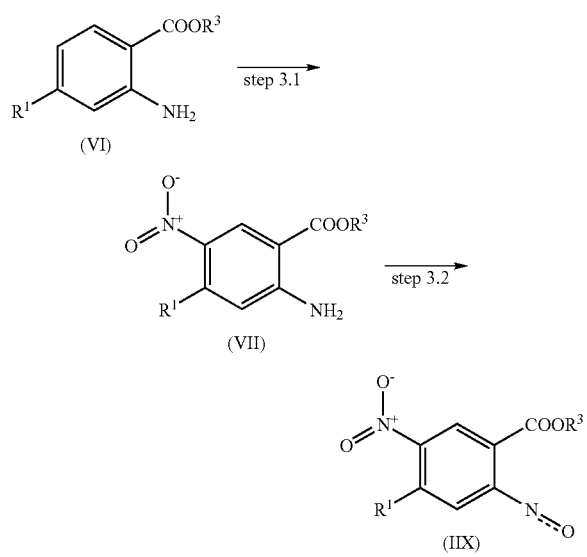

The substituents $R^1$ and $R^2$ of the compounds of formulae (I) to (XII) and further used starting materials have the meaning as defined above for compounds of formula (I); the substituent $R^3$ represents $C_1$-$C_4$ alkyl, preferably methyl.

The processes are described in more detail below.

Step 1.1: A compound of formula (VI) is obtainable by subjecting a compound of formula (XII) to reduction conditions using $H_2$ and a palladium catalyst for example (Valgeirsson, J.; Nielsen, E. Ø.; Peters, D.; Varming, T.; Mathiesen, C.; Kristensen, A. S.; Madsen, U. J. Med. Chem. 2003, 46, 5834-5843), followed by an esterification reaction with an alcohol $R^3OH$, such as MeOH, and an acid, such as HCl, (similar products were prepared, see: Hill, D. T.; Stanley, K. G.; Karoglan Williams, J. E.; Loev, B.; Fowler, P. J.; McCafferty, J. P.; Macko, E.; Berkoff, C. E.; Ladd, C. B. J. Med. Chem. 1983, 26, 865-869.

The following scheme illustrates step 1.1 in more detail.

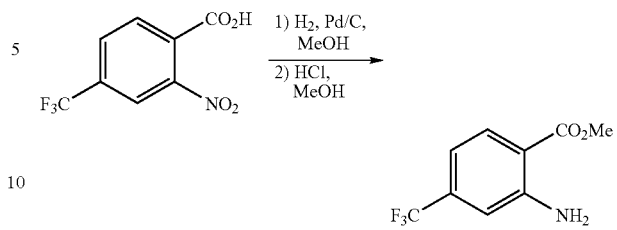

Starting materials of formula (XII) are known and/or obtainable according to known methods and/or obtainable as described in the examples.

Step 1.2: A compound of formula (V) is obtainable be reacting a compound of formula (VI) with Iodine in the presence of $Ag_2SO_4$, optionally in the presence of a solvent, e.g. ethanol, and optionally in the presence of further reaction auxiliaries.

The following scheme illustrates step 1.2 in more detail.

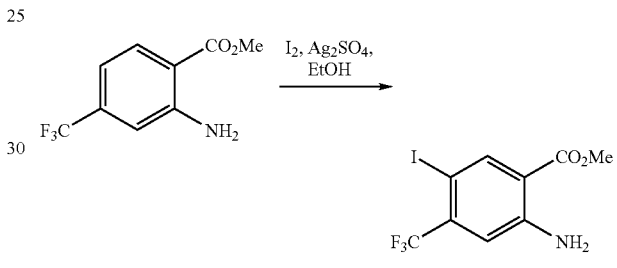

Step 1.3: A compound of formula (II) can be prepared from a compound of formula (V) by subjecting it to Pd-catalyzed reactions of, e.g. Stille Reaction, Suzuki reaction or Heck reaction. In such cases, it might be suitable to protect the amino group, e.g. by converting it to an acetamide group.

Suitable coupling reagents such as tributylethoxyvinyltin, tributyl(vinyl)tin, tetrahydro-2-(2-propynyloxy)-2H-pyran, trimethylsilylethynyl, tributylstannanyl or (4,4,5,5-tetramethyl-1,3,2-dioxaborolan-2-yl)-pyrazol intermediates, tributylstannanylpyrrole, 3-furanboronic acid are known.

Suitable palladium catalyst, i.e. tetrakis-triphenylphosphine palladium (0), bis(triphenylphosphine)palladium (II) chloride, bis(dibenzylidenacetone)palladium, [1,1'-dichloro [1,1'-bis(diphenylphosphino)-ferrocene]palladium (II) dichloromethane complex are known. Depending on the substitution pattern, the reaction can be carried out in the presence of CuI.

Suitable bases, such as triethylamine or potassium carbonate may be employed when required.

Suitable solvents are dichloromethane, dioxane, tetrahydrofuran, toluene.

The following scheme illustrates step 1.2 in more detail.

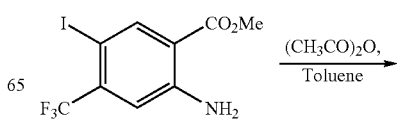

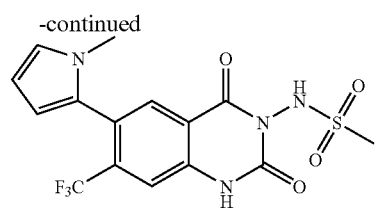

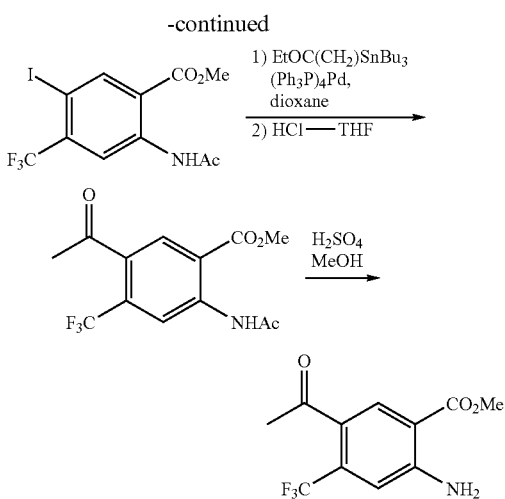

Step 1.4: A compound of formula (IV) is obtainable by reacting a compound of formula (II) with 4-chlorophenyl-chloroformate, optionally in the presence of a diluent, and optionally in the presence of a reaction auxiliary.

The following scheme illustrates step 1.4 in more detail.

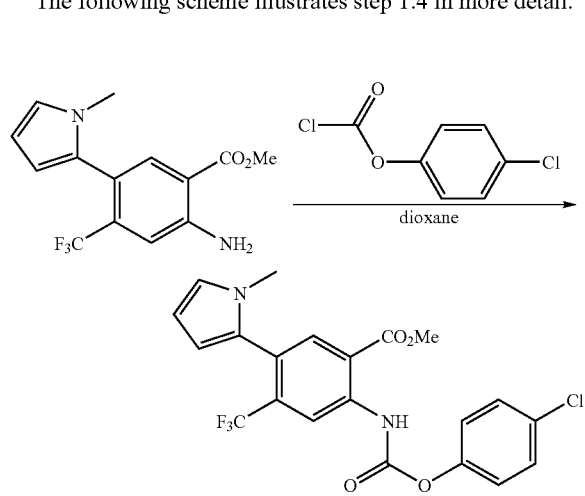

Step 1.5: A compound of formula (I) is obtainable by subjecting a compound of formula (IV) to a cyclocondensation with sulfonylhydrazine H$_2$N—NH—SO$_2$—CH$_3$, in a suitable inert solvent such as tetrahydrofuran or dioxane, in the presence of or followed by addition of a base, e.g. aqueous sodium hydroxide solution or an organic base such as triethylamine or Huenig's base.

The following scheme illustrates step 1.5 in more detail.

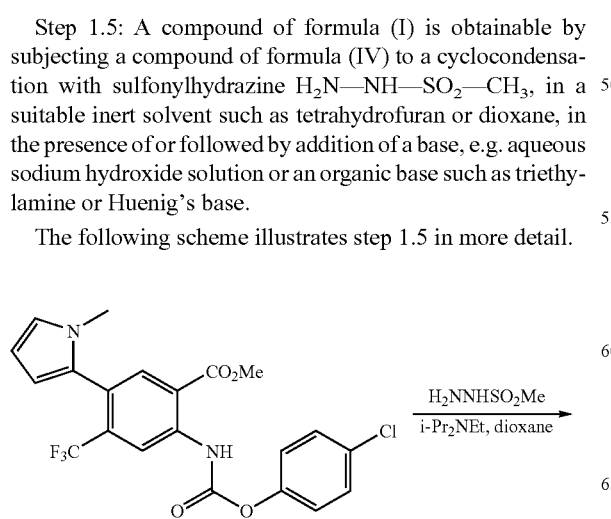

Step 1.6, 1.7: A compound of formula (III) is obtainable by conversion of a compound of formula (II) with phosgene or triphosgene optionally in the presence of a diluent and optionally in the presence of a reaction auxiliary. Subsequent cyclocondensation with sulfonylhydrazine H$_2$N—NH—SO$_2$—CH$_3$, optionally in an inert solvent such as tetrahydrofuran or dioxane, in the presence of or followed by addition of a base, e.g. aqueous sodium hydroxide solution or an organic base such as triethylamine or Huenig's base results in the formation of a compound of formula (I). Steps 1.6 and 1.7 may be performed with or without isolating the resulting intermediates.

The following scheme illustrates steps 1.6, 1.7 in more detail.

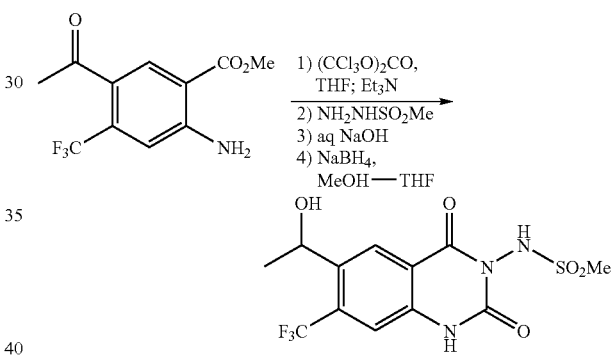

Step 2.1: A compound of formula (IX) is obtainable by reacting a compound of formula (IIX) with sulfonylhydrazine H$_2$N—NH—SO$_2$—CH$_3$ optionally in an inert solvent such as tetrahydrofuran or dioxane, in the presence of or followed by addition of a base, e.g. aqueous sodium hydroxide solution or an organic base such as triethylamine or Huenig's base results in the formation of a compound of formula (I). Step 2.1 may be performed with or without isolating the resulting intermediates.

The following scheme illustrates step 2.1 in more detail.

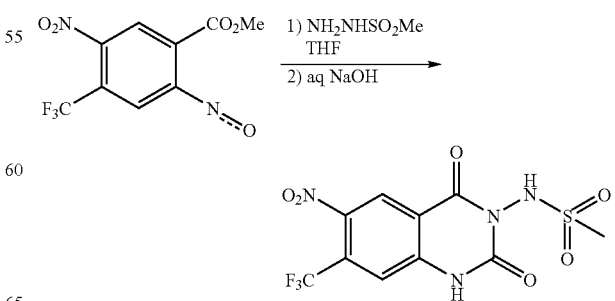

Step 2.2: A compound of formula (X) is obtainable by reducing a compound of formula (IX), for example with hydrogen, optionally in the presence of an diluent, such as EtOH—CH₃COOH, and optionally in the presence of a catalyst, such as Pd/C.

The following scheme illustrates step 2.2 in more detail.

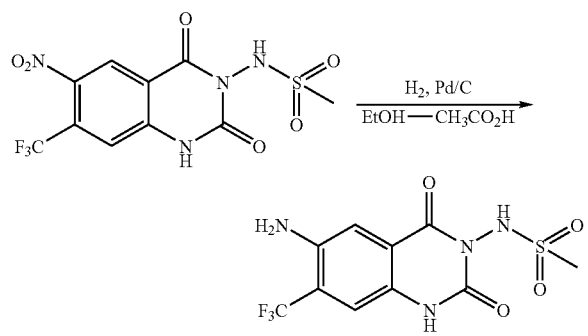

Step 2.3: A compound of formula (XI) is obtainable via a Sandmeyer-type reaction with a compound of formula (X).

The following scheme illustrates step 2.3 in more detail.

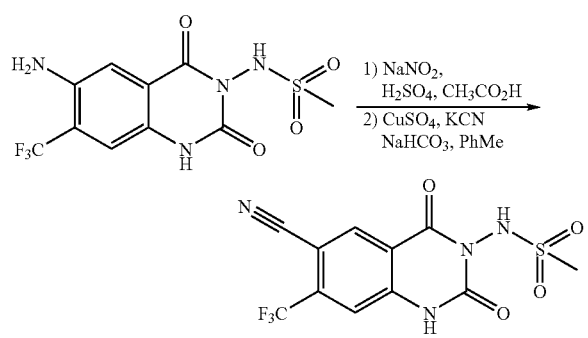

Step 2.4: A compound of formula (I') is obtainable by reducing a compound of formula (XI) for example with hydrogen, optionally in the presence of a catalyst, such as Raney Nickel, optionally in the presence of a diluent, and in the presence of acetic anhydride.

The following scheme illustrates step 2.4 in more detail.

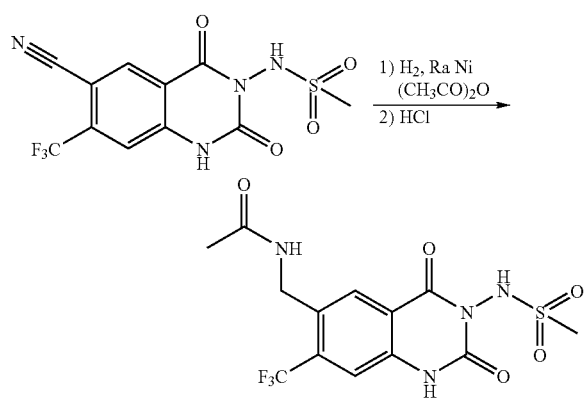

Step 2.5: The compound of formula (I')—wherein R² represents Acylaminomethyl—may be converted to other compounds of formula (I) by known reactions, e.g. cyclisation, substitution, oxidation and/or reduction steps.

The following scheme illustrates step 2.5 in more detail.

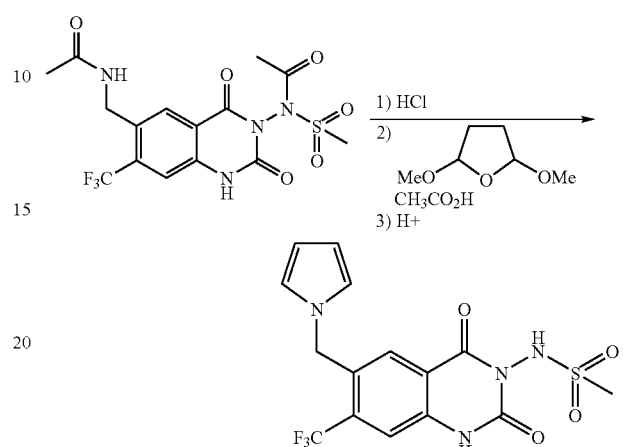

Step 3.1: A compound of formula (VII) is obtainable by nitration of a compound of formula (VI), e.g. by using nitric acid and sulfuric acid, optionally in the presence of a diluent. In such a case, it might be suitable to protect the amino group, e.g. by converting it to an acetamide group. The starting material of formula (VI) is obtainable, e.g. according to step 1.1.

The following scheme illustrates step 3.1 in more detail.

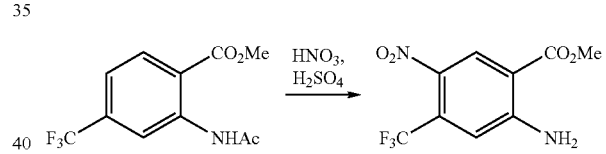

Step 3.2: A compound of formula (IIX) is obtainable by reacting a compound of formula (VII) with phosgene in a diluent, e.g. toluene.

The following scheme illustrates step 3.2 in more detail.

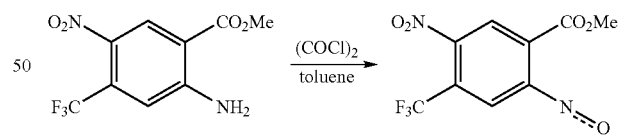

With regard to the use of protecting groups throughout the reaction steps described, the formation of salts, e.g. for the purposes of purification, and the synthesis of isomers the following considerations may apply:

Protecting groups: In the reaction steps described above, one or more functional groups, for example carboxy, hydroxy, amino, or mercapto, may need to be protected in the starting materials by protecting groups. The protecting groups employed may already be present in precursors and should protect the functional groups concerned against unwanted secondary reactions, such as acylations, etherifications, esterifications, oxidations, solvolysis, and similar reactions. It is a characteristic of protecting groups that they lend themselves readily, i.e. without undesired secondary reactions, to removal, typically by solvolysis, reduction, photolysis or also by enzyme activity, for example under conditions analogous to physiological conditions, and that they are not present in the end-products. The specialist knows, or can easily establish, which protecting groups are suitable with the reactions mentioned hereinabove and hereinafter. The protection of such functional groups by such protecting groups, the protecting groups themselves, and their removal reactions are described for example in standard reference works, such as J. F. W. McOmie, "Protective Groups in Organic Chemistry", Plenum Press, London and New York 1973, in T. W. Greene and P. G. M. Wuts, "Protective Groups in Organic Synthesis", Third edition, Wiley, New York 1999, in "The Peptides"; Volume 3 (editors: E. Gross and J. Meienhofer), Academic Press, London and New York 1981, in "Methoden der organischen Chemie" (*Methods of organic chemistry*), Houben Weyl, 4th edition, Volume 15/I, Georg Thieme Verlag, Stuttgart 1974, in H.-D. Jakubke and H. Jescheit, "Aminosäuren, Peptide, Proteine" (*Amino acids, peptides, proteins*), Verlag Chemie, Weinheim, Deerfield Beach, and Basel 1982, and in Jochen Lehmann, "Chemie der Kohlenhydrate: Monosaccharide und Derivate" (*Chemistry of carbohydrates: monosaccharides and derivatives*), Georg Thieme Verlag, Stuttgart 1974.

Salts: Acid addition salts may be produced from the free bases in known manner, and vice-versa.

Isomers: Compounds of formula I in optically pure form can be obtained from the corresponding racemates according to well-known procedures, e.g. HPLC with chiral matrix. Alternatively, optically pure starting materials can be used. Stereoisomeric mixtures, e.g. mixtures of diastereomers, can be separated into their corresponding isomers in a manner known per se by means of suitable separation methods. Diastereomeric mixtures for example may be separated into their individual diastereomers by means of fractionated crystallization, chromatography, solvent distribution, and similar procedures. This separation may take place either at the level of a starting compound or in a compound of formula I itself. Enantiomers may be separated through the formation of diastereomeric salts, for example by salt formation with an enantiomer-pure chiral acid, or by means of chromatography, for example by HPLC, using chromatographic substrates with chiral ligands.

Certain intermediates of the reaction steps described above are novel and useful for the manufacture of compounds of formula (I). Hence, these compounds are subject to a further aspect of the invention.

Compound of Formula (II')

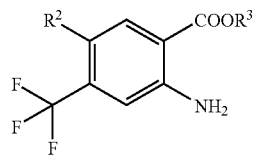

(II')

wherein
$R^2$ has the meaning given above for compounds of formula (I) and
$R^3$ represents hydrogen or $C_1$-$C_4$ alkyl, preferably methyl.

Compound of Formula (III')

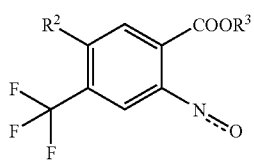

(III')

wherein
$R^2$ has the meaning given above for compounds of formula (I) and
$R^3$ represents hydrogen or $C_1$-$C_4$ alkyl, preferably methyl.

Compound of Formula (IV')

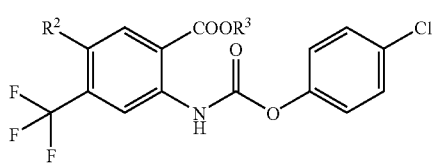

(IV')

wherein
$R^2$ has the meaning given above for compounds of formula (I) and
$R^3$ represents hydrogen or $C_1$-$C_4$ alkyl, preferably methyl.

Compound of Formula (VII)

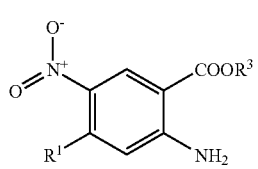

(VII)

wherein
$R^1$ has the meaning given above for compounds of formula (I) and
$R^3$ represents hydrogen or $C_1$-$C_4$ alkyl, preferably methyl.

Compound of Formula (IIX)

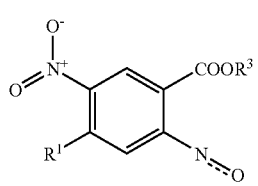

(IIX)

wherein
$R^1$ has the meaning given above for compounds of formula (I) and
$R^3$ represents hydrogen or $C_1$-$C_4$ alkyl, preferably methyl.

Compound of Formula (IX)

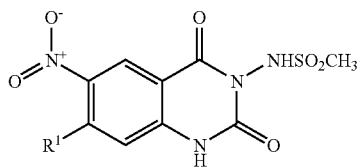

wherein $R^1$ has the meaning given above for compounds of formula (I).

Compound of Formula (X)

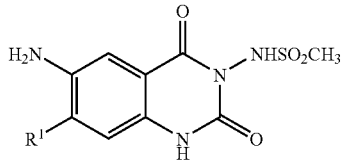

wherein $R^1$ has the meaning given above for compounds of formula (I).

Compound of Formula (XI)

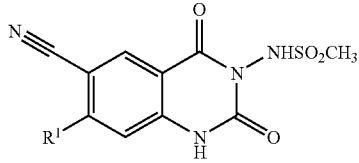

wherein $R^1$ has the meaning given above for compounds of formula (I).

The compounds of the invention exhibit pharmacological activity and are, therefore, useful as pharmaceuticals. In particular, the compounds are potent competitive AMPA receptor antagonists.

The compounds of the invention are especially effective as pharmaceuticals in the treatment of epilepsy, esp. in partial seizures (simple, complex and partial evolving to secondarily generalized seizures) and generalized seizures [absence (typical and atypical), myoclonic, clonic, tonic, tonic-clonic and atonic].

The compounds of the invention are also especially effective as pharmaceuticals in the treatment of psychosis in schizophrenia, in bipolar disorder, in Parkinson's Disease and in drug-induced psychosis and in postictal psychosis, as well as in the improvement of positive and negative symptoms and effective in treatment-resistant patients (cf. Kalkman H O, Loetscher E GAD67: the link between GABA-deficit hypothesis and the dopaminergic- and glutamatergic theories of psychosis. J. Neural. Transm. 2003, 1110, 803-812).

Furthermore, the compounds of the invention are useful as pharmaceuticals in the treatment of any pathology, disorder or clinical condition involving altered AMPA receptor function or AMPA receptor mediated neuronal damage, e.g. neurodegenerative disorders, such as multiple sclerosis, amyotrophic lateral sclerosis, Parkinson's Disease, Huntington's Disease or Alzheimers Disease, schizophrenia, esp. chronic schizophrenia, anxiety, depression, bipolar mood disorders, sleep disorders, cognitive disorders, emesis, tinnitus, pain, neuronal pain, migraine, anesthetics, myopia, tumor growth, withdrawal symptoms, ischemic and hypoxic conditions such as stroke, subarachnoid hemorrhage, perinatal hypoxia, brain and spinal cord trauma, head injury, high intracranial pressure, and any surgical procedure potentially associated with hypoxia of the central nervous system, and conditions produced by the actions of environmental, exogenous neurotoxins, including those produced by infections as well as those produced by metabolic changes and hepatic encephalopathy associated with liver failure.

As i.v. formulation, the compounds are useful for treatment of status epilepticus and as anaesthetic, in particular for treatment of acute brain trauma and other brain lesions requiring deep anaesthesia.

Further, properly isotope-labeled agents of the invention exhibit valuable properties as histopathological labeling agents, imaging agents and/or biomarkers, hereinafter "markers", for the selective labeling of the AMPA receptor. More particularly the agents of the invention are useful as markers for labeling the central and peripheral AMPA receptors in vitro or in vivo. In particular, compounds of the invention which are properly isotopically labeled are useful as PET markers. Such PET markers are labeled with one or more atoms selected from the group consisting of $^{11}C$, $^{13}N$, $^{15}O$, $^{18}F$.

The agents of the invention are therefore useful, for instance, for determining the levels of receptor occupancy of a drug acting at the AMPA receptor, or diagnostic purposes for diseases resulting from an imbalance or dysfunction of AMPA receptors, and for monitoring the effectiveness of pharmacotherapies of such diseases.

In accordance with the above, the present invention provides an agent of the invention for use as a marker for neuroimaging.

In a further aspect, the present invention provides a composition for labeling brain and peripheral nervous system structures involving AMPA receptors in vivo and in vitro comprising an agent of the invention.

In still a further aspect, the present invention provides a method for labeling brain and peripheral nervous system structures involving AMPA receptors in vitro or in vivo, which comprises contacting brain tissue with an agent of the invention.

The method of the invention may comprise a further step aimed at determining whether the agent of the invention labeled the target structure. Said further step may be effected by observing the target structure using positron emission tomography (PET) or single photon emission computed tomography (SPECT), or any device allowing detection of radioactive radiations.

For all these indications, the appropriate dosage will, of course, vary depending upon, for example, the compound of the invention employed, the host, the mode of administration and the nature and severity of the conditions being treated. However, in general, satisfactory results in animals are indicated to be obtained at daily dosages from about 0.1 to about 30 mg/kg animal body weight. In larger mammals, for example humans, an indicated daily dosage is in the range from about 5 mg to about 2 g of a compound of the invention conveniently administered, for example, in divided doses up to four times a day.

The active agents of the invention may be administered by any conventional route, in particular enterally, preferably orally, e.g. in the form of tablets or capsules, or parenterally, e.g. in the form of injectable solutions or suspensions.

In accordance with the foregoing, the present invention provides compounds for use as a pharmaceutical, in particular for use in the treatment of any pathology, disorder or clinical condition involving AMPA receptors in their etiology or involving AMPA-receptor mediated neuronal damage, and especially for use in any of the specific indications hereinbefore cited.

The present invention also provides a pharmaceutical composition comprising compounds in association with at least one pharmaceutical carrier or diluent. Such compositions may be manufactured in conventional manner. Unit dosage forms contain, for example, from about 1 mg to about 400 mg of an active agent according to the invention.

The present invention furthermore provides the use of a compound according to the invention, for the manufacture of a medicament for the treatment of any pathology, disorder or clinical condition involving AMPA receptors in their etiology or involving AMPA-receptor mediated neuronal damage.

Moreover the present invention provides a method for the treatment of any pathology, disorder or clinical condition involving AMPA receptors in their etiology or involving AMPA-receptor mediated neuronal damage, in a subject in need of such treatment, which comprises administering to such subject a therapeutically effective amount of a compound according to the invention.

Furthermore, the compounds of the invention can be combined with other drugs useful for the above mentioned indications, e.g. in the case of epilepsy with other anti-epileptic drugs like barbiturates and derivatives thereof, benzodiazepines, carboxamides, hydantoins, succinimides, valproic acid and other fatty acid derivates, Lamotrigine, Levetiracetam and derivatives thereof, Topiramate, Pregabalin, Gabapentin, Zonisamide, Sultiam, Felbamate and other AMPA-antagonists. The compounds of the invention can also be combined with neuroleptic drugs selected from the list consisting of atypical antipsychotic drugs such as clozapine, olanzapine, risperidone and typical antipsychotic drugs such as haloperidol. Thus, in further aspects, the present invention relates to Combinations comprising a compound of formula (I) and Anti-epileptic Drugs, suitable for the treatment of Neurological Disorders Combinations comprising a compound of formula (I) for affective and attention disorders Combinations comprising a compound of formula (I) suitable for the treatment of neurological/psychiatric disorders Combinations comprising a compound of formula (I) suitable for the treatment of ocular disorders, in particular myopia Combinations comprising a compound of formula (I) suitable for the treatment of pain, especially neuropathic pain Combinations comprising a compound of formula (I) suitable for the treatment of psychiatric/neurological disorders, in particular schizophrenia.

Combinations comprising a compound of formula (I) suitable for the treatment of neurological disorders, in particular tinnitus Combinations comprising a compound of formula (I) comprising nootropics suitable for the treatment of dementia.

Combinations comprising a compound of formula (I) suitable for treatment of acute brain lesions, e.g. brain trauma, stroke, hypoxia.

Combinations comprising a compound of formula (I) suitable as anaesthetic.

These combinations and their uses are explained in more detail herein after. In each case the term "AMPA receptor antagonist" refers to compounds as defined by formula (I). Preferred AMPA receptor antagonists are the compounds as identified in the examples.

Combinations Comprising Anti-Epileptic Drugs for the Treatment of Neurological Disorders The present invention also relates to combinations suitable for the treatment of neurological disorders, in particular epilepsy. Epilepsy is characterized by abnormal discharges of cerebral neurons and typically manifested as various types of seizures. 20 to 30% of epilepsy patients are refractory to current therapy.

Surprisingly, the effect of a combination which comprises two anti-epileptic drugs selected from the list consisting of barbiturates and derivatives thereof, benzodiazepines, carboxamides, hydantoins, succinimides, valproic acid and other fatty acid derivates, AMPA antagonists and other anti-epileptic drugs is greater than the additive effect of the combined anti-epileptic drugs. Furthermore, the combinations disclosed herein can be used to treat epilepsy which is refractory to monotherapy employing one of the combinations alone.

Hence, the invention relates to a combination, such as a combined preparation or pharmaceutical composition, which comprises two anti-epileptics selected from the list consisting of barbiturates and derivatives thereof, benzodiazepines, carboxamides, hydantoins, succinimides, valproic acid and other fatty acid derivates, AMPA antagonists and other anti-epileptic drugs, in which the active ingredients are present in each case in free form or in the form of a pharmaceutically acceptable salt and optionally at least one pharmaceutically acceptable carrier; for simultaneous, separate or sequential use.

The term "barbiturates and derivatives thereof" as used herein includes, but is not limited to phenobarbital, pentobarbital, mepobarbital and primidon. The term "benzodiazepines" as used herein includes, but is not limited to clonazepam, clobazam, diazepam and lorazepam. The term "carboxamides" as used herein includes, but is not limited to carbamazepine, oxcarbazepine, 10-hydroxy-10,11-dihydro-carbamazepine and the compounds of formula (II)

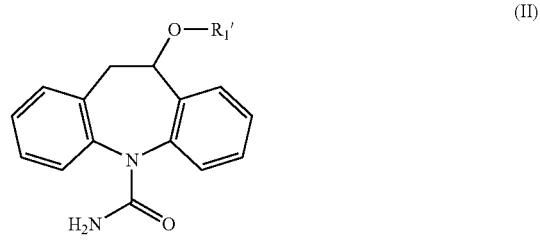

(II)

wherein $R_1'$ represents $C_1$-$C_3$alkyl carbonyl. The term "hydantoins" as used herein includes, but is not limited to phenyloin. The term "succinimides" as used herein includes, but is not limited to ethosuximide, phensuximide and mesuximide. The term "valproic acid and other fatty acid derivates" as used herein includes, but is not limited to valproic acid sodium salt, tiagabine hydrochloride monohydrate and vigabatrine. The term "other anti-epileptic drugs" as used herein includes, but is not limited to levetiracetam, lamotrigine, gabapentin, sultiam, felbamate, the 1,2,3-1H-triazoles disclosed in EP 114 347, esp. rufinamide [1-(2,6-difluorobenzyl)-1H-[1,2,3]triazole-4-carboxylic acid amide] and the 2-aryl-8-oxodihydropurines disclosed in WO99/28320. The term "AMPA antagonists" as used herein includes, but is not limited to the 1H-quinazoline-2,4-diones of formula I

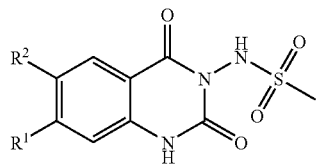

wherein R1 and R2 are as defined above, and their salts; CX 691, EGIS 8332 (7-acetyl-5-(4-aminophenyl)-8,9-dihydro-8-methyl-7H-1,3-dioxolo[4,5-h][2,3]benzodiazepine-8-carbonitrile), GYKI 47261 (4-(8-chloro-2-methyl-11H-imidazo[1,2-c][2,3]benzodiazepin-6-yl)benzenamine), Irampanel (BIIR 561; N,N-dimethyl-2-[2-(3-phenyl-1,2,4-oxadiazol-5-yl)phenoxy]ethanamine), KRP 199 (7-[4-[[[[(4-carboxyphenyl)amino]carbonyl]oxy]methyl]-1H-imidazol-1-yl]-3,4-dihydro-3-oxo-6-(trifluoromethyl)-2-quinoxalinecarboxylic acid), NS 1209 (2-[[[5-[4-[(dimethylamino)sulfonyl]phenyl]-1,2,6,7,8,9-hexahydro-8-methyl-2-oxo -3H-pyrrolo[3,2-h]isoquinolin-3-ylidene]amino]oxy]-4-hydroxybutanoic acid monosodium salt, e.g. prepared as described in WO 98/14447), topiramate (TOPAMAX, 2,3:4,5-bis-O-(1-methylethylidene)-beta-D-fructopyranose sulfamate, preparation, e.g. as described in U.S. Pat. No. 535,475) talampanel ((R)-7-acetyl-5-(4-aminophenyl)-8,9-dihydro-8-methyl-7H-1,3-dioxolo[4,5-h][2,3]benzodiazepine, preparation, e.g. as described in EP 492-485 and 1,2,3,4-tetrahydro-7-nitro-2,3-dioxo-5-quinoxalinyl)methyl]amino]methyl]phosphonic acid dehydrate.

Phenobarbital, can be administered, e.g., in the form as marketed, e.g. under the trademark Luminal™. Primidon can be administered, e.g., in the form as marketed, e.g. under the trademark Mylepsinum™. Clonazepam can be administered, e.g., in the form as marketed, e.g. under the trademark Antelepsin™. Diazepam can be administered, e.g., in the form as marketed, e.g. under the trademark Diazepam Desitin™. Lorazepam can be administered, e.g., in the form as marketed, e.g. under the trademark Tavor™. Carbamazepine can be administered, e.g., in the form as marketed, e.g. under the trademark Tegretal™ or Tegretol™. Oxcarbazepine can be administered, e.g., in the form as marketed, e.g. under the trademark Trileptal™. Oxcarbazepine is well known from the literature [see for example Schuetz H. et al., Xenobiotica (GB), 16(8), 769-778 (1986)]. The preparation of the compound of formula II wherein $R_1'$ is $C_1$-$C_3$alkyl carbonyl and its pharmaceutically acceptable salts is described, e.g., in U.S. Pat. No. 5,753,646. 10-Hydroxy-10,11-dihydrocarbamazepine can be prepared as disclosed in U.S. Pat. No. 3,637, 661. 10-Hydroxy-10,11-dihydrocarbamazepine may be administered, e.g., in the form as described in U.S. Pat. No. 6,316,417. Phenyloin can be administered, e.g., in the form as marketed, e.g. under the trademark Epanutin™. Ethosuximide can be administered, e.g., in the form as marketed, e.g. under the trademark Suxinutin™. Mesuximide can be administered, e.g., in the form as marketed, e.g. under the trademark Petinutin™. Valproic acid sodium salt can be administered, e.g., in the form as marketed, e.g. under the trademark Leptilan™. Tiagabine hydrochloride monohydrate can be administered, e.g., in the form as marketed, e.g. under the trademark Gabitril™. Vigabatrine can be administered, e.g., in the form as marketed, e.g. under the trademark Sabril™. Levetiracetam can be administered, e.g., in the form as marketed, e.g. under the trademark Keppra™. Lamotrigine can be administered, e.g., in the form as marketed, e.g. under the trademark Lamictal™. Gabapentin can be administered, e.g., in the form as marketed, e.g. under the trademark Neurontin™. Sultiam can be administered, e.g., in the form as marketed, e.g. under the trademark Ospolot™. Felbamate can be administered, e.g., in the form as marketed, e.g. under the trademark Taloxa™. Topiramate can be administered, e.g., in the form as marketed, e.g. under the trademark Topamax™. The 1,2, 3-1H-triazoles disclosed in EP 114 347 may be administered, e.g., in the form as described in U.S. Pat. No. 6,455,556. The 2-aryl-8-oxodihydropurines disclosed in WO99/28320 may be administered, e.g., in the form as described in WO99/28320. The compounds of formula I as well as their production process and pharmaceutical compositions thereof are known e.g. from WO 98/17672.

The structure of the active ingredients identified by code nos., generic or trade names may be taken from the actual edition of the standard compendium "The Merck Index" or from databases, e.g. Patents International (e.g. IMS World Publications). The corresponding content thereof is hereby incorporated by reference. Any person skilled in the art is fully enabled to identify the active ingredients and, based on these references, likewise enabled to manufacture and test the pharmaceutical indications and properties in standard test models, both in vitro and in vivo.

The term "a combined preparation", as used herein defines especially a "kit of parts" in the sense that the first and second active ingredient as defined above can be dosed independently or by use of different fixed combinations with distinguished amounts of the ingredients, i.e., simultaneously or at different time points. The parts of the kit of parts can then, e.g., be administered simultaneously or chronologically staggered, that is at different time points and with equal or different time intervals for any part of the kit of parts. Very preferably, the time intervals are chosen such that the effect on the treated disease in the combined use of the parts is larger than the effect which would be obtained by use of only any one of the active ingredients. The ratio of the total amounts of the active ingredient 1 to the active ingredient 2 to be administered in the combined preparation can be varied, e.g., in order to cope with the needs of a patient sub-population to be treated or the needs of the single patient which different needs can be due to age, sex, body weight, etc. of the patients. Preferably, there is at least one beneficial effect, e.g., a mutual enhancing of the effect of the first and second active ingredient, in particular a synergism, e.g. a more than additive effect, additional advantageous effects, less side effects, a combined therapeutical effect in a non-effective dosage of one or both of the first and second active ingredient, and especially a strong synergism the first and second active ingredient.

It will be understood that in the discussion of methods, references to the active ingredients are meant to also include the pharmaceutically acceptable salts. If these active ingredients have, for example, at least one basic center, they can form acid addition salts. Corresponding acid addition salts can also be formed having, if desired, an additionally present basic center. The active ingredients having an acid group (for example COOH) can also form salts with bases. The active ingredient or a pharmaceutically acceptable salt thereof may also be used in form of a hydrate or include other solvents used for crystallization.

A pharmaceutical combination which comprises two antiepileptics selected from the list consisting of barbiturates and derivatives thereof, benzodiazepines, carboxamides, hydantoins, succinimides, valproic acid and other fatty acid derivates, AMPA antagonists and other anti-epileptic drugs, in which the active ingredients are present in each case in free form or in the form of a pharmaceutically acceptable salt, if at least one salt-forming group is present, will be referred to hereinafter as a COMBINATION OF THE INVENTION.

Surprisingly, the administration of a COMBINATION OF THE INVENTION results in a beneficial, especially a synergistic, therapeutic effect or in other surprising beneficial effects, e.g. less side effects, compared to a monotherapy applying only one of the pharmaceutically active ingredients used in the COMBINATION OF THE INVENTION.

The pharmacological activity of a COMBINATION OF THE INVENTION may, for example, be evidenced in pre-clinical studies known as such, e.g. the Audiogenic Seizure Test or the methods described in the Examples.

The pharmacological activity of a COMBINATION OF THE INVENTION may, for example, be demonstrated in a clinical study. Such clinical studies are preferably randomized, double-blind, clinical studies in patients with epilepsy. Such studies demonstrate, in particular, the synergism of the active ingredients of the COMBINATIONS OF THE INVENTION. The beneficial effects on epilepsy can be determined directly through the results of these studies or by changes in the study design which are known as such to a person skilled in the art. The studies are, in particular, suitable to compare the effects of a monotherapy using the active ingredients and a COMBINATION OF THE INVENTION.

A further benefit is that lower doses of the active ingredients of the COMBINATION OF THE INVENTION can be used, for example, that the dosages need not only often be smaller but are also applied less frequently, or can be used in order to diminish the incidence of side effects. This is in accordance with the desires and requirements of the patients to be treated. The COMBINATIONs OF THE INVENTION can be used, in particular, for the treatment of epilepsy which is refractory to monotherapy.

Very preferred is a COMBINATION OF THE INVENTION comprising as active ingredients two anti-epileptic drugs, wherein a first anti-epileptic is selected from carboxamides, especially carbamazepine, oxcarbazepine, 10-hydroxy-10,11-dihydrocarbamazepine, a compound of formula II wherein $R_1'$ represents acetoxy, tiagabine hydrochloride monohydrate, phenobarbital, levetiracetam, pregabaline, brivaracetam and lamotrigine, and a second anti-epileptic is an AMPA antagonist.

It is one objective of this invention to provide a pharmaceutical composition comprising a quantity, which is jointly therapeutically effective against epilepsy, comprising at least two anti-epileptics or a pharmaceutically acceptable salt thereof and at least one pharmaceutically acceptable carrier. In this composition, the first and second active ingredient can be administered together, one after the other or separately in one combined unit dosage form or in two separate unit dosage forms. The unit dosage form may also be a fixed combination.

The pharmaceutical compositions according to the invention can be prepared in a manner known per se and are those suitable for enteral, such as oral or rectal, and parenteral administration to mammals (warm-blooded animals), including Man, comprising a therapeutically effective amount of at least one pharmacologically active ingredient, alone or in combination with one or more pharmaceutically acceptable carriers, especially suitable for enteral or parenteral application. The preferred route of administration of the dosage forms of the present invention is orally.

The novel pharmaceutical composition contain, for example, from about 10% to about 100%, preferably from about 20% to about 60%, of the active ingredients. Pharmaceutical preparations for the combination therapy for enteral or parenteral administration are, for example, those in unit dosage forms, such as sugar-coated tablets, tablets, capsules or suppositories, and furthermore ampoules. If not indicated otherwise, these are prepared in a manner known per se, for example by means of conventional mixing, granulating, sugar-coating, dissolving or lyophilizing processes. It will be appreciated that the unit content of active ingredient or ingredients contained in an individual dose of each dosage form need not in itself constitute an effective amount since the necessary effective amount can be reached by administration of a plurality of dosage units.

In preparing the compositions for oral dosage form, any of the usual pharmaceutical media may be employed, such as, for example, water, glycols, oils or alcohols; or carriers such as starches, sugars, microcrystalline cellulose, diluents, granulating agents, lubricants, binders, disintegrating agents and the like in the case of oral solid preparations such as, for example, powders, capsules and tablets. Because of their ease of administration, tablets and capsules represent the most advantageous oral dosage unit form in which case solid pharmaceutical carriers are obviously employed.

Furthermore, the present invention relates to the use of a COMBINATION OF THE INVENTION for the preparation of a medicament for the treatment of epilepsy.

Additionally, the present invention provides a method of treating a warm-blooded animal having epilepsy comprising administering to the animal a COMBINATION OF THE INVENTION in a quantity which is jointly therapeutically effective against epilepsy and in which the compounds can also be present in the form of their pharmaceutically acceptable salts.

Moreover, the present invention provides a commercial package comprising as active ingredients COMBINATION OF THE INVENTION, together with instructions for simultaneous, separate or sequential use thereof in the treatment of epilepsy.

In particular, a therapeutically effective amount of each of the active ingredients of the COMBINATION OF THE INVENTION may be administered simultaneously or sequentially and in any order, and the components may be administered separately or as a fixed combination. For example, the method of treatment of diseases according to the invention may comprise (i) administration of the first active ingredient in free or pharmaceutically acceptable salt form and (ii) administration of the second active ingredient in free or pharmaceutically acceptable salt form, simultaneously or sequentially in any order, in jointly therapeutically effective amounts, preferably in synergistically effective amounts, e.g. in daily dosages corresponding to the amounts described herein. The individual active ingredients of the COMBINATION OF THE INVENTION can be administered separately at different times during the course of therapy or concurrently in divided or single combination forms. Furthermore, the term administering also encompasses the use of a prodrug of an active ingredient that convert in vivo to the active ingredient. The instant invention is therefore to be understood as embracing all such regimes of simultaneous or alternating treatment and the term "administering" is to be interpreted accordingly.

In one preferred embodiment of the invention, the COMBINATION OF THE INVENTION is used for the treatment of treatment of epilepsy which is refractory to monotherapy.

The effective dosage of each of the active ingredients employed in the COMBINATION OF THE INVENTION may vary depending on the particular compound or pharmaceutical composition employed, the mode of administration, the severity of the condition being treated. Thus, the dosage regimen for the COMBINATION OF THE INVENTION is selected in accordance with a variety of factors including the route of administration and the renal and hepatic function of the patient. A physician, clinician or veterinarian of ordinary skill can readily determine and prescribe the effective amount of the single active ingredients required to prevent, counter or arrest the progress of the condition. Optimal precision in achieving concentration of the active ingredients within the range that yields efficacy without toxicity requires a regimen based on the kinetics of the active ingredients' availability to target sites. This involves a consideration of the distribution, equilibrium, and elimination of the active ingredients.

When the combination partners employed in the COMBINATION OF THE INVENTION are applied in the form as marketed single drugs, their dosage and mode of administration can take place in accordance with the information provided on the packet leaflet of the respective marketed drug in order to result in the beneficial effect described herein, if not mentioned herein otherwise. In particular, Phenobarbital may be administered to an adult patient in a total daily dosage between about 1 to about 3 mg/kg body weight and to a pediatric patient in a total daily dosage between about 3 to about 4 mg/kg body weight, split into two separate units.

Primidone may be administered to an adult patient and to children being at least 9 years old in a total daily dosage of 0.75 to 1.5 g.

Clonazepam may be administered to an adult patient in a total daily dosage between about 3 to about 8 mg and to a pediatric patient in a total daily dosage between about 0.5 to about 3 mg, split into three of four separate units.

Diazepam may be administered to an adult patient in a total daily dosage between about 5 to about 10 mg and to a pediatric patient in a total daily dosage between about 5 to about 10 mg.

Lorazepam may be administered to an adult patient in a total daily dosage between about 0.044 mg/kg body weight to about 0.05 mg/kg body weight.

Carbamazepine may be administered to an adult patient in a total daily dosage between about 600 to about 2000 mg and to a pediatric patient older than 6 years in a total daily dosage between about 400 to about 600 mg.

Oxcarbazepine may be administered to an adult patient in a total daily dosage between about 600 to about 2400 mg and to a pediatric patient in a total daily dosage between about 30 to about 46 mg/kg body weight.

Phenyloin may be administered to an adult patient in a total daily dosage between about 100 to about 300 mg and to a pediatric patient in a total daily dosage between about 100 to about 200 mg.

Ethosuximide may be administered to an adult patient in a total daily dosage of about 15 mg/kg body weight and to a pediatric patient in a total daily dosage of about 20 mg/kg body weight.

Valproic acid sodium salt may be administered to an adult patient in a total daily dosage of about 20 mg/kg body weight and to a pediatric patient in a total daily dosage of about 30 mg/kg body weight.

Tiagabine hydrochloride monohydrate may be administered to an adult patient in a total daily dosage between about 15 to about 70 mg.

Vigabatrine may be administered to an adult patient in a total daily dosage between about 2 to about 3 g.

Levetiracetam may be administered to a patient who is older than 16 years in a total daily dosage between about 1000 to about 3000 mg.

Lamotrigine may be administered to a patient who is older than 12 years in a total daily dosage between about 100 to about 200 mg.

Gabapentin may be administered to a patient in a total daily dosage between about 900 to about 2400 mg.

Sultiam may be administered to a patient in a total daily dosage between about 5 to about 10 mg/kg body weight.

Felbamate may be administered to a patient who is older than 14 years in a total daily dosage of between about 2400 to about 3600 mg.

Topiramate may be administered to an adult patient in a total daily dosage of between about 250 to about 500 mg.

Combinations for Affective and Attention Disorders

The present invention also relates to combinations suitable for the treatment of neurological/psychiatric disorders, in particular affective and attention disorders.

Surprisingly, the effect of a combination which comprises at least one AMPA receptor antagonist and at least one compound selected from the group consisting of lithium, valproic acid sodium salt, conventional antipsychotics, atypical antipsychotics, lamotrigine, methylphenidate, antidepressants and antiepileptics is greater than the additive effect of the combined drugs. Furthermore, the combinations disclosed herein can be used to treat affective and attention disorders which is refractory to monotherapy employing one of the combination partners alone.

Hence, the invention relates to a combination, such as a combined preparation or pharmaceutical composition, which comprises at least one AMPA receptor antagonist and at least one compound selected from the group consisting of lithium, valproic acid sodium salt, conventional antipsychotics, atypical antipsychotics, lamotrigine, methylphenidate, antidepressants and antiepileptics, in which the active ingredients are present in each case in free form or in the form of a pharmaceutically acceptable salt and optionally at least one pharmaceutically acceptable carrier; for simultaneous, separate or sequential use.

The term "affective and attention disorders" as used herein includes, but is not limited to bipolar disorder, e.g. manic-depressive psychoses, mania with or without psychotic feature, attention deficit hyperactivity disorder (ADHD), and other attention disorders, e.g. autism, as well as those behavioural states characterized by social withdrawal, e.g., negative symptoms.

The term "lithium" as used herein includes, but is not limited to lithium acetate, lithium carbonate, lithium chloride, lithium citrate and lithium sulfate. The term "conventional antipsychotics" as used herein includes, but is not limited to haloperidol and fluphenazine. The term "atypical antipsychotics" as used herein includes, but is not limited to olanzapine, quetiapine and risperidone. The term "antidepressants" as used herein includes, but is not limited to tricyclic antidepressants, selective serotonin reuptake inhibitors (SSRI's), or selective serotonin and norepinephrine reuptake inhibitors (SNRI-s). A tricyclic antidepressant suitable for the present invention is especially selected from amitriptyline, butriptyline, clomipramine, desipramine, dibenzepin, dothiepin, doxepin, imipramine, nortriptyline, opipramol, protriptyline, trimipramine, maprotiline, mianserin, and mirtazepine. An SSRI suitable for the present invention is especially selected from fluoxetine, fluvoxamine, sertraline, paroxetine, citalopram and escitalopram, and an SNRI selected from venlafaxine and duloxetine.

The term "anti-epileptics" as used herein includes, but is not limited to barbiturates and derivatives thereof, benzodiazepines, carboxamides, hydantoins, succinimides, valproic acid and other fatty acid derivates, AMPA antagonists and other anti-epileptic drugs, in which the active ingredients are present in each case in free form or in the form of a pharmaceutically acceptable salt and optionally at least one pharmaceutically acceptable carrier; for simultaneous, separate or sequential use.

The term "barbiturates and derivatives thereof" as used herein includes, but is not limited to phenobarbital, pentobarbital, mepobarbital and primidon. The term "benzodiazepines" as used herein includes, but is not limited to clonazepam, diazepam and lorazepam. The term "carboxamides" as used herein includes, but is not limited to carbamazepine, oxcarbazepine, 10-hydroxy-10,11-dihydrocarbamazepine and the compounds of formula II

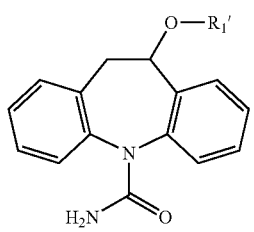

(II)

wherein $R_1'$ represents $C_1$-$C_3$alkyl carbonyl. The term "hydantoins" as used herein includes, but is not limited to phenyloin. The term "succinimides" as used herein includes, but is not limited to ethosuximide, phensuximide and mesuximide. The term "valproic acid and other fatty acid derivates" as used herein includes, but is not limited to valproic acid sodium salt, tiagabine hydrochloride monohydrate and vigabatrine. The term "other anti-epileptic drugs" as used herein includes, but is not limited to levetiracetam, lamotrigine, gabapentin, sultiam, felbamate, the 1,2,3-1H-triazoles disclosed in EP 114 347, esp. rufinamide [1-(2,6-difluorobenzyl)-1H-[1,2,3]triazole-4-carboxylic acid amide] and the 2-aryl-8-oxodihydropurines disclosed in WO99/28320.

Lithium acetate can be administered, e.g., in the form as marketed, e.g. under the trademark Quilonorm™. Lithium carbonate can be administered, e.g., in the form as marketed, e.g. under the trademark Eskalith™. Lithium citrate can be administered, e.g., in the form as marketed, e.g. under the trademark Litarex™. Lithium sulfate can be administered, e.g., in the form as marketed, e.g. under the trademark Lithium-Duriles™, or, e.g., by transdermal release (U.S. Pat. No. 6,375,990). Valproic acid sodium salt can be administered, e.g., in the form as marketed, e.g. under the trademark Divalproex Sodium™. Haloperidol can be administered, e.g., in the form as marketed, e.g. under the trademark Haloperidol STADA™. Olanzapine can be administered, e.g., in the form as marketed, e.g. under the trademark Zyprexa™. Risperidone can be administered, e.g., in the form as marketed, e.g. under the trademark Risperdal™. Quetiapine can be administered, e.g., in the form as marketed, e.g. under the trademark Seroquel™. Fluphenazine can be administered, e.g., in the form of its dihydrochloride as marketed, e.g. under the trademark Prolixin™. Lamotrigine can be administered, e.g., in the form as marketed, e.g. under the trademark Lamictal™. Fluoxetine can be administered, e.g., in the form of its hydrochloride as marketed, e.g. under the trademark Prozac™. Paroxetine can be administered, e.g., in the form as marketed, e.g. under the trademark Paxil™. Methylphenidate can be administered, e.g., in the form as marketed, e.g. under the trademark Ritalin™.

Methylphenidate is the most commonly prescribed psychotropic medication for children in the United States, primarily for the treatment of children diagnosed with attention deficit disorder (ADD) and Attention Deficit Hyperactivity Disorder (ADHD), and thus, is widely available. Methylphenidate is described in U.S. Pat. Nos. 2,838,519 and 2,957,880. U.S. Pat. Nos. 5,922,736; 5,908,850; 5,773,478; 6,113,879 describe administering d-threo methylphenidate to treat nervous system disorders. U.S. Pat. Nos. 6,100,401; 6,121,453; and 6,162,919 describe processes for preparing substantially the single enantiomer d-threo methylphenidate. U.S. Pat. Nos. 5,874,090 and 5,837,284 describe sustained release formulations of methylphenidate. All these citations are included herein by reference.

Topiramate can be administered, e.g., in the form as marketed, e.g. under the trademark Topamax™. The compounds of formula I as well as their production process and pharmaceutical compositions thereof are known e.g. from WO 98/17672.

The structure of the active ingredients identified by code nos., generic or trade names and their preparation may be taken from the actual edition of the standard compendium "The Merck Index" (e.g. M. J. O'Neil et al., ed., 'The Merck Index', 13$^{th}$ ed., Merck Research Laboratories, 2001) or from databases, e.g. Patents International (e.g. IMS World Publications). The corresponding content thereof is hereby incorporated by reference. Any person skilled in the art is fully enabled to identify the active ingredients and, based on these references, likewise enabled to manufacture and test the pharmaceutical indications and properties in standard test models, both in vitro and in vivo.

The term "a combined preparation", as used herein defines especially a "kit of parts" in the sense that the first and second active ingredient as defined above can be dosed independently or by use of different fixed combinations with distinguished amounts of the ingredients, i.e., simultaneously or at different time points. The parts of the kit of parts can then, e.g., be administered simultaneously or chronologically staggered, that is at different time points and with equal or different time intervals for any part of the kit of parts. Very preferably, the time intervals are chosen such that the effect on the treated disease in the combined use of the parts is larger than the effect which would be obtained by use of only any one of the active ingredients. The ratio of the total amounts of the active ingredient 1 to the active ingredient 2 to be administered in the combined preparation can be varied, e.g., in order to cope with the needs of a patient sub-population to be treated or the needs of the single patient which different needs can be due to age, sex, body weight, etc. of the patients. Preferably, there is at least one beneficial effect, e.g., a mutual enhancing of the effect of the first and second active ingredient, in particular a synergism, e.g. a more than additive effect, additional advantageous effects, less side effects, a combined therapeutic effect in a non-effective dosage of one or both of the first and second active ingredient, and especially a strong synergism the first and second active ingredient.

It will be understood that in the discussion of methods, references to the active ingredients are meant to also include the pharmaceutically acceptable salts. If these active ingredients have, for example, at least one basic center, they can form acid addition salts. Corresponding acid addition salts can also be formed having, if desired, an additionally present basic center. The active ingredients having an acid group (for example COOH) can also form salts with bases. The active ingredient or a pharmaceutically acceptable salt thereof may also be used in form of a hydrate or include other solvents used for crystallization.

A pharmaceutical combination which comprises at least one AMPA receptor antagonist and at least one compound selected from the group consisting of lithium, valproic acid sodium salt, conventional antipsychotics, atypical antipsychotics, lamotrigine, methylphenidate and antidepressants, in which the active ingredients are present in each case in free form or in the form of a pharmaceutically acceptable salt, if at least one salt-forming group is present, will be referred to hereinafter as a COMBINATION OF THE INVENTION.

Surprisingly, the administration of a COMBINATION OF THE INVENTION results in a beneficial, especially a synergistic, therapeutic effect or in other surprising beneficial effects, e.g. less side effects, compared to a monotherapy applying only one of the pharmaceutically active ingredients used in the COMBINATION OF THE INVENTION.

The activity of the COMBINATION OF THE INVENTION in the treatment of affective disorders is evidenced, for example, in the preclinical tests suitable for detecting drugs reversing psycho-motor stimulatory effects.

Test 1: NMDA-Antagonist Induced Locomotion:

Male rats are used. In principle 8 treatment groups are formed:

1) AMPA receptor antagonist followed by solvent 2 and solvent 3 to study the effects of the AMPA receptor antagonist on locomotor activity.

2) Solvent 1, combination partner and solvent 3 to study the effects of the combination partner on locomotor activity.

3) Solvent 1, solvent 2, followed by the competitive NMDA receptor antagonist (S)-2-amino-3-(2'-chloro-5-phosphonomethyl-biphenyl-3-yl)-propionic acid, hereinafter SDZ 220-581 (10 mg/kg) to study the induction of hyperlocomotor activity.

4) AMPA receptor antagonist followed by solvent 2 and SDZ 220-581.

5) Solvent 1 followed by combination partner and SDZ 220-581.

6) The COMBINATION OF THE INVENTION (doses of each active ingredient at doses close to threshold) followed by solvent 3.

7) The COMBINATION OF THE INVENTION (doses of each active ingredient at doses close to threshold) followed by SDZ 220-581 (10 mg/kg).

8) Solvent 1 solvent 2 solvent 3.

Rats are randomly allocated to these pretreatment groups (n=10/dose group). Drugs are administered subcutaneous (s.c.), 15 min prior to SDZ 220-581. Immediately after the animals received SDZ 220-581, they are placed into the activity monitor for a period of 60 min. Locomotor activity is analysed over the initial 30 minutes.

Locomotion is recorded with a videotracking system. Animals are on a normal 12/12 h day-night cycle, with light on at 06:00 H. Experiments are performed in a dimly lit room between 07:00 H and 15:00 H. Animals are placed in a round arena (diameter 42 cm, height 32 cm) made of grey polyvinylchloride plastic.

Test 2: NMDA-Channel Blocker Induced Head Swaying and Circling:

Adult male rats are used. The animals are randomized to the following treatment groups (n=10 per group):

1) AMPA receptor antagonist (t=−15 min) followed by solvent 2 (t=−15 min) and solvent 3 (t=0 min) to study whether head swaying and circling is induced by the AMPA receptor antagonist given alone.

2) Solvent 1 (t=−15 min), combination partner (t=−15 min) and solvent 3 (t=0 min) to study whether head swaying and circling is induced by the combination partner given alone.

3) Solvent 1 (t=−15 min), solvent 2 (t=−15 min), followed by phencyclidine (PCP; an NMDA channel blocker, dosed 3 and 10 mg/kg, t=0 min) to induce circling and head swaying.

4) AMPA receptor antagonist (t=−15 min) followed by solvent 2 (t=−15 min) and PCP (t=0 min).

5) Solvent 1 (t=−15 min) followed by combination partner (t=−15 min) and PCP (t=0 min).

6) The COMBINATION OF THE INVENTION (doses of each active ingredients at doses close to threshold (t=−15 min)) followed by solvent 3 (t=0 min).

7) The COMBINATION OF THE INVENTION (doses of each active ingredients at doses close to threshold (t=−15 min)) followed by PCP (3 and 10 mg/kg, t=0 min).

8) Solvent 1 (t=−15 min), solvent 2 (t=−15 min), solvent 3 (t=0 min).

COMBINATION OF THE INVENTION (at t=−15 min) and PCP (at t=0 min) are administered s.c. in a volume of 1 mL/kg. Video-recordings of the animals behavior over the period 0-30 min following PCP are scored by an observer who is unaware about the animals pretreatment. Head-swaying (rocking the head repeatedly by at least 2 cm left and right) and circling (turning around by using the forepaws, whereas the hindpaws remain more or less on the original position) are scored as present (1) or absent (O), every five minutes for the duration of 1 min. The scores for individual animals is summed and group scores used for statistical analysis (t-test with Bonferroni correction).

NMDA-antagonist induced locomotor responses reflect a psychosis/mania-like state. Blockade of this activity indicates an anti-psychotic, anti-manic activity. Furthermore, enhancement of head-swaying and circling suggest a behavioral disinhibition (=anxiolytic-/antidepressant-like) and sociotropic activity. Therefore, the compounds are useful in the treatment of affective disorders including bipolar disorders, e.g. manic-depressive psychoses, extreme psychotic states e.g. mania with psychotic feature and excessive mood swings where behavioral stabilization is desired. In addition, the COMBINATION OF THE INVENTION are indicated in ADHD (attention deficit hyperactivity disorders) and other attention disorders, e.g. autism, and as well as those behavioral states characterized by social withdrawal e.g. negative symptoms.

The pharmacological activity of a COMBINATION OF THE INVENTION may also be demonstrated in a clinical study. Such clinical studies are preferably randomized, double-blind, clinical studies in patients with affective and attention disorders. Such studies demonstrate, in particular, the synergism of the active ingredients of the COMBINATIONS OF THE INVENTION. The beneficial effects on affective and attention disorders can be determined directly through the results of these studies or by changes in the study design which are known as such to a person skilled in the art. The studies are, in particular, suitable to compare the effects of a monotherapy using the active ingredients and a COMBINATION OF THE INVENTION.

A further benefit is that lower doses of the active ingredients of the COMBINATION OF THE INVENTION can be used, for example, that the dosages need not only often be smaller but are also applied less frequently, or can be used in order to diminish the incidence of side effects. This is in accordance with the desires and requirements of the patients to be treated. The COMBINATIONs OF THE INVENTION can be used, in particular, for the treatment of affective and attention disorders which is refractory to monotherapy.

It is one objective of this invention to provide a pharmaceutical composition comprising a quantity, which is jointly therapeutically effective against affective and attention disorders, comprises at least one AMPA receptor antagonist, at least one compound selected from the group consisting of lithium, valproic acid sodium salt, conventional antipsychotics, atypical antipsychotics, lamotrigine, methylphenidate and antidepressants and at least one pharmaceutically acceptable carrier. In this composition, the first and second active ingredient can be administered together, one after the other or separately in one combined unit dosage form or in two separate unit dosage forms. The unit dosage form may also be a fixed combination.

The pharmaceutical compositions according to the invention can be prepared in a manner known per se and are those suitable for enteral, such as oral or rectal, and parenteral administration to mammals (warm-blooded animals), including man, comprising a therapeutically effective amount of at least one pharmacologically active ingredient, alone or in combination with one or more pharmaceutically acceptable carries, especially suitable for enteral or parenteral application. The preferred route of administration of the dosage forms of the present invention is orally.

The novel pharmaceutical composition contain, for example, from about 10% to about 100%, preferably from about 20% to about 60%, of the active ingredients. Pharmaceutical preparations for the combination therapy for enteral or parenteral administration are, for example, those in unit dosage forms, such as sugar-coated tablets, tablets, capsules or suppositories, and furthermore ampoules. If not indicated otherwise, these are prepared in a manner known per se, for example by means of conventional mixing, granulating, sugar-coating, dissolving or lyophilizing processes. It will be appreciated that the unit content of active ingredient or ingredients contained in an individual dose of each dosage form need not in itself constitute an effective amount since the necessary effective amount can be reached by administration of a plurality of dosage units.

In preparing the compositions for oral dosage form, any of the usual pharmaceutical media may be employed, such as, for example, water, glycols, oils or alcohols; or carriers such as starches, sugars, microcristalline cellulose, diluents, granulating agents, lubricants, binders, disintegrating agents and the like in the case of oral solid preparations such as, for example, powders, capsules and tablets. Because of their ease of administration, tablets and capsules represent the most advantageous oral dosage unit form in which case solid pharmaceutical carriers are obviously employed.

Furthermore, the present invention relates to the use of a COMBINATION OF THE INVENTION for the preparation of a medicament for the treatment of affective and attention disorders.

Additionally, the present invention provides a method of treating a warm-blooded animal having affective and attention disorders comprising administering to the animal a COMBINATION OF THE INVENTION in a quantity which is jointly therapeutically effective against affective and attention disorders and in which the compounds can also be present in the form of their pharmaceutically acceptable salts.

Moreover, the present invention provides a commercial package comprising as active ingredients COMBINATION OF THE INVENTION, together with instructions for simultaneous, separate or sequential use thereof in the treatment of affective and attention disorders.

In particular, a therapeutically effective amount of each of the active ingredients of the COMBINATION OF THE INVENTION may be administered simultaneously or sequentially and in any order, and the components may be administered separately or as a fixed combination. For example, the method of treatment of affective and attention disorders according to the invention may comprise (i) administration of the first active ingredient in free or pharmaceutically acceptable salt form and (ii) administration of the second active ingredient in free or pharmaceutically acceptable salt form, simultaneously or sequentially in any order, in jointly therapeutically effective amounts, preferably in synergistically effective amounts, e.g. in daily dosages corresponding to the amounts described herein. The individual active ingredients of the COMBINATION OF THE INVENTION can be administered separately at different times during the course of therapy or concurrently in divided or single combination forms. Furthermore, the term administering also encompasses the use of a pro-drug of an active ingredient that convert in vivo to the active ingredient. The instant invention is therefore to be understood as embracing all such regimes of simultaneous or alternating treatment and the term "administering" is to be interpreted accordingly.

In one preferred embodiment of the invention, the COMBINATION OF THE INVENTION is used for the treatment of affective and attention disorders which is refractory to monotherapy.

The effective dosage of each of the active ingredients employed in the COMBINATION OF THE INVENTION may vary depending on the particular compound or pharmaceutical composition employed, the mode of administration, the severity of the condition being treated. Thus, the dosage regimen for the COMBINATION OF THE INVENTION is selected in accordance with a variety of factors including the route of administration and the renal and hepatic function of the patient. A physician, clinician or veterinarian of ordinary skill can readily determine and prescribe the effective amount of the single active ingredients required to prevent, counter or arrest the progress of the condition. Optimal precision in achieving concentration of the active ingredients within the range that yields efficacy without toxicity requires a regimen based on the kinetics of the active ingredients' availability to target sites. This involves a consideration of the distribution, equilibrium, and elimination of the active ingredients.

When the combination partners employed in the COMBINATION OF THE INVENTION are applied in the form as marketed single drugs, their dosage and mode of administration can take place in accordance with the information provided on the packet leaflet of the respective marketed drug in order to result in the beneficial effect described herein, if not mentioned herein otherwise. In particular, Topiramate may be administered to an adult patient in a total daily dosage of between about 250 to about 500 mg.

Haloperidol may be administered to a patient in a total daily dosage of between about 2.5 to about 30 mg.

Lithium can be administered to a patient in a total daily dosage of between about 0.5 to about 2 g.

Olanzapine can be administered to a patient in a total daily dosage of between about 2.5 to about 20 mg.

Quetiapine can be administered to a patient in a total daily dosage of between about 500 to about 600 mg.

Risperidone may be administered to a patient in a total daily dosage of between about 2 to about 6 mg.

Valproic acid sodium salt may be administered to a patient in a total daily dosage of between about 2000 to about 3000 mg.

Amitriptyline may be administered to a patient in a total daily dosage of between about 30 to about 300 mg.

Clomipramine may be administered to a patient in a total daily dosage of between about 30 to about 150 mg.

Desipramine may be administered to a patient in a total daily dosage of between about 25 to about 200 mg.

{[(7-Nitro-2,3-dioxo-1,2,3,4-tetrahydro-quinoxalin-5-yl-methyl)-amino]-methyl}-phosphonic acid may be administered to a patient in a total daily dosage of about 60 to about 400 mg.

Combinations for Anxiety

The present invention also relates to combinations suitable for the treatment of neurological/psychiatric disorders, in particular anxiety disorders or other psychiatric disorders with underlying anxiety symptomatologies.

Surprisingly, the effect of a combination which comprises at least one AMPA receptor antagonist and at least one compound selected from the group consisting of benzodiazepines, selective serotonin reuptake inhibitors (SSRIs), selective serotonin and norepinephrine reuptake inhibitors (SNRIs), buspirone and pregabalin is greater than the additive effect of the combined drugs. Furthermore, the combinations disclosed herein can be used to treat anxiety disorders or other psychiatric disorders with underlying anxiety symptomatologies which are refractory to monotherapy employing one of the combination partners alone.

Hence, the invention relates to a combination, such as a combined preparation or pharmaceutical composition, which comprises at least one AMPA receptor antagonist and at least one compound selected from the group consisting of benzodiazepines, SSRIs, SNRIs, buspirone and pregabalin, in which the active ingredients are present in each case in free form or in the form of a pharmaceutically acceptable salt and optionally at least one pharmaceutically acceptable carrier; for simultaneous, separate or sequential use.

The term "anxiety or other psychiatric disorders with underlying anxiety symptomatologies" as used herein includes, but is not restricted to anxiety disorders, such as general anxiety disorder, social anxiety disorder, post traumatic stress disorder, obsessive compulsive disorder, panic and anxiety occurring following cessation of psychostimulants or intake of other psychotropics with abuse potential.

An SSRI suitable for the present invention is especially selected from fluoxetine, fuvoxamine, sertraline, paroxetine, citalopram and escitalopram.

An SNRI suitable for the present invention is especially selected from venlafaxine and duloxetine.

The term "benzodiazepines" as used herein includes, but is not limited to clonazepam, diazepam and lorazepam.

Buspirone can be administered in free form or as a salt, e.g. as its hydrochloride, e.g., in the form as marketed, e.g. under the trademark Anxut™, Buspar™ or Bespar™. It can be prepared and administered, e.g., as described in U.S. Pat. No. 3,717,634. Topiramate can be administered, e.g., in the form as marketed, e.g. under the trademark Topamax™. The compounds of formula I as well as their production process and pharmaceutical compositions thereof are known e.g. from WO 98/17672. Fluoxetine can be administered, e.g., in the form of its hydrochloride as marketed, e.g. under the trademark Prozac™. It can be prepared and administered, e.g., as described in CA 2002182. Paroxetine ((3S,4R)-3-[(1,3-benzodioxol-5-yloxy)methyl]-4-(4-fluorophenyl)piperidine) can be administered, e.g., in the form as marketed, e.g. under the trademark Paxil™. It can be prepared and administered, e.g., as described in U.S. Pat. No. 3,912,743. Sertraline can be administered, e.g., in the form as marketed, e.g. under the trademark Zoloft™. It can be prepared and administered, e.g., as described in U.S. Pat. No. 4,536,518. Clonazepam can be administered, e.g., in the form as marketed, e.g. under the trademark Antelepsin™. Diazepam can be administered, e.g., in the form as marketed, e.g. under the trademark Diazepam Desitin™. Lorazepam can be administered, e.g., in the form as marketed, e.g. under the trademark Tavor™. Citalopram can be administered in free form or as a salt, e.g. as its hydrobromide, e.g., in the form as marketed, e.g. under the trademark Cipramil™. Escitalopram can be administered, e.g., in the form as marketed, e.g. under the trademark Cipralex™. It can be prepared and administered, e.g., as described in AU623144. Venlafaxine can be administered, e.g., in the form as marketed, e.g. under the trademark Trevilor™. Duloxetine can be administered, e.g., in the form as marketed, e.g. under the trademark Cymbalta™. It may be prepared and administered, e.g., as described in CA 1302421.

The structure of the active ingredients identified by code nos., generic or trade names may be taken from the actual edition of the standard compendium "The Merck Index" or from databases, e.g. Patents International (e.g. IMS World Publications). The corresponding content thereof is hereby incorporated by reference. Any person skilled in the art is fully enabled to identify the active ingredients and, based on these references, likewise enabled to manufacture and test the pharmaceutical indications and properties in standard test models, both in vitro and in vivo.

The term "a combined preparation", as used herein defines especially a "kit of parts" in the sense that the first and second active ingredient as defined above can be dosed independently or by use of different fixed combinations with distinguished amounts of the ingredients, i.e., simultaneously or at different time points. The parts of the kit of parts can then, e.g., be administered simultaneously or chronologically staggered, that is at different time points and with equal or different time intervals for any part of the kit of parts. Very preferably, the time intervals are chosen such that the effect on the treated disease in the combined use of the parts is larger than the effect which would be obtained by use of only any one of the active ingredients. The ratio of the total amounts of the active ingredient 1 to the active ingredient 2 to be administered in the combined preparation can be varied, e.g., in order to cope with the needs of a patient sub-population to be treated or the needs of the single patient which different needs can be due to age, sex, body weight, etc. of the patients. Preferably, there is at least one beneficial effect, e.g., a mutual enhancing of the effect of the first and second active ingredient, in particular a synergism, e.g. a more than additive effect, additional advantageous effects, less side effects, a combined therapeutical effect in a non-effective dosage of one or both of the first and second active ingredient, and especially a strong synergism the first and second active ingredient.

It will be understood that in the discussion of methods, references to the active ingredients are meant to also include the pharmaceutically acceptable salts. If these active ingredients have, for example, at least one basic center, they can form acid addition salts. Corresponding acid addition salts can also be formed having, if desired, an additionally present basic center. The active ingredients having an acid group (for example COOH) can also form salts with bases. The active ingredient or a pharmaceutically acceptable salt thereof may also be used in form of a hydrate or include other solvents used for crystallization.

A pharmaceutical combination which comprises at least one AMPA receptor antagonist and at least one compound selected from the group consisting of benzodiazepines, SSRIs, SNRIs, buspirone and pregabalin in which the active ingredients are present in each case in free form or in the form of a pharmaceutically acceptable salt, if at least one salt-forming group is present, will be referred to hereinafter as a COMBINATION OF THE INVENTION.

Surprisingly, the administration of a COMBINATION OF THE INVENTION results in a beneficial, especially a synergistic, therapeutic effect or in other surprising beneficial effects, e.g. less side effects, compared to a monotherapy applying only one of the pharmaceutically active ingredients used in the COMBINATION OF THE INVENTION.

The pharmacological activity of the COMBINATION OF THE INVENTION in the treatment of anxiety symptomatologies is evidenced, for example, in preclinical studies known as such, e.g. the stress induced hyperthermia model.

The following Example serves to illustrate the invention without limiting the invention in its scope.

Male mice are used. Treated animals were placed in their home cage for 1 h. This time interval may depend on the combination partner and may therefore be longer or shorter. After this pretreatment time, the core body temperature is measured using a rectal probe. Subsequently, the animal is placed back in the cage and the measurement is repeated after 15 min. The first rectal measurement including handling is a stressful situation for the animal which causes the body temperature to rise. Anxiolytic compounds are known to prevent the increase in core body temperature in response to the first measurement. In principle 4 treatment groups are formed:

1) Solvent followed by solvent.

2) Solvent pretreatment followed by the combination partner.

3) AMPA receptor antagonist followed by solvent.

4) The COMBINATION OF THE INVENTION (low doses of each active ingredients)

Mice are randomly allocated to these pretreatment groups (n=10/dose group). Drugs are administered subcutaneous (s.c.) or orally (p.o.) at doses close to threshold when administered alone.

The pharmacological activity of a COMBINATION OF THE INVENTION may, for example, also be demonstrated in a clinical study. Such clinical studies are preferably randomized, double-blind, clinical studies in patients with anxiety or other psychiatric disorders with underlying anxiety symptomatologies. Such studies demonstrate, in particular, the synergism of the active ingredients of the COMBINATIONS OF THE INVENTION. The beneficial effects on anxiety or other psychiatric disorders with underlying anxiety symptomatologies can be determined directly through the results of these studies or by changes in the study design which are known as such to a person skilled in the art. The studies are, in particular, suitable to compare the effects of a monotherapy using the active ingredients and a COMBINATION OF THE INVENTION.

A further benefit is that lower doses of the active ingredients of the COMBINATION OF THE INVENTION can be used, for example, that the dosages need not only often be smaller but are also applied less frequently, or can be used in order to diminish the incidence of side effects. This is in accordance with the desires and requirements of the patients to be treated. The COMBINATIONs OF THE INVENTION can be used, in particular, for the treatment of anxiety or other psychiatric disorders with underlying anxiety symptomatologies which is refractory to monotherapy.

It is one objective of this invention to provide a pharmaceutical composition comprising a quantity, which is jointly therapeutically effective against anxiety and other psychiatric disorders with underlying anxiety symptomatologies, comprising at least one AMPA receptor antagonist, at least one compound selected from the group consisting of benzodiazepines, selective serotonin reuptake inhibitors (SSRIs), selective serotonin and norepinephrine reuptake inhibitors (SNRIs), buspirone and pregabalin and at least one pharmaceutically acceptable carrier. In this composition, the first and second active ingredient can be administered together, one after the other or separately in one combined unit dosage form or in two separate unit dosage forms. The unit dosage form may also be a fixed combination.

The pharmaceutical compositions according to the invention can be prepared in a manner known per se and are those suitable for enteral, such as oral or rectal, and parenteral administration to mammals (warm-blooded animals), including humans, comprising a therapeutically effective amount of at least one pharmacologically active ingredient, alone or in combination with one or more pharmaceutically acceptable carries, especially suitable for enteral or parenteral application. The preferred route of administration of the dosage forms of the present invention is orally.

The novel pharmaceutical composition contain, for example, from about 10% to about 100%, preferably from about 20% to about 60%, of the active ingredients. Pharmaceutical preparations for the combination therapy for enteral or parenteral administration are, for example, those in unit dosage forms, such as sugar-coated tablets, tablets, capsules or suppositories, and furthermore ampoules. If not indicated otherwise, these are prepared in a manner known per se, for example by means of conventional mixing, granulating, sugar-coating, dissolving or lyophilizing processes. It will be appreciated that the unit content of active ingredient or ingredients contained in an individual dose of each dosage form need not in itself constitute an effective amount since the necessary effective amount can be reached by administration of a plurality of dosage units.

In preparing the compositions for oral dosage form, any of the usual pharmaceutical media may be employed, such as, for example, water, glycols, oils or alcohols; or carriers such as starches, sugars, microcristalline cellulose, diluents, granulating agents, lubricants, binders, disintegrating agents and the like in the case of oral solid preparations such as, for example, powders, capsules and tablets. Because of their ease of administration, tablets and capsules represent the most advantageous oral dosage unit form in which case solid pharmaceutical carriers are obviously employed.

Furthermore, the present invention relates to the use of a COMBINATION OF THE INVENTION for the preparation of a medicament for the treatment of anxiety or other psychiatric disorders with underlying anxiety symptomatologies.

Additionally, the present invention provides a method of treating a warm-blooded animal having anxiety modelled in a particular paradigm comprising administering to the animal a COMBINATION OF THE INVENTION in a quantity which is jointly therapeutically effective against anxiety or other psychiatric disorders with underlying anxiety symptomatologies and in which the compounds can also be present in the form of their pharmaceutically acceptable salts.

Moreover, the present invention provides a commercial package comprising as active ingredients COMBINATION OF THE INVENTION, together with instructions for simultaneous, separate or sequential use thereof in the treatment of anxiety or other psychiatric disorders with underlying anxiety symptomatologies.

In particular, a therapeutically effective amount of each of the active ingredients of the COMBINATION OF THE INVENTION may be administered simultaneously or sequentially and in any order, and the components may be administered separately or as a fixed combination. For example, the method of treatment of anxiety or other psychiatric disorders with underlying anxiety symptomatologies according to the invention may comprise (i) administration of the first active ingredient in free or pharmaceutically acceptable salt form and (ii) administration of the second active ingredient in free or pharmaceutically acceptable salt form, simultaneously or sequentially in any order, in jointly therapeutically effective amounts, preferably in synergistically effective amounts, e.g. in daily dosages corresponding to the amounts described herein. The individual active ingredients of the COMBINATION OF THE INVENTION can be administered separately at different times during the course of therapy or concurrently in divided or single combination forms. Furthermore, the term administering also encompasses the use of a pro-drug of an active ingredient that convert in vivo to the active ingredient. The instant invention is therefore to be understood as embracing all such regimes of simultaneous or alternating treatment and the term "administering" is to be interpreted accordingly.

In one preferred embodiment of the invention, the COMBINATION OF THE INVENTION is used for the treatment of anxiety or other psychiatric disorders with underlying anxiety symptomatologies which are refractory to monotherapy.

The effective dosage of each of the active ingredients employed in the COMBINATION OF THE INVENTION may vary depending on the particular compound or pharmaceutical composition employed, the mode of administration, the severity of the condition being treated. Thus, the dosage regimen the COMBINATION OF THE INVENTION is selected in accordance with a variety of factors including the route of administration and the renal and hepatic function of the patient. A physician, clinician or veterinarian of ordinary skill can readily determine and prescribe the effective amount of the single active ingredients required to prevent, counter or arrest the progress of the condition. Optimal precision in achieving concentration of the active ingredients within the range that yields efficacy without toxicity requires a regimen based on the kinetics of the active ingredients' availability to target sites. This involves a consideration of the distribution, equilibrium, and elimination of the active ingredients.

When the combination partners employed in the COMBINATION OF THE INVENTION are applied in the form as marketed single drugs, their dosage and mode of administration can take place in accordance with the information provided on the packet leaflet of the respective marketed drug in order to result in the beneficial effect described herein, if not mentioned herein otherwise. In particular, Topiramate may be administered to an adult patient in a total daily dosage of between about 250 to about 500 mg. Buspirone may be administered in a total daily dosage of between about 15 to about 60 mg.

Clonazepam may be administered to an adult patient in a total daily dosage between about 3 to about 8 mg and to a pediatric patient in a total daily dosage between about 0.5 to about 3 mg, split into three of four separate units.

Diazepam may be administered to an adult patient in a total daily dosage between about 5 to about 10 mg and to a pediatric patient in a total daily dosage between about 5 to about 10 mg.

Lorazepam may be administered to an adult patient in a total daily dosage between about. 0.044 mg/kg body weight to about 0.05 mg/kg body weight.

Citalopram may be administered in a total daily dosage of between about 20 to about 60 mg.

Paroxetine may be administered in a total daily dosage of between about 20 to about 50 mg.

Venlafaxine may be administered in a total daily dosage of between about 70 to about 150 mg.

{[(7-Nitro-2,3-dioxo-1,2,3,4-tetrahydro-quinoxalin-5-yl-methyl)-amino]-methyl}-phosphonic acid may be administered to a patient in a total daily dosage of about 60 to about 400 mg.

Combinations for Myopia

The present invention also relates to combinations suitable for the treatment of ocular disorders, in particular myopia.

Myopia (nearsightedness) is an error of visual focusing that makes distant objects appear blurred. A nearsighted person can easily read the Jaeger eye chart (the chart for near reading), but finds the Snellen eye chart (the chart for distance) difficult to read. This blurred vision occurs when the physical length of the eye is greater than the optical length. For this reason, nearsightedness often develops in the rapidly growing school-aged child or teenager, and progresses during the growth years, requiring frequent changes in glasses or contact lenses. It usually stops progressing as growth is completed in the early twenties. Nearsightedness affects males and females equally, and those with a family history of nearsightedness are more likely to develop it. Nearsightedness can often be compensated for by the use of eyeglasses or contact lenses, which shift the focus point to the retina. Furthermore, there are several surgical procedures that reshape the cornea, shifting the focus point from in front of the retina to the retina. Most eyes with nearsightedness are entirely healthy, but a small number of people with myopia develop a form of retinal degeneration.

Surprisingly, the effect of a combination which comprises at least one AMPA receptor antagonist and at least one least one compound selected from the group consisting of pirenzepine, telenzepine, ortho-methoxy-sila-hexocyclium, gamma-amino butyric acid (GABA) and GABA agonists is greater than the additive effect of the combined drugs. Furthermore, the combinations disclosed herein can be used to treat myopia which is refractory to monotherapy employing one of the combination partners alone.

Hence, the invention relates to a combination, such as a combined preparation or pharmaceutical composition, which comprises at least one AMPA receptor antagonist and at least one compound selected from the group consisting of pirenzepine, telenzepine, ortho-methoxy-sila-hexocyclium, gamma-amino butyric acid (GABA) and GABA agonists, in which the active ingredients are present in each case in free form or in the form of a pharmaceutically acceptable salt and optionally at least one pharmaceutically acceptable carrier; for simultaneous, separate or sequential use.

Topiramate can be administered, e.g., in the form as marketed, e.g. under the trademark Topamax™. The compounds of formula I as well as their production process and pharmaceutical compositions thereof are known e.g. from WO 98/17672.

Pirenzepine, telenzepine and ortho-methoxy-sila-hexocyclium can be applied as described in U.S. Pat. No. 5,122,522.

The term "gamma-amino butyric acid (GABA) and GABA agonists" as used herein includes, but is not limited to the compounds disclosed in WO03/032975.

The structure of the active ingredients identified by code nos., generic or trade names may be taken from the actual edition of the standard compendium "The Merck Index" or from databases, e.g. Patents International (e.g. IMS World Publications). The corresponding content thereof is hereby incorporated by reference. Any person skilled in the art is fully enabled to identify the active ingredients and, based on these references, likewise enabled to manufacture and test the pharmaceutical indications and properties in standard test models, both in vitro and in vivo.

The term "a combined preparation", as used herein defines especially a "kit of parts" in the sense that the first and second active ingredient as defined above can be dosed independently or by use of different fixed combinations with distinguished amounts of the ingredients, i.e., simultaneously or at different time points. The parts of the kit of parts can then, e.g., be administered simultaneously or chronologically staggered, that is at different time points and with equal or different time intervals for any part of the kit of parts. Very preferably, the time intervals are chosen such that the effect on the treated disease in the combined use of the parts is larger than the effect which would be obtained by use of only any one of the active ingredients. The ratio of the total amounts of the active ingredient 1 to the active ingredient 2 to be administered in the combined preparation can be varied, e.g., in order to cope with the needs of a patient sub-population to be treated or the needs of the single patient which different needs can be due to age, sex, body weight, etc. of the patients. Preferably, there is at least one beneficial effect, e.g., a mutual enhancing of the effect of the first and second active ingredient, in particular a synergism, e.g. a more than additive effect, additional advantageous effects, less side effects, a combined therapeutical effect in a non-effective dosage of one or both of the first and second active ingredient, and especially a strong synergism the first and second active ingredient.

It will be understood that in the discussion of methods, references to the active ingredients are meant to also include the pharmaceutically acceptable salts. If these active ingredients have, for example, at least one basic center, they can form acid addition salts. Corresponding acid addition salts can also be formed having, if desired, an additionally present basic center. The active ingredients having an acid group (for example COOH) can also form salts with bases. The active ingredient or a pharmaceutically acceptable salt thereof may also be used in form of a hydrate or include other solvents used for crystallization.

A pharmaceutical combination which comprises at least one AMPA receptor antagonist and at least one compound selected from the group consisting of pirenzepine, telenzepine, ortho-methoxy-sila-hexocyclium, gamma-amino butyric acid (GABA) and GABA agonists, in which the active ingredients are present in each case in free form or in the form of a pharmaceutically acceptable salt, if at least one salt-forming group is present, will be referred to hereinafter as a COMBINATION OF THE INVENTION.

Surprisingly, the administration of a COMBINATION OF THE INVENTION results in a beneficial, especially a synergistic, therapeutic effect or in other surprising beneficial effects, e.g. less side effects, compared to a monotherapy applying only one of the pharmaceutically active ingredients used in the COMBINATION OF THE INVENTION.

The pharmacological activity of a COMBINATION OF THE INVENTION may, for example, be evidenced in pre-clinical studies known as such, e.g. the methods described herein.

The activity against myopia of the compounds is, e.g., indicated in standard tests, e.g. in the model according to R. A. Stone et al. [Proc. Natl. Acad. Sci. (USA) 86, 704-706 (1989)] wherein experimental myopia is produced in chicken, on administration of about 0.1 to about 1 mg/kg of a COMBINATION OF THE INVENTION in eye drops.

Furthermore, the pharmacological activity of a COMBINATION OF THE INVENTION may, for example, be demonstrated in a clinical study. Such clinical studies are preferably randomized, double-blind, clinical studies in patients with myopia. Such studies demonstrate, in particular, the synergism of the active ingredients of the COMBINATIONS OF THE INVENTION. The beneficial effects on myopia can be determined directly through the results of these studies or by changes in the study design which are known as such to a person skilled in the art. The studies are, in particular, suitable to compare the effects of a monotherapy using the active ingredients and a COMBINATION OF THE INVENTION.

A further benefit is that lower doses of the active ingredients of the COMBINATION OF THE INVENTION can be used, for example, that the dosages need not only often be smaller but are also applied less frequently, or can be used in order to diminish the incidence of side effects. This is in accordance with the desires and requirements of the patients to be treated. The COMBINATIONs OF THE INVENTION can be used, in particular, for the treatment of myopia which is refractory to monotherapy.

In one embodiment of the invention, the AMPA receptor antagonists used in the present invention are competitive AMPA receptor antagonists.

It is one objective of this invention to provide a pharmaceutical composition comprising a quantity, which is jointly therapeutically effective against myopia, comprising at least one AMPA receptor antagonist, at least one compound selected from the group consisting of pirenzepine, telenzepine, ortho-methoxy-sila-hexocyclium, gamma-amino butyric acid (GABA) and GABA agonists and at least one pharmaceutically acceptable carrier. In this composition, the first and second active ingredient can be administered together, one after the other or separately in one combined unit dosage form or in two separate unit dosage forms. The unit dosage form may also be a fixed combination.

The pharmaceutical compositions according to the invention can be prepared in a manner known per se comprising a therapeutically effective amount of at least one pharmacologically active ingredient, alone or in combination with one or more pharmaceutically acceptable carries. The COMBINATIONs OF THE INVENTION are preferably applied topically to the eye in ca. 0.002 to ca. 0.02% opthalmologic solutions. The ophthalmic vehicle is such that the COMBINATION OF THE INVENTION is maintained in contact with the ocular surface for a sufficient time period to allow the COMBINATION OF THE INVENTION to penetrate the corneal and internal regions of the eye. The pharmaceutically acceptable ophthalmic vehicle may be e.g. an ointment, vegetable oil, or encapsulating material.

Furthermore, the present invention relates to the use of a COMBINATION OF THE INVENTION for the preparation of a medicament for the treatment of myopia.

Additionally, the present invention provides a method of treating a warm-blooded animal having myopia comprising administering to the animal a COMBINATION OF THE INVENTION in a quantity which is jointly therapeutically effective against myopia and in which the compounds can also be present in the form of their pharmaceutically acceptable salts.

Additionally, the present invention provides a method of controlling postnatal growth of an eye of a maturing warm-blooded animal, especially a human, which method comprises administering a COMBINATION OF THE INVENTION in a quantity which is jointly therapeutically effective for controlling postnatal growth.

Moreover, the present invention provides a commercial package comprising as active ingredients COMBINATION OF THE INVENTION, together with instructions for simultaneous, separate or sequential use thereof in the treatment of myopia.

In particular, a therapeutically effective amount of each of the active ingredients of the COMBINATION OF THE INVENTION may be administered simultaneously or sequentially and in any order, and the components may be administered separately or as a fixed combination. For example, the method of treatment of myopia according to the invention may comprise (i) administration of the first active ingredient in free or pharmaceutically acceptable salt form and (ii) administration of the second active ingredient in free or pharmaceutically acceptable salt form, simultaneously or sequentially in any order, in jointly therapeutically effective amounts, preferably in synergistically effective amounts, e.g. in daily dosages corresponding to the amounts described herein. The individual active ingredients of the COMBINATION OF THE INVENTION can be administered separately at different times during the course of therapy or concurrently in divided or single combination forms. Furthermore, the term administering also encompasses the use of a pro-drug of an active ingredient that convert in vivo to the active ingredient. The instant invention is therefore to be understood as embracing all such regimes of simultaneous or alternating treatment and the term "administering" is to be interpreted accordingly.

In one preferred embodiment of the invention, the COMBINATION OF THE INVENTION is used for the treatment of myopia which is refractory to monotherapy.

The effective dosage of each of the active ingredients employed in the COMBINATION OF THE INVENTION may vary depending on the particular compound or pharmaceutical composition employed, the mode of administration, the severity of the condition being treated. Thus, the dosage regimen the COMBINATION OF THE INVENTION is selected in accordance with a variety of factors including the route of administration and the renal and hepatic function of the patient. A physician, clinician, ophthalmologist or veterinarian of ordinary skill can readily determine and prescribe the effective amount of the single active ingredients required to prevent, counter or arrest the progress of the condition. Optimal precision in achieving concentration of the active ingredients within the range that yields efficacy without toxicity requires a regimen based on the kinetics of the active ingredients' availability to target sites. This involves a consideration of the distribution, equilibrium, and elimination of the active ingredients.

When the combination partners employed in the COMBINATION OF THE INVENTION are applied in the form as marketed single drugs, their dosage and mode of administration can take place in accordance with the information provided on the packet leaflet of the respective marketed drug in order to result in the beneficial effect described herein, if not mentioned herein otherwise. In particular, Topiramate may be administered to an adult patient in a total daily dosage of between about 250 to about 500 mg.

Example 1

Eye Drops: Eye Drops Containing the Ingredients Indicated Below is Prepared by Conventional Techniques

| Composition | mg/ml |
| --- | --- |
| COMBINATION OF THE INVENTION | 1.0 |
| Glycerol | 25.0 |
| Benzalkonium chloride | 0.105 |
| Hydroxypropylmethylcellulose | 1.0 |
| Water for injection to | 1.0 ml |

When the combination partners employed in the COMBINATION OF THE INVENTION are applied in the form as marketed single drugs, their dosage and mode of administration can take place in accordance with the information provided on the packet leaflet of the respective marketed drug in order to result in the beneficial effect described herein, if not mentioned herein otherwise.

Combinations for Neuropathic Pain

The present invention also relates to combinations suitable for the treatment of pain, especially neuropathic pain.

The present invention relates to combinations suitable for the treatment of pain of various genesis or aetiology.

The term "pain of various genesis or aetiology" includes, but is not limited to, inflammatory pain, hyperalgesia and, in particular, chronic pain, and means in particular pain consequential to trauma, e.g. associated with burns, sprains, fracture or the like, subsequent to surgical intervention, e.g. as post-operative analgesics, as well as inflammatory pain of diverse genesis, e.g. bone and joint pain (osteoarthritis), myofascial pain (e.g. muscular injury), lower back pain, chronic inflammatory pain, fibromyalgia, chronic neuropathic pain, e.g. diabetic neuropathy, phantom limb pain and perioperative pain (general surgery, gynecologic surgery) as well as pain associated with, e.g., angina, menstruation or cancer.

The term "neuropathic pain" as used herein includes, but is not restricted to, pain that frequently accompanies nerve lesions resulting from a range of pathologies including amputation or conditions such as diabetes, post-herpetic neuralgia or trigeminal neuralgia. The hyperalgesia and allodynia associated with neuropathic pain is particularly intractable and poorly treated in the clinic by treatments such as opiates.

Surprisingly, the effect of a combination which comprises at least one AMPA receptor antagonist and at least one combination partner selected from the group consisting of cyclooxygenase inhibitors, vanilloid receptor antagonists, opioids, tricyclic antidepressants, anticonvulsants, cathepsin S inhibitors and $GABA_B$ receptor agonists is greater than the additive effect of the combined drugs. Furthermore, the combinations disclosed herein can be used to treat pain, which is refractory to monotherapy employing one of the combination partners alone.

Hence, the invention relates to a combination, such as a combined preparation or pharmaceutical composition, which comprises at least one AMPA receptor antagonist and at least one combination partner selected from the group consisting of cyclooxygenase inhibitors, vanilloid receptor antagonists, opioids, tricyclic antidepressants, anticonvulsants, cathepsin S inhibitors and GABA$_B$ receptor agonists, in which the active ingredients are present in each case in free form or in the form of a pharmaceutically acceptable salt and optionally at least one pharmaceutically acceptable carrier; for simultaneous, separate or sequential use.

The term "pain" relates in particular, but is not limited, to neuropathic pain.

The term cyclooxigenase inhibitors as used herein includes, but is not limited to specific COX-2 inhibitors, e.g. celecoxib and rofecoxib, and nonsteroidal anti-inflammatory drugs (NSAIDs), e.g. acetylsalicylic acid and propionic acid derivatives.

The term "tricyclic antidepressants" as used herein includes, but is not limited to Anafranil®, Asendin®, Aventyl®, Elavil®, Endep®, Norfranil®, Norpramin®, Pamelor®, Sinequan®, Surmontil®, Tipramine®, Tofranil®, Vivactil® and Tofranil-PM®.

The term "anticonvulsants" as used herein includes, but is not limited to oxcarbazepine and gabapentin.

The term "cathepsin S inhibitors" as used herein includes, but is not limited to the compounds disclosed in WO03/020287.

The term "GABA$_B$ receptor agonists" as used herein includes, but is not limited to L-baclofen.

The term "opioid" as used herein refers to all drugs, both natural and synthetic, with morphine-like actions. An opioid suitable for the present invention is especially selected from the group comprising alfentanil, allylprodine, alphaprodine, anileridine, benzylmorphine, bezitramide, buprenorphine, butorphanol, clonitazene, codeine, cyclorphan, desomorphine, dextromoramide, dezocine, diampromide, dihydrocodeine, dihydromorphine, eptazocine, ethylmorphine, fentanyl, hydrocodone, hydromorphone, hydroxypethidine, levophenacylmorphan, levorphanol, lofentanil, methylmorphine, morphine, necomorphine, normethadone, normorphine, opium, oxycodone, oxymorphone, pholcodine, profadol and sufentanil.

For instance, alfentanil can be administered, e.g., in the form as marketed, e.g. under the trademark Rapifen™; allylprodine can be administered, e.g., in the form as marketed, e.g. under the trademark Alperidine™; anileridine can be administered, e.g., in the form as marketed, e.g. under the trademark Leritine™; benzylmorphine can be administered, e.g., in the form as marketed, e.g. under the trademark Peronine™; bezitramide can be administered, e.g., in the form as marketed, e.g. under the trademark Burgodin™; buprenorphine can be administered, e.g., in the form as marketed, e.g. under the trademark Buprenex™; butorphanol can be administered, e.g., in the form as marketed, e.g. under the trademark Torate™; dextromoramide can be administered, e.g., in the form as marketed, e.g. under the trademark Palfium™; dezocine can be administered, e.g., in the form as marketed, e.g. under the trademark Dalgan™; dihydrocodeine can be administered, e.g., in the form as marketed, e.g. under the trademark Novicodin™; dihydromorphine can be administered, e.g., in the form as marketed, e.g. under the trademark Paramorphan™; eptazocine can be administered, e.g., in the form as marketed, e.g. under the trademark Sedapain™; ethylmorphine can be administered, e.g., in the form as marketed, e.g. under the trademark Dionin™; fentanyl can be administered, e.g., in the form as marketed, e.g. under the trademark Fentanest™ or Leptanal™; hydrocodone can be administered, e.g., in the form as marketed, e.g. under the trademark Bekadid™ or Calmodid™; hydromorphone can be administered, e.g., in the form as marketed, e.g. under the trademark Novolaudon™; hydroxypethidine can be administered, e.g., in the form as marketed, e.g. under the trademark Bemidone™; levorphanol can be administered, e.g., in the form as marketed, e.g. under the trademark Dromoran™; normethadone can be administered, e.g., in the form as marketed, e.g. under the trademark Ticarda™; oxycodone can be administered, e.g., in the form as marketed, e.g. under the trademark Dihydrone™ and oxymorphone can be administered, e.g., in the form as marketed, e.g. under the trademark Numorphan™.

Topiramate can be administered, e.g., in the form as marketed, e.g. under the trademark Topamax™. The compounds of formula I as well as their production process and pharmaceutical compositions thereof are known e.g. from WO 98/17672.

The structure of the active ingredients identified by code nos., generic or trade names may be taken from the actual edition of the standard compendium "The Merck Index" or from databases, e.g. Patents International (e.g. IMS World Publications). The corresponding content thereof is hereby incorporated by reference. Any person skilled in the art is fully enabled to identify the active ingredients and, based on these references, likewise enabled to manufacture and test the pharmaceutical indications and properties in standard test models, both in vitro and in vivo.

The term "a combined preparation", as used herein defines especially a "kit of parts" in the sense that the first and second active ingredient as defined above can be dosed independently or by use of different fixed combinations with distinguished amounts of the ingredients, i.e., simultaneously or at different time points. The parts of the kit of parts can then, e.g., be administered simultaneously or chronologically staggered, that is at different time points and with equal or different time intervals for any part of the kit of parts. Very preferably, the time intervals are chosen such that the effect on the treated disease in the combined use of the parts is larger than the effect which would be obtained by use of only any one of the active ingredients. The ratio of the total amounts of the active ingredient 1 to the active ingredient 2 to be administered in the combined preparation can be varied, e.g., in order to cope with the needs of a patient sub-population to be treated or the needs of the single patient which different needs can be due to age, sex, body weight, etc. of the patients. Preferably, there is at least one beneficial effect, e.g., a mutual enhancing of the effect of the first and second active ingredient, in particular a synergism, e.g. a more than additive effect, additional advantageous effects, less side effects, a combined therapeutically effect in a non-effective dosage of one or both of the first and second active ingredient, and especially a strong synergism the first and second active ingredient.

It will be understood that in the discussion of methods, references to the active ingredients are meant to also include the pharmaceutically acceptable salts. If these active ingredients have, for example, at least one basic center, they can form acid addition salts. Corresponding acid addition salts can also be formed having, if desired, an additionally present basic center. The active ingredients having an acid group (for example COOH) can also form salts with bases. The active ingredient or a pharmaceutically acceptable salt thereof may also be used in form of a hydrate or include other solvents used for crystallization.

A pharmaceutical combination which comprises at least one AMPA receptor antagonist and at least one combination partner selected from the group consisting of cyclooxygenase inhibitors, vanilloid receptor antagonists, opioids, tricyclic antidepressants, anticonvulsants, cathepsin S inhibitors and GABA$_B$ receptor agonists, in which the active ingredients are present in each case in free form or in the form of a pharmaceutically acceptable salt, if at least one salt-forming group is present, will be referred to hereinafter as a COMBINATION OF THE INVENTION.

Surprisingly, the administration of a COMBINATION OF THE INVENTION results in a beneficial, especially a synergistic, therapeutic effect or in other surprising beneficial effects, e.g. less side effects, compared to a monotherapy applying only one of the pharmaceutically active ingredients used in the COMBINATION OF THE INVENTION.

The pharmacological activity of a COMBINATION OF THE INVENTION may, for example, be evidenced in preclinical studies known as such, e.g. the methods described in the Examples.

The pharmacological activity of a COMBINATION OF THE INVENTION may, for example, be demonstrated in a clinical study. Such clinical studies are preferably randomized, double-blind, clinical studies in patients with pain. Such studies demonstrate, in particular, the synergism of the active ingredients of the COMBINATIONS OF THE INVENTION. The beneficial effects on pain can be determined directly through the results of these studies or by changes in the study design which are known as such to a person skilled in the art. The studies are, in particular, suitable to compare the effects of a monotherapy using the active ingredients and a COMBINATION OF THE INVENTION.

A further benefit is that lower doses of the active ingredients of the COMBINATION OF THE INVENTION can be used, for example, that the dosages need not only often be smaller but are also applied less frequently, or can be used in order to diminish the incidence of side effects. This is in accordance with the desires and requirements of the patients to be treated. The COMBINATIONs OF THE INVENTION can be used, in particular, for the treatment of pain which is refractory to monotherapy.

In one embodiment of the invention, the AMPA receptor antagonists used in the present invention are competitive AMPA receptor antagonists.

In another embodiment of the present invention, the AMPA receptor antagonists is selected from EGIS 8332 (7-acetyl-5-(4-aminophenyl)-8,9-dihydro-8-methyl-7H-1,3-dioxolo[4,5-h][2,3]benzodiazepine-8-carbonitrile), GYKI 47261 4-(7-chloro-2-methyl-4H-3,10,10a-triaza-benzo[f]azulen-9-yl)-phenylamine), irampanel (BIIR 561; N,N-dimethyl-2-[2-(3-phenyl-1,2,4-oxadiazol-5-yl)phenoxy]ethanamine), KRP 199 (7-[4-[[[[(4-carboxyphenyl)-amino]carbonyl]oxy]methyl]-1H-imidazol-1-yl]-3,4-dihydro-3-oxo-6-(trifluoromethyl)-2-quinoxalinecarboxylic acid), NS 1209 (2-[[[5-[4-[(dimethylamino)-sulfonyl]phenyl]-1,2,6,7,8,9-hexahydro-8-methyl-2-oxo-3H-pyrrolo[3,2-h]isoquinolin-3-ylidene]amino]oxy]-4-hydroxybutanoic acid monosodium salt, e.g. prepared as described in WO 98/14447), topiramate (TOPAMAX, 2,3:4,5-bis-O-(1-methylethylidene)-beta-D-fructopyranose sulfamate, preparation, e.g. as described in U.S. Pat. No. 535,475), talampanel (LY-300164, (R)-7-acetyl-5-(4-aminophenyl)-8,9-dihydro-8-methyl-7H-1,3-dioxolo[4,5-h][2,3]benzo-diazepine, preparation, e.g. as described in EP 492-485), YM90K (6-imidazol-1-yl-7-nitro-1,4-dihydro-quinoxaline-2,3-dione), S-34730 (7-chloro-6-sulfamoyl-2-(1H)-quinolinone-3-phosphonic acid), Zonampanel (YM-872; (7-imidazol-1-yl-6-nitro-2,3-dioxo-3,4-dihydro-2H-quinoxalin-1-yl)-acetic acid), GYKI-52466 (4-(8-methyl-9H-1,3-dioxa-6,7-diaza-cyclohepta[f]inden-5-yl)-phenylamine), ZK-200775 (MPQX, (7-morpholin-4-yl-2,3-dioxo-6-trifluoromethyl-3,4-dihydro-2H-quinoxalin-1-ylmethyl)-phosphonic acid), CP-465022 (3-(2-chlorophenyl)-2-[2-(6-diethylaminomethyl-pyridin-2-yl)-vinyl]-6-fluoro-3H-quinazolin-4-one), SYM-2189 (4-(4-aminophenyl)-6-methoxy-1-methyl-1H-phthalazine-2-carboxylic acid propylamide), SYM-2206 (8-(4-amino-phenyl)-5-methyl-5H-[1,3]dioxolo[4,5-g]phthalazine-6-carboxylic acid propylamide, RPR-117824 ((4-oxo-2-phosphono-5,10-dihydro-4H-imidazo[1,2-a]indeno[1,2-e]pyrazin-9-yl)-acetic acid), LY-293558 (6-[2-(1H-tetrazol-5-yl)-ethyl]-decahydro-isoquinoline-3-carboxylic acid), and 1,2,3,4-tetrahydro-7-nitro-2,3-dioxo-5-quinoxalinyl)methyl]amino]methyl]phosphonic acid dehydrate.

It is one objective of this invention to provide a pharmaceutical composition comprising a quantity, which is jointly therapeutically effective against pain, comprising at least one AMPA receptor antagonist and at least one combination partner selected from the group consisting of cyclooxygenase inhibitors, vanilloid receptor antagonists, opioids, tricyclic antidepressants, anticonvulsants, cathepsin S inhibitors and $GABA_B$ receptor agonists, and at least one pharmaceutically acceptable carrier. In this composition, the first and second active ingredient can be administered together, one after the other or separately in one combined unit dosage form or in two separate unit dosage forms. The unit dosage form may also be a fixed combination.

The pharmaceutical compositions according to the invention can be prepared in a manner known per se and are those suitable for enteral, such as oral or rectal, and parenteral administration to mammals (warm-blooded animals), including man, comprising a therapeutically effective amount of at least one pharmacologically active ingredient, alone or in combination with one or more pharmaceutically acceptable carries, especially suitable for enteral or parenteral application. The preferred route of administration of the dosage forms of the present invention is orally. The novel pharmaceutical composition contain, for example, from about 10% to about 100%, preferably from about 20% to about 60%, of the active ingredients. Pharmaceutical preparations for the combination therapy for enteral or parenteral administration are, for example, those in unit dosage forms, such as sugar-coated tablets, tablets, capsules or suppositories, and furthermore ampoules. If not indicated otherwise, these are prepared in a manner known per se, for example by means of conventional mixing, granulating, sugar-coating, dissolving or lyophilizing processes. It will be appreciated that the unit content of active ingredient or ingredients contained in an individual dose of each dosage form need not in itself constitute an effective amount since the necessary effective amount can be reached by administration of a plurality of dosage units.

In preparing the compositions for oral dosage form, any of the usual pharmaceutical media may be employed, such as, for example, water, glycols, oils or alcohols; or carriers such as starches, sugars, microcristalline cellulose, diluents, granulating agents, lubricants, binders, disintegrating agents and the like in the case of oral solid preparations such as, for example, powders, capsules and tablets. Because of their ease of administration, tablets and capsules represent the most advantageous oral dosage unit form in which case solid pharmaceutical carriers are obviously employed.

Furthermore, the present invention relates to the use of a COMBINATION OF THE INVENTION for the preparation of a medicament for the treatment of pain.

Additionally, the present invention provides a method of treating a warm-blooded animal having pain comprising administering to the animal a COMBINATION OF THE INVENTION in a quantity which is jointly therapeutically effective against pain and in which the compounds can also be present in the form of their pharmaceutically acceptable salts.

Moreover, the present invention provides a commercial package comprising as active ingredients COMBINATION OF THE INVENTION, together with instructions for simultaneous, separate or sequential use thereof in the treatment of pain.

In particular, a therapeutically effective amount of each of the active ingredients of the COMBINATION OF THE INVENTION may be administered simultaneously or sequentially and in any order, and the components may be administered separately or as a fixed combination. For example, the method of treatment of pain according to the invention may comprise (i) administration of the first active ingredient in free or pharmaceutically acceptable salt form and (ii) administration of the second active ingredient in free or pharmaceutically acceptable salt form, simultaneously or sequentially in any order, in jointly therapeutically effective amounts, preferably in synergistically effective amounts, e.g. in daily dosages corresponding to the amounts described herein. The individual active ingredients of the COMBINATION OF THE INVENTION can be administered separately at different times during the course of therapy or concurrently in divided or single combination forms. Furthermore, the term administering also encompasses the use of a pro-drug of an active ingredient that convert in vivo to the active ingredient. The instant invention is therefore to be understood as embracing all such regimes of simultaneous or alternating treatment and the term "administering" is to be interpreted accordingly.

In one preferred embodiment of the invention, the COMBINATION OF THE INVENTION is used for the treatment of pain which is refractory to monotherapy.

The effective dosage of each of the active ingredients employed in the COMBINATION OF THE INVENTION may vary depending on the particular compound or pharmaceutical composition employed, the mode of administration, the severity of the condition being treated. Thus, the dosage regimen the COMBINATION OF THE INVENTION is selected in accordance with a variety of factors including the route of administration and the renal and hepatic function of the patient. A physician, clinician or veterinarian of ordinary skill can readily determine and prescribe the effective amount of the single active ingredients required to prevent, counter or arrest the progress of the condition. Optimal precision in achieving concentration of the active ingredients within the range that yields efficacy without toxicity requires a regimen based on the kinetics of the active ingredients' availability to target sites. This involves a consideration of the distribution, equilibrium, and elimination of the active ingredients.

When the combination partners employed in the COMBINATION OF THE INVENTION are applied in the form as marketed single drugs, their dosage and mode of administration can take place in accordance with the information provided on the packet leaflet of the respective marketed drug in order to result in the beneficial effect described herein, if not mentioned herein otherwise. In particular, Topiramate may be administered to an adult patient in a total daily dosage of between about 250 to about 500 mg.

The pharmacological activity of a COMBINATION OF THE INVENTION may, for example, be demonstrated in a preclinical model such as the "Chronic neuropathic pain model": Wistar rats are anaesthetised with enflurane and a small incision is made mid-way up one thigh to expose the sciatic nerve. The nerve is cleared of connective tissue and tightly ligated so that the dorsal ⅓ to ½ of the nerve thickness is held within the ligature. The muscle and skin are closed with sutures and clips and the wound dusted with antibiotic powder. This procedure produces a mechanical hyperalgesia which develops within 2-3 days and is maintained for at least 4 weeks. Mechanical hyperalgesia is assessed by measuring paw withdrawal thresholds on both the ipsilateral (ligated) and contralateral (unligated) hindpaw to an increasing pressure stimulus applied to the paw using an analgesymeter (Ugo-Basile) with a wedge-shaped probe (area 1.75 $mm^2$) and a cut-off threshold of 250 g. The end point is taken as the first sign of pain response (struggling, vocalisation or paw withdrawal). Hyperalgesia is indicated by the difference in ipsilateral and contralateral withdrawal thresholds. Reversal of established hyperalgesia by administered compounds is measured 12-14 days following surgery, using 6 animals per treatment group.

In principal 4 treatment groups are formed:

1) Solvent followed by solvent.

2) Solvent pretreatment followed by the combination partner.

3) AMPA receptor antagonist followed by solvent.

4) The COMBINATION OF THE INVENTION (low doses of each active ingredients).

Paw withdrawal thresholds are measured prior to and then up to 6 hours following drug or solvent administration. Statistical analysis is carried out on withdrawal threshold readings using ANOVA followed by Tukey's HSD test comparing drug treated and time-matched vehicle treated animals.

When the combination partners employed in the COMBINATION OF THE INVENTION are applied in the form as marketed single drugs, their dosage and mode of administration can take place in accordance with the information provided on the packet leaflet of the respective marketed drug in order to result in the beneficial effect described herein, if not mentioned herein otherwise.

Combinations for Schizophrenia

The present invention also relates to combinations suitable for the treatment of psychiatric/neurological disorders, in particular schizophrenia.

Surprisingly, the effect of a combination which comprises at least one AMPA receptor antagonist and at least one compound selected from the group consisting of (a) anti-epileptic drugs selected from barbiturates and derivatives thereof, benzodiazepines, carboxamides, hydantoins, succinimides, valproic acid and other fatty acid derivates and other anti-epileptic drugs, (b) conventional antipsychotics and (c) atypical antipsychotics is greater than the additive effect of the combined drugs. Furthermore, the combinations disclosed herein can be used to treat schizophrenia which is refractory to monotherapy employing one of the combination partners alone.

Hence, the invention relates to a combination, such as a combined preparation or pharmaceutical composition, which comprises at least one AMPA receptor antagonist and at least one compound selected from the group consisting of (a) anti-epileptic drugs selected from barbiturates and derivatives thereof, benzodiazepines, carboxamides, hydantoins, succinimides, valproic acid and other fatty acid derivates and other anti-epileptic drugs, (b) conventional antipsychotics and (c) atypical antipsychotics, in which the active ingredients are present in each case in free form or in the form of a pharmaceutically acceptable salt and optionally at least one pharmaceutically acceptable carrier; for simultaneous, separate or sequential use.

The term "barbiturates and derivatives thereof" as used herein includes, but is not limited to phenobarbital, pentobarbital, mepobarbital and primidon. The term "benzodiazepines" as used herein includes, but is not limited to clonazepam, diazepam and lorazepam. The term "carboxamides" as used herein includes, but is not limited to carbamazepine, oxcarbazepine, 10-hydroxy-10,11-dihydrocarbamazepine and the compounds of formula II

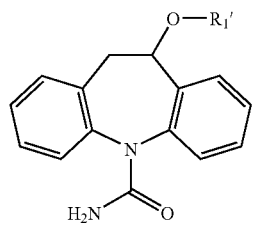

(II)

wherein $R_1'$ represents $C_1$-$C_3$alkyl carbonyl. The term "hydantoins" as used herein includes, but is not limited to phenyloin. The term "succinimides" as used herein includes, but is not limited to ethosuximide, phensuximide and mesuximide. The term "valproic acid and other fatty acid derivates" as used herein includes, but is not limited to valproic acid sodium salt, tiagabine hydrochloride monohydrate and vigabatrine. The term "other anti-epileptic drugs" as used herein includes, but is not limited to levetiracetam, lamotrigine, gabapentin, sultiam, felbamate, the 1,2,3-1H-triazoles disclosed in EP 114 347 and the 2-aryl-8-oxodihydropurines disclosed in WO99/28320.

The term "conventional antipsychotics" as used herein includes, but is not limited to haloperidol, fluphenazine, thiotixene and flupentixol.

The term "atypical antipsychotics" as used herein relates to clozaril, risperidone, olanzapine, quetiapine, ziprasidone and aripiprazol.

The structure of the active ingredients identified by code nos., generic or trade names and their preparation may be taken from the actual edition of the standard compendium "The Merck Index" (e.g. M. J. O'Neil et al., ed., 'The Merck Index', 13$^{th}$ ed., Merck Research Laboratories, 2001) or from databases, e.g. Patents International (e.g. IMS World Publications). The corresponding content thereof is hereby incorporated by reference. Any person skilled in the art is fully enabled to identify the active ingredients and, based on these references, likewise enabled to manufacture and test the pharmaceutical indications and properties in standard test models, both in vitro and in vivo.

Phenobarbital, can be administered, e.g., in the form as marketed, e.g. under the trademark Luminal™. Primidon can be administered, e.g., in the form as marketed, e.g. under the trademark Mylepsinum™. Clonazepam can be administered, e.g., in the form as marketed, e.g. under the trademark Antelepsin™. Diazepam can be administered, e.g., in the form as marketed, e.g. under the trademark Diazepam Desitin™. Lorazepam can be administered, e.g., in the form as marketed, e.g. under the trademark Tavor™. Carbamazepine can be administered, e.g., in the form as marketed, e.g. under the trademark Tegretal™ or Tegretol™. Oxcarbazepine can be administered, e.g., in the form as marketed, e.g. under the trademark Trileptal™. Oxcarbazepine is well known from the literature [see for example Schuetz H. et al., Xenobiotica (GB), 16(8), 769-778 (1986)]. The preparation of the compound of formula II wherein $R_1'$ is $C_1$-$C_3$alkyl carbonyl and its pharmaceutically acceptable salts is described, e.g., in U.S. Pat. No. 5,753,646. 10-Hydroxy-10,11-dihydrocarbamazepine can be prepared as disclosed in U.S. Pat. No. 3,637,661. 10-Hydroxy-10,11-dihydrocarbamazepine may be administered, e.g., in the form as described in U.S. Pat. No. 6,316,417. Phenyloin can be administered, e.g., in the form as marketed, e.g. under the trademark Epanutin™. Ethosuximide can be administered, e.g., in the form as marketed, e.g. under the trademark Suxinutin™. Mesuximide can be administered, e.g., in the form as marketed, e.g. under the trademark Petinutin™. Valproic acid sodium salt can be administered, e.g., in the form as marketed, e.g. under the trademark Leptilan™. Tiagabine hydrochloride monohydrate can be administered, e.g., in the form as marketed, e.g. under the trademark Gabitril™. Vigabatrine can be administered, e.g., in the form as marketed, e.g. under the trademark Sabril™. Levetiracetam can be administered, e.g., in the form as marketed, e.g. under the trademark Keppra™. Lamotrigine can be administered, e.g., in the form as marketed, e.g. under the trademark Lamictal™. Gabapentin can be administered, e.g., in the form as marketed, e.g. under the trademark Neurontin™. Sultiam can be administered, e.g., in the form as marketed, e.g. under the trademark Ospolot™. Felbamate can be administered, e.g., in the form as marketed, e.g. under the trademark Taloxa™. Topiramate can be administered, e.g., in the form as marketed, e.g. under the trademark Topamax™. The 1,2,3-1H-triazoles disclosed in EP 114 347 may be administered, e.g., in the form as described in U.S. Pat. No. 6,455,556. The 2-aryl-8-oxodihydropurines disclosed in WO99/28320 may be administered, e.g., in the form as described in WO99/28320. Haloperidol can be administered, e.g., in the form as marketed, e.g. under the trademark Haloperidol STADA™. Fluphenazine can be administered, e.g., in the form of its dihydrochloride as marketed, e.g. under the trademark Prolixin™. Thiothixene can be administered, e.g., in the form as marketed, e.g. under the trademark Navane™. It can be prepared, e.g., as described in U.S. Pat. No. 3,310,553. Flupentixol can be administered for instance in the form of its dihydrochloride, e.g., in the form as marketed, e.g. under the trademark Emergil™ or in the form of its decanoate, e.g., in the form as marketed, e.g. under the trademark Depixol™. It can be prepared, e.g., as described in BP 925,538. Clozaril can be administered, e.g., in the form as marketed, e.g. under the trademark Leponex™. It can be prepared, e.g., as described in U.S. Pat. No. 3,539,573. Risperidone can be administered, e.g., in the form as marketed, e.g. under the trademark Risperdal™. Olanzapine can be administered, e.g., in the form as marketed, e.g. under the trademark Zyprexa™. Quetiapine can be administered, e.g., in the form as marketed, e.g. under the trademark Seroquel™. Ziprasidone can be administered, e.g., in the form as marketed, e.g. under the trademark Geodon™. It can be prepared, e.g., as described in GB 281,309. Aripiprazole can be administered, e.g., in the form as marketed, e.g. under the trademark Abilify™. It can be prepared, e.g., as described in U.S. Pat. No. 5,006,528. Topiramate can be administered, e.g., in the form as marketed, e.g. under the trademark Topamax™. The compounds of formula I as well as their production process and pharmaceutical compositions thereof are known e.g. from WO 98/17672.

The term "a combined preparation", as used herein defines especially a "kit of parts" in the sense that the first and second active ingredient as defined above can be dosed independently or by use of different fixed combinations with distinguished amounts of the ingredients, i.e., simultaneously or at different time points. The parts of the kit of parts can then, e.g., be administered simultaneously or chronologically staggered, that is at different time points and with equal or different time intervals for any part of the kit of parts. Very preferably, the time intervals are chosen such that the effect on the treated disease in the combined use of the parts is larger than the effect which would be obtained by use of only any one of the active ingredients. The ratio of the total amounts of the active ingredient 1 to the active ingredient 2 to be administered in the combined preparation can be varied, e.g., in order to cope with the needs of a patient sub-population to be treated or the needs of the single patient which different needs can be due to age, sex, body weight, etc. of the patients. Preferably, there is at least one beneficial effect, e.g., a mutual enhancing of the effect of the first and second active ingredient, in particular a synergism, e.g. a more than additive effect, additional advantageous effects, less side effects, a combined therapeutically effect in a non-effective dosage of one or both of the first and second active ingredient, and especially a strong synergism the first and second active ingredient.

It will be understood that in the discussion of methods, references to the active ingredients are meant to also include the pharmaceutically acceptable salts. If these active ingredients have, for example, at least one basic center, they can form acid addition salts. Corresponding acid addition salts can also be formed having, if desired, an additionally present basic center. The active ingredients having an acid group (for example COOH) can also form salts with bases. The active ingredient or a pharmaceutically acceptable salt thereof may also be used in form of a hydrate or include other solvents used for crystallization.

A pharmaceutical combination which comprises at least one AMPA antagonist and at least one compound selected from the group consisting of (a) anti-epileptic drugs selected from barbiturates and derivatives thereof, benzodiazepines, carboxamides, hydantoins, succinimides, valproic acid and other fatty acid derivates and other anti-epileptic drugs, (b) conventional antipsychotics and (c) atypical antipsychotics, in which the active ingredients are present in each case in free form or in the form of a pharmaceutically acceptable salt, if at least one salt-forming group is present, will be referred to hereinafter as a COMBINATION OF THE INVENTION.

Surprisingly, the administration of a COMBINATION OF THE INVENTION results in a beneficial, especially a synergistic, therapeutic effect or in other surprising beneficial effects, e.g. less side effects, compared to a monotherapy applying only one of the pharmaceutically active ingredients used in the COMBINATION OF THE INVENTION.

The antipsychotic potential of a COMBINATION OF THE INVENTION may, for example, be evidenced in preclinical studies known as such, e.g. the methods described herein.

The antipsychotic potential of the COMBINATION OF THE INVENTION is indicated in standard tests, e.g. in the amphetamine-induced hyperlocomotion test. Blockade of amphetamine-induced hyperlocomotion is well known as screening paradigm for antischizophrenic activity.

Male rats are used. In principle 4 treatment groups are formed:

1) AMPA receptor antagonist followed by solvent 2 and solvent 3 to study the effects of the AMPA receptor antagonist on locomotor activity.

2) Solvent 1, combination partner and solvent 3 to study the effects of the combination partner on locomotor activity.

3) Solvent 1, solvent 2, followed by amphetamine to study the induction of hyperlocomotor activity.

4) AMPA receptor antagonist followed by solvent 2 and amphetamine.

5) Solvent 1 followed by combination partner and amphetamine.

6) The COMBINATION OF THE INVENTION (doses of each active ingredients at doses close to threshold) followed by solvent 3.

7) The COMBINATION OF THE INVENTION (doses of each active ingredients at doses close to threshold) followed by amphetamine.

8) Solvent 1 solvent 2 solvent 3.

Rats are randomly allocated to these pretreatment groups (n=10/dose group). Drugs are administered subcutaneous (s.c.), 15 min prior to SDZ 220-581. Immediately after the animals received amphetamine, they are placed into the activity monitor for a period of 60 min. Locomotor activity is analysed over the initial 30 minutes.

Threshold doses of each active ingredient of the combination partners are used. Amphetamine is dosed at 1 mg/kg s.c. Locomotion is recorded with a videotracking system. Animals are on a normal 12/12 h. day-night cycle, with light on at 06:00 H. Experiments are performed in a dimly lit room between 07:00 H and 15:00 H. Animals are placed in a round arena (diameter 42 cm, height 32 cm) made of grey polyvinylchloride plastic. The camera is placed such, that four animals (one per arena) can be recorded simultaneously.

Comparison between groups is done with Student's t-test, corrected for multiple testing using the Bonferroni procedure.

Furthermore, the pharmacological activity of a COMBINATION OF THE INVENTION may, for example, be demonstrated in a clinical study. Such clinical studies are preferably randomized, double-blind, clinical studies in patients with schizophrenia. Such studies demonstrate, in particular, the synergism of the active ingredients of the COMBINATIONS OF THE INVENTION. The beneficial effects on schizophrenia can be determined directly through the results of these studies or by changes in the study design which are known as such to a person skilled in the art. The studies are, in particular, suitable to compare the effects of a monotherapy using the active ingredients and a COMBINATION OF THE INVENTION.

The COMBINATIONs OF THE INVENTION provide, in particular, benefits in the treatment of positive symptoms, negative symptoms, mood symptoms and/or cognitive symptoms of schizophrenia and/or psychosis. Furthermore, some of the COMBINATIONs OF THE INVENTION show beneficial effects in the control of impulsive and/or violent behavior of schizophrenic patients.

A further benefit is that lower doses of the active ingredients of the COMBINATION OF THE INVENTION can be used, for example, that the dosages need not only often be smaller but are also applied less frequently, or can be used in order to diminish the incidence of side effects. This is in accordance with the desires and requirements of the patients to be treated. The COMBINATIONs OF THE INVENTION can be used, in particular, for the treatment of schizophrenia which is refractory to monotherapy.

It is one objective of this invention to provide a pharmaceutical composition comprising a quantity, which is jointly therapeutically effective against schizophrenia, comprises at least one AMPA antagonist, at least one compound selected from the group specified above and at least one pharmaceutically acceptable carrier. In this composition, the first and second active ingredient can be administered together, one after the other or separately in one combined unit dosage form or in two separate unit dosage forms. The unit dosage form may also be a fixed combination.

The pharmaceutical compositions according to the invention can be prepared in a manner known per se and are those suitable for enteral, such as oral or rectal, and parenteral administration to mammals (warm-blooded animals), including humans, comprising a therapeutically effective amount of at least one pharmacologically active ingredient, alone or in combination with one or more pharmaceutically acceptable carries, especially suitable for enteral or parenteral application. The preferred route of administration of the dosage forms of the present invention is orally.

The novel pharmaceutical composition contain, for example, from about 10% to about 100%, preferably from about 20% to about 60%, of the active ingredients. Pharmaceutical preparations for the combination therapy for enteral or parenteral administration are, for example, those in unit dosage forms, such as sugar-coated tablets, tablets, capsules or suppositories, and furthermore ampoules. If not indicated otherwise, these are prepared in a manner known per se, for example by means of conventional mixing, granulating, sugar-coating, dissolving or lyophilizing processes. It will be appreciated that the unit content of active ingredient or ingredients contained in an individual dose of each dosage form need not in itself constitute an effective amount since the necessary effective amount can be reached by administration of a plurality of dosage units.

In preparing the compositions for oral dosage form, any of the usual pharmaceutical media may be employed, such as, for example, water, glycols, oils or alcohols; or carriers such as starches, sugars, microcrystalline cellulose, diluents, granulating agents, lubricants, binders, disintegrating agents and the like in the case of oral solid preparations such as, for example, powders, capsules and tablets. Because of their ease of administration, tablets and capsules represent the most advantageous oral dosage unit form in which case solid pharmaceutical carriers are obviously employed.

Furthermore, the present invention relates to the use of a COMBINATION OF THE INVENTION for the preparation of a medicament for the treatment of schizophrenia.

Additionally, the present invention provides a method of treating a warm-blooded animal having schizophrenia comprising administering to the animal a COMBINATION OF THE INVENTION in a quantity which is jointly therapeutically effective against schizophrenia and in which the compounds can also be present in the form of their pharmaceutically acceptable salts.

Moreover, the present invention provides a commercial package comprising as active ingredients COMBINATION OF THE INVENTION, together with instructions for simultaneous, separate or sequential use thereof in the treatment of schizophrenia.

In particular, a therapeutically effective amount of each of the active ingredients of the COMBINATION OF THE INVENTION may be administered simultaneously or sequentially and in any order, and the components may be administered separately or as a fixed combination. For example, the method of treatment of schizophrenia according to the invention may comprise (i) administration of the first active ingredient in free or pharmaceutically acceptable salt form and (ii) administration of the second active ingredient in free or pharmaceutically acceptable salt form, simultaneously or sequentially in any order, in jointly therapeutically effective amounts, preferably in synergistically effective amounts, e.g. in daily dosages corresponding to the amounts described herein. The individual active ingredients of the COMBINATION OF THE INVENTION can be administered separately at different times during the course of therapy or concurrently in divided or single combination forms. Furthermore, the term administering also encompasses the use of a pro-drug of an active ingredient that convert in vivo to the active ingredient. The instant invention is therefore to be understood as embracing all such regimes of simultaneous or alternating treatment and the term "administering" is to be interpreted accordingly.

In one preferred embodiment of the invention, the COMBINATION OF THE INVENTION is used for the treatment of treatment of schizophrenia which is refractory to monotherapy.

The effective dosage of each of the active ingredients employed in the COMBINATION OF THE INVENTION may vary depending on the particular compound or pharmaceutical composition employed, the mode of administration, the severity of the condition being treated. Thus, the dosage regimen the COMBINATION OF THE INVENTION is selected in accordance with a variety of factors including the route of administration and the renal and hepatic function of the patient. A physician, clinician or veterinarian of ordinary skill can readily determine and prescribe the effective amount of the single active ingredients required to prevent, counter or arrest the progress of the condition. Optimal precision in achieving concentration of the active ingredients within the range that yields efficacy without toxicity requires a regimen based on the kinetics of the active ingredients' availability to target sites. This involves a consideration of the distribution, equilibrium, and elimination of the active ingredients.

When the combination partners employed in the COMBINATION OF THE INVENTION are applied in the form as marketed single drugs, their dosage and mode of administration can take place in accordance with the information provided on the packet leaflet of the respective marketed drug in order to result in the beneficial effect described herein, if not mentioned herein otherwise. In particular, Phenobarbital may be administered to an adult patient in a total daily dosage between about 1 to about 3 mg/kg body weight and to a pediatric patient in a total daily dosage between about 3 to about 4 mg/kg body weight, split into two separate units.

Primidone may be administered to an adult patient and to children being at least 9 years old in a total daily dosage of 0.75 to 1.5 g.

Clonazepam may be administered to an adult patient in a total daily dosage between about 3 to about 8 mg and to a pediatric patient in a total daily dosage between about 0.5 to about 3 mg, split into three of four separate units.

Diazepam may be administered to an adult patient in a total daily dosage between about 5 to about 10 mg and to a pediatric patient in a total daily dosage between about 5 to about 10 mg.

Lorazepam may be administered to an adult patient in a total daily dosage between about. 0.044 mg/kg body weight to about 0.05 mg/kg body weight.

Carbamazepine may be administered to an adult patient in a total daily dosage between about 600 to about 2000 mg and to a pediatric patient older than 6 years in a total daily dosage between about 400 to about 600 mg.

Oxcarbazepine may be administered to an adult patient in a total daily dosage between about 600 to about 2400 mg and to a pediatric patient in a total daily dosage between about 30 to about 46 mg/kg body weight.

Phenyloin may be administered to an adult patient in a total daily dosage between about 100 to about 300 mg and to a pediatric patient in a total daily dosage between about 100 to about 200 mg.

Ethosuximide may be administered to an adult patient in a total daily dosage of about 15 mg/kg body weight and to a pediatric patient in a total daily dosage of about 20 mg/kg body weight.

Valproic acid sodium salt may be administered to an adult patient in a total daily dosage of about 20 mg/kg body weight and to a pediatric patient in a total daily dosage of about 30 mg/kg body weight.

Tiagabine hydrochloride monohydrate may be administered to an adult patient in a total daily dosage between about 15 to about 70 mg.

Vigabatrine may be administered to an adult patient in a total daily dosage between about 2 to about 3 g.

Levetiracetam may be administered to a patient who is older than 16 years in a total daily dosage between about 1000 to about 3000 mg.

Lamotrigine may be administered to a patient who is older than 12 years in a total daily dosage between about 100 to about 200 mg.

Gabapentin may be administered to a patient in a total daily dosage between about 900 to about 2400 mg.

Sultiam may be administered to a patient in a total daily dosage between about 5 to about 10 mg/kg body weight.

Felbamate may be administered to a patient who is older than 14 years in a total daily dosage of between about 2400 to about 3600 mg.

Topiramate may be administered to an adult patient in a total daily dosage of between about 250 to about 500 mg.

Clozaril may be administered to an adult patient in a total daily dosage of between about 300 to about 900 mg.

Haloperidol may be administered to a patient in a total daily dosage of between about 2.5 to about 30 mg.

Olanzapine can be administered to a patient in a total daily dosage of between about 2.5 to about 20 mg.

Quetiapine can be administered to a patient in a total daily dosage of between about 500 to about 600 mg.

Risperidone may be administered to a patient in a total daily dosage of between about 2 to about 6 mg.

{[(7-Nitro-2,3-dioxo-1,2,3,4-tetrahydro-quinoxalin-5-yl-methyl)-amino]-methyl}-phosphonic acid may be administered to a patient in a total daily dosage of about 60 to about 400 mg.

Talampanel may be administered to a patient in a total daily dosage of between 25 to about 75 mg Combinations for Tinnitus The present invention also relates to combinations suitable for the treatment of neurological disorders, in particular tinnitus.

Tinnitus is the medical term for roaring, buzzing, clicking, whistling, hissing, or high pitched ringing in the ears or inside the head. Tinnitus may be constant or occur intermittently in one or both ears. Although there are many theories about how tinnitus occurs, there is no scientific consensus to its origin. Some causes of tinnitus result from a blow to the head, large doses of aspirin, anemia, noise exposure, stress, impacted wax, hypertension and certain types of medications and tumors.

Surprisingly, the effect of a combination which comprises at least one AMPA receptor antagonist and at least one compound selected from the group consisting of anti-anxiety drugs, antidepressants, antihistamines, anticonvulsants, vasodilators, zinc salts and anesthetics is greater than the additive effect of the combined drugs. Furthermore, the combinations disclosed herein can be used to treat tinnitus which is refractory to monotherapy employing one of the combination partners alone.

Hence, the invention relates to a combination, such as a combined preparation or pharmaceutical composition, which comprises at least one AMPA receptor antagonist and at least one compound selected from the group consisting of anti-anxiety drugs, antidepressants, antihistamines, anticonvulsants, vasodilators, zinc salts and anesthetics, in which the active ingredients are present in each case in free form or in the form of a pharmaceutically acceptable salt and optionally at least one pharmaceutically acceptable carrier; for simultaneous, separate or sequential use.

The term "anti-anxiety drug" as used herein includes, but is not limited to alprazolam.

The term "antidepressants" as used herein includes, but is not limited to nortriptyline (N-methyl-3-(10,11-dihydro-5H-dibenzo[a,d]cyclohepten-5-yliden)propylamine).

The term "anticonvulsants" as used herein includes, but is not limited to oxcarbazepine.

The term "anesthetics" as used herein includes, but is not limited to lidocaine.

The term "vasodilators" as used herein includes, but is not limited to pentoxifylline.

The term "zinc salts" as used herein includes, but is not limited to zinc sulfate.

Topiramate can be administered, e.g., in the form as marketed, e.g. under the trademark Topamax™. The compounds of formula I as well as their production process and pharmaceutical compositions thereof are known, e.g., from WO 98/17672. Alprazolam can be administered, e.g., in the form as marketed, e.g. under the trademark Xanax™. Nortriptyline can be administered, e.g., in the form as marketed, e.g. under the trademark Nortrilen™.

Oxcarbazepine can be administered, e.g., in the form as marketed, e.g. under the trademark Trileptal™. Lidocaine can be administered in the form of its hydrochloride, e.g., in the form as marketed as injection solution, e.g. under the trademark Heweneural™.

zinc sulfate can be administered, e.g., in the form as marketed, e.g. under the trademark Zink-Sandoz™.

Pentoxifyllin can be administered, e.g., in the form as marketed, e.g. under the trademark Trental™.

The structure of the active ingredients identified by code nos., generic or trade names may be taken from the actual edition of the standard compendium "The Merck Index" or from databases, e.g. Patents International (e.g. IMS World Publications). The corresponding content thereof is hereby incorporated by reference. Any person skilled in the art is fully enabled to identify the active ingredients and, based on these references, likewise enabled to manufacture and test the pharmaceutical indications and properties in standard test models, both in vitro and in vivo.

The term "a combined preparation", as used herein defines especially a "kit of parts" in the sense that the first and second active ingredient as defined above can be dosed independently or by use of different fixed combinations with distinguished amounts of the ingredients, i.e., simultaneously or at different time points. The parts of the kit of parts can then, e.g., be administered simultaneously or chronologically staggered, that is at different time points and with equal or different time intervals for any part of the kit of parts. Very preferably, the time intervals are chosen such that the effect on the treated disease in the combined use of the parts is larger than the effect which would be obtained by use of only any one of the active ingredients. The ratio of the total amounts of the active ingredient 1 to the active ingredient 2 to be administered in the combined preparation can be varied, e.g., in order to cope with the needs of a patient sub-population to be treated or the needs of the single patient which different needs can be due to age, sex, body weight, etc. of the patients. Preferably, there is at least one beneficial effect, e.g., a mutual enhancing of the effect of the first and second active ingredient, in particular a synergism, e.g. a more than additive effect, additional advantageous effects, less side effects, a combined therapeutically effect in a non-effective dosage of one or both of the first and second active ingredient, and especially a strong synergism the first and second active ingredient.

It will be understood that in the discussion of methods, references to the active ingredients are meant to also include the pharmaceutically acceptable salts. If these active ingredients have, for example, at least one basic center, they can form acid addition salts. Corresponding acid addition salts can also be formed having, if desired, an additionally present basic center. The active ingredients having an acid group (for example COOH) can also form salts with bases. The active ingredient or a pharmaceutically acceptable salt thereof may also be used in form of a hydrate or include other solvents used for crystallization.

A pharmaceutical combination which comprises at least one AMPA receptor antagonist and at least one compound selected from the group consisting of anti-anxiety drugs, antidepressants, antihistamines, anticonvulsants, vasodilators, zinc salts and anesthetics, in which the active ingredients are present in each case in free form or in the form of a pharmaceutically acceptable salt, if at least one salt-forming group is present, will be referred to hereinafter as a COMBINATION OF THE INVENTION.

Surprisingly, the administration of a COMBINATION OF THE INVENTION results in a beneficial, especially a synergistic, therapeutic effect or in other surprising beneficial effects, e.g. less side effects, compared to a monotherapy applying only one of the pharmaceutically active ingredients used in the COMBINATION OF THE INVENTION.

The pharmacological activity of a COMBINATION OF THE INVENTION may, for example, be evidenced in preclinical studies known as such, e.g., the methods described herein.

The activity in tinnitus of the COMBINATION OF THE INVENTION can be shown in standard tests, e.g. in the salicylate-induced tinnitus model.

It has been demonstrated [C. A. Bauer et al., Hearing Research 147 (2000) 175-182] that chronic salicylate exposure causes upregulation of glutamic acid decarboxylase (GAD) expression in the rat inferior colliculus (IC), associated with the development of tinnitus.

Furthermore, electrophysiological recordings from auditory neurons using patch clamp recording techniques [D. Peruzzi et al. Neuroscience 101 (2000) 403-416, X. Lin et al., Journal of Neurophysiology 79 (1998) 2503-2512] and single neuron recordings [J. J. Eggermont and M. Kenmochi, Hearing Research 117 (1998) 149-160] showed that the excitability of neurons is changed following salicylate and quinine treatment.

Administration of salicylate or quinine caused an increase in the firing rate auditory neurons measured by extracellular electrophysiological recording techniques. Using in vitro electrophysiological recording techniques superfusion with salicylate increases the excitability of the recorded neurons. On administration of the COMBINATIONS OF THE INVENTION at concentrations of about 1 nM to 100 µM, the effects of salicylate were reversed.

Furthermore, the pharmacological activity of a COMBINATION OF THE INVENTION may, for example, be demonstrated in a clinical study. Such clinical studies are preferably randomized, double-blind, clinical studies in patients with tinnitus. Such studies demonstrate, in particular, the synergism of the active ingredients of the COMBINATIONS OF THE INVENTION. The beneficial effects on tinnitus can be determined directly through the results of these studies or by changes in the study design which are known as such to a person skilled in the art. The studies are, in particular, suitable to compare the effects of a monotherapy using the active ingredients and a COMBINATION OF THE INVENTION.

A further benefit is that lower doses of the active ingredients of the COMBINATION OF THE INVENTION can be used, for example, that the dosages need not only often be smaller but are also applied less frequently, or can be used in order to diminish the incidence of side effects. This is in accordance with the desires and requirements of the patients to be treated. The COMBINATIONs OF THE INVENTION can be used, in particular, for the treatment of tinnitus which is refractory to monotherapy.

It is one objective of this invention to provide a pharmaceutical composition comprising a quantity, which is jointly therapeutically effective against tinnitus, comprising at least one AMPA antagonist and at least one compound selected from the group consisting of anti-anxiety drugs, antidepressants, antihistamines, anticonvulsants, vasodilators, zinc salts and anesthetics, in which the active ingredients are present in each case in free form or in the form of a pharmaceutically acceptable salt and optionally at least one pharmaceutically acceptable carrier. In this composition, the first and second active ingredient can be administered together, one after the other or separately in one combined unit dosage form or in two separate unit dosage forms. The unit dosage form may also be a fixed combination.

The pharmaceutical compositions according to the invention can be prepared in a manner known per se and are those suitable for enteral, such as oral or rectal, and parenteral administration to mammals (warm-blooded animals), including man, comprising a therapeutically effective amount of at least one pharmacologically active ingredient, alone or in combination with one or more pharmaceutically acceptable carries, especially suitable for enteral or parenteral application or local application into the ear showing the tinnitus. The preferred route of administration of the dosage forms of the present invention is orally.

The novel pharmaceutical composition contain, for example, from about 10% to about 100%, preferably from about 20% to about 60%, of the active ingredients. Pharmaceutical preparations for the combination therapy for enteral or parenteral administration are, for example, those in unit dosage forms, such as sugar-coated tablets, tablets, capsules or suppositories, and furthermore ampoules. If not indicated otherwise, these are prepared in a manner known per se, for example by means of conventional mixing, granulating, sugar-coating, dissolving or lyophilizing processes. It will be appreciated that the unit content of active ingredient or ingredients contained in an individual dose of each dosage form need not in itself constitute an effective amount since the necessary effective amount can be reached by administration of a plurality of dosage units.

In preparing the compositions for oral dosage form, any of the usual pharmaceutical media may be employed, such as, for example, water, glycols, oils or alcohols; or carriers such as starches, sugars, microcristalline cellulose, diluents, granulating agents, lubricants, binders, disintegrating agents and the like in the case of oral solid preparations such as, for example, powders, capsules and tablets. Because of their ease of administration, tablets and capsules represent the most advantageous oral dosage unit form in which case solid pharmaceutical carriers are obviously employed.

Unit dosage forms may contain, for example, from about 2.5 mg to about 500 mg of the active ingredients.

Furthermore, the present invention relates to the use of a COMBINATION OF THE INVENTION for the preparation of a medicament for the treatment of tinnitus.

Additionally, the present invention provides a method of treating a warm-blooded animal having tinnitus comprising administering to the animal a COMBINATION OF THE INVENTION in a quantity which is jointly therapeutically effective against tinnitus and in which the compounds can also be present in the form of their pharmaceutically acceptable salts.

Moreover, the present invention provides a commercial package comprising as active ingredients COMBINATION OF THE INVENTION, together with instructions for simultaneous, separate or sequential use thereof in the treatment of tinnitus.

In particular, a therapeutically effective amount of each of the active ingredients of the COMBINATION OF THE INVENTION may be administered simultaneously or sequentially and in any order, and the components may be administered separately or as a fixed combination. For example, the method of treatment of tinnitus according to the invention may comprise (i) administration of the first active ingredient in free or pharmaceutically acceptable salt form and (ii) administration of the second active ingredient in free or pharmaceutically acceptable salt form, simultaneously or sequentially in any order, in jointly therapeutically effective amounts, preferably in synergistically effective amounts, e.g. in daily dosages corresponding to the amounts described herein. The individual active ingredients of the COMBINATION OF THE INVENTION can be administered separately at different times during the course of therapy or concurrently in divided or single combination forms. Furthermore, the term administering also encompasses the use of a pro-drug of an active ingredient that convert in vivo to the active ingredient. The instant invention is therefore to be understood as embracing all such regimes of simultaneous or alternating treatment and the term "administering" is to be interpreted accordingly.

In one preferred embodiment of the invention, the COMBINATION OF THE INVENTION is used for the treatment of treatment of tinnitus which is refractory to monotherapy.

The effective dosage of each of the active ingredients employed in the COMBINATION OF THE INVENTION may vary depending on the particular compound or pharmaceutical composition employed, the mode of administration, the severity of the condition being treated. Thus, the dosage regimen the COMBINATION OF THE INVENTION is selected in accordance with a variety of factors including the route of administration and the renal and hepatic function of the patient. A physician, clinician or veterinarian of ordinary skill can readily determine and prescribe the effective amount of the single active ingredients required to prevent, counter or arrest the progress of the condition. Optimal precision in achieving concentration of the active ingredients within the range that yields efficacy without toxicity requires a regimen based on the kinetics of the active ingredients' availability to target sites. This involves a consideration of the distribution, equilibrium, and elimination of the active ingredients.

When the combination partners employed in the COMBINATION OF THE INVENTION are applied in the form as marketed single drugs, their dosage and mode of administration can take place in accordance with the information provided on the packet leaflet of the respective marketed drug in order to result in the beneficial effect described herein, if not mentioned herein otherwise. In particular, Topiramate may be administered to an adult patient in a total daily dosage of between about 250 to about 500 mg. {[(7-Nitro-2,3-dioxo-1,2,3,4-tetrahydro-quinoxalin-5-ylm-ethyl)-amino]-methyl}-phosphonic acid may be administered to a patient in a total daily dosage of about 60 to about 400 mg.

Combinations Comprising Nootropics Suitable for the Treatment of Dementia

The present invention also relates to combinations comprising nootropics suitable for the treatment of dementia.

Surprisingly, dementia can be treated by administration of an AMPA receptor antagonist in combination with nootropics. Hence, the present invention relates to a method for the treatment and/or prevention dementia comprising the step of administering to a warm-blooded animal, including a human, in need thereof an effective amount of AMPA receptor antagonist in combination with nootropics.

The term "dementia" as used herein includes, but is not restricted to, Alzheimer's dementia with or without psychotic symptoms. In particular, the methods and materials described herein are suitable for the treatment of behavioral disturbances observed with such types of dementia.

The term "nootropics" as used herein includes, but is not limited to nootropical plant extracts, calcium antagonists, cholinesterase inhibitors, dihydroergotoxin, nicergoline, piracetame, purine derivates, pyritinol, vincamine and vinpocetine. In a preferred embodiment of the invention, the combination partner is a cholinesterase inhibitor.

The term "nootropical plant extracts" as used herein includes, but is not limited to extracts from Ginkgo leafs. The term "calcium antagonists" as used herein includes, but is not limited to cinnarizine and nimodipine. The term "cholinesterase inhibitors" as used herein includes, but is not limited to donepezil hydrochloride, rivastigmine and galantamine hydrobromide. The term "purine derivates" as used herein includes, but is not limited to pentifyllin.

Extracts from Ginkgo leafs can be administered, e.g., in the form as marketed, e.g. under the trademark Ginkodilat™ according to the information provided by the package insert. Cinnarizine can be administered, e.g., in the form as marketed, e.g. under the trademark Cinnarizin Forte-Ratiopharm™. Nimodipine can be administered, e.g., in the form as marketed, e.g. under the trademark Nimotop™. Donepezil hydrochloride can be administered, e.g., in the form as marketed, e.g. under the trademark Aricept™. Rivastigmine can be prepared as disclosed in U.S. Pat. No. 5,602,176. It can be administered, e.g., in the form as marketed, e.g. under the trademark Exelon™. Galantamine hydrobromide can be administered, e.g., in the form as marketed, e.g. under the trademark Reminyl™. Dihydroergotoxin can be administered, e.g., in the form as marketed, e.g. under the trademark Hydergin™. Nicergoline can be administered, e.g., in the form as marketed, e.g. under the trademark Sermion™. Piracetam can be administered, e.g., in the form as marketed, e.g. under the trademark Cerebroforte™. Pentifyllin can be administered, e.g., in the form as marketed, e.g. under the trademark Cosaldon™. Pyritinol can be administered, e.g., in the form as marketed, e.g. under the trademark Encephabol™. Vinpocetin can be administered, e.g., in the form as marketed, e.g. under the trademark Cavinton™.

The structure of the active ingredients identified by code nos., generic or trade names mentioned herein may be taken from the actual edition of the standard compendium "The Merck Index" or from databases, e.g. Patents International (e.g. IMS World Publications). The corresponding content thereof is hereby incorporated by reference. Any person skilled in the art is fully enabled to identify the active ingredients and, based on these references, likewise enabled to manufacture and test the pharmaceutical indications and properties in standard test models, both in vitro and in vivo.

Hence, in one aspect the invention relates to a combination, such as a combined preparation or pharmaceutical composition, which comprises at least one AMPA receptor antagonist and at least one nootropic, in which the active ingredients are present in each case in free form or in the form of a pharmaceutically acceptable salt and optionally at least one pharmaceutically acceptable carrier; for simultaneous, separate or sequential use.

The term "a combined preparation", as used herein defines especially a "kit of parts" in the sense that the first and second active ingredient as defined above can be dosed independently or by use of different fixed combinations with distinguished amounts of the ingredients, i.e., simultaneously or at different time points. The parts of the kit of parts can then, e.g., be administered simultaneously or chronologically staggered, that is at different time points and with equal or different time intervals for any part of the kit of parts. Very preferably, the time intervals are chosen such that the effect on the treated disease in the combined use of the parts is larger than the effect which would be obtained by use of only any one of the active ingredients. The ratio of the total amounts of the active ingredient 1 to the active ingredient 2 to be administered in the combined preparation can be varied, e.g., in order to cope with the needs of a patient sub-population to be treated or the needs of the single patient which different needs can be due to age, sex, body weight, etc. of the patients. Preferably, there is at least one beneficial effect, e.g., a mutual enhancing of the effect of the first and second active ingredient, in particular a synergism, e.g. a more than additive effect, additional advantageous effects, less side effects, a combined therapeutic effect in a non-effective dosage of one or both of the first and second active ingredient, and especially a strong synergism the first and second active ingredient.

It will be understood that in the discussion of methods, references to the active ingredients are meant to also include the pharmaceutically acceptable salts. If these active ingredients have, for example, at least one basic center, they can form acid addition salts. Corresponding acid addition salts can also be formed having, if desired, an additionally present basic center. The active ingredients having an acid group (for example COOH) can also form salts with bases. The active ingredient or a pharmaceutically acceptable salt thereof may also be used in form of a hydrate or include other solvents used for crystallization.

A pharmaceutical combination which comprises at least one AMPA receptor antagonist and at least one nootropic in which the active ingredients are present in each case in free form or in the form of a pharmaceutically acceptable salt, if at least one salt-forming group is present, will be referred to hereinafter as a COMBINATION OF THE INVENTION.

The pharmacological activity of an AMPA receptor antagonist or a COMBINATION OF THE INVENTION may, for example, also be demonstrated in a clinical study. Such clinical studies are preferably randomized, double-blind, clinical studies in patients with Alzheimer's Disease. Such studies demonstrate, in particular, the synergism of the active ingredients of the COMBINATIONS OF THE INVENTION. The beneficial effects on Alzheimer's Disease can be determined directly through the results of these studies or by changes in the study design which are known as such to a person skilled in the art. The studies are, in particular, suitable to compare the effects of a monotherapy using the active ingredients and a COMBINATION OF THE INVENTION.

A further benefit is that lower doses of the active ingredients of the COMBINATION OF THE INVENTION can be used, for example, that the dosages need not only often be smaller but are also applied less frequently, or can be used in order to diminish the incidence of side effects. This is in accordance with the desires and requirements of the patients to be treated. The COMBINATIONs OF THE INVENTION can be used, in particular, for the treatment of dementia which is refractory to monotherapy.

It is one objective of this invention to provide a pharmaceutical composition comprising a quantity, which is jointly therapeutically effective against dementia, comprising at least one AMPA receptor antagonist, at least one nootropic and at least one pharmaceutically acceptable carrier. In this composition, the first and second active ingredient can be administered together, one after the other or separately in one combined unit dosage form or in two separate unit dosage forms. The unit dosage form may also be a fixed combination.

The pharmaceutical compositions according to the invention can be prepared in a manner known per se and are those suitable for enteral, such as oral or rectal, and parenteral administration to mammals (warm-blooded animals), including man, comprising a therapeutically effective amount of at least one pharmacologically active ingredient, alone or in combination with one or more pharmaceutically acceptable carries, especially suitable for enteral or parenteral application. The preferred route of administration of the dosage forms of the present invention is orally.

The novel pharmaceutical composition contain, for example, from about 10% to about 100%, preferably from about 20% to about 60%, of the active ingredients. Pharmaceutical preparations for the combination therapy for enteral or parenteral administration are, for example, those in unit dosage forms, such as sugar-coated tablets, tablets, capsules or suppositories, and furthermore ampoules. If not indicated otherwise, these are prepared in a manner known per se, for example by means of conventional mixing, granulating, sugar-coating, dissolving or lyophilizing processes. It will be appreciated that the unit content of active ingredient or ingredients contained in an individual dose of each dosage form need not in itself constitute an effective amount since the necessary effective amount can be reached by administration of a plurality of dosage units.

In preparing the compositions for oral dosage form, any of the usual pharmaceutical media may be employed, such as, for example, water, glycols, oils or alcohols; or carriers such as starches, sugars, microcristalline cellulose, diluents, granulating agents, lubricants, binders, disintegrating agents and the like in the case of oral solid preparations such as, for example, powders, capsules and tablets. Because of their ease of administration, tablets and capsules represent the most advantageous oral dosage unit form in which case solid pharmaceutical carriers are obviously employed.

Furthermore, the present invention relates to the use of a COMBINATION OF THE INVENTION for the preparation of a medicament for the treatment of dementia.

Additionally, the present invention provides a method of treating a warm-blooded animal having dementia comprising administering to the animal a COMBINATION OF THE INVENTION in a quantity which is jointly therapeutically effective against dementia and in which the compounds can also be present in the form of their pharmaceutically acceptable salts.

Moreover, the present invention provides a commercial package comprising as active ingredients COMBINATION OF THE INVENTION, together with instructions for simultaneous, separate or sequential use thereof in the treatment of dementia.

In one preferred embodiment of the invention, the COMBINATION OF THE INVENTION is used for the treatment of dementia which is refractory to monotherapy.

In particular, a therapeutically effective amount of each of the active ingredients of the COMBINATION OF THE INVENTION may be administered simultaneously or sequentially and in any order, and the components may be administered separately or as a fixed combination. For example, the method of treatment of dementia according to the invention may comprise (i) administration of the first active ingredient in free or pharmaceutically acceptable salt form and (ii) administration of the second active ingredient in free or pharmaceutically acceptable salt form, simultaneously or sequentially in any order, in jointly therapeutically effective amounts, preferably in synergistically effective amounts, e.g. in daily dosages corresponding to the amounts described herein. The individual active ingredients of the COMBINATION OF THE INVENTION can be administered separately at different times during the course of therapy or concurrently in divided or single combination forms. Furthermore, the term administering also encompasses the use of a pro-drug of an active ingredient that convert in vivo to the active ingredient. The instant invention is therefore to be understood as embracing all such regimes of simultaneous or alternating treatment and the term "administering" is to be interpreted accordingly.

The effective dosage of each of the active ingredients employed in the COMBINATION OF THE INVENTION may vary depending on the particular compound or pharmaceutical composition employed, the mode of administration, the severity of the condition being treated. Thus, the dosage regimen the COMBINATION OF THE INVENTION is selected in accordance with a variety of factors including the route of administration and the renal and hepatic function of the patient. A physician, clinician or veterinarian of ordinary skill can readily determine and prescribe the effective amount of the single active ingredients required to prevent, counter or arrest the progress of the condition. Optimal precision in achieving concentration of the active ingredients within the range that yields efficacy without toxicity requires a regimen based on the kinetics of the active ingredients' availability to target sites. This involves a consideration of the distribution, equilibrium, and elimination of the active ingredients.

When the combination partners employed in the COMBINATION OF THE INVENTION are applied in the form as marketed single drugs, their dosage and mode of administration can take place in accordance with the information provided on the packet leaflet of the respective marketed drug in order to result in the beneficial effect described herein, if not mentioned herein otherwise. In particular, Cinnarizine may be administered to a patient in a total daily dosage of between about 75 to about 150 mg.

Nimodipine may be administered to a patient in a total daily dosage of between about 60 to about 120 mg.

Donepezil hydrochloride may be administered to a patient in a total daily dosage of between about 5 mg and 10 mg.

Rivastigmine may be administered to a patient in a total daily dosage of between about 6 and about 12 mg.

Galantamine may be administered to a patient in a total daily dosage of between about 12 and 24 mg, e.g. 12 mg twice daily.

Dihydroergotoxin may be administered in the form of its methansulfonate to a patient in a total daily dosage of between about 4 mg and 10 mg, e.g. about 8 mg.

Nicergoline may be administered in the form of its tartrate by intramuscular injection to a patient in a total daily dosage of between about 4 mg and 8 mg.

Piracetam may be administered to a patient in a total daily dosage of between about 1200 and 5000 mg, e.g. 4800 mg/day.

Pentifyllin may be administered to a patient in a total daily dosage of between about 400 and 800 mg.

Pyritinol may be administered in the form of its hydrochloride to a patient in a total daily dosage of about 600 mg.

Vinpocetin may be administered to a patient in a total daily dosage of between about 10 and 15 mg.

The following examples illustrate, without limitation, the invention as described throughout this specification.

The following abbreviations are used:

CNQX 7-Nitro-2,3-dioxo-1,2,3,4-tetrahydro-quinoxaline-6-carbonitrile d day

DAST (diethylamino)sulfur trifluoride

DCM dichloromethane

DME 1,2-dimethoxyethane

DMSO dimethyl sulfoxide equiv equivalent

ESI-MS electrospray ionization mass spectrum

EtOAc ethyl acetate

EtOH ethanol

HEPES 4-(2-Hydroxyethyl)piperazine-1-ethanesulphonic acid

H hour

HPLC High Performance Liquid Chromatography

IR Infrared spectroscopy

MeOH methanol min minute m.p. melting point

MPLC Medium pressure liquid chromatography m/z mass-to-charge ratio

RP reversed phase rt retention time r.t. room temperature

SPL Sound Pressure Level

TFA trifluoroacetic acid

Example 1

N-(6-Acetyl-2,4-dioxo-7-trifluoromethyl-1,4-dihydro-2H-quinazolin-3-yl)-methanesulfonamide 2-Amino-4-trifluoromethyl-benzoic acid

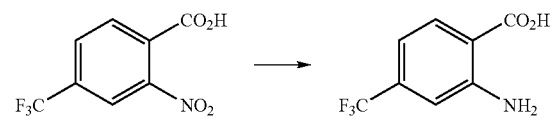

A solution of 2-nitro-4-trifluoromethyl-benzoic acid (100 g, 425 mmol) in MeOH (600 mL) was treated with palladium on carbon (10%) and the mixture was stirred at r.t. for 2 h under hydrogen (7 bars). The mixture was then filtered and concentrated in vacuo to give 2-amino-4-trifluoromethylbenzoic acid (87.2 g, 425 mmol, 100%) as a yellow solid, m.p. 172-173° C., ESI-MS: m/z 206 [M+H]⁺.

2-Amino-4-trifluoromethyl-benzoic acid methyl ester

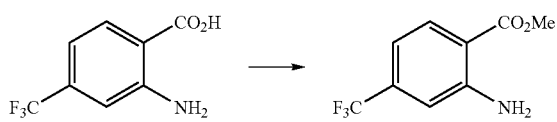

To a solution of 2-amino-4-trifluoromethyl-benzoic acid (72.0 g, 351 mmol) in MeOH (1000 mL) was added dropwise concentrated sulfuric acid (50 mL). The mixture was heated to reflux for 16 h under nitrogen, allowed to cool to r.t., and then concentrated in vacuo to ¼ of its volume. The mixture was taken up in EtOAc and washed with water, 10% aqueous solution of sodium carbonate, and brine. It was then dried over anhydrous sodium sulfate, filtered and concentrated in vacuo. Purification by column chromatography (silica gel 60, hexanes/EtOAc 9:1) furnished 2-amino-4-trifluoromethyl-benzoic acid methyl ester (57.8 g, 264 mmol, 75%) as a white powder, m.p. 59° C., ESI-MS: m/z 218 [M−H]⁻.

2-Amino-5-iodo-4-trifluoromethyl-benzoic acid methyl ester

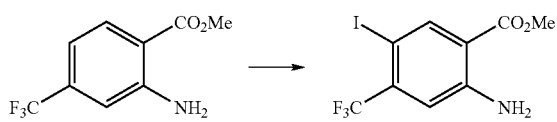

A mixture of 2-amino-4-trifluoromethyl-benzoic acid methyl ester (51.5 g, 235 mmol), iodine (55.1 g, 217 mmol) and silver sulfate (73.3 g, 234 mmol) in EtOH (1560 mL) was stirred for 1 h at r.t. under nitrogen. The suspension was then filtered and the filtrate diluted with EtOAc and washed once with a 10% aqueous sodium thiosulfate solution. The organic layer was dried over anhydrous sodium sulfate, filtered and concentrated in vacuo to give 2-amino-5-iodo-4-trifluoromethyl-benzoic acid methyl ester (67.5 g, 196 mmol, 83%) as a brown solid, m.p. 101-103° C., ESI-MS: m/z 346 [M+H]⁺.

2-Acetylamino-5-iodo-4-trifluoromethyl-benzoic acid methyl ester

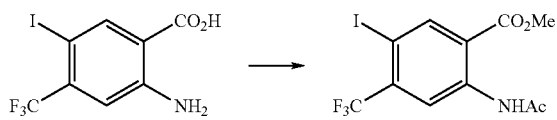

A solution of 2-amino-5-iodo-4-trifluoromethyl-benzoic acid methyl ester (42.0 g, 122 mmol) in toluene (400 mL) was treated with acetic anhydride (12.8 mL, 135 mmol) and the mixture was heated to reflux for 16 h under nitrogen. It was then allowed to cool to r.t. and diluted with water. The mixture was rendered neutral by adding small portions of sodium hydrogencarbonate, and the organic layer was separated. The aqueous phase was extracted with EtOAc, and the combined organic phases were dried over anhydrous sodium sulfate, filtered and concentrated in vacuo. The crude product was recrystallized in hexanes to give 2-acetylamino-5-iodo-4-trifluoromethyl-benzoic acid methyl ester (43.4 g, 112 mmol, 92%) as a white powder, m.p. 96-98° C., ESI-MS: m/z 388 [M+H]⁺.

2-Acetylamino-5-(1-ethoxy-vinyl)-4-trifluoromethyl-benzoic acid methyl ester

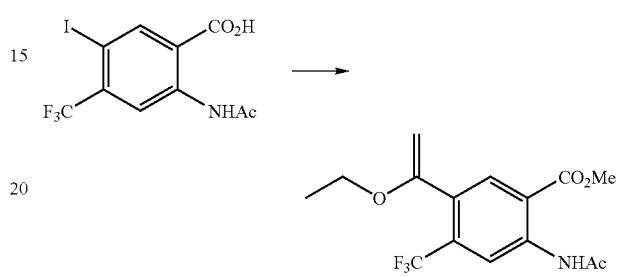

A solution of 2-acetylamino-5-iodo-4-trifluoromethyl-benzoic acid methyl ester (17.8 g, 46.1 mmol), tetrakis-(triphenylphosphine)-palladium (2.67 g, 2.30 mmol), and tributyl-(ethoxyvinyl)-tin (25.0 g, 69.2 mmol) in dioxane (100 mL) was heated to 110° C. for 20 h under nitrogen. The mixture was allowed to cool to r.t., and then filtered. The filtrate was concentrated in vacuo and the crude product was purified by column chromatography (silica gel 60, hexanes/EtOAc 3:1) to give crude 2-acetylamino-5-(1-ethoxy-vinyl)-4-trifluoromethyl-benzoic acid methyl ester as an orange solid, m.p. 65-73° C., ESI-MS: m/z 332 [M+H]⁺. This crude product was used without further purification in the next step.

5-Acetyl-2-acetylamino-4-trifluoromethyl-benzoic acid methyl ester

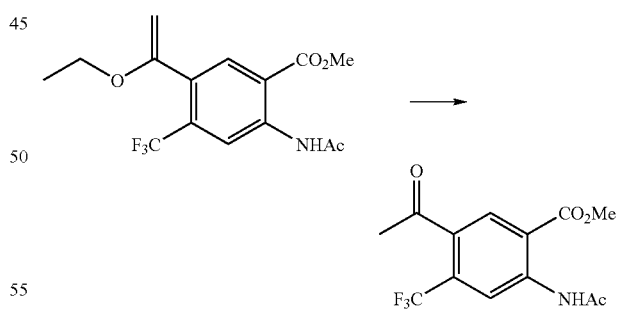

A solution of crude 2-acetylamino-5-(1-ethoxy-vinyl)-4-trifluoromethyl-benzoic acid methyl ester from above in THF (100 mL) was treated with aqueous hydrochloric acid (1N, 50 mL), and the mixture was stirred at r.t. for 1 h under nitrogen. The mixture was then poured into EtOAc and washed once with water. The organic phase was dried over anhydrous sodium sulfate, filtered and concentrated in vacuo. The crude product was purified by column chromatography (silica gel 60, hexanes/EtOAc 2:1) to give 5-acetyl-2-acetylamino-4- trifluoromethyl-benzoic acid methyl ester (10.7 g, 35.1 mmol, 76% over two steps) as a white powder, m.p. 66-69° C., ESI-MS: m/z 326 [M+Na]+.

5-Acetyl-2-amino-4-trifluoromethyl-benzoic acid methyl ester

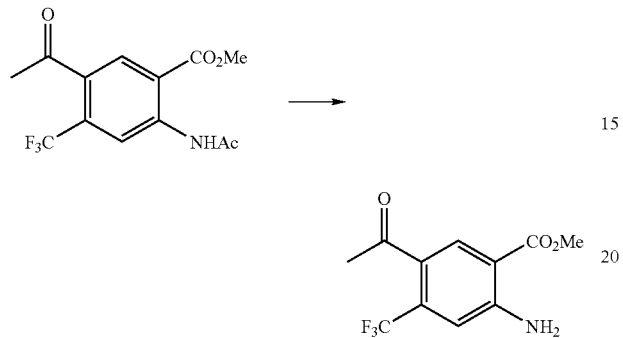

A solution of 5-acetyl-2-acetylamino-4-trifluoromethyl-benzoic acid methyl ester (11.5 g, 37.8 mmol) in MeOH (120 mL)/water (24 mL) was cooled to 0° C. and concentrated sulfuric acid (15.0 mL, 271 mmol) was added dropwise. Upon completion of the addition, the mixture was heated to reflux for 45 min under nitrogen, and then allowed to cool to r.t. The mixture was diluted with EtOAc and washed once with water. The organic layer was dried over anhydrous sodium sulfate, filtered, and concentrated in vacuo providing 5-acetyl-2-amino-4-trifluoromethyl-benzoic acid methyl ester (9.87 g, 37.8 mmol, quantitative) as a white solid, m.p. 118-121° C., ESI-MS: m/z 262 [M+H]+.

N-(6-Acetyl-2,4-dioxo-7-trifluoromethyl-1,4-dihydro-2H-quinazolin-3-yl)-methanesulfonamide

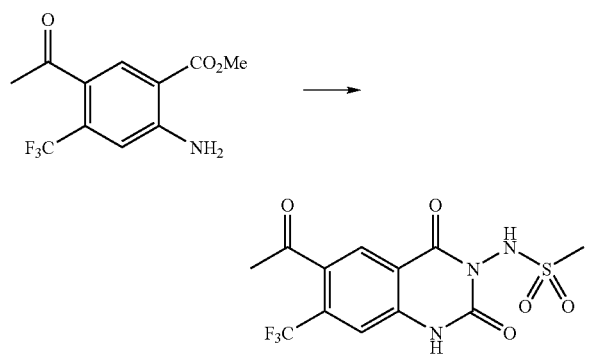

A solution of 5-acetyl-2-amino-4-trifluoromethyl-benzoic acid methyl ester (10.2 g, 39.0 mmol) in THF (250 mL) was treated with (CCl3O)2CO (3.86 g, 12.9 mmol) and the mixture was stirred at r.t. for 15 min under nitrogen. To this solution was added Et3N (5.55 mL, 39.0 mmol) and the mixture was stirred for another 3 h at r.t. The mixture was then treated with CH3SO2NHNH2 (4.38 g, 39.0 mmol) and stirred for 1 h at r.t. Aqueous sodium hydroxide (1M, 78 mL, 78.0 mmol) was subsequently added and the solution was stirred for 18 h at r.t. The mixture was acidified with aqueous hydrochloric acid (4N) until pH=3-4, and then diluted with EtOAc. It was then washed once with water, and the organic phase was then dried over anhydrous sodium sulfate, filtered and concentrated until the product precipitated. The suspension was then cooled to 0° C., and then filtered. The white solid was dried in vacuo to give N-(6-acetyl-2,4-dioxo-7-trifluoromethyl-1,4-dihydro-2H-quinazolin-3-yl)-methanesulfonamide (12.1 g, 33.2 mmol, 85%), m.p. 258-265° C., ESI-MS: m/z 366 [M+H]+.

Example 2

N-[6-(1-Hydroxy-ethyl)-2,4-dioxo-7-trifluoromethyl-1,4-dihydro-2H-quinazolin-3-yl]-methanesulfonamide

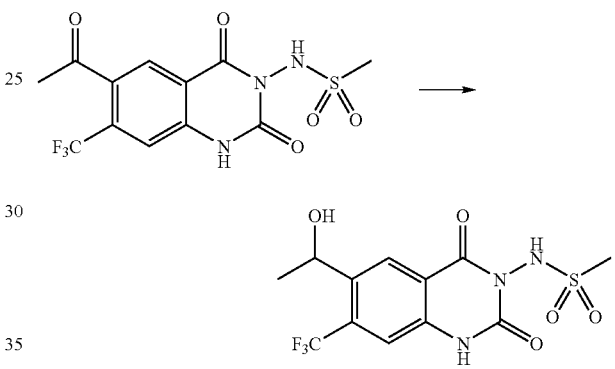

A solution of N-(6-acetyl-2,4-dioxo-7-trifluoromethyl-1,4-dihydro-2H-quinazolin-3-yl)-methanesulfonamide (12.1 g, 33.1 mmol) in THF (150 mL)/MeOH (150 mL) under nitrogen was treated with sodium borohydride (25.0 g, 660 mmol) portionwise over 18 h at r.t. The suspension was then poured into a mixture of ice/concentrated EtOAc. The combined organic layers were dried over anhydrous sodium sulfate, filtered and concentrated in vacuo. The crude product was purified by column chromatography (silica gel 60, DCM/MeOH 9:1) affording colorless crystals, which were recrystallized in EtOAc to provide N-[6-(1-hydroxy-ethyl)-2,4-dioxo-7-trifluoromethyl-1,4-dihydro-2H-quinazolin-3-yl]-methanesulfonamide (8.85 g, 24.1 mmol, 73%) as a white powder, m.p. 263-268° C., $^1$H-NMR (DMSO-$d_6$, 400 MHz) 8.41 (s, 1H), 7.49 (s, 1H), 5.66 (m, 1H), 5.03 (br s, 1H), 3.18 (s, 3H), 1.36 (d, J=6.2 Hz, 3H).

The racemic mixture of N-[6-(1-hydroxy-ethyl)-2,4-dioxo-7-trifluoromethyl-1,4-dihydro-2H-quinazolin-3-yl]-methanesulfonamide (5.28 g, 144 mmol) was purified by chiral preparative HPLC (Chiracel OJ, hexanes/EtOH 7:3, 1.0 mL/min) providing 2.34 g (63.7 mmol) of enantiomer 1 (S)—N-[6-(1-Hydroxy-ethyl)-2,4-dioxo-7-trifluoromethyl-1,4-dihydro-2H-quinazolin-3-yl]-methanesulfonamide (retention time 8.99 min, $[\alpha]_{589}$=−39.3) and 2.05 g (55.8 mmol) of enantiomer 2 (R)—N-[6-(1-Hydroxy-ethyl)-2,4-dioxo-7-trifluoromethyl-1,4-dihydro-2H-quinazolin-3-yl]-methanesulfonamide (retention time 12.77 min, $[\alpha]_{589}$=+38.8).

Example 3

N-[6-(1-Methoxy-ethyl)-2,4-dioxo-7-trifluoromethyl-1,4-dihydro-2H-quinazolin-3-yl]-methanesulfonamide

2-Acetylamino-5-(1-hydroxy-ethyl)-4-trifluoromethyl-benzoic acid methyl ester

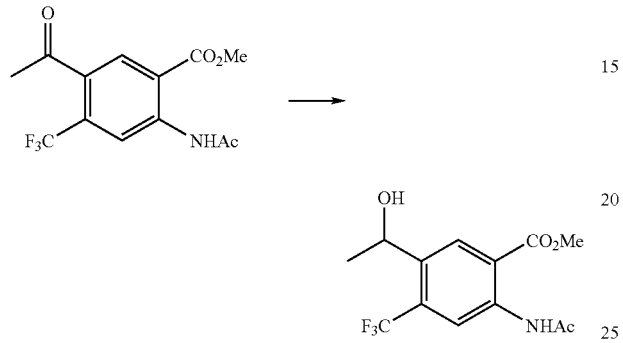

A suspension of 5-acetyl-2-acetylamino-4-trifluoromethyl-benzoic acid methyl ester (1.0 g, 3.3 mmol) and 100 mg of palladium on carbon (10%) in THF (10 mL) was stirred at r.t. for 2 h under hydrogen (5 bars). The mixture was then filtered and concentrated in vacuo. The crude product was purified by column chromatography (silica gel 60, hexanes/EtOAc 2:1) to give 2-acetylamino-5-(1-hydroxy-ethyl)-4-trifluoromethyl-benzoic acid methyl ester (917 mg, 3.0 mmol, 91%) as a white solid, m.p. 120-122° C., ESI-MS: m/z 306 [M+H]$^+$.

2-Amino-5-(1-methoxy-ethyl)-4-trifluoromethyl-benzoic acid methyl ester

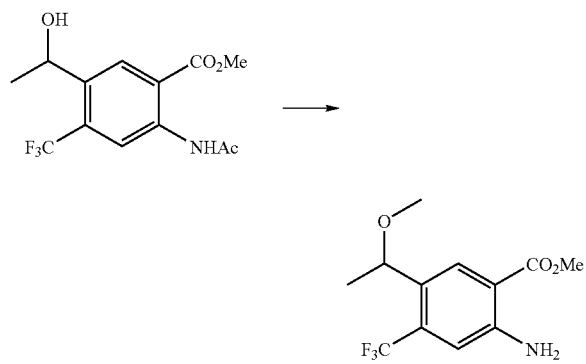

A solution of 2-acetylamino-5-(1-hydroxy-ethyl)-4-trifluoromethyl-benzoic acid methyl ester (600 mg, 1.97 mmol) and Et$_3$N (412 µL, 3.0 mmol) in DCM (6 mL) was cooled to 0° C. and treated with methanesulfonyl chloride (194 µL, 2.46 mmol) dropwise. The mixture was allowed to warm to r.t. and stirred for 2 h. The mixture was then diluted with DCM, and washed once with water, dried over anhydrous sodium sulfate, filtered and concentrated in vacuo to give a brown oil which was taken up in MeOH. This solution was allowed to stand for 60 h at r.t. The mixture was then concentrated in vacuo and the crude product was purified by column chromatography (silica gel 60, hexanes/EtOAc 5:1) to give 2-amino-5-(1-methoxy-ethyl)-4-trifluoromethyl-benzoic acid methyl ester (196 mg, 0.71 mmol, 36%) as a white powder, m.p. 112-114° C., ESI-MS: m/z 278 [M+H]$^+$.

N-[6-(1-methoxy-ethyl)-2,4-dioxo-7-trifluoromethyl-1,4-dihydro-2H-quinazolin-3-yl]-methanesulfonamide

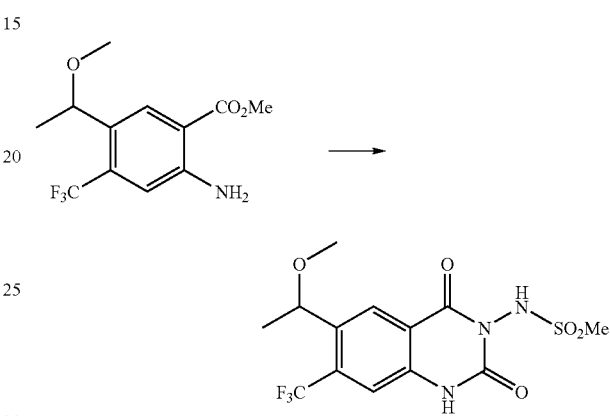

A solution of 2-amino-5-(1-methoxy-ethyl)-4-trifluoromethyl-benzoic acid methyl ester (190 mg, 0.69 mmol) in THF was treated with (CCl$_3$O)$_2$CO (178 mg, 0.6 mmol) and the mixture was stirred at r.t. for 15 min under argon. To this solution was added Et$_3$N (84 µL, 0.6 mmol) and the mixture was stirred for another 3 h at r.t. The mixture was then treated with CH$_3$SO$_2$NHNH$_2$ (66 mg, 0.6 mmol) and stirred for 1 h at r.t. Aqueous sodium hydroxide (1M, 3 mL, 3 mmol) was subsequently added and the solution was stirred for 18 h at r.t. The mixture was acidified with aqueous hydrochloric acid (4N) until pH=3-4, and then diluted with EtOAc. The layers were separated and the organic phase was then washed once with water, dried over anhydrous sodium sulfate, filtered and concentrated in vacuo. The crude product was purified by column chromatography (silica gel 60, hexanes/EtOAc 2:1) to give a pale yellow solid, which was dissolved in EtOAc. Pentane was then added until a white product precipitated. This mixture was allowed to stand at 0° C. for 16 h, and the white solid was then filtered and dried in vacuo at 60° C. to provide N-[6-(1-methoxy-ethyl)-2,4-dioxo-7-trifluoromethyl-1,4-dihydro-2H-quinazolin-3-yl]-methanesulfonamide (180 mg, 0.47 mmol, 68%) as a white powder, m.p. 233-236° C., ESI-MS: m/z 382 [M+H]$^+$.

A resolution of the racemate was done using chiral chromatography to yield the two enantiomers. HPLC analyses were performed using a system comprising a Merck-Hitaschi L-6200A pump coupled to a Merck-Hitaschi L-4500 Diode Array detector and a Merck-Hitaschi Lahrom D-7000 spectrometer, a 50 µL loop injection valve and a Chiralcel OJ-H column (250×4.6 mm) running a mixture of hexane/ethanol/methanol 90:5:5+0.1% trifluoroacetic acid. The solvent flow was 0.5 mL/min. Enantiomer 1: r.t.=48.19 min, Enantiomer 2: r.t.=52.56 min.

Example 4

N-[6-(1-Ethoxy-ethyl)-2,4-dioxo-7-trifluoromethyl-1,4-dihydro-2H-quinazolin-3-yl]-methanesulfonamide 2-Amino-5-(1-ethoxy-ethyl)-4-trifluoromethyl-benzoic acid methyl ester

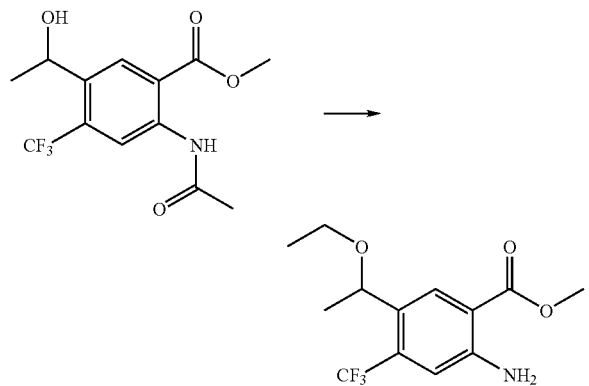

A solution of 2-acetylamino-5-(1-hydroxy-ethyl)-4-trifluoromethyl-benzoic acid methyl ester (500 mg, 1.64 mmol) in EtOH (5 mL) was treated with p-toluenesulfonic acid monohydrate (100 mg, 0.518 mmol) and stirred at r.t. for 5 d. The reaction mixture was taken into EtOAc and washed with sat. aq NaHCO$_3$. The organic phase was dried (Na$_2$SO$_4$), filtered and concentrated in vacuo. The residue was purified by column chromatography (silica gel, 5:1 hexanes/EtOAc) to give title product (270 mg, 57%) as colorless crystals. m.p.: 100-103° C., API-ES: m/z 292 [M+H]$^+$.

N-[6-(1-Ethoxy-ethyl)-2,4-dioxo-7-trifluoromethyl-1,4-dihydro-2H-quinazolin-3-yl]-methanesulfonamide

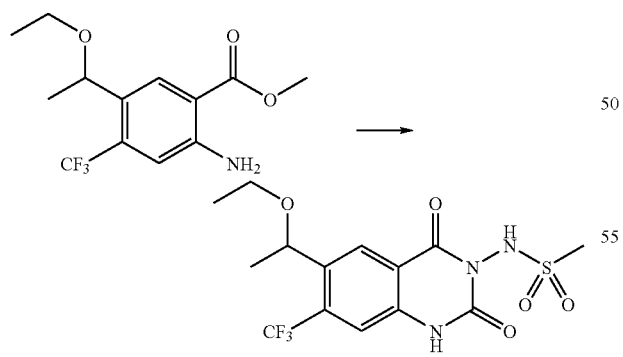

2-Amino-5-(1-ethoxy-ethyl)-4-trifluoromethyl-benzoic acid methyl ester (250 mg, 0.857 mmol) was converted to N-[6-(1-ethoxy-ethyl)-2,4-dioxo-7-trifluoromethyl-1,4-dihydro-2H-quinazolin-3-yl]-methanesulfonamide as a colorless foam (272 mg, 80%) following the same procedure described for N-[6-(1-methoxy-ethyl)-2,4-dioxo-7-trifluoromethyl-1,4-dihydro-2H-quinazolin-3-yl]-methanesulfonamide. m.p.: 105-112° C., API-ES: m/z 396 [M+H]$^+$.

Example 5

N-[6-(Isopropoxy-ethyl)-2,4-dioxo-7-trifluoromethyl-1,4-dihydro-2H-quinazolin-3-yl]-methanesulfonamide 2-Acetylamino-5-(1-hydroxy-ethyl)-4-trifluoromethyl-benzoic acid methyl ester

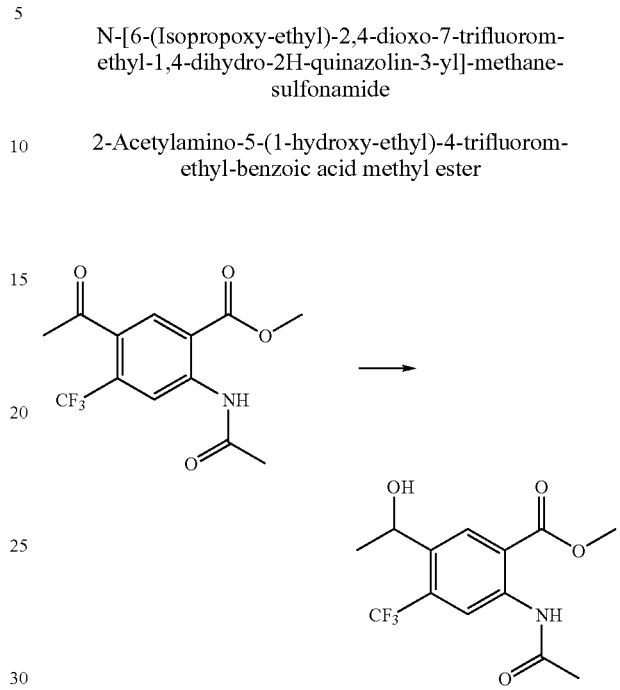

A solution of 5-acetyl-2-acetylamino-4-trifluoromethyl-benzoic acid methyl ester (4 g, 13.2 mmol) in THF (40 mL) was hydrogenated at r.t. for 2 h over Pd—C (10%, 250 mg). The reaction mixture was filtered on a sintered funnel. The filtrate was concentrated in vacuo. The residue was purified by column chromatography (silica gel, 2:1 hexanes/EtOAc) to give the title product (3.66 g, 91% yield) as colorless crystals. m.p.: 120-123° C., ESI-MS: m/z 306 [M+H]$^+$.

2-Amino-5-(1-isopropoxy-ethyl)-4-trifluoromethyl-benzoic acid methyl ester

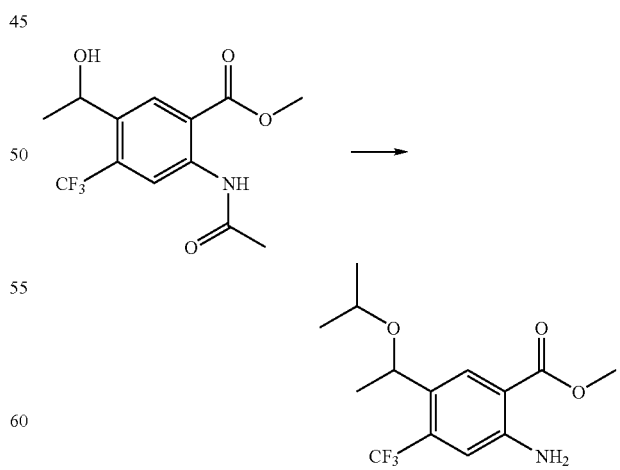

A solution of 2-acetylamino-5-(1-hydroxy-ethyl)-4-trifluoromethyl-benzoic acid methyl ester (500 mg, 1.64 mmol) in i-PrOH (5 mL) was treated by addition of p-toluenesulfonic acid monohydrate (99.9 mg, 0.517 mmol) and stirred at 80° C.

for 18 h. The reaction mixture was cooled then concentrated in vacuo. The residue was purified by column chromatography (silica gel, 5:1 hexanes/EtOAc) to give title product (69 mg, 14% yield) as colorless crystals. m.p.: 87-90° C., API-ES: m/z 306 [M+H]⁺.

N-[6-(1-Isopropoxy-ethyl)-2,4-dioxo-7-trifluoromethyl-1,4-dihydro-2H-quinazolin-3-yl]-methanesulfonamide

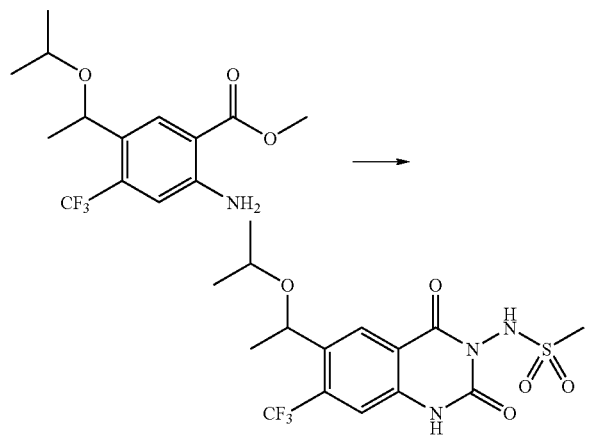

2-Amino-5-(1-isopropoxy-ethyl)-4-trifluoromethyl-benzoic acid methyl ester (65 mg, 0.213 mmol) was converted to N-[6-(1-isopropoxy-ethyl)-2,4-dioxo-7-trifluoromethyl-1,4-dihydro-2H-quinazolin-3-yl]-methanesulfonamide as a colorless foam (52 mg, 60% yield) following the same procedure described for N-[6-(1-methoxy-ethyl)-2,4-dioxo-7-trifluoromethyl-1,4-dihydro-2H-quinazolin-3-yl]-methanesulfonamide. m.p.: 110-115° C., API-ES: m/z 410 [M+H]⁺.

HPLC analyses were performed using a system comprising a Merck-Hitaschi L-6200A pump coupled to a Merck-Hitaschi L-4500 Diode Array detector and a Merck-Hitaschi Lahrom D-7000 spectrometer, a 50 µL loop injection valve and a Chiralpak AS-H column (250×4.6 mm) running a mixture of hexane/ethanol 90:10+0.1% trifluoroacetic acid. The solvent flow was 1.0 mL/min. Enantiomer 1: r.t.=9.68 min, Enantiomer 2: r.t.=13.84 min.

Example 6

N-(2,4-Dioxo-6-propionyl-7-trifluoromethyl-1,4-dihydro-2H-quinazolin-3-yl)-methanesulfonamide

2-Acetylamino-4-trifluoromethyl-5-vinyl-benzoic acid methyl ester

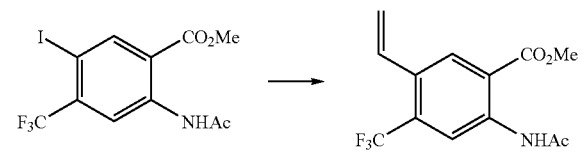

A solution of 2-acetylamino-5-iodo-4-trifluoromethyl-benzoic acid methyl ester (18.0 g, 46.5 mmol) in dry toluene (72 mL) was degassed for 5 min at the ultrasound bath. The solution was then treated with tributyl(vinyl)tin (28 mL, 93 mmol) and tetrakis-(triphenylphosphine)-palladium (2.77 g, 2.33 mmol), and heated to reflux for 2 h. The mixture was allowed to cool to r.t. and potassium fluoride dihydrate (22 g) was then added. This suspension was stirred for 30 min at r.t. and was then filtered on a short pad of silica gel. The filter was washed with diethyl ether and the filtrate was concentrated in vacuo. The crude product was taken up in hexanes and the suspension was filtered. The filtrate was concentrated in vacuo again and allowed to stand at r.t. for 7 d. The solid formed was filtered, washed with hexanes and combined with the product previously isolated to give 2-acetylamino-4-trifluoromethyl-5-vinyl-benzoic acid methyl ester (10.0 g, 34.8 mmol, 75%) as a beige solid, m.p. 79-81° C., ESI-MS: m/z 288 [M+H]⁺.

2-Acetylamino-5-formyl-4-trifluoromethyl-benzoic acid methyl ester

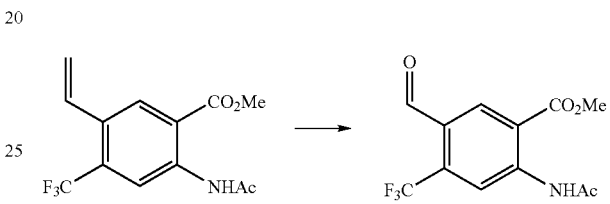

A solution of 2-acetylamino-4-trifluoromethyl-5-vinyl-benzoic acid methyl ester (708 mg, 2.46 mmol) in DCM (70 mL) was cooled to −68° C. and a flow of ozone was passed through the mixture until it turned dark green. A flow of oxygen was then passed through the mixture for 30 min and dimethyl sulfide (360 µL, 4.86 mmol) was added. This mixture was stirred for 30 min at r.t. and triphenylphosphine (327 mg, 1.23 mmol) was added. The solution was allowed to stand for 60 h at r.t. under argon. It was then concentrated in vacuo and the crude product was purified by flash chromatography (silica gel 60, hexanes/EtOAc 100:0→80:20) to afford 2-acetylamino-5-formyl-4-trifluoromethyl-benzoic acid methyl ester (591 mg, 2.04 mmol, 83%) as a beige powder, m.p. 106-108° C., ESI-MS: m/z 290 [M+H]⁺.

2-Acetylamino-5-(1-hydroxy-propyl)-4-trifluoromethyl-benzoic acid methyl ester

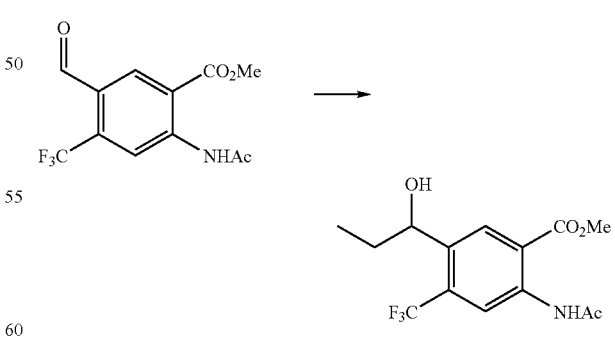

A solution of 2-acetylamino-5-formyl-4-trifluoromethyl-benzoic acid methyl ester (840 mg, 2.90 mmol) in dry diethyl ether (29 mL) was cooled to 0° C. and a solution of ethylmagnesium bromide (1M in THF, 5.8 mL, 5.8 mmol) was added dropwise. The mixture was stirred for 1 h at 0° C. and the reaction was quenched by adding aqueous ammonium chloride solution. This mixture was extracted once with EtOAc and the organic phase was then washed with brine, dried over anhydrous sodium sulfate, filtered and concentrated in vacuo. The crude product was purified by flash chromatography (silica gel 60, hexanes/EtOAc 80:20→70:30) to furnish 2-acetylamino-5-(1-hydroxy-propyl)-4-trifluoromethyl-benzoic acid methyl ester (262 mg, 0.82 mmol, 28%) as a white solid, m.p. 120-122° C., ESI-MS: m/z 320 [M+H]$^+$.

2-Acetylamino-5-propionyl-4-trifluoromethyl-benzoic acid methyl ester

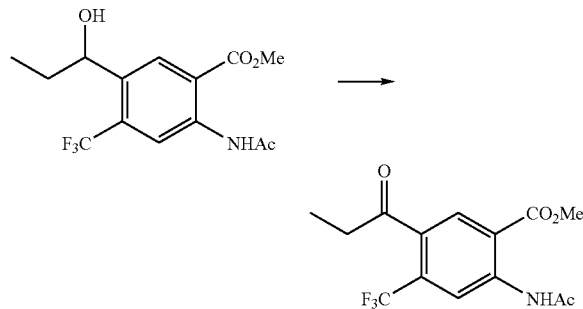

A solution of 2-acetylamino-5-(1-hydroxy-propyl)-4-trifluoromethyl-benzoic acid methyl ester (262 mg, 0.82 mmol) in DCM (1.3 mL) was added to a solution of Dess-Martin periodinane (556 mg, 1.31 mmol) in DCM (2.6 mL) and the mixture was stirred for 1 h at r.t. It was then poured into aqueous sodium thiosulfate and this mixture was extracted with EtOAc. The organic phase was then washed twice with aqueous potassium hydrogencarbonate (pH=8), once with brine, dried over anhydrous sodium sulfate, filtered and concentrated in vacuo to give crude 2-acetylamino-5-propionyl-4-trifluoromethyl-benzoic acid methyl ester as a white solid which was used without further purification in the next step, ESI-MS: m/z 318 [M+H]$^+$.

2-Amino-5-propionyl-4-trifluoromethyl-benzoic acid methyl ester

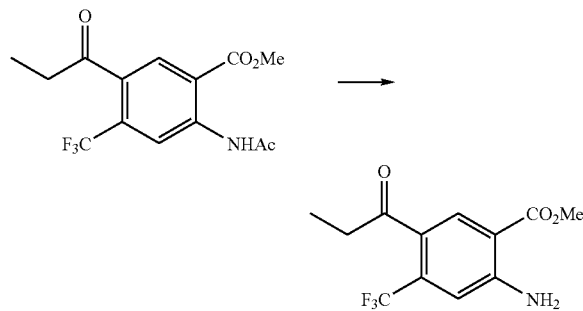

A solution of 2-acetylamino-5-propionyl-4-trifluoromethyl-benzoic acid methyl ester (260 mg, 0.82 mmol) in MeOH (2.6 mL) and water (0.54 mL) was treated with concentrated sulfuric acid (0.26 mL) and the mixture was heated to 60° C. for 1 h. It was then allowed to cool to r.t., and diluted with EtOAc. This mixture was washed once with aqueous sodium hydrogencarbonate (pH=8), once with brine, dried over anhydrous sodium sulfate, filtered and concentrated in vacuo. The crude product was purified by flash chromatography (silica gel 60, hexanes/EtOAc 100:0→80:20) to furnish 2-amino-5-propionyl-4-trifluoromethyl-benzoic acid methyl ester (185 mg, 0.67 mmol, 82%) as a white powder, m.p. 141-144° C., ESI-MS: m/z 276 [M+H]$^+$.

N-(2,4-Dioxo-6-propionyl-7-trifluoromethyl-1,4-dihydro-2H-quinazolin-3-yl)-methanesulfonamide

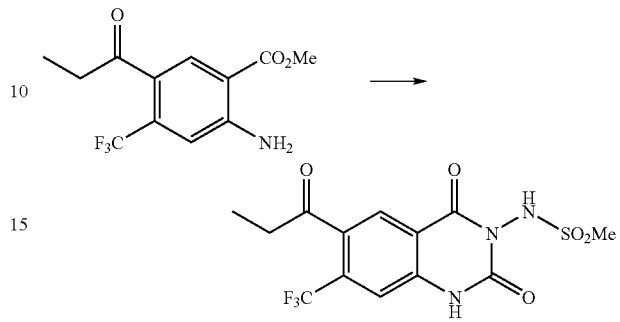

A solution of 2-methyl-5-propionyl-4-trifluoromethyl-benzoic acid methyl ester (180 mg, 0.65 mmol) in THF (2.6 mL) was treated with (CCl$_3$O)$_2$CO (65.3 mg, 0.22 mmol) at r.t. under argon. The mixture was stirred for 15 min and Et$_3$N (91 µL, 0.65 mmol) was added. The suspension was stirred for another 3 h and CH$_3$SO$_2$NHNH$_2$ (73.5 mg, 0.65 mmol) was added. After 20 h, an aqueous solution of sodium hydroxide (1N, 0.87 mL) was added and the yellow suspension was stirred for 4 h at r.t. The pH of the mixture was then adjusted to 4-5 with an aqueous solution of hydrochloric acid (1N), and it was then diluted with EtOAc. The layers were separated and the organic phase was washed once with water, once with brine, dried over anhydrous sodium sulfate, filtered and concentrated in vacuo. The crude product was recrystallized in DCM to give N-(2,4-dioxo-6-propionyl-7-trifluoromethyl-1,4-dihydro-2H-quinazolin-3-yl)-methanesulfonamide (195 mg, 0.51 mmol, 79%) as a white solid, m.p. 234-236° C., ESI-MS: m/z 380 [M+H]$^+$.

Example 7

N-[6-(1-Hydroxy-propyl)-2,4-dioxo-7-trifluoromethyl-1,4-dihydro-2H-quinazolin-3-yl]-methanesulfonamide

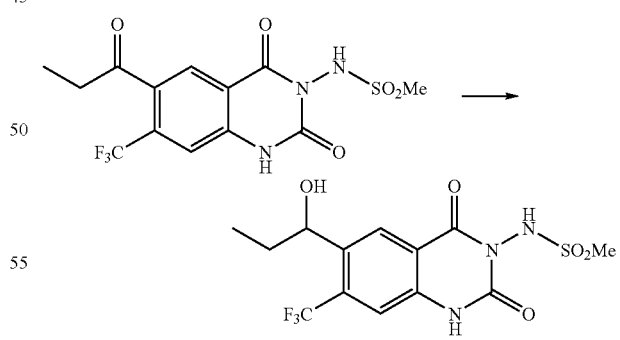

To a solution of N-(2,4-dioxo-6-propionyl-7-trifluoromethyl-1,4-dihydro-2H-quinazolin-3-yl)-methanesulfonamide (50 mg, 0.132 mmol) in THF (1 mL) and MeOH (1 mL) was added sodium borohydride (80 mg, 2.11 mmol). The resultant mixture was stirred for 20 h. After that time, it was then diluted with EtOAc and water and the pH was adjusted to 4-5 with an aqueous hydrochloric acid solution (1N). The organic phase was separated and washed once with brine, dried over anhydrous sodium sulfate, filtered and concentrated in vacuo. Purification of the crude product by flash chromatography (silica gel 60, DCM/MeOH 100:0→90:10) to afford N-[6-(1-hydroxy-propyl)-2,4-dioxo-7-trifluoromethyl-1,4-dihydro-2H-quinazolin-3-yl]-methanesulfonamide (39 mg, 0.102 mmol, 78%) as a white powder, m.p. 219-222° C., $^1$H-NMR (DMSO-d$_6$, 400 MHz) 11.93 (br s, 1H), 10.38 (br s, 1H), 8.33 (s, 1H), 7.50 (s, 1H), 5.63 (m, 1H), 5.27 (m, 1H), 3.17 (s, 3H), 1.60 (m, 2H), 0.93 (m, 3H).

Example 8

N-[2,4-Dioxo-6-(1-propoxy-propyl)-7-trifluoromethyl-1,4-dihydro-2H-quinazolin-3-yl]-methanesulfonamide 2-Amino-5-(1-propoxy-propyl)-4-trifluoromethyl-benzoic acid methyl ester

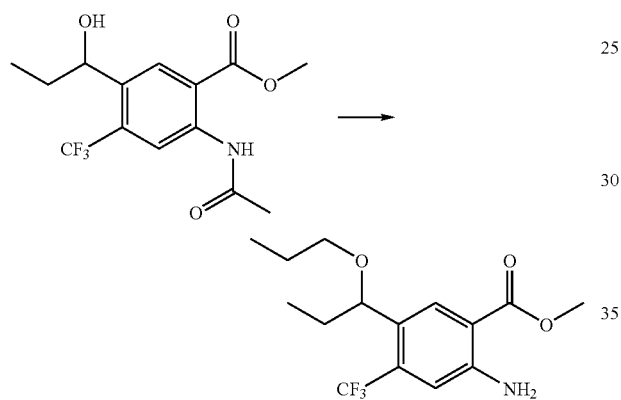

A solution of 2-acetylamino-5-(1-hydroxy-propyl)-4-trifluoromethyl-benzoic acid methyl ester (200 mg, 0.626 mmol) in 1-propanol (2 mL) at r.t. was treated with p-toluenesulfonic acid monohydrate (38 mg, 0.198 mmol) and the reaction was stirred for 10 d at r.t. The reaction mixture was diluted with water and EtOAc and basified to pH 8 with sat. aq KHCO$_3$. The organic phase was washed with brine, dried (Na$_2$SO$_4$), filtered and concentrated in vacuo. The residue was purified by flash chromatography (20 g silica gel, EtOAc/hexanes (0:1→3:7)) to give the title product (88 mg, 44% yield) as light yellow oil. ESI-MS: m/z 320 [M+H]$^+$, m/z 318 [M–H]$^-$.

N-[2,4-Dioxo-6-(1-propoxy-propyl)-7-trifluoromethyl-1,4-dihydro-2H-quinazolin-3-yl]-methanesulfonamide

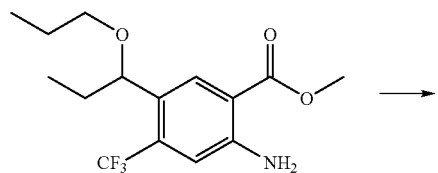

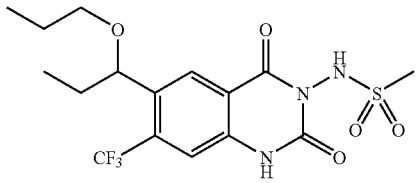

2-Amino-5-(1-propoxy-propyl)-4-trifluoromethyl-benzoic acid methyl ester (86 mg, 0.269 mmol) was converted to N-[2,4-dioxo-6-(1-propoxy-propyl)-7-trifluoromethyl-1,4-dihydro-2H-quinazolin-3-yl]-methanesulfonamide as a colorless foam (95 mg, 83% yield) following the same procedure described for N-[6-(1-methoxy-ethyl)-2,4-dioxo-7-trifluoromethyl-1,4-dihydro-2H-quinazolin-3-yl]-methanesulfonamide. ESI-MS: m/z 424 [M+H]$^+$, m/z 422 [M–H]$^-$.

Example 9

N-[6-(1-isopropoxy-propyl)-2,4-dioxo-7-trifluoromethyl-1,4-dihydro-2H-quinazolin-3-yl]-methanesulfonamide 2-Amino-5-(1-isopropoxy-propyl)-4-trifluoromethyl-benzoic acid methyl ester

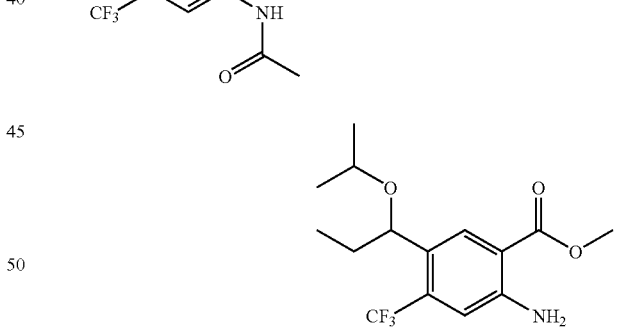

A solution of 2-acetylamino-5-(1-hydroxy-propyl)-4-trifluoromethyl-benzoic acid methyl ester (394 mg, 1.23 mmol) in 2-propanol (2 mL) at room temperature was treated with p-toluenesulfonic acid monohydrate (75.3 mg, 0.39 mmol) and the reaction was stirred for 13 d at r.t. The reaction mixture was diluted with water and EtOAc and basified to pH 8 with sat. aq KHCO$_3$. The organic phase was washed with brine, dried (Na$_2$SO$_4$), filtered and concentrated in vacuo. The residue was purified by flash chromatography (20 g of silica gel, EtOAc/hexanes (0:1→3:7)) to give the title product (48 mg, 12%). as colorless crystals. m.p.: 54-56° C., ESI-MS: m/z 320 [M+H]$^+$.

N-[6-(1-isopropoxy-propyl)-2,4-dioxo-7-trifluoromethyl-1,4-dihydro-2H-quinazolin-3-yl]-methanesulfonamide

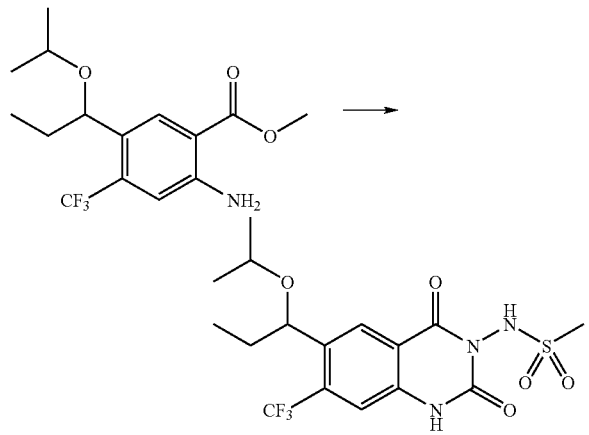

2-Amino-5-(1-isopropoxy-propyl)-4-trifluoromethyl-benzoic acid methyl ester (46 mg, 0.144 mmol) was converted to N-[6-(1-isopropoxy-propyl)-2,4-dioxo-7-trifluoromethyl-1,4-dihydro-2H-quinazolin-3-yl]-methanesulfonamide as a colorless foam (36 mg, 59%) following the same procedure described for N-[6-(1-methoxy-ethyl)-2,4-dioxo-7-trifluoromethyl-1,4-dihydro-2H-quinazolin-3-yl]-methanesulfonamide. ESI-MS: m/z 424 [M+H]$^+$, m/z 422 [M−H]$^−$.

Example 10

N-(6-Butyryl-2,4-dioxo-7-trifluoromethyl-1,4-dihydro-2H-quinazolin-3-yl)-methanesulfonamide 2-Acetylamino-5-(1-hydroxy-butyl)-4-trifluoromethyl-benzoic acid methyl ester

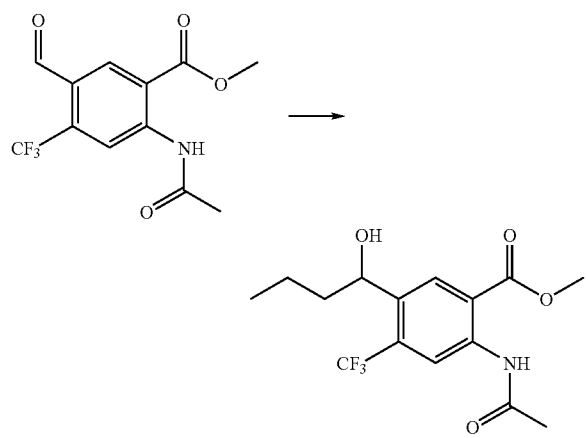

To a solution of 2-acetylamino-5-formyl-4-trifluoromethyl-benzoic acid methyl ester (1.52 g, 5.26 mmol) in absolute Et$_2$O (52 mL), under argon, was added a solution of propylmagnesium chloride (2.0 M in Et$_2$O, 5.3 mL, 11 mmol) over 5 min at 20° C. An immediate crystallisation occurred along with an exotherm. The reaction mixture was cooled to 20° C. using an ice/water bath. The reaction mixture was stirred at r.t. for 1 h then poured onto sat. aq NH$_4$Cl and EtOAc. The pH was adjusted to 7 with sat. aq NH$_4$Cl and the layers were separated. The organic phase was washed with brine, dried (Na$_2$SO$_4$), filtered and concentrated in vacuo. The residue was purified by flash column chromatography (25 g silica gel, hexanes/EtOAc (1:0→7:3)) to give product as colorless crystals (409 mg, 23%). m.p.: 97-101° C., ESI-MS: m/z 334 [M+H]$^+$, m/z 332 [M−H]$^−$.

2-Acetylamino-5-butyryl-4-trifluoromethyl-benzoic acid methyl ester

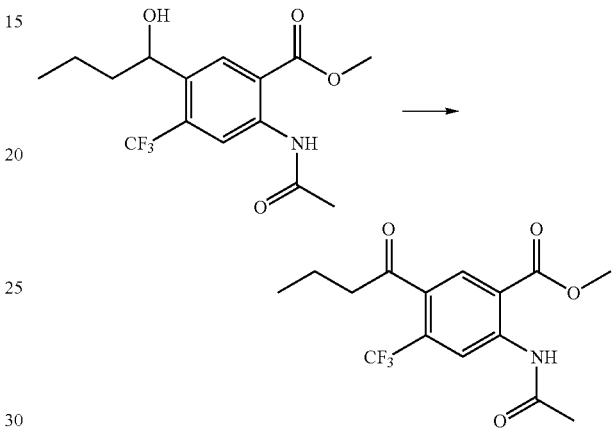

To a solution of Dess-Martin periodinane (514 mg, 1.18 mmol) in DCM (2.5 mL) at r.t. was added 2-acetylamino-5-(1-hydroxy-butyl)-4-trifluoromethyl-benzoic acid methyl ester (245 mg, 0.735 mmol). The reaction was stirred at r.t. for 1 h then diluted with EtOAc and poured onto 1:1 mixture water/sat. aq Na$_2$SO$_3$. The organic phase was washed twice with aq KHCO$_3$, brine, dried (Na$_2$SO$_4$) and filtered. The filtrate was concentrated in vacuo to give the title compound (237 mg, 97% yield) as a beige product. ESI-MS: m/z 332 [M+H]$^+$, m/z 330 [M−H]$^−$.

2-Amino-5-butyryl-4-trifluoromethyl-benzoic acid methyl ester

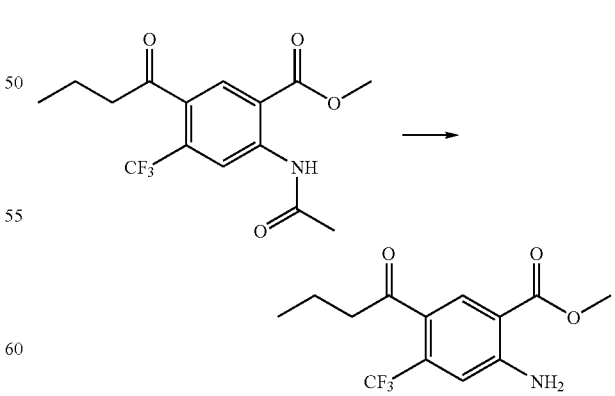

2-Acetylamino-5-butyryl-4-trifluoromethyl-benzoic acid methyl ester (234 mg, 0.706 mmol) was dissolved in MeOH (2.4 mL). Water (500 uL) was added, followed by dropwise addition of concd H$_2$SO$_4$ (254 uL). The reaction mixture was heated to 60° C. for 1 h to give a light yellow suspension. The reaction mixture was diluted with EtOAc, poured onto water/EtOAc and the pH was adjusted to 8 with sat. aq KHCO₃. The organic phase was washed with brine, dried (Na₂SO₄) and filtered. The filtrate was concentrated in vacuo. The obtained residue was purified by flash column chromatography (10 g silica gel, hexanes/EtOAc (1:0→7:3)) to afford the title compound (168 mg, 82%) as a colorless foam. ESI-MS: m/z 290 [M+H]⁺, m/z 288 [M−H]⁻.

N-(6-Butyryl-2,4-dioxo-7-trifluoromethyl-1,4-dihydro-2H-quinazolin-3-yl)-methanesulfonamide

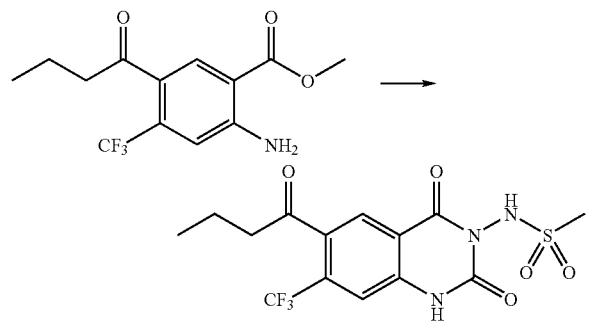

2-Amino-5-butyryl-4-trifluoromethyl-benzoic acid methyl ester (165 mg, 0.570 mmol) was converted to N-(6-butyryl-2,4-dioxo-7-trifluoromethyl-1,4-dihydro-2H-quinazolin-3-yl)-methanesulfonamide as colorless crystals (188 mg, 84% yield) following the same procedure described for N-[6-(1-methoxy-ethyl)-2,4-dioxo-7-trifluoromethyl-1,4-dihydro-2H-quinazolin-3-yl]-methanesulfonamide. m.p.: 236-239° C., ESI-MS: m/z 394 [M+H]⁺, m/z 392 [M−H]⁻.

Example 11

N-[6-(1-Hydroxy-butyl)-2,4-dioxo-7-trifluoromethyl-1,4-dihydro-2H-quinazolin-3-yl]-methanesulfonamide

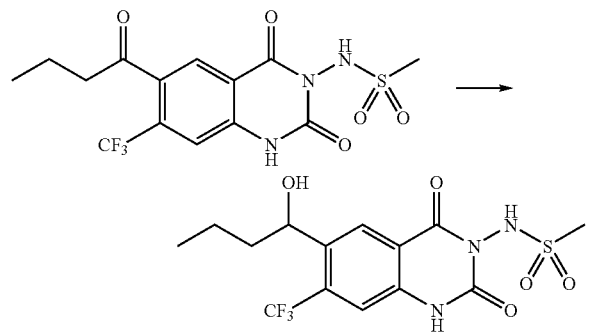

To a solution of N-(6-butyryl-2,4-dioxo-7-trifluoromethyl-1,4-dihydro-2H-quinazolin-3-yl)-methanesulfonamide (131 mg, 0.333 mmol) in THF (3 mL) and MeOH (3 mL) was added NaBH₄ (131 mg, 3.32 mmol) portionwise over 10 min at r.t. The reaction mixture was stirred at r.t. for 18 h, poured onto a mixture of water and EtOAc then adjusted to pH 3-4 by addition of 1N aq HCl. The organic phase was washed twice with brine, dried (Na₂SO₄), filtered and the filtrate was concentrated in vacuo. The residue was purified by flash column chromatography (10 g silica gel, DCM/MeOH (1:0→9:1) to afford the title compound (94 mg, 71%) as colorless crystals. m.p.: 223-226° C., ESI-MS: m/z 396 [M+H]⁺, m/z 394 [M−H]⁻.

Example 12

N-[2,4-Dioxo-6-(tetrahydro-furan-2-yl)-7-trifluoromethyl-1,4-dihydro-2H-quinazolin-3-yl]-methanesulfonamide Tributyl-(4,5-dihydro-furan-2-yl)-stannane

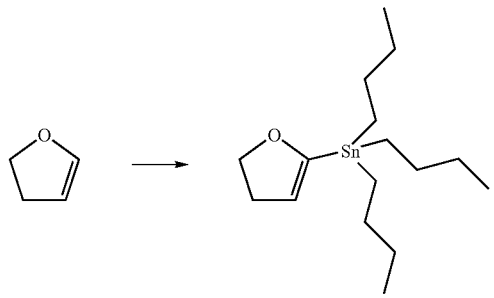

A solution of 2,3-dihydrofuran (10.7 mL, 141 mmol) in anhyd THF (80 mL) was cooled to −60° C. A solution of t-BuLi (1.7 M in pentane, 100 mL, 170 mmol) was added dropwise. The yellow solution was stirred at −60° C. for 10 min then at 0° C. for 50 min. The reaction mixture was cooled down to −60° C. and Bu₃SnCl (52.7 mL, 185 mmol) was added dropwise to give a colorless solution that was stirred at 0° C. for 90 min. Sat. aq NH₄Cl was added dropwise and the reaction mixture was extracted with Et₂O. The aqueous phase was further extracted with Et₂O and the combined organic phases were dried (Na₂SO₄), filtered and concentrated in vacuo. The crude residue was distilled under 24 mbar vacuum at 150° C. and the residue was distilled again under 22 mbar vacuum at 154° C. to yield the title compound (55 g, 100%) as a light yellow liquid.

2-Acetylamino-5-(4,5-dihydro-furan-2-yl)-4-trifluoromethyl-benzoic acid methyl ester

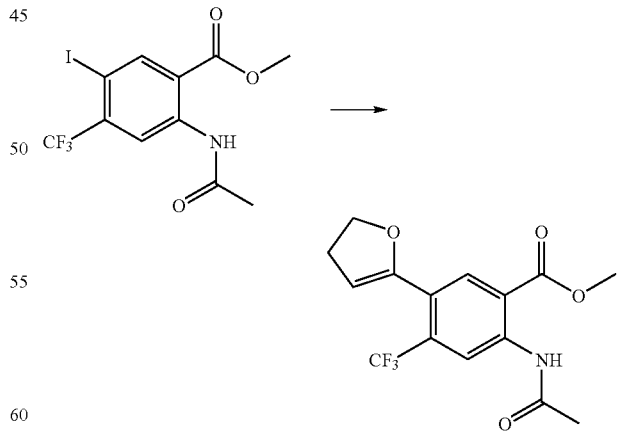

To a solution of 2-acetylamino-5-iodo-4-trifluoromethyl-benzoic acid methyl ester (10 g, 25.8 mmol) in dioxane were added tributyl-(4,5-dihydro-furan-2-yl)-stannane (13.9 g, 38.7 mmol), (Ph₃P)₄Pd then Et₃N (4.52 mL, 32.3 mmol). The reaction mixture was heated at reflux for 18 h to give a brown suspension that was allowed to cool to r.t. The reaction mixture was filtered through a sintered funnel and the filtrate was concentrated under in vacuo. The residue was purified by flash column chromatography (silica gel, 1:4 EtOAc/hexanes) to give the title compound (7.3 g, 86%) as beige crystals, m.p.: 120-125° C., API-ES: m/z 330 [M+H]+

2-Acetylamino-5-(tetrahydro-furan-2-yl)-4-trifluoromethyl-benzoic acid methyl ester

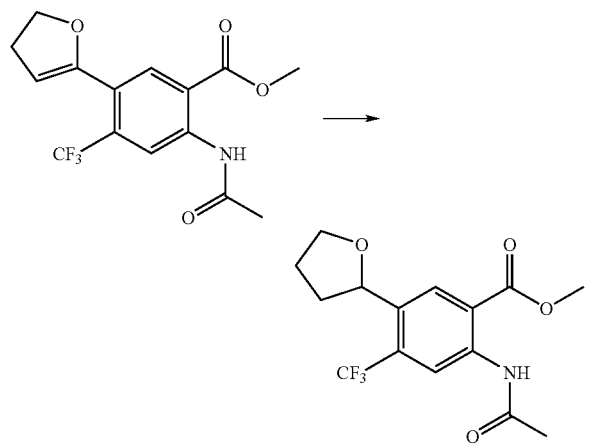

A solution of 2-acetylamino-5-(4,5-dihydro-furan-2-yl)-4-trifluoromethyl-benzoic acid methyl ester (13.2 g, 40.1 mmol) in dry THF (250 mL) was shaken under H₂ (5 bars) at r.t. in the presence of Raney nickel. (6.0 g, B113W, Degussa) for 46 h. The reaction mixture was then filtered through a sintered funnel and the filtrate was concentrated in vacuo to give the title product (7.5 g, 100%) as a yellow oil. API-ES: m/z 332 [M+H]+.

2-Amino-5-(tetrahydro-furan-2-yl)-4-trifluoromethyl-benzoic acid methyl ester

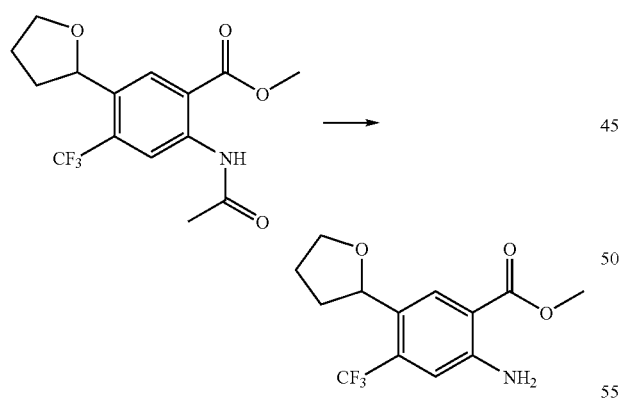

A solution of 2-acetylamino-5-(tetrahydro-furan-2-yl)-4-trifluoromethyl-benzoic acid methyl ester (8.25 g, 24.9 mmol) in MeOH (100 mL) and water (10 mL) was cooled to 0° C. Concd H₂SO₄ (6.88 mL, 125 mmol) was added dropwise. The solution was refluxed for 45 min, cooled to r.t., diluted with ice/water and extracted with EtOAc. The organic phase was dried (Na₂SO₄), filtered and concentrated in vacuo. The residue was purified by flash column chromatography (silica gel, 1:4 EtOAc/hexanes) to give the title product (5.06 g, 68%) as colorless crystals. m.p.: 131-136° C., API-ES: m/z 290 [M+H]+.

N-[2,4-Dioxo-6-(tetrahydro-furan-2-yl)-7-trifluoromethyl-1,4-dihydro-2H-quinazolin-3-yl]-methanesulfonamide

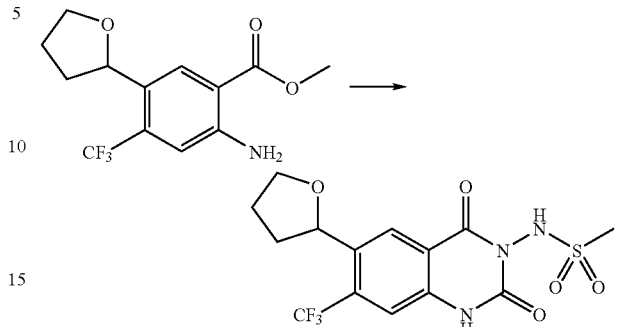

A solution of 2-amino-5-(tetrahydro-furan-2-yl)-4-trifluoromethyl-benzoic acid methyl ester (2 g, 6.91 mmol) in anhydrous THF (30 mL) was treated with (CCl₃O)₂CO (684 mg, 2.28 mmol). The resultant yellow solution was stirred at r.t. for 15 min and Et₃N (967 uL, 6.91 mmol) was then added. A thick suspension developed that was diluted with anhydrous THF (20 mL). The suspension was stirred for 3 h at r.t. CH₃SO₂NHNH₂ (777 mg, 6.91 mmol) was added and the reaction was stirred for 1 h. The reaction mixture was then treated with aq NaOH (1 N, 14 mL, 14 mmol) and the resultant orange-red solution was stirred for 1 h at r.t. The reaction mixture was acidified to pH 3-4 with aq HCl (4 N) and extracted with EtOAc. The organic phase was dried (Na₂SO₄), filtered and concentrated in vacuo. The residue was taken into DCM and triturated. The colorless suspension was collected by vacuum filtration and further dried in vacuo at 60° C. to give the title product (2.36 g, 87%) as colorless crystals. m.p.: 254-257° C., API-ES: m/z 394 [M+H].

The enantiomers were separated by chiral chromatography. HPLC analyses were performed using a system comprising a Merck-Hitaschi L-6200A pump coupled to a Merck-Hitaschi L-4500 Diode Array detector and a Merck-Hitaschi Lahrom D-7000 spectrometer, a 50 µL loop injection valve and a Chiralpak AD-H column (250×4.6 mm) running a mixture of hexane/ethanol/methanol 80:10:10. The solvent flow was 1.0 mL/min. Enantiomer 1: r.t.=12.13 min, Enantiomer 2: r.t.=15.84 min.

The following products were synthesized by analogous procedures.

Example 13

N-[7-Difluoromethyl-6-(1-ethoxy-ethyl)-2,4-dioxo-1,4-dihydro-2H-quinazolin-3-yl]-methanesulfonamide

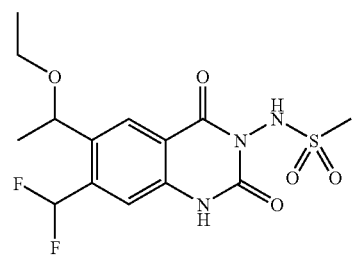

ESI-MS: m/z 378 [M+H]+, ¹H-NMR (CDCl₃, 400 MHz) 9.42 (s, 1H), 8.29 (s, 1H), 7.62 (s, 1H), 7.43 (s, 1H), 7.15 (t,

J=54.7 Hz, 1H), 4.77 (q, J=6.4 Hz, 1H), 3.33-3.48 (m, 2H), 3.39 (s, 3H), 1.53 (d, J=6.6 Hz, 3H), 1.23 (t, J=6.9 Hz, 3H).

Example 14

N-[2,4-Dioxo-6-(1-propoxy-ethyl)-7-trifluoromethyl-1,4-dihydro-2H-quinazolin-3-yl]-methanesulfonamide

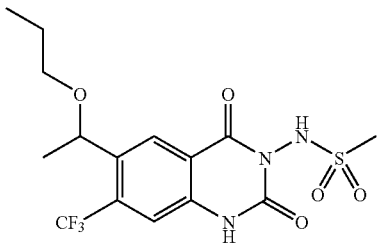

m.p.: 95-105° C., API-ES: m/z 410 [M+H]⁺.

Example 15

N-[6-(1-Butoxy-ethyl)-2,4-dioxo-7-trifluoromethyl-1,4-dihydro-2H-quinazolin-3-yl]-methanesulfonamide

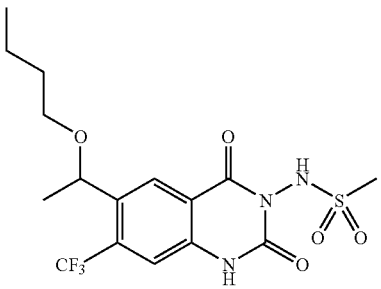

m.p.: 84-90° C., API-ES: m/z 424 [M+H]⁺.

Example 16

N-[6-(1-Isobutoxy-ethyl)-2,4-dioxo-7-trifluoromethyl-1,4-dihydro-2H-quinazolin-3-yl]-methanesulfonamide

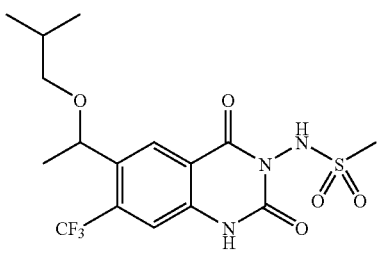

API-ES: m/z 424 [M+H]⁺, ¹H-NMR (DMSO-d₆, 400 MHz) 11.98 (s, 1H), 10.39 (s, 1H), 8.26 (s, 1H), 7.53 (s, 1H), 4.70 (m, 1H), 3.18 (s, 3H), 3.12 (m, 1H), 2.91 (m, 1H), 1.77 (m, 1H), 1.39 (d, J=6.3 Hz, 3H), 0.85 (t, J=5.9 Hz, 6H).

Example 17

N-[6-(1-Cyclopentyloxy-ethyl)-2,4-dioxo-7-trifluoromethyl-1,4-dihydro-2H-quinazolin-3-yl]-methanesulfonamide

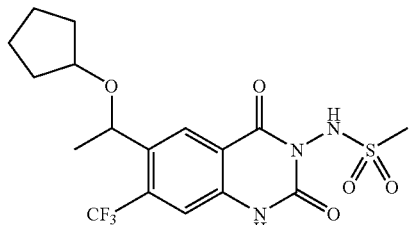

m.p.: 188-192° C., API-ES: m/z 436 [M+H]⁺.

Example 18

N-[6-(1-Ethoxy-propyl)-2,4-dioxo-7-trifluoromethyl-1,4-dihydro-2H-quinazolin-3-yl]-methanesulfonamide

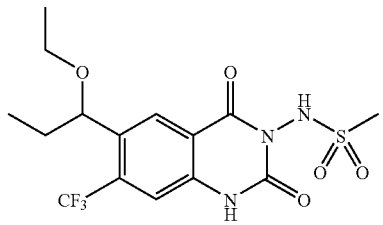

ESI-MS: m/z 410 [M+H]⁺, ¹H-NMR (DMSO-d₆, 400 MHz) 11.98 (s, 1H), 10.38 (s, 1H), 8.20 (s, 1H), 7.54 (s, 1H), 4.48 (br s, 1H), 3.23-3.31 (m, 2H), 3.19 (s, 3H), 1.56-1.72 (m, 2H), 1.10 (t, J=7 Hz, 3H), 0.92 (t, J=7 Hz, 3H).

Example 19

N-[6-(1-methoxy-butyl)-2,4-dioxo-7-trifluoromethyl-1,4-dihydro-2H-quinazolin-3-yl]-methanesulfonamide

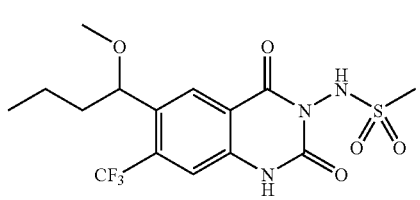

ESI-MS: m/z 410 [M+H]⁺, ¹H-NMR (CDCl₃, 400 MHz) 9.48 (s, 1H), 8.50 (s, 1H), 7.65 (s, 1H), 7.45 (s, 1H), 4.57 (m, 1H), 3.39 (s, 3H), 3.22 (s, 3H), 1.39-1.76 (m, 4H), 0.96 (t, J=8 Hz, 3H).

Example 20

N-[2,4-Dioxo-6-(2,2,2,-trifluoro-acetyl)-7-trifluoromethyl-1,4-dihydro-2H-quinazolin-3-yl]-methanesulfonamide

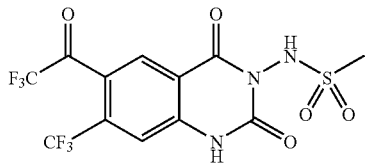

m.p.: 262-265° C., ESI-MS: m/z 418 [M−H]⁻.

Example 21

N-(6-Isobutyryl-2,4-dioxo-7-trifluoromethyl-1,4-dihydro-2H-quinazolin-3-yl)-methanesulfonamide

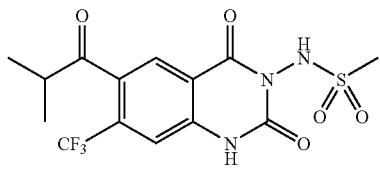

m.p.: 228-231° C., ESI-MS: m/z 394 [M+H]⁺.

Example 22

N-[6-(1-Hydroxy-2-methyl-propyl)-2,4-dioxo-7-trifluoromethyl-1,4-dihydro-2H-quinazolin-3-yl]-methanesulfonamide

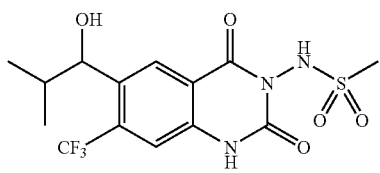

m.p.: 232-235° C., ESI-MS: m/z 396 [M+H]⁺.

Example 23

N-[6-(1-Methoxy-2-methyl-propyl)-2,4-dioxo-7-trifluoromethyl-1,4-dihydro-2H-quinazolin-3-yl]-methanesulfonamide

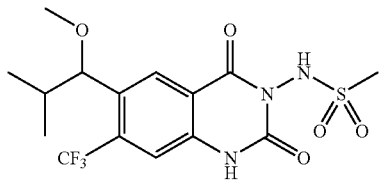

m.p.: 227-229° C., ESI-MS: m/z 410 [M+H]⁺.

Example 24

N-[2,4-Dioxo-6-(tetrahydro-pyran-2-yl)-7-trifluoromethyl-1,4-dihydro-2H-quinazolin-3-yl]-methanesulfonamide

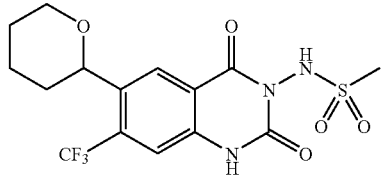

m.p.: 275-280° C., ESI-MS: m/z 408 [M+H]⁺.

Example 25

N-[6-(3-Hydroxy-propyl)-2,4-dioxo-7-trifluoromethyl-1,4-dihydro-2H-quinazolin-3-yl]-methanesulfonamide 2-Amino-5-[3-(tetrahydro-pyran-2-yloxy)-prop-1-ynyl]-4-trifluoromethyl-benzoic acid methyl ester

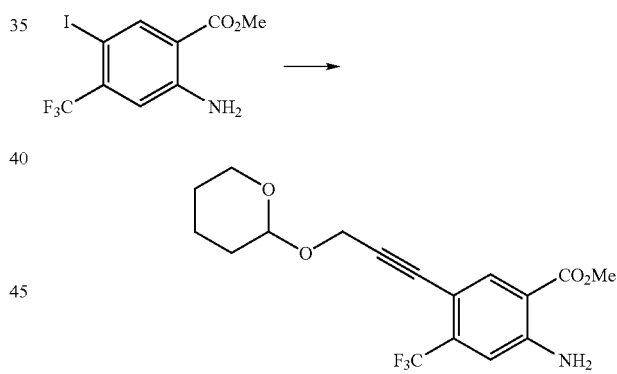

A solution of 2-amino-5-iodo-4-trifluoromethyl-benzoic acid methyl ester (2.0 g, 5.80 mmol), tetrahydro-2-(2-propynyloxy)-2H-pyran (2.44 mL, 17.4 mmol), copper iodide (55.0 mg, 0.29 mmol) and bis(triphenylphosphine)palladium (II) dichloride (407 mg, 0.58 mmol) in dioxane (15 mL) and Et₃N (15 mL) was heated to reflux for 16 h under nitrogen. The mixture was then allowed to cool to r.t., filtered and the filtrate was diluted with AcOEt. This mixture was washed once with water. The organic phase was then dried over anhydrous sodium sulfate, filtered and concentrated in vacuo. The crude product was purified by flash chromatography (silica gel 60, hexanes/EtOAc 5:1) to give an orange oil, which was recrystallized in hexanes to provide 2-amino-5-[3-(tetrahydro-pyran-2-yloxy)-prop-1-ynyl]-4-trifluoromethyl-benzoic acid methyl ester (1.50 g, 4.20 mmol, 72%) as a pale brown powder, m.p. 88° C., ESI-MS: m/z 358 [M+H]⁺.

2-Amino-5-[3-(tetrahydro-pyran-2-yloxy)-propyl]-4-trifluoromethyl-benzoic acid methyl ester

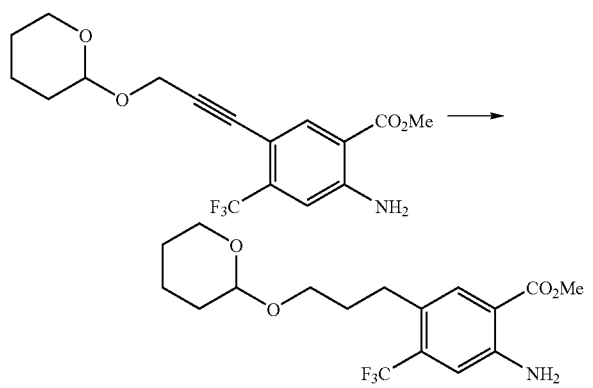

A suspension of 2-amino-5-[3-(tetrahydro-pyran-2-yloxy)-prop-1-ynyl]-4-trifluoromethyl-benzoic acid methyl ester (2.20 g, 6.16 mmol) and palladium on carbon (250 mg, 10%) in THF (15 mL) was stirred at r.t. for 30 min under hydrogen (5 bars). The mixture was then filtered and concentrated in vacuo. The crude product was purified by flash chromatography (silica gel 60, hexanes/EtOAc 5:1) to afford 2-amino-5-[3-(tetrahydro-pyran-2-yloxy)-propyl]-4-trifluoromethyl-benzoic acid methyl ester (1.99 g, 5.51 mmol, 89%) as a colorless oil, ESI-MS: m/z 384 [M+Na]$^+$, rt 6.20 min).

N-[6-(3-Hydroxy-propyl)-2,4-dioxo-7-trifluoromethyl-1,4-dihydro-2H-quinazolin-3-yl]-methanesulfonamide

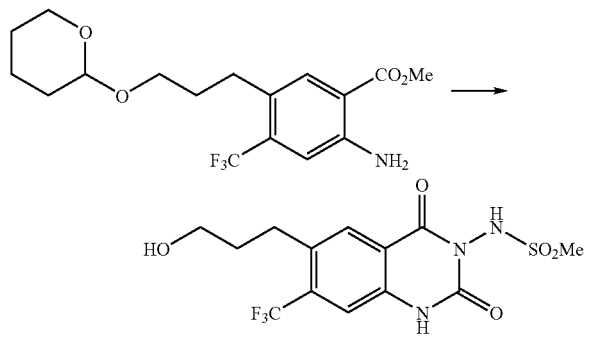

A solution of 2-amino-5-[3-(tetrahydro-pyran-2-yloxy)-propyl]-4-trifluoromethyl-benzoic acid methyl ester (1.00 g, 2.77 mmol) in THF (10 mL) was treated with (CCl$_3$O)$_2$CO (279 mg, 0.94 mmol) and the mixture was stirred at r.t. for 15 min under nitrogen. To this solution was added dropwise Et$_3$N (0.39 mL, 2.77 mmol) and the mixture was further diluted with THF (20 mL), and stirred for another 3 h at r.t. The mixture was then treated with CH$_3$SO$_2$NHNH$_2$ (305 mg, 2.77 mmol) and stirred for 16 h at r.t. Aqueous sodium hydroxide (1M, 10 mL, 10 mmol) was subsequently added and the solution was stirred for 3 h at r.t. The mixture was acidified with aqueous hydrochloric acid (4N) until pH=3-4, and then diluted with EtOAc. The layers were separated and the organic phase was washed once with water and then dried over anhydrous sodium sulfate, filtered and concentrated in vacuo. The white solid obtained was taken up in EtOAc and stirred at r.t. for 1 h. The suspension was filtered and the white solid was dried. This solid was then taken up in THF and this solution was acidified with aqueous hydrochloric acid (4M).

The mixture was concentrated in vacuo to give a white solid, which was recrystallized in EtOAc. This solid was then purified by flash chromatography (silica gel 60, hexanes/EtOAc 2:1) to provide N-[6-(3-hydroxy-propyl)-2,4-dioxo-7-trifluoromethyl-1,4-dihydro-2H-quinazolin-3-yl]-methanesulfonamide (100 mg, 0.26 mmol, 9%) as a white powder, m.p. 243-247° C., ESI-MS: m/z 382 [M+H]+, 1H-NMR (DMSO-d6, 400 MHz) 8.04 (s, 1H), 7.53 (s, 1H), 4.60 (m, 1H), 3.48 (m, 2H), 3.18 (s, 3H), 2.83, (m, 2H), 1.74 (m, 2H).

Example 26

N-[6-(1-Hydroxy-3-methoxy-propyl)-2,4-dioxo-7-trifluoromethyl-1,4-dihydro-2H-quinazolin-3-yl]-methanesulfonamide

2-Amino-5-(3-methoxy-prop-1-ynyl)-4-trifluoromethyl-benzoic acid methyl ester

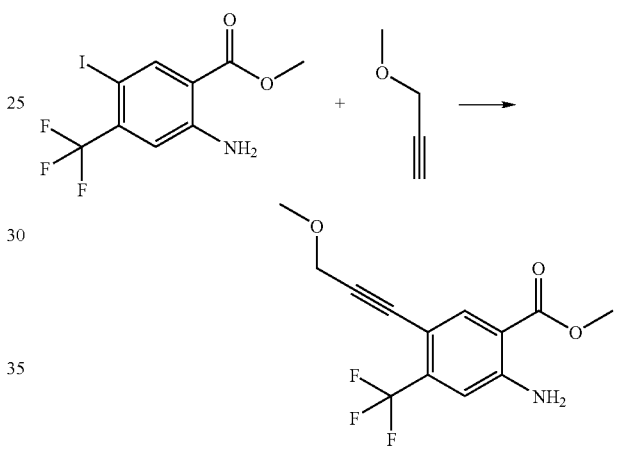

A solution of 2-amino-5-iodo-4-trifluoromethyl-benzoic acid methyl ester (3.0 g, 8.69 mmol) and Et$_3$N (22 mL) in dry dioxane (22 mL) was purged with argon during 15 min. (Ph$_3$P)$_2$PdCl$_2$ (305 mg, 0.435 mmol), CuI (166 mg) and 3-methoxy-propyne (2.20 mL, 26.08 mmol) were added and the mixture was heated to 55° C. for 100 min. After cooling, the reaction mixture was filtered and the filtrate diluted with EtOAc, washed with water and brine and dried (Na$_2$SO$_4$). Evaporation of the volatiles gave a residue which was purified by MPLC (silica gel, cyclohexane/EtOAc 4:1) to yield the title compound (1.94 g, 78%) as a beige solid, m.p. 107-111° C.

2-Amino-5-(3-methoxy-propionyl)-4-trifluoromethyl-benzoic acid methyl ester

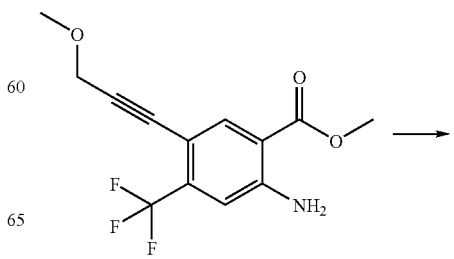

-continued

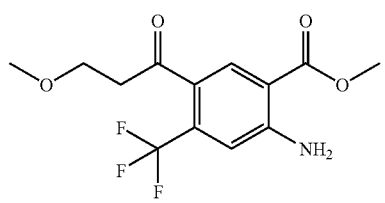

To a solution of 2-amino-5-(3-methoxy-prop-1-ynyl)-4-trifluoromethyl-benzoic acid methyl ester (1.19 g, 4.15 mmol) in MeOH (100 mL) were added successively a solution of sodium sulfide (0.1 M, 12.4 mL, 1.24 mmol), followed by 10% aq HCl-solution (3.70 mL, 12.45 mmol). The reaction mixture was heated to 75° C. for 29 h, cooled and filtered over Celite. Evaporation of the filtrate gave a yellow oil which was purified by MPLC (oRP-C18 column (particle size 5-21 μM) with 1:1 CH$_3$CN/water. The fractions containing the product were combined, the acetonitrile was distilled off and the residual water phase was extracted with EtOAc. The organic phase was washed with brine and dried (Na$_2$SO$_4$) and the solvent was removed in vacuo to provide the title compound (0.167 g, 13%) as a white powder, mp 89-91° C. IR (FTIR microscope in transmission): 1696 m, 1674 s cm$^{-1}$.

2-Isocyanato-5-(3-methoxy-propionyl)-4-trifluoromethyl-benzoic acid methyl ester

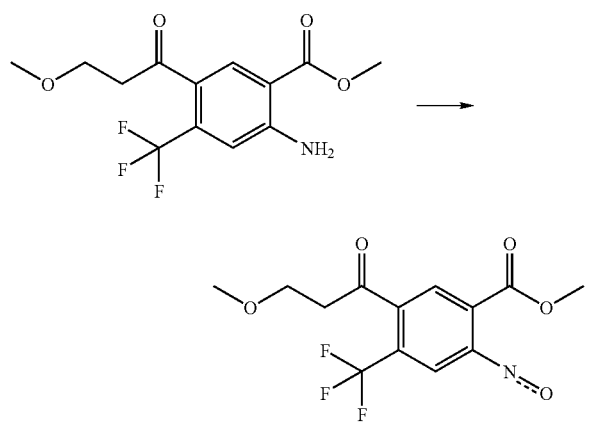

In a dried flask purged with argon, a solution of 2-amino-5-(3-methoxy-propionyl)-4-trifluoromethyl-benzoic acid methyl ester (154 mg, 0.504 mmol) in dry toluene (4.7 mL) was cooled to 0° C. and treated dropwise with a solution of phosgene in toluene (20%, 4.9 mL). A slow stream of phosgene was introduced and the reaction mixture was heated to reflux for 2 h. Argon was blown through the yellow solution and the solvent distilled off leaving the title compound (168 mg, 100%) as an oily residue, sufficiently pure for the next step. $^1$H-NMR (CDCl$_3$, 360 MHz): 8.20 (s, 1H), 7.45 (s, 1H), 4.00 (s, 3H), 3.75 (t, J=8 Hz, 2H), 3.35 (s, 31H), 3.10 (t, J=8 Hz, 2H).

N-[6-(3-Methoxy-propionyl)-2,4-dioxo-7-trifluoromethyl-1,4-dihydro-2H-quinazolin-3-yl]-methanesulfonamide

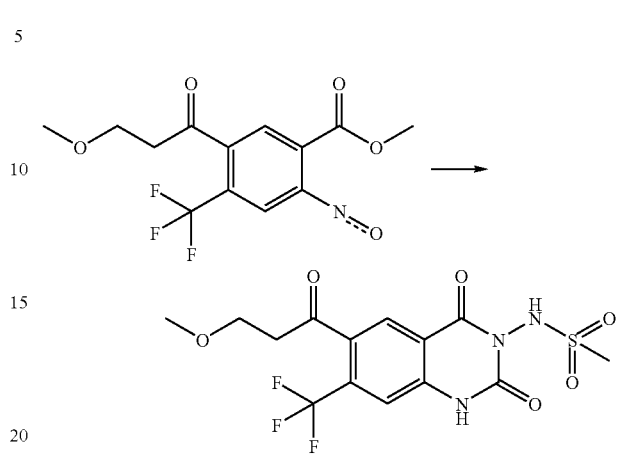

A solution of CH$_3$SO$_2$NHNH$_2$ (61 mg, 0.555 mmol) in THF (1 mL) was slowly added dropwise to a solution of 2-isocyanato-5-(3-methoxy-propionyl)-4-trifluoromethyl-benzoic acid methyl ester (167 mg, 0.505 mmol) in dry THF (2.6 mL). After stirring the mixture at r.t. for 105 min, aq NaOH (1 M, 0.53 mL) was added and stirring was continued for 60 min. The reaction mixture was concentrated and the residue was taken in EtOAc and washed with water. The aqueous phase was extracted with EtOAc (3×), all organic phases are combined, washed with brine and dried (Na$_2$SO$_4$) and the solvent was evaporated to dryness yielding the title compound (194 mg, 94%) as a white powder, mp 186-191° C.

N-[6-(1-Hydroxy-3-methoxy-propyl)-2,4-dioxo-7-trifluoromethyl-1,4-dihydro-2H-quinazolin-3-yl]-methanesulfonamide

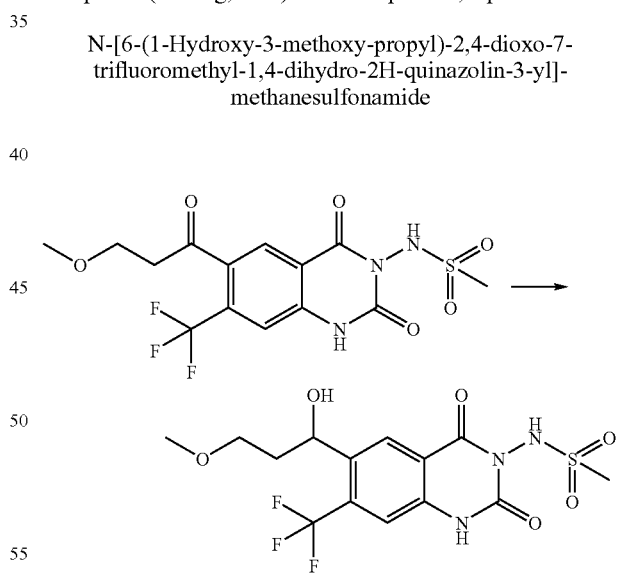

A solution of N-[6-(3-methoxy-propionyl)-2,4-dioxo-7-trifluoromethyl-1,4-dihydro-2H-quinazolin-3-yl]-methanesulfonamide (118 mg, 0.288 mmol) in MeOH (3 mL) at r.t. was treated with NaBH$_4$ (77 mg, 2.03 mmol), added portionwise over a period of 3 h. After disappearance of the starting material, the reaction mixture was acidified with 2M aq HCl and diluted with water. The aqueous phase was extracted with EtOAc (2×), the organic phases were combined, washed with brine and dried (Na$_2$SO$_4$) and evaporated. The white powder obtained was purified by MPLC(RP-C18 column (particle size 5-21 μM) with CH₃CN/water 1:2. The fractions containing the product were combined, the acetonitrile is distilled off and the residual water phase was extracted with EtOAc. The organic phase was washed with brine and dried (Na$_2$SO$_4$) and the solvent was removed in vacuo to provide the title compound (112 mg, 94%) as a white powder, mp 180-184° C. $^1$H-NMR (DMSO-d6, 400 MHz): 11.80 (br s, 1H), 10.35 (br s, 1H), 8.33 (s, 1H), 7.45 (s, 1H), 5.65 (d, J=6 Hz, 1H), 4.98-4.92 (m, 1H), 3.60-3.52 (m, 1H), 3.42-3.35 (m, 1H), 3.20 (s, 3H), 3.15 (s, 3H), 1.86-1.67 (m, 2H).

HPLC Method Used for the Following Examples, Unless Otherwise Noted in the Example:

HPLC analyses were performed using a system comprising Gilson 331 pumps coupled to a Gilson U/VIS 152 detector and a Finnigan AQA spectrometer (ESI), a 50 μL loop injection valve and a Waters XTerra MS C18 3.5 μm 4.6×50 mm column running a gradient from 5% to 90% acetonitrile containing 0.05% TFA as follows: 0 to 1 min: 5% CH$_3$CN; 1 to 6 min: from 5 to 90% CH$_3$CN; from 6 to 8 min: 90% CH$_3$CN. The solvent flow was 1.5 mL/min. Retention times (rt) were recorded for all new compounds.

For examples 51-54, the HPLC analyses were performed using the following system and method: LC-MS system: Capillary LC Agilent connected to Finnigan LTQ linear ion trap; Column: Xterra MS C18 1×50 mm 2.5 μm kept at 50 C; Flow: 35 uL/min; Mobile Phase: A: water+3 mM ammonium acetate+0.05% formic acid; B: acetonitrile+0.05% formic acid; Gradient: 0 to 100% B in 9 min, 1 min at 100% B, back to 100% A, 5 min re-equilibration at 100% A.

Example 27

N-[7-Trifluoromethyl-6-(2-methyl-2H-pyrazol-3-yl)-2,4-dioxo-1,4-dihydro-2H-quinazolin-3-yl]-methanesulfonamide The 1-methyl-5-tributylstannanyl-1H-pyrazole required for the coupling reaction described below was prepared according to the following procedure:

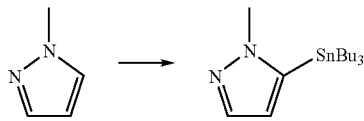

To a solution of diisopropylamine (4.2 mL, 1.2 equiv) in THF (70 mL) at −78° C. was added n-BuLi (18.6 mL, 1.6 M in hexanes, 1.2 equiv). The mixture was stirred for 15 min prior to the addition of a solution of methylpyrrazole (2 mL, 24.36 mmol) in THF. After 30 min, Bu$_3$SnCl (7.9 mL, 1.2 equiv) was added and the mixture was then allowed to reach r.t. over 30 min and was stirred overnight at this temperature. The mixture was poured into water (250 mL) and then extracted twice with EtOAc. The organic phases were combined, washed with saturated NaHCO$_3$ and dried (Na$_2$SO$_4$). Concentration in vacuo and drying afforded a yellow oil (9.1 g) which was used without further purification.

(*Yagi and coll. Heterocycles* 1997, 45(8), 1643-1646.)

2-Amino-4-trifluoromethyl-5-(2-methyl-2H-pyrazol-3-yl)-benzoic acid methyl ester

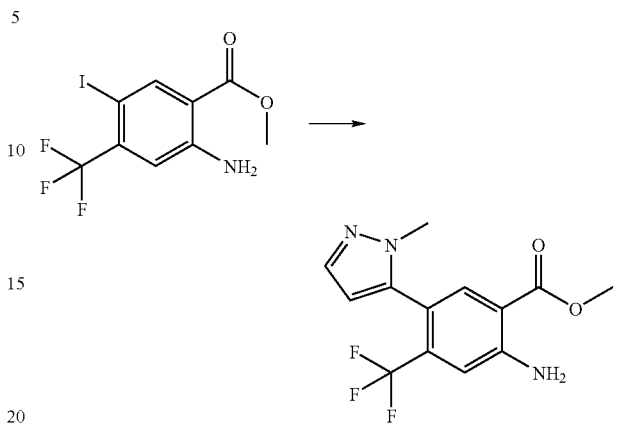

2-Amino-5-iodo-4-trifluoromethyl-benzoic acid methyl ester (7 g, 20.29 mmol) and 1-methyl-5-tributylstannanyl-1H-pyrazole (9.03 g, 1.2 equiv) were weighed in air and added in a flame-dried flask. Bis(triphenylphosphine)palladium (II) dichloride (2.18 g, 0.15 equiv) and dioxane (100 mL) were added and the mixture was stirred for 18 h at 100° C. The mixture was evaporated to dryness. The crude product was purified by flash chromatography (hexanes to EtOAc/hexanes (4:6)) to provide 2-amino-4-trifluoromethyl-5-(2-methyl-2H-pyrazol-3-yl)-benzoic acid methyl ester (4.6 g, 76%) as an orange solid. (ESI-MS: m/z 300.3 [M+H]$^+$, rt 5.15 min).

N-[7-Trifluoromethyl-6-(2-methyl-2H-pyrazol-3-yl)-2,4-dioxo-1,4-dihydro-2H-quinazolin-3-yl]-methanesulfonamide

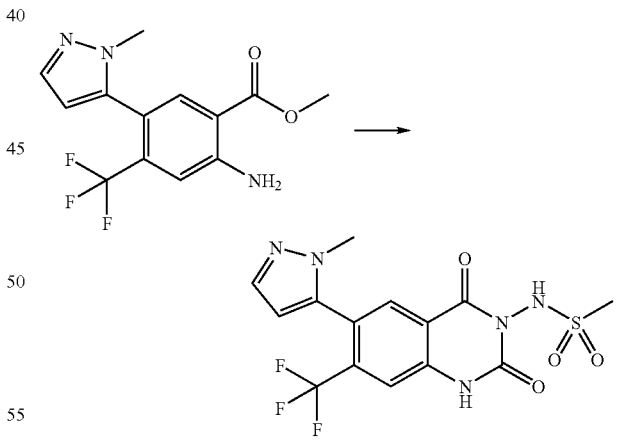

2-Amino-4-trifluoromethyl-5-(2-methyl-2H-pyrazol-3-yl)-benzoic acid methyl ester (4.6 g, 15.4 mmol) in DCM (60 mL) and Et$_3$N (10.7 mL, 5 equiv), (CCl$_3$O)$_2$CO (3.9 g, 0.85 equiv) was added portionwise. The mixture was stirred at r.t. for 2 h before concentration in vacuo to dryness. The resulting paste was dissolved in THF (60 mL) and CH$_3$SO$_2$NHNH$_2$ (2.02 g, 1.2 equiv) was added. The mixture was stirred at r.t. for 1 h. An aqueous NaOH solution (1N, 15.4 mL, 1 equiv) was added and the mixture was stirred for 1 h at r.t. The mixture was then poured into water and the aqueous phase was extracted with AcOEt. The aqueous layer was acidified to pH 3 by addition of 2N aq HCl and then extracted with AcOEt. The organic phases were combined, dried (Na$_2$SO$_4$) and concentrated in vacuo to afford a crude solid (7 g). The crude product was purified by flash chromatography (EtOAc/hexanes (1:9) to EtOAc). The fractions containing the final compound were concentrated in vacuo in order to afford an off-white solid. This solid was sonicated in DCM and the resulting precipitate was filtered off and dried in vacuo to afford the title compound (3.0 g, 48%) as an off-white solid. (ESI-MS: m/z 404.3 [M+H]$^+$, rt 4.20 min). $^1$H-NMR (DMSO-d$_6$, 400 MHz) 11.7 (s, 1H), 10.45 (s, 1H), 8.0 (s, 1H), 7.70 (s, 1H), 7.55 (s, 1H), 6.35 (s, 1H), 3.60 (s, 3H), 3.20 (s, 3H).

Example 28

N-[6-(1-Methyl-1H-[1,2,3]triazol-4-yl)-2,4-dioxo-7-trifluoromethyl-1,4-dihydro-2H-quinazolin-3-yl]-methanesulfonamide 2-Amino-4-trifluoromethyl-5-trimethylsilanylethynyl-benzoic acid methyl ester

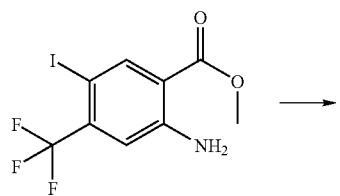

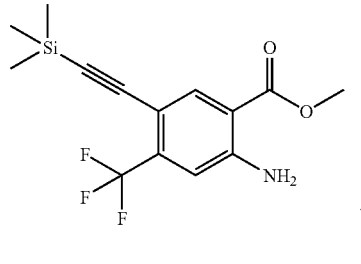

To a solution of 2-amino-5-iodo-4-trifluoromethyl-benzoic acid methyl ester (2.0 g, 5.80 mmol) in DCM (60 mL) were added Et$_3$N (10 mL), trimethylsilyl ethynyl (1.2 mL, 1.5 equiv), Cl$_2$Pd(PPh$_3$)$_2$ (391 mg, 0.1 equiv) and CuI (112 mg, 0.1 equiv). The resulting mixture was stirred for 2 h at r.t. The solution was concentrated in vacuo to afford a brown oil. The crude product was purified by flash chromatography (hexanes to EtOAc/hexanes (25:75)) to provide 2-amino-4-trifluoromethyl-5-trimethylsilanylethynyl-benzoic acid methyl ester (1.65 g, 90%) as an orange solid. (ESI-MS: m/z 357.4 [M+H]$^+$, rt 6.77 min).

2-Amino-5-ethynyl-4-trifluoromethyl-benzoic acid methyl ester

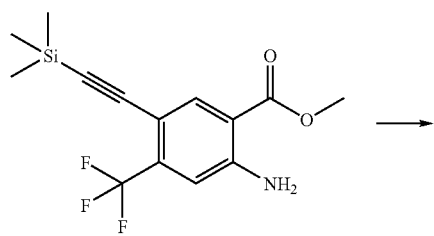

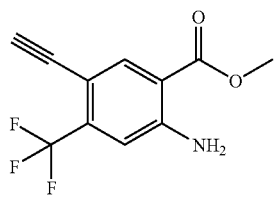

To a solution of 2-amino-4-trifluoromethyl-5-trimethylsilanylethynyl-benzoic acid methyl ester (1.65 g, 5.23 mmol) in THF (20 mL) was added a solution of TBAF in THF (1M, 10.5 mL, 2 equiv) and the resulting solution was stirred at r.t. for 10 min. The solvent was removed in vacuo and the crude oil was dissolved in AcOEt. The organic phase was washed with saturated NH$_4$Cl and water, dried (Na2SO4) and concentrated in vacuo to afford a dark red oil. The crude product was purified by flash chromatography (EtOAc/hexanes (1:3)) to furnish 2-amino-5-ethynyl-4-trifluoromethyl-benzoic acid methyl ester (750 mg, 55%) as an orange oil. (ESI-MS: m/z 285.3 [M+CH$_3$CN+H]$^+$, rt 5.60 min).

2-Amino-4-trifluoromethyl-5-(1-trimethylsilanylmethyl-1H-[1,2,3]triazol-4-yl)-benzoic acid methyl ester

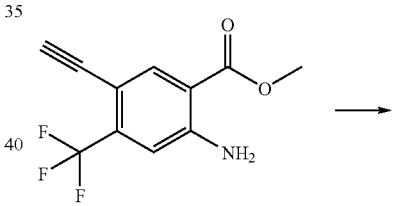

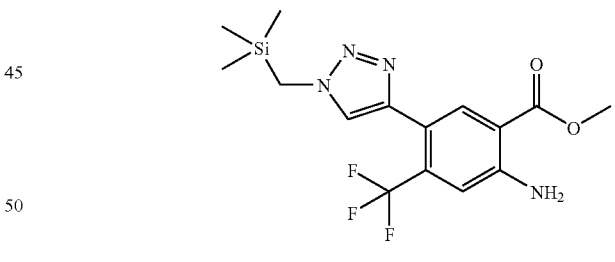

To a solution of 2-amino-5-ethynyl-4-trifluoromethyl-benzoic acid methyl ester (300 mg, 1.23 mmol) in t-BuOH/H$_2$O (1/1, 10 mL) were added portions of sodium ascorbate (3×80 mg), of CuSO$_4$ (3×10 mg) and trimethylsilyl azide (3×240 mg, 3×1.5 equiv) every 0.5 d. The resulting mixture was stirred at r.t. for 2 d. The mixture was diluted with water and then extracted with AcOEt. The organic phase was dried (Na$_2$SO$_4$) and concentrated in vacuo to afford 2-amino-4-trifluoromethyl-5-(1-trimethylsilanylmethyl-1H-[1,2,3]triazol-4-yl)-benzoic acid methyl ester (420 mg, 91%) as a brown pasty solid which was used in the next step without further purification. (ESI-MS: m/z 415.6 [M+CH$_3$CN+H]$^+$, rt 5.80 min).

2-Amino-5-(1-methyl-1H-[1,2,3]triazol-4-yl)-4-trifluoromethyl-benzoic acid methyl ester

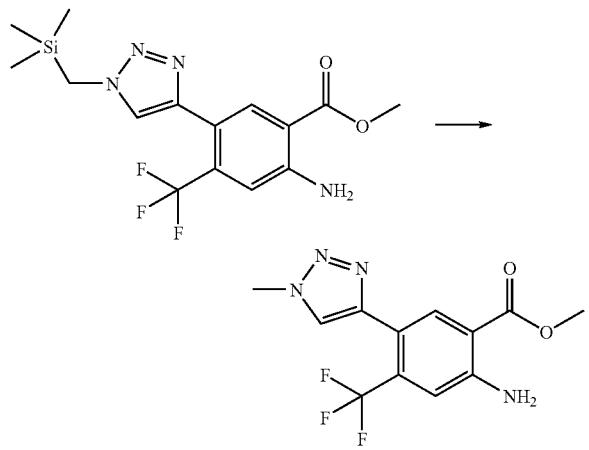

2-Amino-4-trifluoromethyl-5-(1-trimethylsilanylmethyl-1H-[1,2,3]triazol-4-yl)-benzoic acid methyl ester (420 mg, 1.12 mmol) was dissolved in THF (10 mL). After addition of a solution of TBAF in THF (1M, 2.25 mL, 2 equiv), the mixture was stirred at r.t. for 30 min. The solvent was removed in vacuo and the residue was taken in AcOEt. The organic phase was washed with water, dried (Na$_2$SO$_4$) and concentrated in vacuo to give a brown oil. The crude product was purified by flash chromatography (EtOAc/hexanes (1:9) to EtOAc/hexanes (6:4)) to yield 2-amino-5-(1-methyl-1H-[1,2,3]triazol-4-yl)-4-trifluoromethyl-benzoic acid methyl ester (240 mg, 71%) as a yellow solid. (ESI-MS: m/z 301.3 [M+H]$^+$, rt 4.62 min).

2-(4-Chloro-phenoxycarbonylamino)-5-(1-methyl-1H-[1,2,3]triazol-4-yl)-4-trifluoromethyl-benzoic acid methyl ester

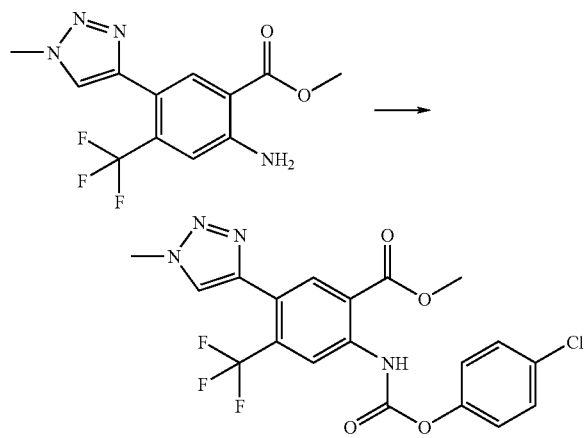

2-Amino-5-(1-methyl-1H-[1,2,3]triazol-4-yl)-4-trifluoromethyl-benzoic acid methyl ester (240 mg, 0.8 mmol) was dissolved in dioxane and chlorophenyl chloroformate (222 µL, 2 equiv) was added. The mixture was stirred for 1 h at 100° C. The solvent was removed in vacuo and hexanes (15 mL) was added. After sonication, the precipitate was removed by filtration, washed with hexanes and dried in high-vacuo to afford the title compound (260 mg, 71.5%) as an off-white solid. (ESI-MS: m/z 455.5 [M+H]$^+$, rt 6.26 min).

N-[6-(1-Methyl-1H-[1,2,3]triazol-4-yl)-2,4-dioxo-7-trifluoromethyl-1,4-dihydro-2H-quinazolin-3-yl]-methanesulfonamide

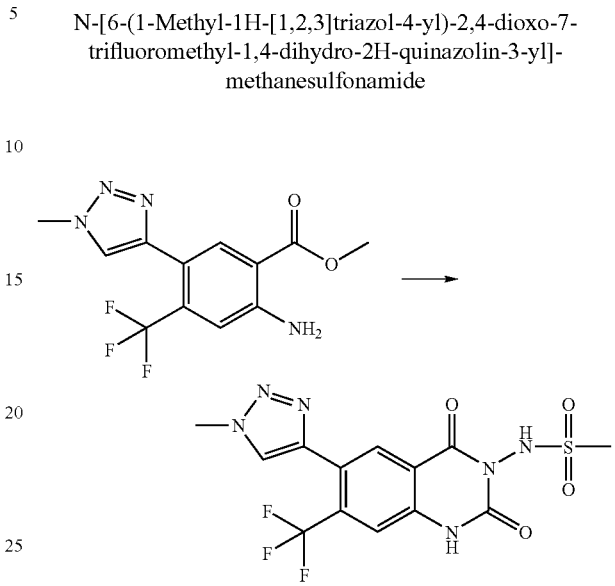

2-(4-Chloro-phenoxycarbonylamino)-5-(1-methyl-1H-[1,2,3]triazol-4-yl)-4-trifluoromethyl-benzoic acid methyl ester (260 mg, 0.57 mmol) was dissolved in dioxane (15 mL). After addition of i-Pr$_2$NEt (294 µL, 3 equiv) and CH$_3$SO$_2$NHNH$_2$ (126 mg, 2 equiv), the solution was stirred for 2 h at 100° C. The solvent was removed in vacuo and the crude product was dried in vacuo for 2 h. DCM (5 mL) was then added and, after sonication, the solution was put in the freezer for 16 h. The resulting solid was filtered off, washed with DCM and dried to afford N-[6-(1-methyl-1H-[1,2,3]triazol-4-yl)-2,4-dioxo-7-trifluoromethyl-1,4-dihydro-2H-quinazolin-3-yl]-methanesulfonamide (180 mg, 78%) as an off-white solid. (ESI-MS: m/z 446.5 [M+CH$_3$CN+H]$^+$, rt 3.71 min). $^1$H-NMR (DMSO-d$_6$, 400 MHz) 8.33 (s, 1H), 8.28 (s, 1H), 7.64 (s, 1H), 4.13 (s, 3H), 3.16 (s, 3H).

Example 29

N-[6-(5-Methyl-2H-pyrazol-3-yl)-2,4-dioxo-7-trifluoromethyl-1,4-dihydro-2H-quinazolin-3-yl]-methanesulfonamide Synthesis of 3-Methyl-5-tributylstannanyl-1-(2-trimethylsilanylmethoxy-ethyl)-1H-pyrazole 3-Methyl-1-(2-trimethylsilanylmethoxy-ethyl)-1H-pyrazole and 5-Methyl-1-(2-trimethylsilanylmethoxy-ethyl)-1H-pyrazole

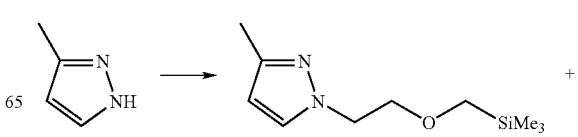

-continued

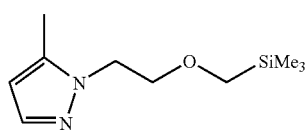

To a suspension of NaH (60% in mineral oil, 1.31 g, 1 equiv) in THF (50 mL), 3-methylpyrazole (2.64 mL, 32.8 mmol) was added dropwise. After 1 h, SEM-Cl (5.81 mL, 1 equiv) was added and the mixture was stirred at 0° C. for 30 min and at r.t for 2 h. Water was added and the aqueous phase was then extracted with AcOEt (3 times). The organic phases were combined, washed with brine, dried (Na$_2$SO$_4$) and concentrated in vacuo. The crude product was purified by flash chromatography (hexanes to EtOAc/hexanes (25/75)) to provide a mixture of 3-methyl-1-(2-trimethylsilanylmethoxy-ethyl)-11H-pyrazole and 5-methyl-1-(2-trimethylsilanyl-methoxy-ethyl)-1H-pyrazole (1:1 NMR ratio) (5.32 g, 75%) as a colorless syrup. (TLC rf 0.55 in EtOAc/hexanes 1:4)

3-Methyl-5-tributylstannanyl-1-(2-trimethylsilanyl-methoxy-ethyl)-11H-pyrazole

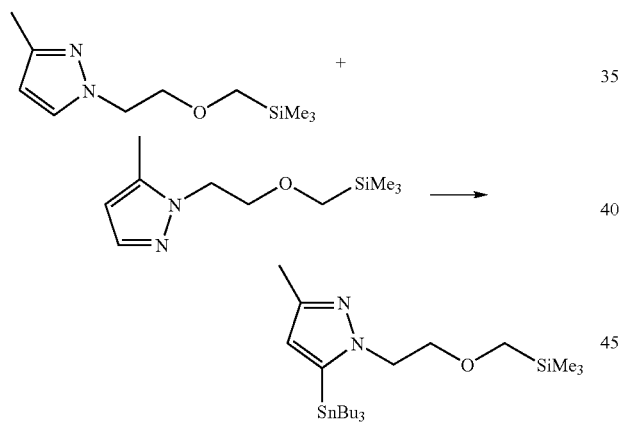

To a solution containing a 1:1 mixture of 3-methyl-1-(2-trimethylsilanylmethoxy-ethyl)-1H-pyrazole and 5-methyl-1-(2-trimethylsilanylmethoxy-ethyl)-1H-pyrazole (1.5 g, 7.06 mmol) in THF (20 mL) at −78° C. was added dropwise n-BuLi (1.6M in hexanes, 4.4 mL, 1 equiv) while keeping the temperature below −70° C. The mixture was then stirred 30 min at −78° C. prior to the addition of tributyltin chloride (1.9 mL, 1 equiv) (the temperature was maintained below −70° C.). The mixture was stirred at −78° C. for 30 min and for 2 h at r.t. Hexanes was added to the mixture and the insoluble material was removed by filtration. Concentration of the solution in vacuo gave a colorless syrup. The crude product was purified by flash chromatography (hexanes to EtOAc/hexanes (20/80)) to provide 3-methyl-5-tributylstannanyl-1-(2-trimethylsilanylmethoxy-ethyl)-1H-pyrazole (847 mg, 24%) as a colorless syrup. (TLC rf 0.33 in EtOAc/hexanes 5:95).

2-Amino-5-[5-methyl-2-(2-trimethylsilanylmethoxy-ethyl)-2H-pyrazol-3-yl]-4-trifluoromethyl-benzoic acid methyl ester

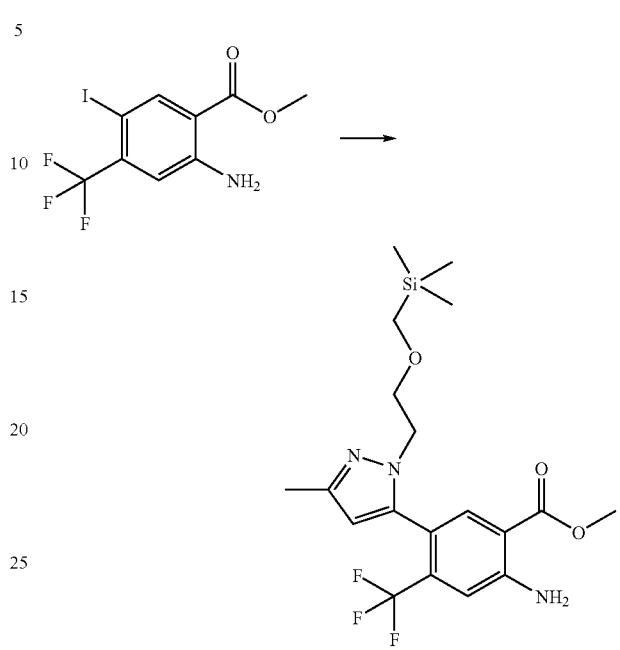

2-Amino-5-iodo-4-trifluoromethyl-benzoic acid methyl ester (583 mg, 1.69 mmol) and 3-methyl-5-tributylstannanyl-1-(2-trimethylsilanylmethoxy-ethyl)-1H-pyrazole (847 mg, 1 equiv) were weighed in air and added to a flame-dried flask. Bistriphenylphosphinedichloropalladium (119 mg, 0.1 equiv) was added. Dioxane (15 mL) was added and the mixture was stirred for 18 h at 90° C. The mixture was evaporated to dryness. The crude product was purified by flash chromatography (hexanes to EtOAc/hexanes (1:4)) to furnish 2-amino-5-[5-methyl-2-(2-trimethylsilanylmethoxy-ethyl)-2H-pyrazol-3-yl]-4-trifluoromethyl-benzoic acid methyl ester (426 mg, 59%) as a yellow paste (ESI-MS: m/z 430.5 [M+H]$^+$, rt 6.54 min).

N-{6-[5-Methyl-2-(2-trimethylsilanylmethoxy-ethyl)-2H-pyrazol-3-yl]-2,4-dioxo-7-trifluoromethyl-1,4-dihydro-2H-quinazolin-3-yl}-methanesulfonamide

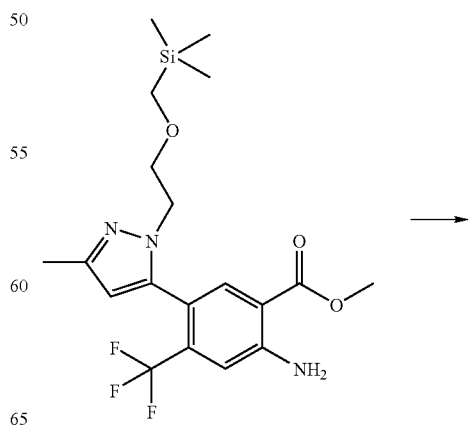

-continued

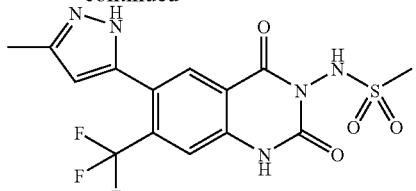

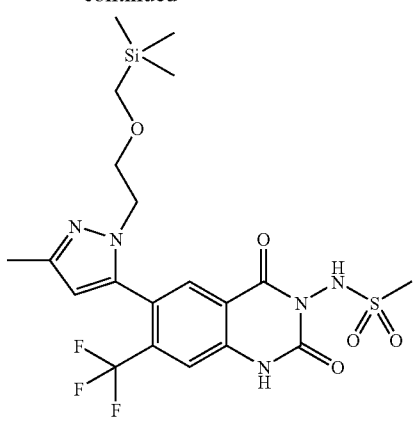

To a solution of 2-amino-5-[5-methyl-2-(2-trimethylsilanylmethoxy-ethyl)-2H-pyrazol-3-yl]-4-trifluoromethyl-benzoic acid methyl ester (426 mg, 0.99 mmol) in DCM (10 mL) containing Et$_3$N (0.55 mL, 4 equiv) was added (CCl$_3$O)$_2$CO (147 mg, 0.5 equiv) portionwise. The mixture was stirred at r.t. for 2 h and then concentrated in vacuo to dryness. The resulting paste was dissolved in THF (10 mL) and CH$_3$SO$_2$NHNH$_2$ (109 mg, 1 equiv) was added. After stirring the mixture at r.t. for 1 h, an aqueous solution of NaOH (1N, 1 mL, 1 equiv) was added. The mixture was stirred for 2 h at r.t. Then, the mixture was poured into water and the aqueous phase was extracted with AcOEt (3 times). The organic phases were combined, dried (Na$_2$SO$_4$) and concentrated in vacuo to afford a crude solid. The crude product was purified by flash chromatography (hexanes to EtOAc/hexanes (3:1)) to provide N-{6-[5-methyl-2-(2-trimethylsilanylmethoxy-ethyl)-2H-pyrazol-3-yl]-2,4-dioxo-7-trifluoromethyl-1,4-dihydro-2H-quinazolin-3-yl}-methanesulfonamide (140 mg, 26%) as a yellow paste. (ESI-MS: m/z 534.6 [M+H]$^+$, rt 5.69 min).

N-[6-(5-Methyl-2H-pyrazol-3-yl)-2,4-dioxo-7-trifluoromethyl-1,4-dihydro-2H-quinazolin-3-yl]-methanesulfonamide

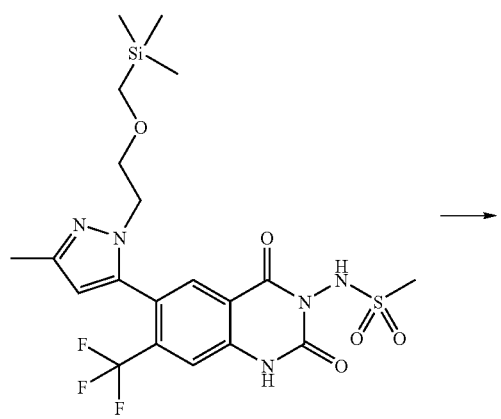

To a solution of N-{6-[5-methyl-2-(2-trimethylsilanylmethoxy-ethyl)-2H-pyrazol-3-yl]-2,4-dioxo-7-trifluoromethyl-1,4-dihydro-2H-quinazolin-3-yl}-methanesulfonamide (140 mg, 0.26 mmol) in dioxane (5 mL) was added a solution of HCl in EtOH (1N, 0.6 mL, 2 equiv). The solution was stirred at 60° C. for 4 h. The solvent was removed in vacuo and the resulting paste was sonicated in 5 mL of DCM. The solid was filtered off, washed with DCM and dried in vacuo to afford N-[6-(5-methyl-2H-pyrazol-3-yl)-2,4-dioxo-7-trifluoromethyl-1,4-dihydro-2H-quinazolin-3-yl]-methanesulfonamide (59 mg, 56%) as a white solid. (ESI-MS: m/z 445.4 [M+CH$_3$CN+H]$^+$, rt 4.16 min)). $^1$H-NMR (DMSO-d$_6$, 400 MHz) 12.0 (s, 1H), 10.36 (s, 1H), 8.13 (s, 1H), 7.62 (s, 1H), 6.22 (s, 1H), 3.15 (s, 3H), 2.28 (s, 3H).

Example 30

N-[6-(2,5-Dimethyl-2H-pyrazol-3-yl)-2,4-dioxo-7-trifluoromethyl-1,4-dihydro-2H-quinazolin-3-yl]-methanesulfonamide Synthesis of 1,3-dimethyl-5-tributylstannanyl-1H-pyrazole 1,3-Dimethyl-1H-pyrazole+1,5-Dimethyl-1H-pyrazole (Butler, D. E.; Alexander, S. M. J. Org. Chem. 1972, 37(2), 215-220)

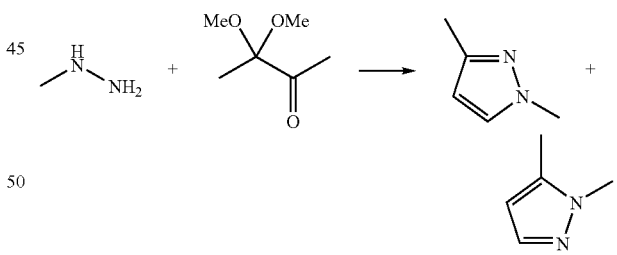

Methylhydrazine (4.25 mL, 80 mmol) was added to 4,4-dimethoxy-2-butanone (10.63 mL, 80 mmol) with keeping the temperature below 25° C. and the mixture was stirred at r.t. for 16 h. The mixture was poured in aq HCl (6N, 16 mL, 1.2 equiv) with stirring. The MeOH was removed in vacuo and then 50% aqueous NaOH was added until the pH was basic. The mixture was extracted with diethyl ether (3 times). The organic phases were combined, dried (Na$_2$SO$_4$) and concentrated in vacuo to afford a mixture of 1,3-dimethyl-1H-pyrazole and 1,5-dimethyl-1H-pyrazole (4:1 NMR ratio) (7.32 g, 95%) as a yellow syrup which was used in the next step without further purification.

1,3-Dimethyl-5-tributylstannanyl-1H-pyrazole

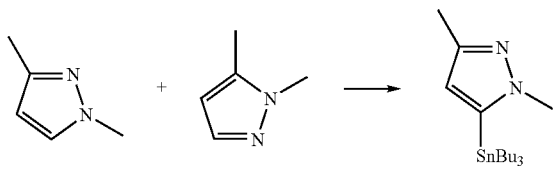

To a solution of LDA (prepared from diisopropylamine (3.6 mL, 1.1 equiv) and n-BuLi (1.6M in hexanes, 14.3 mL, 1.1 equiv) in THF (80 mL) at −78° C. was added dropwise a solution containing a 1:1 mixture of 1,3-dimethyl-1H-pyrazole and 1,5-dimethyl-1H-pyrazole (2 g, 1 equiv) in THF (5 mL) with keeping the temperature below −70° C. At the end of the addition, the mixture was stirred for 30 min at −78° C. before addition of tributyltin chloride (6.16 mL, 1.1 equiv) with keeping the temperature below −70° C. The mixture was then stirred at −78° C. for 30 min and at r.t. for 2 h. The mixture was poured into water and then extracted with AcOEt (3 times). The organic phases were combined, dried ($Na_2SO_4$) and concentrated in vacuo to give a yellow paste. The crude product was purified by flash chromatography (hexanes to EtOAc/hexanes (40:60)) to yield 1,3-dimethyl-5-tributylstannanyl-1H-pyrazole (2.88 g, 36%) as a colorless syrup. (TLC rf 0.46 in EtOAc/hexanes 20:80).

2-Amino-5-(2,5-dimethyl-2H-pyrazol-3-yl)-4-trifluoromethyl-benzoic acid methyl ester

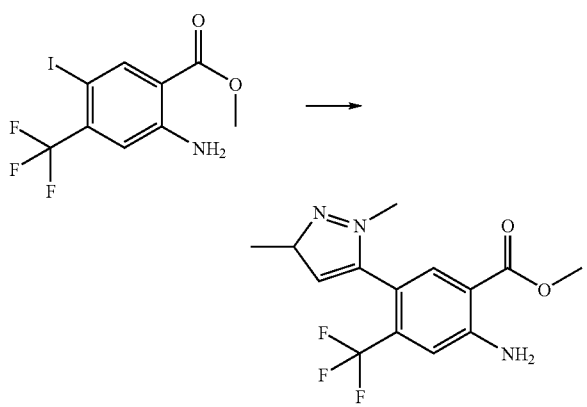

A mixture containing 2-amino-5-iodo-4-trifluoromethyl-benzoic acid methyl ester (1.0 g, 2.9 mmol), 1,3-dimethyl-5-tributylstannanyl-1H-pyrazole (1.34, 1.2 equiv) and bistriphenylphosphinedichloropalladium (207 mg, 0.1 equiv) in dioxane (15 mL) was stirred for 18 h at 80° C.

Bistriphenylphosphinedichloropalladium (0.1 equiv) and another portion of the stannyl derivative (0.4 equiv) were added and the mixture was stirred for 24 h at 80° C. The mixture was evaporated to dryness. The crude product was purified by flash chromatography (hexanes to EtOAc/hexanes (1:1)) to provide 2-amino-5-(2,5-dimethyl-2H-pyrazol-3-yl)-4-trifluoromethyl-benzoic acid methyl ester (651 mg, 72%) as a yellow paste. (ESI-MS: m/z 314.2 [M+H]$^+$, rt 5.12 min).

N-[6-(2,5-Dimethyl-2H-pyrazol-3-yl)-2,4-dioxo-7-trifluoromethyl-1,4-dihydro-2H-quinazolin-3-yl]-methanesulfonamide

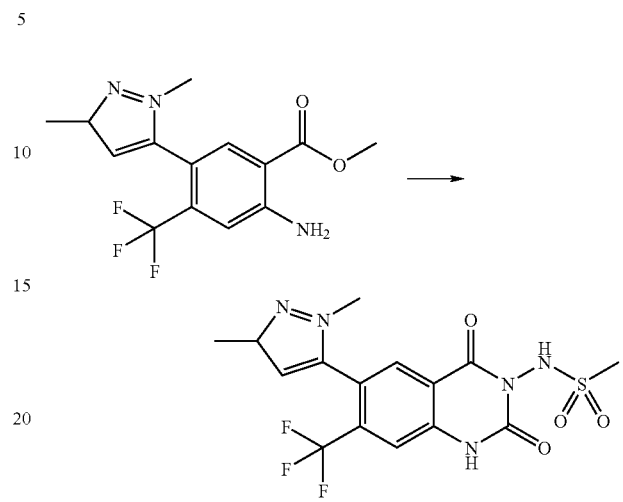

To a solution of 2-amino-5-(2,5-dimethyl-2H-pyrazol-3-yl)-4-trifluoromethyl-benzoic acid methyl ester (610 mg, 1.95 mmol) in DCM (20 mL) containing $Et_3N$ (1.1 mL, 4 equiv) was added $(CCl_3O)_2CO$ (294 mg, 0.5 equiv) portionwise. The mixture was stirred at r.t. for 2 h and was the solvent was removed in vacuo. The resulting paste was dissolved in THF (20 mL) and $CH_3SO_2NHNH_2$ (214 mg, 1 equiv) was added. The mixture was stirred at r.t. for 1 h and an aqueous solution of NaOH (1N, 1.95 mL, 1 equiv) was added. The mixture was stirred at r.t. for 2 h. The mixture was then poured into water and the aqueous phase was extracted with AcOEt. The aqueous layer was acidified to pH 3 by addition of 2N aq HCl and then extracted with AcOEt. The organic phases were combined, dried ($Na_2SO_4$) and concentrated in vacuo to afford a brown syrup. The crude product was purified by flash chromatography (EtOAc/hexanes (25:75) to EtOAc) to furnish N-[6-(2,5-dimethyl-2H-pyrazol-3-yl)-2,4-dioxo-7-trifluoromethyl-1,4-dihydro-2H-quinazolin-3-yl]-methanesulfonamide (213 mg, 26%) as a white powder. (ESI-MS: m/z 418.4 [M+H]$^+$, rt 4.30 min). $^1$H-NMR (DMSO-$d_6$, 400 MHz) 12.1 (s, 1H), 10.38 (s, 1H), 7.91 (s, 1H), 7.64 (s, 1H), 6.08 (s, 1H), 3.47 (s, 3H), 3.16 (s, 3H), 2.17 (s, 3H).

Example 31

N-[6-(1-methyl-1H-pyrazol-4-yl)-2,4-dioxo-7-trifluoromethyl-1,4-dihydro-2H-quinazolin-3-yl]-methanesulfonamide

2-Amino-5-(1-methyl-1H-pyrazol-4-yl)-4-trifluoromethyl-benzoic acid methyl ester

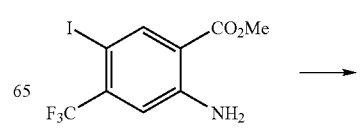

-continued

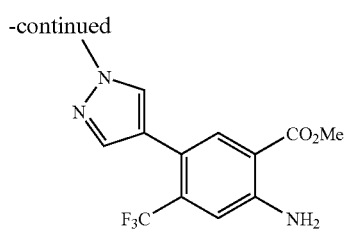

2-Amino-5-iodo-4-trifluoromethyl-benzoic acid methyl ester (300 mg, 0.87 mmol) and 1-methyl-4-(4,4,5,5-tetramethyl-1,3,2-dioxaborolan-2-yl)1H-pyrazole (181 mg, 1.0 equiv), $K_2CO_3$ (303 mg, 2.5 equiv.) and triphenylphosphine (45 mg. 0.2 equiv) were weighed in air and added in a flame-dried flask. Bis(dibenzylidenacetone)palladium (25 mg, 0.05 equiv) was added and the flask was closed by a septum. Dioxane (6 mL) was added and the mixture was stirred for 18 h (TLC control) at 90° C. The catalyst was filtered off and washed with EtOAc, the filtrate was evaporated to dryness. The crude product was purified by column chromatography (silica gel 60, EtOAc/hexanes 1/3 to 1/2) to give 2-amino-5-(1-methyl-1H-pyrazol-4-yl)-4-trifluoromethyl-benzoic acid methyl ester (0.57 mmol, 66%) as a white solid. ESI-MS: m/z 300 [M+H]$^+$, rt: 4.97 min.

2-(4-Chloro-phenoxycarbonylamino)-5-(1-methyl-1H-pyrazol-4-yl)-4-trifluoromethyl-benzoic acid methyl ester

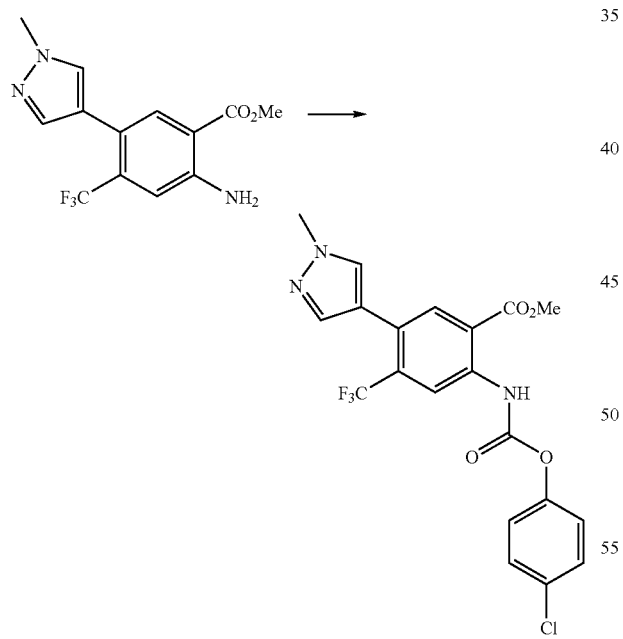

4-Chlorophenyl-chloroformate (155 μL, 2 equiv) was added to a solution of 2-amino-5-(1-methyl-1H-pyrazol-4-yl)-4-trifluoromethyl-benzoic acid methyl ester (170 mg, 0.57 mmol) in dioxane (1.1 mL). The mixture was stirred for 1 h (TLC control) at 85° C. The mixture was evaporated to dryness. The obtained yellow solid was used in the next step without further purification. (rt 6.48 min)

N-[6-(1-Methyl-1H-pyrazol-4-yl)-2,4-dioxo-7-trifluoromethyl-1,4-dihydro-2H-quinazolin-3-yl]-methanesulfonamide

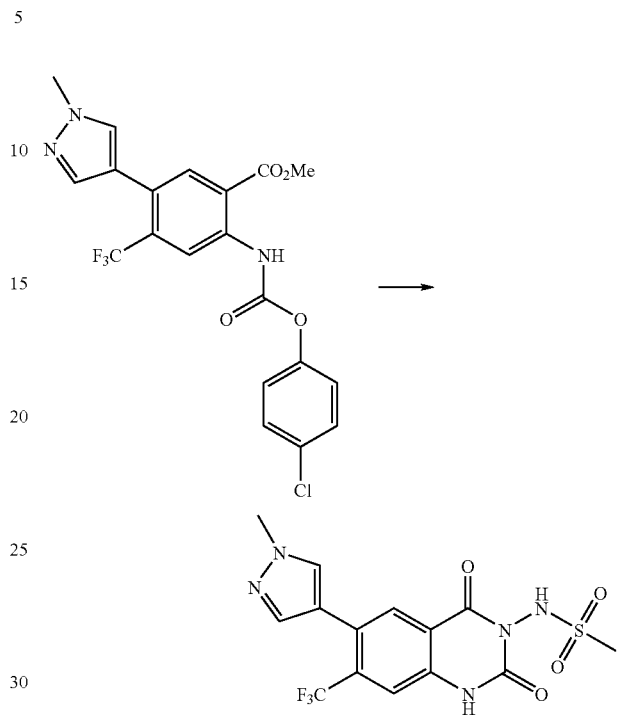

$CH_3SO_2NHNH_2$ (130 mg, 2.4 equiv) and i-$Pr_2NEt$ (169 μL, 2 equiv) were added to a solution of 2-(4-chloro-phenoxycarbonylamino)-5-(1-methyl-1H-pyrazol-4-yl)-4-trifluoromethyl-benzoic acid methyl ester (224 mg, 0.49 mmol) in dioxane (11 mL). The mixture was stirred for 19 h (TLC control) at 90° C. The mixture was evaporated to dryness. The crude product was triturated with hexanes and DCM. The formed precipitate was filtered and washed with hexanes to give N-[6-(1-methyl-1H-pyrazol-4-yl)-2,4-dioxo-7-trifluoromethyl-1,4-dihydro-2H-quinazolin-3-yl]-methanesulfonamide (83 mg, 42%) as a white solid. ESI-MS: m/z 404 [M+H]$^+$, $^1$H-NMR (DMSO-d$_6$, 400 MHz) 7.91 (s, 2H), 7.57 (s, 1H), 7.54 (s, 1H), 3.88 (s, 3H), 3.14 (s, 3H).

Example 32

N-[6-(1-Methyl-1H-pyrrol-2-yl)-2,4-dioxo-7-trifluoromethyl-1,4-dihydro-2H-quinazolin-3-yl]-methanesulfonamide 2-Amino-5-(1-methyl-1H-pyrrol-2-yl)-4-trifluoromethyl-benzoic acid methyl ester

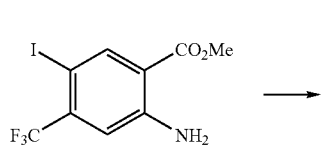

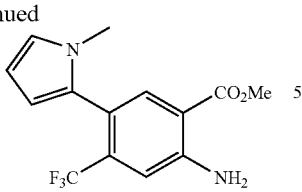

2-Amino-5-iodo-4-trifluoromethyl-benzoic acid methyl ester (400 mg, 1.16 mmol) and 1-methyl-2-tributylstannanyl-1H-pyrrole (643 mg, 1.5 equiv) were weighed in air and added in a flame-dried flask. [Bistriphenylphosphine]dichloropalladium (124.5 mg, 0.15 equiv) was added and the flask was closed by a septum. Dioxane (16 mL) was added and the mixture was stirred for 1 h (TLC control) at 100° C. After 1 h, 1-methyl-2-tributylstannyl-1H-pyrrole (429 mg, 1 equiv) was added and the mixture was stirred for 35 h (TLC control) at 100° C. The solvent was removed in vacuo, the residue was taken in DCM and washed with a saturated solution of $NaHCO_3$, water and brine. The organic phase was dried over $Na_2SO_4$ and evaporated to dryness. The crude product was purified by flash chromatography (hexanes to EtOAc/hexanes (4:6)) to furnish 2-amino-5-(1-methyl-1H-pyrrol-2-yl)-4-trifluoromethyl-benzoic acid methyl ester (50 mg, 14.5%) as a yellow oil. ESI-MS: m/z 299 [M+H]$^+$, rt 5.78 min.

2-(4-Chloro-phenoxycarbonylamino)-5-(1-methyl-1H-pyrrol-2-yl)-4-trifluoromethyl-benzoic acid methyl ester

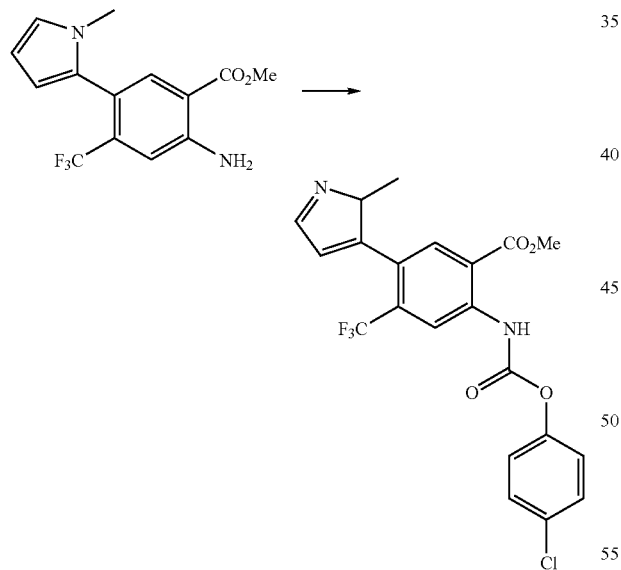

4-Chlorophenyl-chloroformate (24.7 μL, 1 equiv) was added to a solution of 2-amino-5-(1-methyl-1H-pyrrol-2-yl)-4-trifluoromethyl-benzoic acid methyl ester (54 mg, 0.181 mmol) in dioxane (2 mL). The mixture was stirred for 2 h (TLC control) at 100° C. The mixture was evaporated to dryness to provide 2-(4-chloro-phenoxycarbonylamino)-5-(1-methyl-1H-pyrrol-2-yl)-4-trifluoromethyl-benzoic acid methyl ester (70 mg, 0.154 mmol, 85%) as a yellow oil which was used in the next step without further purification. (rt: 7.00 min).

N-[6-(1-Methyl-1H-pyrrol-2-yl)-2,4-dioxo-7-trifluoromethyl-1,4-dihydro-2H-quinazolin-3-yl]-methanesulfonamide

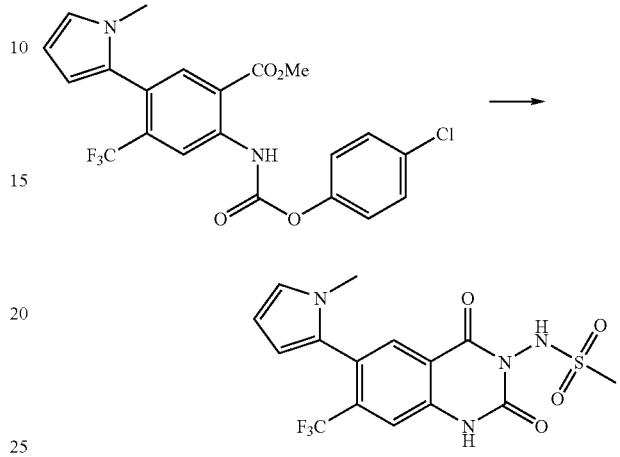

$CH_3SO_2NHNH_2$ (25.5 mg, 1.5 equiv) and i-$Pr_2NEt$ (26.5 μL, 1 equiv) were added to a solution of 2-(4-chloro-phenoxycarbonylamino)-5-(1-methyl-1H-pyrrol-2-yl)-4-trifluoromethyl-benzoic acid methyl ester (70 mg, 0.155 mmol) in dioxane (2 mL). The mixture was stirred for 2 h (TLC control) at 95° C. $CH_3SO_2NHNH_2$ (25.5 mg, 1.5 equiv) and i-$Pr_2NEt$ (26.5 μL, 1 equiv) were then added. The mixture was stirred for 48 h at 95° C. The mixture was evaporated to dryness. The crude product was purified by column chromatography (silica gel 60, EtOAc/hexanes 7/3) to give N-[6-(1-methyl-1H-pyrrol-2-yl)-2,4-dioxo-7-trifluoromethyl-1,4-dihydro-2H-quinazolin-3-yl]-methanesulfonamide (50 mg, 80%) as a yellow solid. ESI-MS: m/z 420 [M+NH$_4$]$^+$, rt: 4.83 min. $^1$H-NMR (DMSO-d$_6$, 400 MHz) 7.91 (s, 2H), 7.57 (s, 1H), 7.54 (s, 1H), 3.88 (s, 3H), 3.14 (s, 3H).

Example 33

N-[2,4-Dioxo-6-(tetrahydro-furan-3-yl)-7-trifluoromethyl-1,4-dihydro-2H-quinazolin-3-yl]-methanesulfonamide 2-Acetylamino-5-furan-3-yl-4-trifluoromethyl-benzoic acid methyl ester

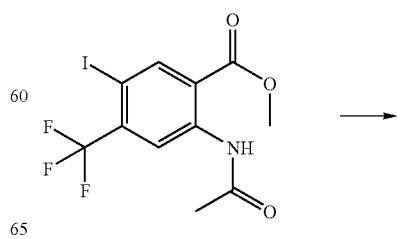

-continued

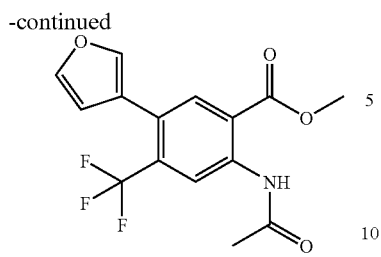

3-Iodo-4-trifluoromethyl-6-acetamidomethylbenzoate (500 mg, 1.29 mmol), 3-furanboronic acid (159 mg, 1.1 equiv) and $Cs_2CO_3$ (1.1 g, 2.5 equiv) were weighed in air and added in a flame-dried flask. Dichloro[1,1'-bis(diphenylphosphino)-ferrocene]palladium (II) dichloromethane complex (52.7 mg, 0.1 equiv) was added, the air was replaced by $N_2$ and the flask was closed by a septum. DME was added and the mixture was stirred for 3 d (TLC control) at 70° C. The mixture was diluted with EtOAc, filtered and the filtrate was concentrated in vacuo. The crude product was purified by flash chromatography (EtOAc/hexanes (1:9)) to provide 2-acetylamino-5-furan-3-yl-4-trifluoromethyl-benzoic acid methyl ester as a white solid (176 mg, 42%) (328 [M+H]$^+$, rt 5.8 min.).

2-Amino-5-furan-3-yl-4-trifluoromethyl-benzoic acid methyl ester

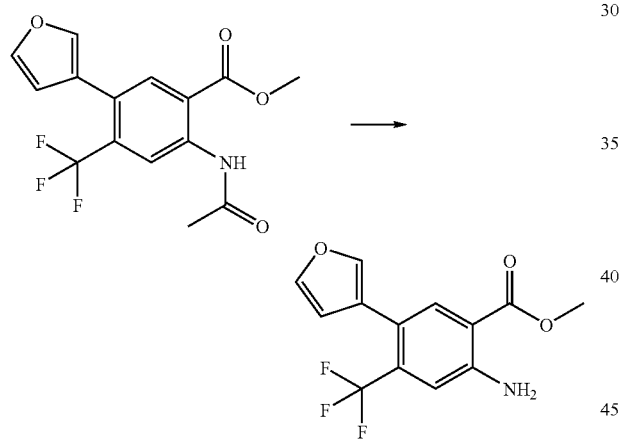

Concentrated $H_2SO_4$ (1.4 mL) was added to a solution of 2-acetylamino-5-furan-3-yl-4-trifluoromethyl-benzoic acid methyl ester (156 mg, 0.47 mmol) in MeOH (15 mL). The mixture was stirred for 1 h (TLC control) at 90° C. The mixture was filtered over Celite and evaporated under reduced pressure. The yellow solid obtained was used in the next step without further purification (rt 5.95 min.).

2-Amino-5-(tetrahydro-furan-3-yl)-4-trifluoromethyl-benzoic acid methyl ester

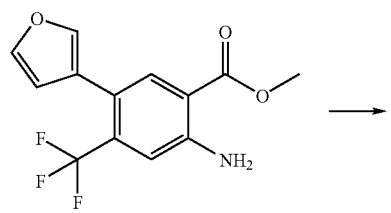

-continued

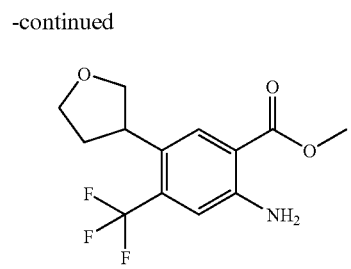

2-Amino-5-furan-3-yl-4-trifluoromethyl-benzoic acid methyl ester (110 mg, 0.38 mmol) was dissolved in THF (15 mL) and, after addition of B113 W (Degussa) Ra/Ni (~200 mg) in $H_2O$ the mixture was stirred for 26 d (TLC control) at 60° C. The mixture was filtered over Celite and evaporated under reduced pressure. The crude product was purified by flash chromatography with hexanes to hexanes/EtOAc 80:20 as eluent to furnish the title compound (51.3 mg, 46% yield) (290 [M+H]$^+$, rt 5.52 min.).

2-(4-Chloro-phenoxycarbonylamino)-5-(tetrahydrofuran-3-yl)-4-trifluoromethyl-benzoic acid methyl ester

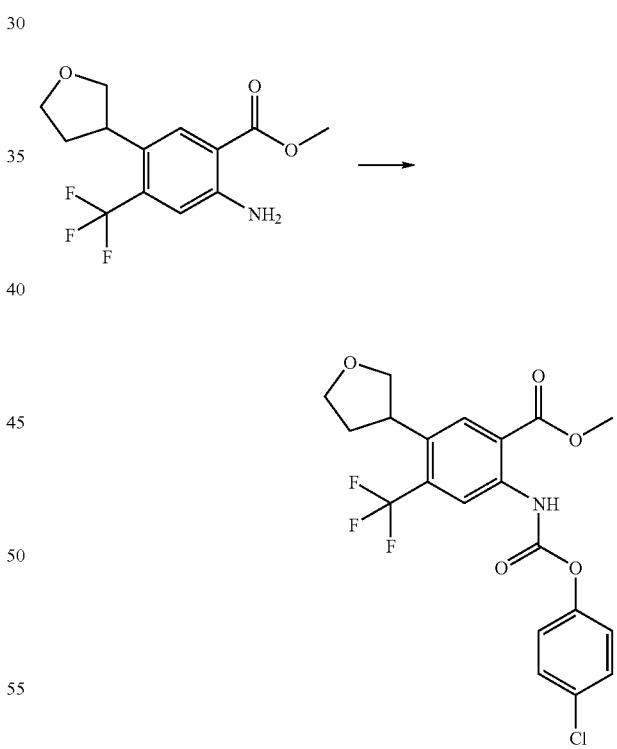

4-Chlorophenyl chloroformate (27.3 μL, 1.1 equiv) was added to a solution of 2-amino-5-(tetrahydro-furan-3-yl)-4-trifluoromethyl-benzoic acid methyl ester (51.3 mg, 0.18 mmol) in dioxane (500 μL). The mixture was then stirred for 2 h (TLC control) at 80° C. The mixture was evaporated to dryness. The product was used in the next step without further purification. (rt 6.87 min.)

111

N-[2,4-Dioxo-6-(tetrahydro-furan-3-yl)-7-trifluoromethyl-1,4-dihydro-2H-quinazolin-3-yl]-methanesulfonamide

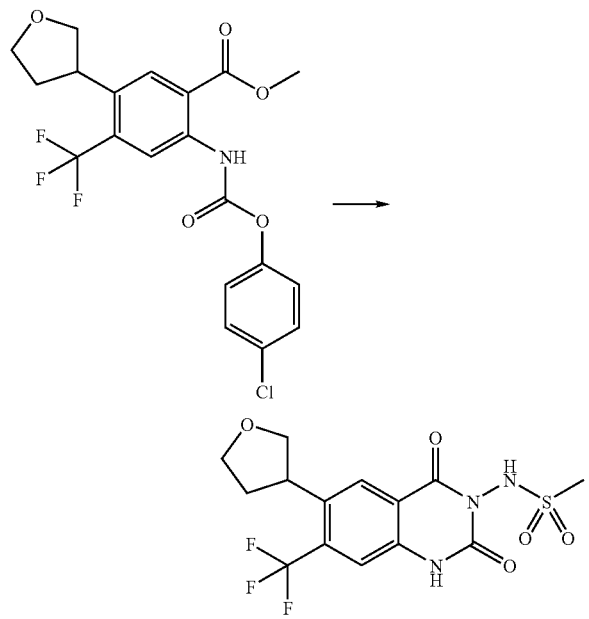

2-(4-Chloro-phenoxycarbonylamino)-5-(tetrahydro-furan-3-yl)-4-trifluoromethyl-benzoic acid methyl ester (80 mg, 0.18 mmol) was dissolved in dioxane (1 mL) and, after addition of CH$_3$SO$_2$NHNH$_2$ (21.8 mg, 1.1 equiv) and i-Pr$_2$NEt (61.7 μL, 2 equiv), the mixture was stirred for 18 h (TLC control) at 80° C. The crude product was purified by flash chromatography with DCM to DCM/MeOH 85:15 as eluent. The obtained product was dried, dissolved in a small quantity of DCM and precipitated with hexanes. The white solid was filtered off and dried to provide the title compound (50 mg, 70% yield) (394 [M+H]$^+$, rt 4.58 min.).

Example 34

N-[6-(3-Cyano-phenyl)-2,4-dioxo-7-trifluoromethyl-1,4-dihydro-2H-quinazolin-3-yl]-methanesulfonamide 4-Acetylamino-3'-cyano-6-trifluoromethyl-biphenyl-3-carboxylic acid methyl ester

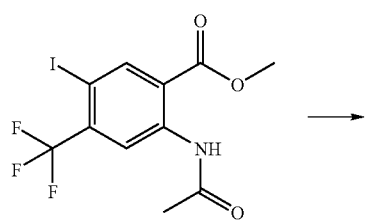

112

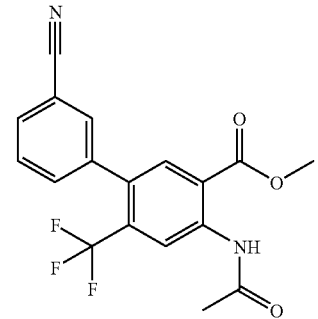

A solution of 2-acetylamino-5-iodo-4-trifluoromethyl-benzoic acid methyl ester (3 g, 7.75 mmol), tetrakis(triphenylphosphine)palladium (0.446 g, 0.775 mmol), and 3-tributylstannanyl-benzonitrile (3.65 g, 9.3 mmol) in dioxane (100 mL) was heated to 110° C. for 96 h under nitrogen. The mixture was allowed to cool to r.t., and then filtered. The filtrate was concentrated in vacuo and the crude product was purified by column chromatography (silica gel 60, hexanes/DCM 9:1) to give 4-acetylamino-3'-cyano-6-trifluoromethyl-biphenyl-3-carboxylic acid methyl ester (1.2 g, 3.3 mmol, 43%) as a yellow oil, ESI-MS: m/z 363 [M+H]$^+$.

4-Amino-3'-cyano-6-trifluoromethyl-biphenyl-3-carboxylic acid methyl ester

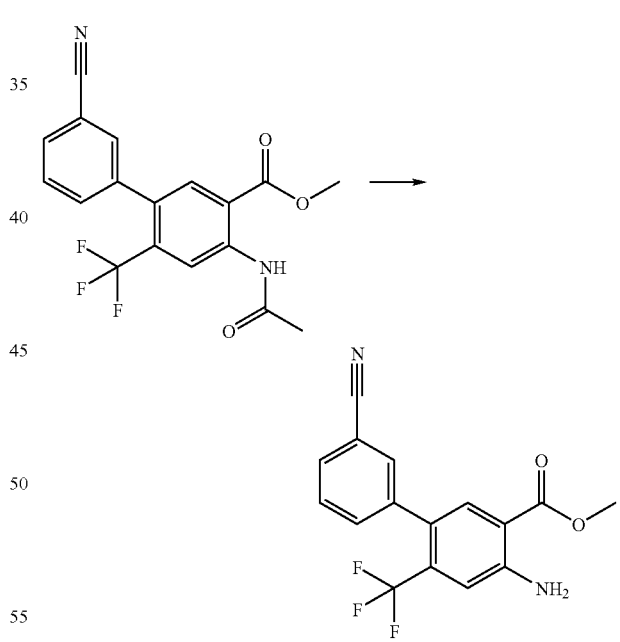

A solution of 4-acetylamino-3'-cyano-6-trifluoromethyl-biphenyl-3-carboxylic acid methyl ester (1.2 g, 3.3 mmol) in MeOH (10 mL)/water (2 mL) was cooled to 0° C., and concentrated sulfuric acid (0.7 mL) was added dropwise. Upon completion of the addition, the mixture was heated to reflux for 2 h under nitrogen, and then allowed to cool to r.t. The mixture was poured on ice water and extracted three times with 25 mL each of EtOAc. The combined organic phases were washed twice with water, dried over anhydrous sodium sulfate, filtered, and concentrated in vacuo providing 4-amino-3'-cyano-6-trifluoromethyl-biphenyl-3-carboxylic acid methyl ester (700 mg, 2.19 mmol, 66%) as a yellow foam, ESI-MS: m/z 321 [M+H]+.

N-[6-(3-Cyano-phenyl)-2,4-dioxo-7-trifluoromethyl-1,4-dihydro-2H-quinazolin-3-yl]-methanesulfonamide

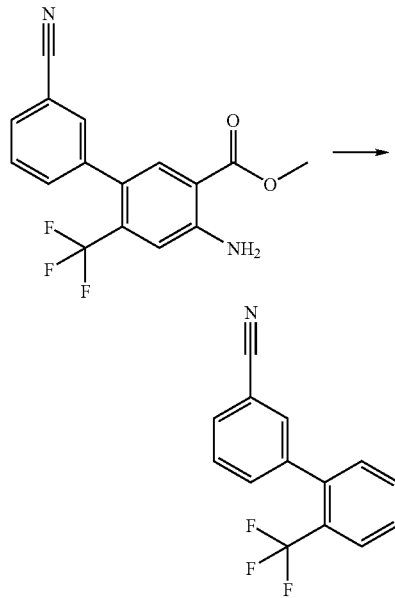

A solution of 4-amino-3'-cyano-6-trifluoromethyl-biphenyl-3-carboxylic acid methyl ester (0.7 g, 2.19 mmol) in dioxane (15 mL) was treated with i-Pr$_2$NEt (0.5 mL, 2.92 mmol) and (CCl$_3$O)$_2$CO (0.655 g, 2.19 mmol) and the mixture was stirred at 60° C. for 1 h under nitrogen. To this solution was added CH$_3$SO$_2$NHNH$_2$ (0.24 g, 2.19 mmol) and stirring was continued for 1 h at 60° C. and for 16 h at r.t. The mixture was concentrated in vacuo, diluted with water and extracted three times with 25 mL each of EtOAc. The combined organic layers were washed twice with water and dried (Na$_2$SO$_4$), filtered and the solvent evaporated. The product was recrystallized from MeOH/DCM 3:1 to give N-[6-(3-cyano-phenyl)-2,4-dioxo-7-trifluoromethyl-1,4-dihydro-2H-quinazolin-3-yl]-methanesulfonamide (0.78 g, 1.84 mmol, 84%), m.p. 291-292° C., ESI-MS: m/z 425 [M+H]+.

Example 35

N-[6-(4-Cyano-phenyl)-2,4-dioxo-7-trifluoromethyl-1,4-dihydro-2H-quinazolin-3-yl]-methanesulfonamide

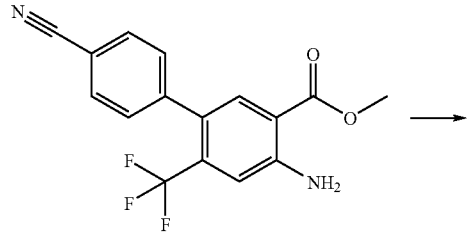

-continued

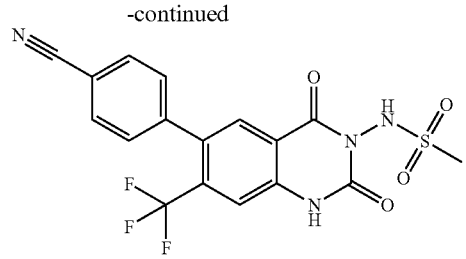

Using a similar procedure starting from 4-tributylstannanyl-benzonitrile the corresponding para-substituted derivative N-[6-(4-cyano-phenyl)-2,4-dioxo-7-trifluoromethyl-1,4-dihydro-2H-quinazolin-3-yl]-methanesulfonamide was prepared, m.p. 145-147° C., ESI-MS: m/z 425 [M+H]+.

Example 36

N-[6-(3-Acetyl-phenyl)-2,4-dioxo-7-trifluoromethyl-1,4-dihydro-2H-quinazolin-3-yl]-methanesulfonamide

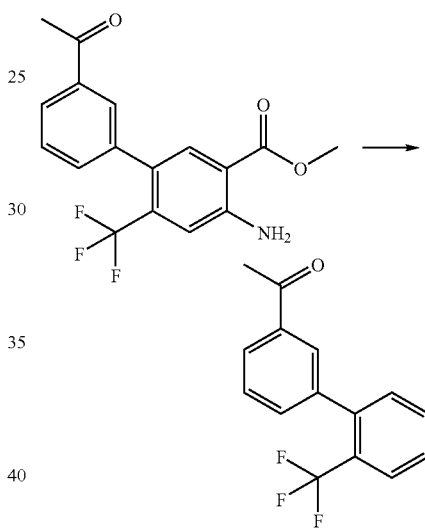

Using a similar procedure starting from 1-(3-tributylstannanyl-phenyl)-ethanone the corresponding methylketone derivative N-[6-(3-acetyl-phenyl)-2,4-dioxo-7-trifluoromethyl-1,4-dihydro-2H-quinazolin-3-yl]-methanesulfonamide was prepared, m.p. 220-222° C., ESI-MS: m/z 442 [M+H]+.

Example 37

N-{6-[3-(1-Hydroxy-ethyl)-phenyl]-2,4-dioxo-7-trifluoromethyl-1,4-dihydro-2H-quinazolin-3-yl}-methanesulfonamide

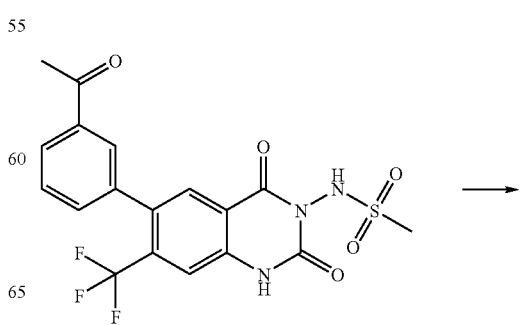

-continued

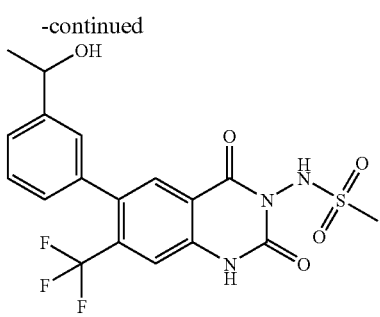

The reduction was effected with sodium borohydride as described in example 1 to give in 89% yield N—{6-[3-(1-hydroxy-ethyl)-phenyl]-2,4-dioxo-7-trifluoromethyl-1,4-dihydro-2H-quinazolin-3-yl}-methane-sulfonamide, m.p. 165-169° C., ESI-MS: m/z 444 [M+H]$^+$.

Example 38

N-[6-(3-Aminomethyl-phenyl)-2,4-dioxo-7-trifluoromethyl-1,4-dihydro-2H-quinazolin-3-yl]-methanesulfonamide

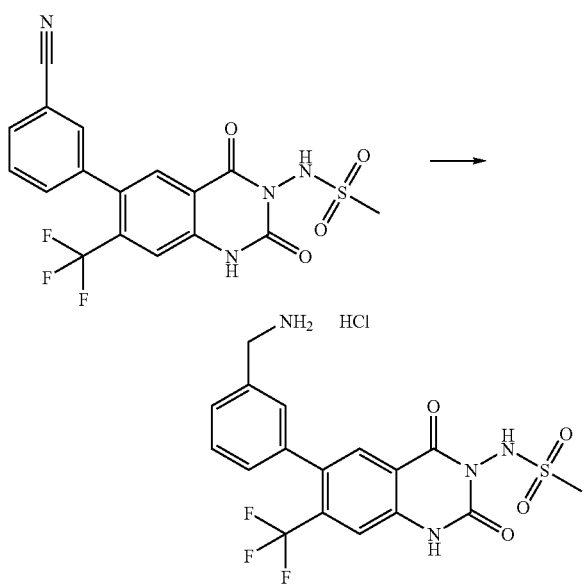

To a solution of N-[6-(3-cyano-phenyl)-2,4-dioxo-7-trifluoromethyl-1,4-dihydro-2H-quinazolin-3-yl]-methanesulfonamide (0.18 g, 0.42 mmol) in MeOH containing 5% ammonia (20 mL) was added Raney nickel (60 mg) and the stirred solution was hydrogenated under normal pressure at ambient temperature during 18 h. The suspension was filtered and the solvent evaporated in vacuo. The crude product was purified by column chromatography (silica gel 60, MeOH/DCM 9:1) and then treated with a solution of 5M HCl in MeOH. Recrystallization yielded N-[6-(3-aminomethyl-phenyl)-2,4-dioxo-7-trifluoromethyl-1,4-dihydro-2H-quinazolin-3-yl]-methanesulfonamide hydrochloride (117 mg, 0.27 mmol, 59%), m.p. 282-284° C., ESI-MS: m/z 429 [M+H]$^+$.

Example 39

N-[6-(3-Dimethylaminomethyl-phenyl)-2,4-dioxo-7-trifluoromethyl-1,4-dihydro-2H-quinazolin-3-yl]-methanesulfonamide

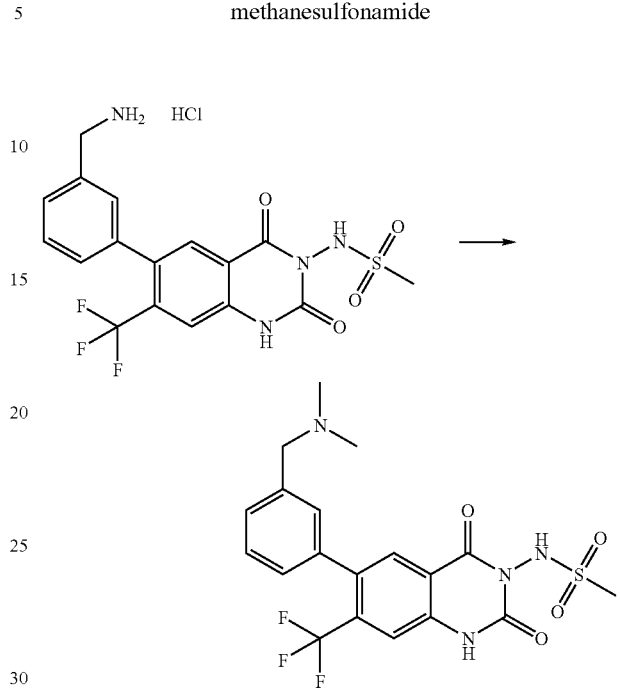

To a solution of N-[6-(3-aminomethyl-phenyl)-2,4-dioxo-7-trifluoromethyl-1,4-dihydro-2H-quinazolin-3-yl]-methanesulfonamide (15 mg, 35 µmol) in dioxane (5 mL) was added formaldehyde solution, (36% in water, 0.013 mL, 175 µmol) and a 1N aqueous solution of sodium dihydrogenphosphite (5 mL). The solution was stirred at 60° C. for 20 min, cooled to ambient temperature and evaporated in vacuo. The crude product was purified via plate chromatography (silica gel 60, MeOH/DCM 9:1) to give N-[6-(3-dimethylaminomethyl-phenyl)-2,4-dioxo-7-trifluoromethyl-1,4-dihydro-2H-quinazolin-3-yl]-methanesulfonamide (12 mg, 26 µmol, 75%), m.p. 346-348° C., ESI-MS: m/z 457 [M+H]$^+$.

Example 40

N-(3-Methanesulfonylamino-2,4-dioxo-7-trifluoromethyl-1,2,3,4-tetrahydro-quinazolin-6-ylmethyl)-acetamide 2-Amino-5-nitro-4-trifluoromethyl-benzoic acid methyl ester

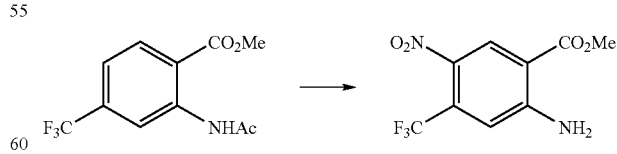

A mixture of concentrated nitric acid (0.49 mL) and concentrated sulfuric acid (3.9 mL) was cooled to −20° C. and 2-acetylamino-4-trifluoromethyl-benzoic acid methyl ester (2.10 g, 8.04 mmol) was added portionwise. The mixture was allowed to warm slowly to r.t. and was then heated to 45° C. for 30 min. The mixture was poured onto ice and the white precipitate was filtered off. The white solid was then dissolved in MeOH (8 mL) and this solution was treated with sulfuric acid (0.8 mL) and heated to reflux for 45 min. The mixture was concentrated in vacuo and was then taken up in EtOAc, washed twice with aqueous potassium hydrogencarbonate, once with brine, dried (Na$_2$SO$_4$), filtered and concentrated in vacuo. The crude product was purified by column chromatography (silica gel 60, toluene/EtOAc 96:4) affording pale yellow crystals that were recrystallized in EtOAc to provide 2-amino-5-nitro-4-trifluoromethyl-benzoic acid methyl ester (116 mg, 0.44 mmol, 5%) as a white solid, m.p. 175-177° C., $^1$H-NMR (DMSO-d$_6$, 400 MHz) 8.59 (s, 1H), 8.04 (br s, 2H), 7.40 (s, 1H), 3.88 (s, 3H).

2-Isocyanato-5-nitro-4-trifluoromethyl-benzoic acid methyl ester

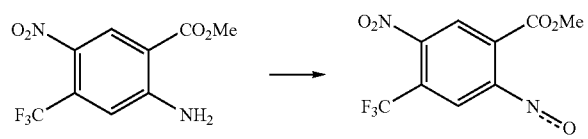

To a suspension of 2-amino-5-nitro-4-trifluoromethyl-benzoic acid methyl ester (100 mg, 0.379 mmol) in dry toluene (1.5 mL) was added a solution of phosgene in toluene (20%, 1.5 mL) at −15° C. After warming to r.t., a stream of phosgene was introduced into the suspension and simultaneously heating was started. At reflux, the stream of phosgene was maintained for one hour, then replaced by a stream of argon for an additional hour. The toluene was distilled off leaving 2-isocyanato-5-nitro-4-trifluoromethyl-benzoic acid methyl ester (110 mg, 100%) as a beige solid. IR (CHCl$_3$): 2260 cm$^{-1}$ (s). $^1$H-NMR (CDCl$_3$, 360 MHz): 4.05 (s, 3H), 7.55 (s, 1H), 8.65 (s, 1H).

N-(6-Nitro-2,4-dioxo-7-trifluoromethyl-1,4-dihydro-2H-quinazolin-3-yl)-methanesulfonamide

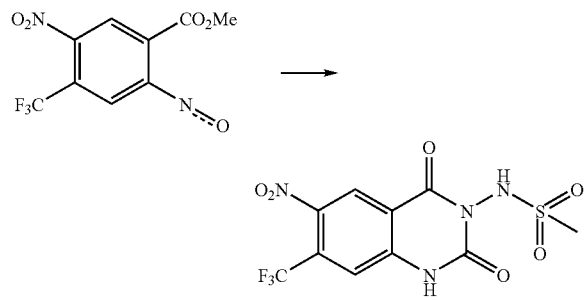

To a solution of 2-isocyanato-5-nitro-4-trifluoromethyl-benzoic acid methyl ester (110 mg, 0.379 mmol) in dry THF (1.7 mL) was added a solution of CH$_3$SO$_2$NHNH$_2$ (41.7 mg, 0.379 mmol) in dry THF (0.6 mL) at r.t. The resultant mixture turned into a white suspension that was stirred for one hour. A 1 M aq NaOH solution (0.379 mL) was added and stirring of the clear solution was continued for 4 h. After addition of 2 M HCl solution (0.472 mL) and evaporation of the THF, the precipitate was filtered and dried at 50° C./0.1 mm yielding N-(6-nitro-2,4-dioxo-7-trifluoromethyl-1,4-dihydro-2H-quinazolin-3-yl)-methanesulfonamide (114 mg, 81%) as a slightly yellow powder, m.p. 220-232° C. (decomp.). $^1$H-NMR (DMSO-d$_6$, 400 MHz): 3.15 (s, 3H), 7.66 (s, 1H), 8.62 (s, 1H), 10.50 (s, 1H), 12.41 (s, 1H).

N-(6-Amino-2,4-dioxo-7-trifluoromethyl-1,4-dihydro-2H-quinazolin-3-yl)-methanesulfonamide

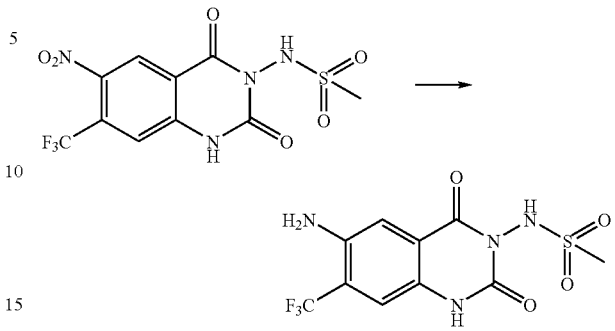

A solution of N-(6-nitro-2,4-dioxo-7-trifluoromethyl-1,4-dihydro-2H-quinazolin-3-yl)-methanesulfonamide (109 mg) in 1:1 EtOH:CH$_3$CO$_2$H (6 mL) was hydrogenated in the presence of 10% palladium on carbon (30 mg). After disappearance of the starting material (TLC control), the reaction mixture was diluted with EtOH and CH$_3$CO$_2$H and slightly warmed up. The catalyst was filtered off and the filtrate concentrated to dryness. Trituration of the residue with EtOAc gave N-(6-amino-2,4-dioxo-7-trifluoromethyl-1,4-dihydro-2H-quinazolin-3-yl)-methanesulfonamide (61 mg, 61%) as a yellow powder, m.p. 240° C. (decomp.). $^1$H-NMR (DMSO-d$_6$, 400 MHz): 3.12 (s, 3H), 5.66 (s, 2H), 7.24 (s, 1H), 7.46 (s, 1H), 10.3 (br s, 1H), 11.4 (br s, 1H).

N-(6-Cyano-2,4-dioxo-7-trifluoromethyl-1,4-dihydro-2H-quinazolin-3-yl)-methanesulfonamide

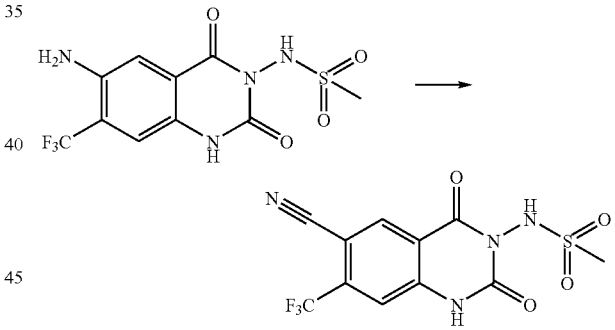

To a suspension of N-(6-amino-2,4-dioxo-7-trifluoromethyl-1,4-dihydro-2H-quinazolin-3-yl)-methanesulfonamide (3 g, 8.87 mmol) in CH$_3$CO$_2$H (6 mL) were added water (8 mL) and conc. sulfuric acid (980 µL, 17.7 mmol). The mixture was cooled to 0° C. A solution of sodium nitrite (680 mg, 9.76 mmol) in water (4 mL) was then added slowly over 5 min and stirring at 0° C. was pursued for 30 min.

In another flask, a solution of copper(II) sulfate (2.65 g, 10.64 mmol) in water (4 mL) was added slowly over a period of 5 min to a solution of potassium cyanide (2.88 g, 44.34 mmol) in water (4 mL) at 0° C. Sodium hydrogencarbonate (7.47 g, 88.69 mmol) and toluene were added to the copper sulfate-potassium cyanide solution and the mixture was stirred at 0° C. for 10 min. To this mixture was added slowly over 1 h the suspension containing the diazonium intermediate and the reaction was stirred at 0° C. for another hour. Subsequently EtOAc (200 mL) was added, the mixture was stirred for 0.5 h and the layers were separated. The organic phase was extracted three time with water. The organic layer was dried and the solvent was evaporated to yield a yellow-orange solid which was re-dissolved in EtOAc and washed with 2M aq HCl. The organic layer was dried once more and the solvent removed in vacuo to yield N-(6-cyano-2,4-dioxo-7-trifluoromethyl-1,4-dihydro-2H-quinazolin-3-yl)-methanesulfonamide (2.8 g, 8.04 mmol, 91%). $^1$H-NMR (DMSO-d$_6$, 400 MHz) 3.22 ppm (s, 3H, SO$_2$—CH$_3$; LC-MS rt=3.07 min; MS: m/z 370.9 [M+Na]$^+$, Column: SunFireC18, 4.6*50 mn, 3.5 um; Positive MS Water/Acetonitrile 95:5 to 5:95 in 5 min, Flow: 1.5 mL/min N-[3-(Acetyl-methanesulfonyl-amino)-2,4-dioxo-7-trifluoromethyl-1,2,3,4-tetrahydro-quinazolin-6-ylmethyl]-acetamide

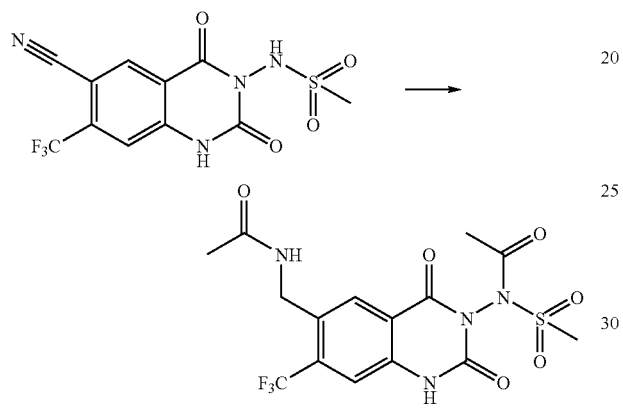

To a solution of N-(6-cyano-2,4-dioxo-7-trifluoromethyl-1,4-dihydro-2H-quinazolin-3-yl)-methanesulfonamide (2.8 g, 8.04 mmol) in acetic anhydride (160 mL) was added Raney Nickel in water (5.24 g, 88.4 mmol) and the mixture was stirred at r.t. under a pressure of hydrogen (5 bar) for 9 h. The reaction mixture was filtered through Hyflo® and washed twice with MeOH. The solvent of the filtrate was evaporated to yield N-[3-(acetyl-methanesulfonyl-amino)-2,4-dioxo-7-trifluoromethyl-1,2,3,4-tetrahydro-quinazolin-6-ylmethyl]-acetamide (4.05 g, 7.52 mmol, 94%) as a light orange solid. $^1$H-NMR (DMSO-d$_6$, 400 MHz) 3.57 ppm (s, 3H, SO$_2$—CH$_3$); LC-MS rt=2.82 min; MS: m/z 458.9 [M+Na]$^+$ Column: SunFireC18, 4.6*50 mn, 3.5 um; Positive MS Water/Acetonitrile 95:5 to 5:95 in 5 min, Flow: 1.5 mL/min N-(3-Methanesulfonylamino-2,4-dioxo-7-trifluoromethyl-1,2,3,4-tetrahydro-quinazolin-6-ylmethyl)-acetamide

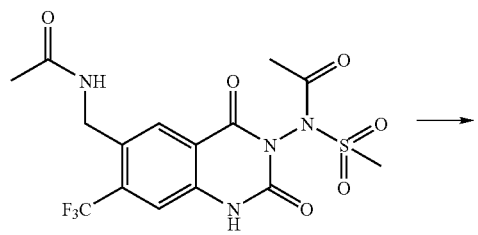

-continued

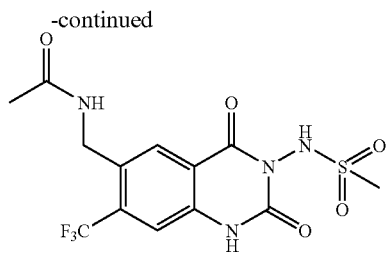

A solution of N-[3-(acetyl-methanesulfonyl-amino)-2,4-dioxo-7-trifluoromethyl-1,2,3,4-tetrahydro-quinazolin-6-ylmethyl]-acetamide (305 mg, 0.70 mmol) in 2M aq HCl (5 mL) was stirred at 80° C. for 1 d. Subsequently, the solvent was evaporated and the crude product was purified by preparative thin-layer chromatography (DCM/MeOH 8/2) to yield N-(3-methanesulfonylamino-2,4-dioxo-7-trifluoromethyl-1,2,3,4-tetrahydro-quinazolin-6-ylmethyl)-acetamide (22 mg, 0.056 mmol, 8%) as a light beige solid. $^1$H-NMR (DMSO-d$_6$, 400 MHz) 3.13 ppm (s, 3H, SO$_2$—CH$_3$); LC-MS rt=2.35 min; MS: m/z 394.9 [M+H]$^+$ Column: SunFireC18, 4.6*50 mn, 3.5 um; Positive MS Water/Acetonitrile 95:5 to 5:95 in 5 min, Flow: 1.5 mL/min Example 41

N-(6-Formylaminomethyl-2,4-dioxo-7-trifluoromethyl-1,4-dihydro-2H-quinazolin-3-yl)-methanesulfonamide N-(6-Aminomethyl-2,4-dioxo-7-trifluoromethyl-1,4-dihydro-2H-quinazolin-3-yl)-methanesulfonamide

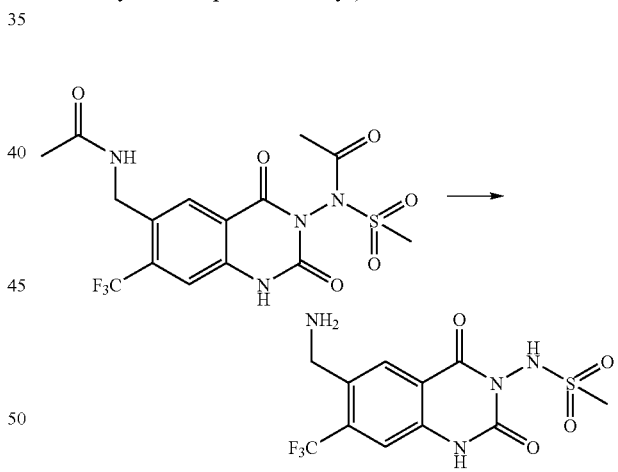

A solution of N-[3-(acetyl-methanesulfonyl-amino)-2,4-dioxo-7-trifluoromethyl-1,2,3,4-tetrahydro-quinazolin-6-ylmethyl]-acetamide (1.8 g, 4.13 mmol) in 2M aq HCl (5.2 mL) was stirred at 80° C. for 2 d. 2M hydrochloric acid (1 mL) was added every half day. Subsequently the solvent was evaporated and the light yellow residue was purified by ion-exchange resin (DOWEX 50*2-100, MeOH): the crude product was dissolved in MeOH, and mixed with a suspension of DOWEX in MeOH and the mixture was stirred at r.t. for 2 h. The resin was then filtered and washed with MeOH (this MeOH fraction was discarded). The resin was suspended in a solution of ammonia in MeOH (7M, 300 mL), stirred for 2 h, filtered and the filtrate was collected. The resin was treated two more times with a solution of ammonia in MeOH as described above and the filtrates were collected. The combined solvent fractions were evaporated to give N-(6-aminomethyl-2,4-dioxo-7-trifluoromethyl-1,4-dihydro-2H-quinazolin-3-yl)-methanesulfonamide (1.12 g, 3.18 mmol, 77%) as a yellow solid, $^1$H-NMR (DMSO-d$_6$, 400 MHz) 3.14 ppm (s, 3H, SO$_2$—C$\underline{H_3}$); LC-MS rt=0.523 mn; MS: m/z 352.9 [M+H]$^+$ Column: SunFireC18, 4.6*50 mn, 3.5 um; Positive MS Water/Acetonitrile 95:5 to 5:95 in 5 min, Flow: 1.5 mL/min N-(6-Formylaminomethyl-2,4-dioxo-7-trifluoromethyl-1,4-dihydro-2H-quinazolin-3-yl)-methanesulfonamide

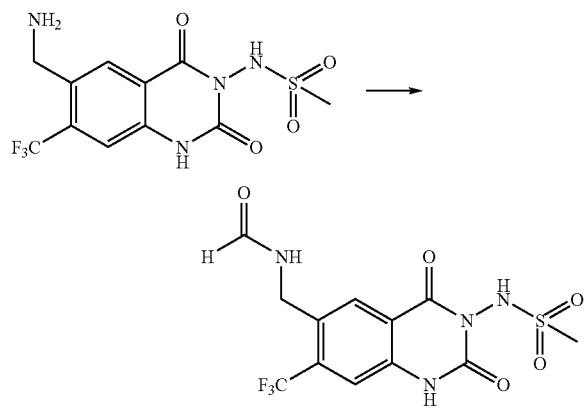

A suspension of N-(6-aminomethyl-2,4-dioxo-7-trifluoromethyl-1,4-dihydro-2H-quinazolin-3-yl)-methanesulfonamide (400 mg, 1.14 mmol) in ethyl formate (27.4 mL, 340.7 mmol) and THF (25 mL) was stirred at 60° C. for 16 h. Subsequently the solvent was evaporated and the residue dried in vacuo for 2 h. The crude product was purified by flash-master chromatography (DCM 100-90/MeOH 0-10, %-gradients) to yield N-(6-formylaminomethyl-2,4-dioxo-7-trifluoromethyl-1,4-dihydro-2H-quinazolin-3-yl)-methanesulfonamide (316 mg, 0.831 mmol, 73%) as a light-yellow solid. $^1$H-NMR (DMSO-d$_6$, 400 MHz) 3.17 ppm (s, 3H, SO$_2$—C$\underline{H_3}$); LC-MS rt=2.32 min; MS: m/z 380.9 [M+H]$^+$ Column: SunFireC18, 4.6*50 mn, 3.5 um; Positive MS Water/Acetonitrile 95:5 to 5:95 in 5 min, Flow: 1.5 mL/min Example 42

N-(2,4-Dioxo-6-pyrrol-1-ylmethyl-7-trifluoromethyl-1,4-dihydro-2H-quinazolin-3-yl)-methanesulfonamide

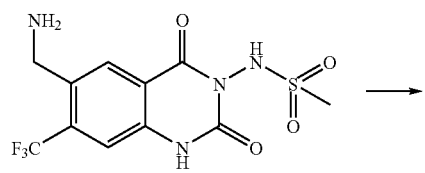

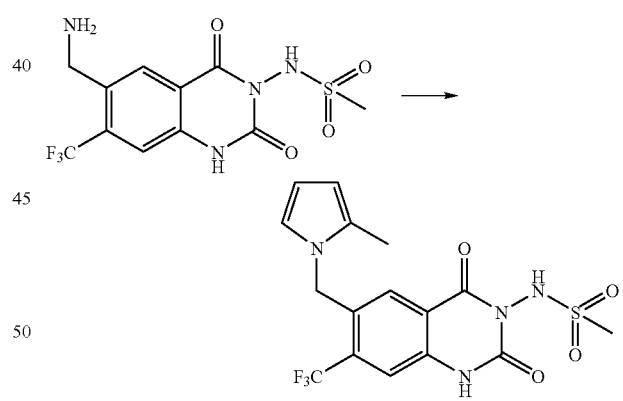

To a solution of N-(6-aminomethyl-2,4-dioxo-7-trifluoromethyl-1,4-dihydro-2H-quinazolin-3-yl)-methanesulfonamide (100 mg, 0.28 mmol) in conc. CH$_3$CO$_2$H (8 mL) was added 2,5-dimethoxytetrahydrofurane (41.3 µL, 0.31 mmol) and the reaction mixture was stirred for 20 min at reflux temperature. Subsequently, the solvent was evaporated and the crude brown residue was recrystallized from EtOAc/cyclohexane to yield N-(2,4-dioxo-6-pyrrol-1-ylmethyl-7-trifluoromethyl-1,4-dihydro-2H-quinazolin-3-yl)-methanesulfonamide (108 mg, 0.27 mmol, 95%) as a light-brown solid. $^1$H-NMR (DMSO-d$_6$, 400 MHz) 3.12 ppm (s, 3H, SO$_2$—C$\underline{H_3}$; LC-MS rt=3.757 mn; MS: m/z 402.9 [M+H]$^+$ Column: SunFireC18, 4.6*50 mn, 3.5 um; Positive MS Water/Acetonitrile 95:5 to 5:95 in 5 min, Flow: 1.5 mL/min Example 43

N-[6-(2-Methyl-pyrrol-1-ylmethyl)-2,4-dioxo-7-trifluoromethyl-1,4-dihydro-2H-quinazolin-3-yl]-methanesulfonamide To a solution of N-(6-aminomethyl-2,4-dioxo-7-trifluoromethyl-1,4-dihydro-2H-quinazolin-3-yl)-methanesulfonamide (150 mg, 0.43 mmol) in conc. CH$_3$CO$_2$H (10 mL) was added 2-methyl-2,5-dimethoxytetrahydrofurane (62.2 mg, 0.43 mmol) and the reaction mixture was stirred for 2 h at reflux temperature. Subsequently, the solvent was evaporated and the crude light-yellow residue was recrystallized from EtOAc/cyclohexane to yield N-[6-(2-methyl-pyrrol-1-ylmethyl)-2,4-dioxo-7-trifluoromethyl-1,4-dihydro-2H-quinazolin-3-yl]-methanesulfonamide (130 mg, 0.312 mmol, 73%) as a light-orange solid. $^1$H-NMR (DMSO-d$_6$, 400 MHz) 3.11 ppm (s, 3H, SO$_2$—C$\underline{H_3}$; LC-MS rt=3.994 mn;

MS: m/z 416.9 [M+H]$^+$ Column: SunFireC18, 4.6*50 mn, 3.5 um; Positive MS Water/Acetonitrile 95:5 to 5:95 in 5 min, Flow: 1.5 mL/min

Example 44

N-[7-Isopropyl-6-(2-methyl-2H-pyrazol-3-yl)-2,4-dioxo-1,4-dihydro-2H-quinazolin-3-yl]-methanesulfonamide 2-Amino-4-isopropyl-5-(2-methyl-2H-pyrazol-3-yl)-benzoic acid methyl ester

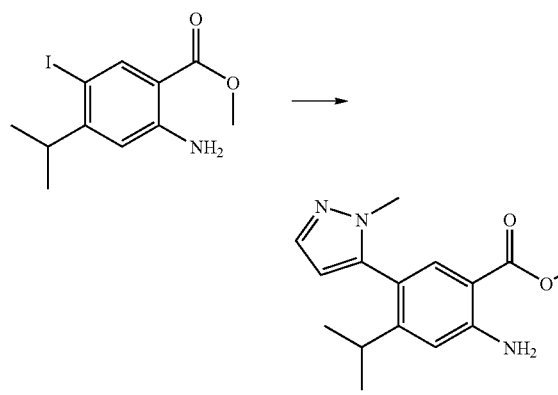

The 2-amino-5-iodo-4-isopropyl-benzoic acid methyl ester required for the coupling reaction described below was prepared according to the procedures described in WO 2004/033435 A1.

The 1-methyl-5-tributylstannanyl-1H-pyrazole required for the coupling reaction was prepared according to the procedure described above.

2-Amino-5-iodo-4-isopropyl-benzoic acid methyl ester (300 mg, 0.94 mmol) and 1-methyl-5-tributylstannanyl-1H-pyrazole (523 mg, 1.5 equiv) were weighed in air and added in a flame-dried flask. [Bistriphenylphosphine]dichloropalladium (67.3 mg, 0.1 equiv) was added and the flask was closed by a septum. Dioxane (1 mL) was added and the mixture was stirred for 18 h (TLC control) at 100° C. The mixture was dissolved with EtOAc, filtered and evaporated to dryness. The crude product was purified by flash chromatography (hexanes to EtOAc/hexanes (4:6)) to yield 2-amino-4-isopropyl-5-(2-methyl-2H-pyrazol-3-yl)-benzoic acid methyl ester (169 mg, 66%) as a yellow solid. (ESI-MS: m/z 274 [M+H]$^+$, rt 5.20 min).

2-(4-Chloro-phenoxycarbonylamino)-4-isopropyl-5-(2-methyl-2H-pyrazol-3-yl)-benzoic acid methyl ester

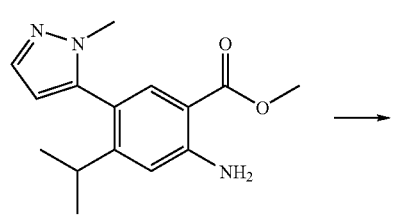

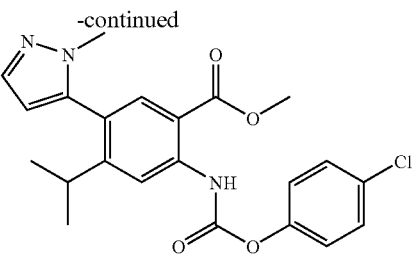

4-Chlorophenyl-chloroformate (88 μL, 1.1 equiv) was added to a solution of 2-amino-4-isopropyl-5-(2-methyl-2H-pyrazol-3-yl)-benzoic acid methyl ester (156 mg, 0.57 mmol) in dioxane (1.5 mL). The mixture was stirred for 2 h (TLC control) at 80° C. The mixture was evaporated to dryness. The obtained yellow solid was used in the next step without further purification. (rt 6.77 min)

N-[7-Isopropyl-6-(2-methyl-2H-pyrazol-3-yl)-2,4-dioxo-1,4-dihydro-2H-quinazolin-3-yl]-methanesulfonamide

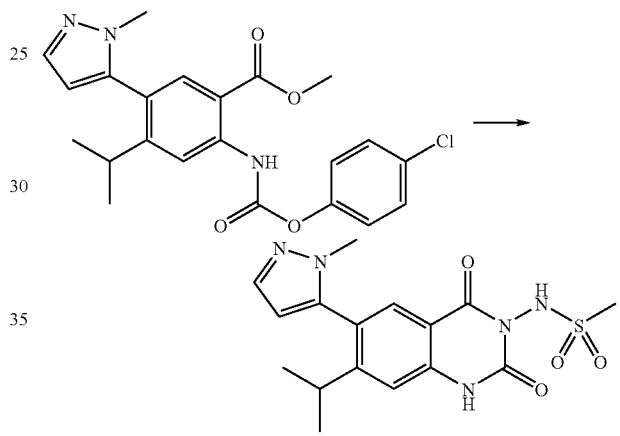

CH$_3$SO$_2$NHNH$_2$ (79.5 mg, 1.1 equiv) and i-Pr$_2$NEt (225 μL, 2 equiv) were added to a solution of 2-(4-chloro-phenoxycarbonylamino)-4-isopropyl-5-(2-methyl-2H-pyrazol-3-yl)-benzoic acid methyl ester (281 mg, 0.65 mmol) in dioxane (8 mL). The mixture was stirred for 16 h (TLC control) at 80° C. The mixture was evaporated to dryness. The crude product was purified by flash chromatography (MeOH/DCM (1:9)) to provide N-[7-isopropyl-6-(2-methyl-2H-pyrazol-3-yl)-2,4-dioxo-1,4-dihydro-2H-quinazolin-3-yl]-methanesulfonamide as a white solid (120 mg, 48%) (ESI-MS: m/z 378 [M+H]$^+$, rt 4.20 min).

The following products were synthesized by analogous procedures.

Example 45

N-[7-Isopropyl-2,4-dioxo-6-(2H-pyrazol-3-yl)-1,4-dihydro-2H-quinazolin-3-yl]-methanesulfonamide

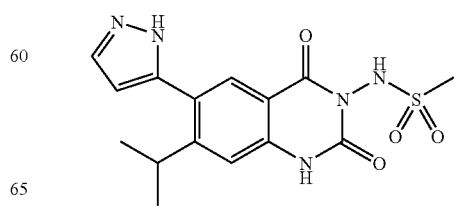

ESI-MS: m/z 364 [M+H]$^+$, rt 4.00 min

Example 46

N-[7-Isopropyl-2,4-dioxo-6-(1H-pyrazol-4-yl)-1,4-dihydro-2H-quinazolin-3-yl]-methanesulfonamide

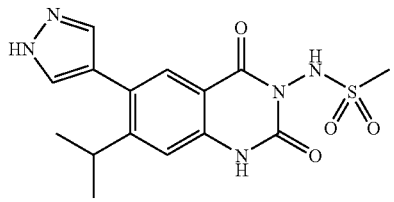

ESI-MS: m/z 364 [M+H]$^+$, rt 3.76 min

Example 47

N-[7-Isopropyl-6-(1-methyl-1H-pyrazol-4-yl)-2,4-dioxo-1,4-dihydro-2H-quinazolin-3-yl]-methanesulfonamide

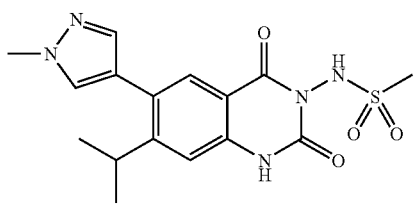

ESI-MS: m/z 378 [M+H]$^+$, rt 3.99 min

Example 48

N-(2,4-Dioxo-6-pyridin-4-yl-7-trifluoromethyl-1,4-dihydro-2H-quinazolin-3-yl)-methanesulfonamide

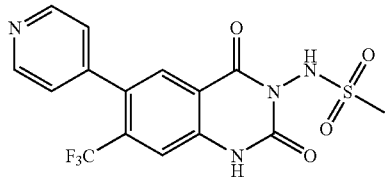

ESI-MS: m/z 401 [M+H]$^+$, rt 0.91 min.

Example 49

N-(2,4-Dioxo-6-pyridin-3-yl-7-trifluoromethyl-1,4-dihydro-2H-quinazolin-3-yl)-methanesulfonamide

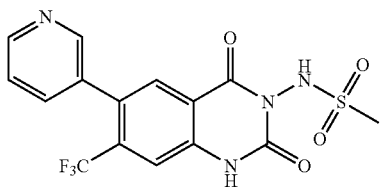

ESI-MS: m/z 401 [M+H]$^+$, rt 0.97 min

Example 50

N-[6-(6-Methoxy-pyridin-3-yl)-2,4-dioxo-7-trifluoromethyl-1,4-dihydro-2H-quinazolin-3-yl]-methanesulfonamide

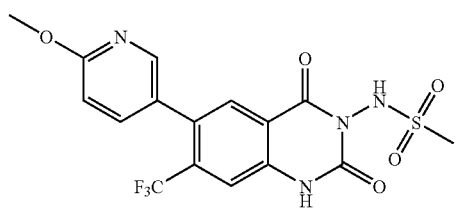

ESI-MS: m/z 431 [M+H]$^+$, rt 4.68 min

Example 51

N-(2,4-Dioxo-6-pyridin-2-yl-7-trifluoromethyl-1,4-dihydro-2H-quinazolin-3yl)-methanesulfonamide

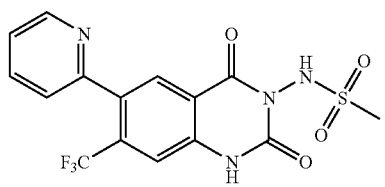

ES-MS: m/z 401 [M+H]$^+$ rt: 8.54 min

Example 52

N-(2,4-Dioxo-6-pyrimidin-4-yl-7-trifluoromethyl-1,4-dihydro-2H-quinazolin-3yl)-methanesulfonamide

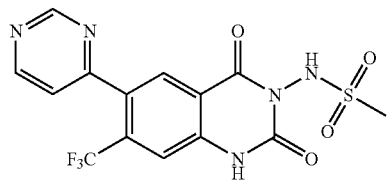

ES-MS: m/z 402 [M+H]$^+$, rt: 7.90 min

Example 53

N-[2,4-Dioxo-6-(1H-pyrrol-2-yl)-7-trifluoromethyl-1,4-dihydro-2H-quinazolin-3-yl]methanesulfonamide

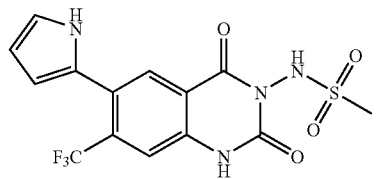

ES-MS: m/z 420 [M+NH$_4$]$^+$, rt 4.67 min

Example 54

N-[6-(1H-Indol-2-yl)-2,4-Dioxo 7-trifluoromethyl-1,4-dihydro-2H-quinazolin-3-yl]methanesulfonamide

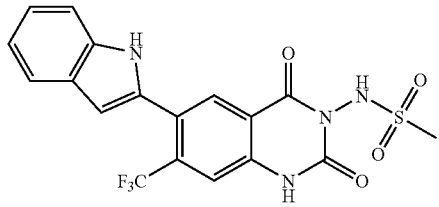

ES-MS: m/z 437 [M–H]⁻, rt: 9.29 min

Example 55

N-[6-(2-Isopropyl-2H-pyrazol-3-yl)-2,4-dioxo-7-trifluoromethyl-1,4-dihydro-2H-quinazolin-3-yl]-methanesulfonamide 1-Isopropyl-1H-pyrazole

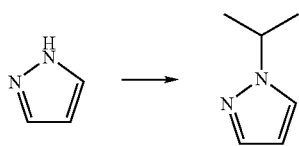

A mixture of pyrazole (5 g, 73.44 mmol), NaHCO$_3$ (12.2 g, 2 eq) and 2-bromopropane (15 mL, 2 eq) was stirred at 120° C. for 90 h. Over this period, 2-bromopropane was added when necessary to keep an adequate volume. The solids were removed by filtration and the resulting solution was distillated. From the distillation, a colorless syrup (4.6 g, bp 148° C., 57%) was collected.

1-Isopropyl-5-tributylstannanyl-1H-pyrazole

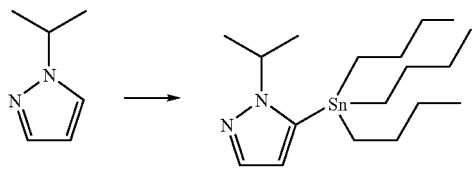

To a cold (–78° C.) solution of LDA (prepared from n-BuLi (7.99 mL, 1.6 M, 1.1 eq) and diisopropylamine (1.82 mL, 1.1 eq)) in THF, a solution of 1-isopropyl-1H-pyrazole (1.28 g, 11.6 mmol) in THF was added dropwise while keeping the temperature below –70° C. At the end of the addition, the mixture was stirred at –78° C. for 30 min. Tributyltin chloride (3.44 mL, 1.1 eq) was then added dropwise while keeping the temperature below –70° C. At the end of the addition, the mixture was stirred for 1 h at –78° C. and for 2 h at r.t. The solvent was removed in vacuo and the crude oil was dissolved into AcOEt. The organic phase was washed with water and dried over Na$_2$SO$_4$. The solution was concentrated in vacuo to afford a yellow oil (3.82 g, 82%).

2-Amino-4-trifluoromethyl-5-(2-isopropyl-2H-pyrazol-3-yl)-benzoic acid methyl ester

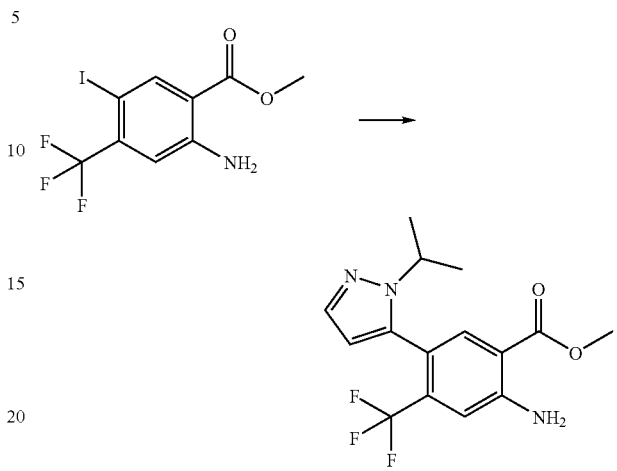

To a solution of 2-amino-4-trifluoromethyl-5-iodo-benzoic acid methyl ester (1.56 g, 4.52 mmol) in dioxane (40 mL) were added 1-isopropyl-5-tributylstannanyl-1H-pyrazole (2.34 g, 1.3 eq) and Pd(dppf)$_2$Cl$_2$ (369 mg, 0.1 eq) and the resulting mixture was stirred at 100° C. for 18 h. A second portion of catalyst (0.1 eq) was added and the mixture was stirred at 100° C. for 24 h. A last portion of catalyst (0.1 equiv) was added and the mixture was kept at 100° C. for 72 h. The solvent was removed in vacuo to provide a dark oil which was purified by flash chromatography (silica gel, EtOAc/hexanes (0:100 to 50:50)) to give the title compound (666 mg, 45%) as an off-white solid (ES-MS: m/z 328.3 [M+H]⁺, rt 5.60 min).

N-[7-Trifluoromethyl-6-(2-isopropyl-2H-pyrazol-3-yl)-2,4-dioxo-1,4-dihydro-2H-quinazolin-3-yl]-methanesulfonamide

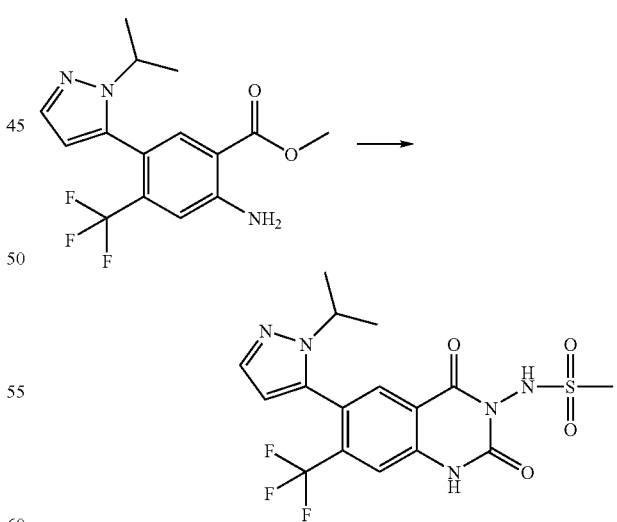

To a solution of 2-amino-4-trifluoromethyl-5-(2-isopropyl-2H-pyrazol-3-yl)-benzoic acid methyl ester (510 mg, 1.56 mmol) in DCM (20 mL) were added Et$_3$N (0.88 mL, 4 equiv) and then (CCl$_3$O)$_2$CO (377 mg, 0.8 equiv). The resulting mixture was stirred at r.t. for 3 h. The solvent was removed in vacuo and the crude intermediate was solubilized in THF. CH$_3$SO$_2$NHNH$_2$ (116 mg, 1.0 equiv) was added and the mixture was stirred at r.t. for 1 h. Then, aq NaOH (1N, 1.56 mL) was added and the mixture was stirred for 30 min. The solvent was removed in vacuo and water was added. The pH was adjusted to pH 3-4 by addition of 1N aq HCl. The aqueous phase was extracted with AcOEt twice. The organic phases were combined, washed with brine, dried ($Na_2SO_4$) and concentrated in vacuo to afford a crude solid. The crude product was purified by flash chromatography (silica gel, EtOAc/hexanes (25:75 to 100:0)) to furnish a white solid (285 mg, 42%). (ES-MS: m/z 432.4 [M+H]$^+$, rt 4.61 min). $^1$H-NMR (DMSO-$d_6$, 400 MHz) 12.05 (bs, 1H); 10.4 (bs, 1H); 7.88 (s, 1H); 7.66 (s, 1H); 7.55 (s, 1H); 6.27 (s, 1H); 4.08 (m, 1H); 3.16 (s, 1H); 1.31 (bd, 6H).

Example 56

N-[6-(2-Hydroxy-2H-pyrazol-3-yl)-2,4-dioxo-7-trifluoromethyl-1,4-dihydro-2H-quinazolin-3-yl]-methanesulfonamide Pyrazol-1-ol

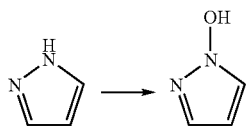

A mixture of pyrazole (10 g, 147 mmol) and mCPBA (36.2 g, 147 mmol) in AcOEt (500 mL) was stirred at r.t. for 10 d. The solution was concentrated in vacuo to afford a yellow paste which was extracted with water (6×100 mL) and concd HCl (100 mL). The aqueous phase was washed with DCM (2×100 mL). The organic layers were combined, concentrated in vacuo and extracted with concd HCl (50 mL). The aqueous phases were combined and 115 g of trisodium phosphate dodecahydrate were added followed by NaOH until pH 10. The aqueous phase was concentrated in vacuo to a volume of 400 mL and was then extracted in continue with DCM/$Et_2O$ (2/3) for 40 h. The organic phase was concentrated in vacuo and the residue dissolved in $CHCl_3$. The insoluble material was removed by filtration and washed with chloroform. The aqueous phase was acidified with 200 mL of concd HCl and then extracted continuously with DCM/$Et_2O$ (2/3) for 70 h. The organic phases were combined and concentrated in vacuo to afford pyrazol-1-ol (4.7 g, 38%) as a yellow syrup.

1-Benzyloxy-1H-pyrazole

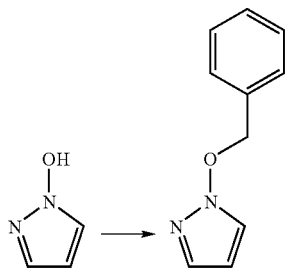

To a mixture of pyrazol-1-ol (1 g, 11.9 mmol) and i-$Pr_2NEt$ (2.02 mL, 11.9 mL) in DCM (15 mL) at 0° C. was added BnBr (4.09 mL, 23.8 mmol). The mixture was allowed to warm up to r.t. and stirred at this temperature for 22 h. The mixture was concentrated in vacuo to afford a yellow paste. The crude product was purified by flash chromatography (silica gel, hexanes/DCM/$Et_2O$ (100:0:0 to 80:10:10), $R_f$ 0.23 in hexanes/DCM/$Et_2O$ (34:3:3)) to provide the title product as a yellow oil (1.17 g, 56%).

1-Benzyloxy-5-tributylstannanyl-1H-pyrazole

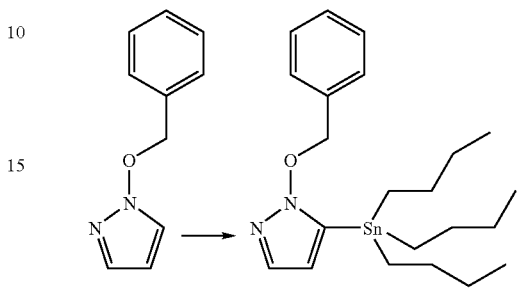

To a solution of 1-benzyloxy-1H-pyrazole (1.17 g, 6.72 mmol) in THF (15 mL) at −78° C. was added dropwise n-BuLi (4.6 mL, 1.6M, 7.4 mmol). The mixture was stirred at −78° C. for 2 h before addition of $Bu_3SnCl$ (1.99 mL, 7.38 mmol). The mixture was kept at this temperature for 1 h and was then allowed to warm up to r.t. and stirred for 1 h. The mixture was concentrated in vacuo and hexanes was added. The insoluble material was removed by filtration and the filtrate was concentrated in vacuo to afford 1-benzyloxy-5-tributylstannanyl-1H-pyrazole (3.3 g, 100%) as a yellow syrup.

2-Amino-5-(2-benzyloxy-2H-pyrazol-3-yl)-4-trifluoromethyl-benzoic acid methyl ester

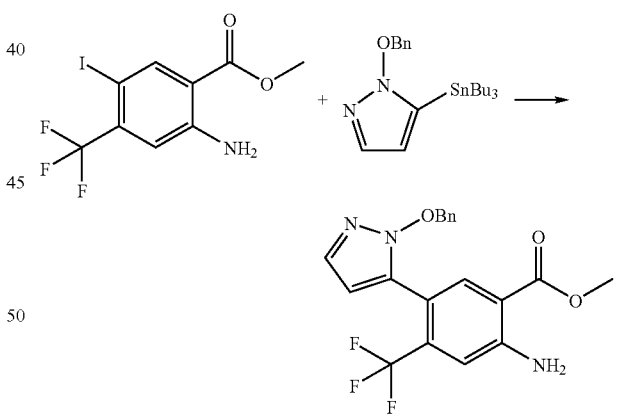

To a solution of 2-amino-4-trifluoromethyl-5-iodo-benzoic acid methyl ester (750 mg, 2.17 mmol) in dioxane (15 mL) were added 1-benzyloxy-5-tributylstannanyl-1H-pyrazole (1.24 g, 2.60 mmol) and Pd(dppf)$_2Cl_2$ (177 mg, 0.217 mmol) and the resulting mixture was stirred at 100° C. for 16 h. An additional portion of catalyst (0.1 equiv) was added and the mixture was stirred at 100° C. for an additional 24 h. The solvent was removed in vacuo to afford a dark oil. The crude product was purified by flash chromatography (silica gel, EtOAc/hexanes (0:100 to 50:50)) to provide the title compound as an off-white solid (263 mg, 31%). ES-MS: m/z 392.3 [M+H]$^+$, rt 6.48 min.

131

N-[6-(2-Benzyloxy-2H-pyrazol-3-yl)-2,4-dioxo-7-trifluoromethyl-1,4-dihydro-2H-quinazolin-3-yl]-methanesulfonamide

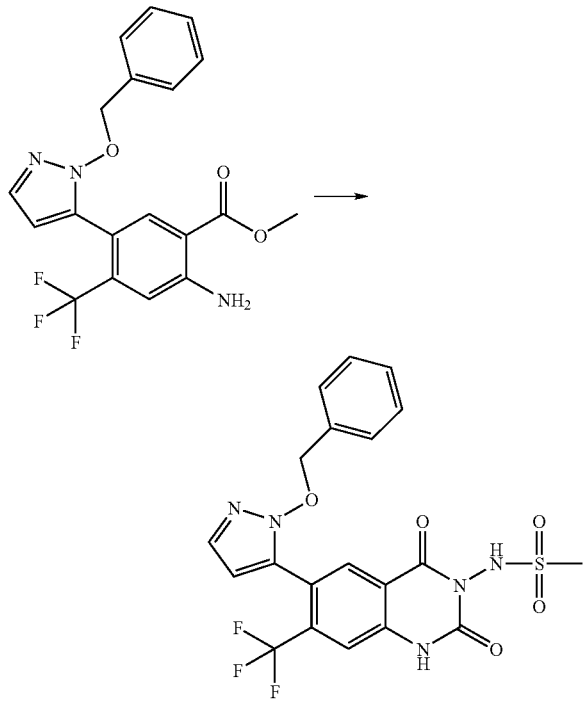

To a solution of 2-amino-5-(2-benzyloxy-2H-pyrazol-3-yl)-4-trifluoromethyl-benzoic acid methyl ester (263 mg, 0.672 mmol) in DCM (15 mL) were added successively Et$_3$N (0.37 mL, 2.69 mmol) and then (CCl$_3$O)$_2$CO (163 mg, 0.53 mmol). The resulting mixture was stirred at r.t. for 2.5 h. The solvent was removed in vacuo and the residue was solubilised in THF. CH$_3$SO$_2$NHNH$_2$ (98 mg, 0.87 mmol) was added. After stirring the mixture at r.t. for 2.5 h, it was treated with aq NaOH (1N, 0.87 mL) for 30 min. The solvent was removed in vacuo and water was added. The pH was adjusted to 3-4 by addition of 1N aq HCl. The aqueous phase was extracted with AcOEt (2×). The organic phases were combined, washed with brine, dried (Na$_2$SO$_4$) and concentrated in vacuo to afford a yellow syrup. The crude product was purified by flash chromatography (silica gel, DCM/MeOH (100:0 to 90:10)) to provide the title compound as an off-white solid (100 mg, 30%). ES-MS: m/z 496.3 [M+H]$^+$, rt 5.81 min.

N-[6-(2-Hydroxy-2H-pyrazol-3-yl)-2,4-dioxo-7-trifluoromethyl-1,4-dihydro-2H-quinazolin-3-yl]-methanesulfonamide

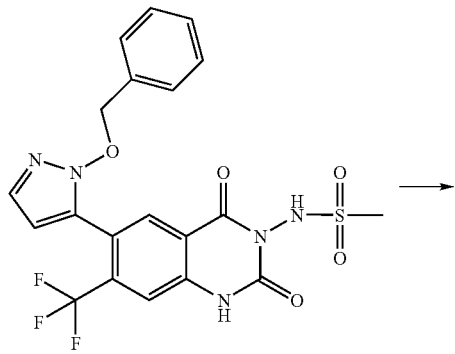

132

-continued

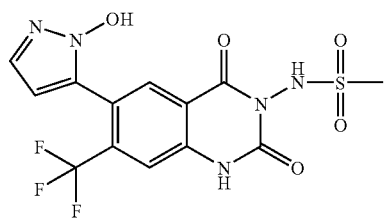

N-[6-(2-Benzyloxy-2H-pyrazol-3-yl)-2,4-dioxo-7-trifluoromethyl-1,4-dihydro-2H-quinazolin-3-yl]-methanesulfonamide (100 mg, 0.202 mmol) was hydrogenated over 10% Pd/C in MeOH (5 mL) for 16 h at r.t. The catalyst was removed by filtration over Celite. The solution was concentrated in vacuo and the resulting resin was dissolved in DCM (1 mL). Hexanes (4 mL) was added and the precipitate was filtered off, washed with hexanes and dried to afford the title compound as a grey powder (66 mg, 81% yield). ES-MS: m/z 447.3 [M+CH$_3$CN+H]$^+$, rt 4.90 min. $^1$H-NMR (DMSO-d$_6$, 400 MHz) 8.00 (s, H), 7.63 (s, 1H), 7.26 (d, J=2.34 Hz, 1H), 6.30 (d, J=1.89 Hz, 1H), 3.17 (s, 3H).

Example 57

N-{6-[2-(2-Methoxy-ethyl)-2H-pyrazol-3-yl]-2,4-dioxo-7-trifluoromethyl-1,4-dihydro-2H-quinazolin-3-yl}-methanesulfonamide 2-Acetylamino-5-((E)-3-dimethylamino-acryloyl)-4-trifluoromethyl-benzoic acid methyl ester

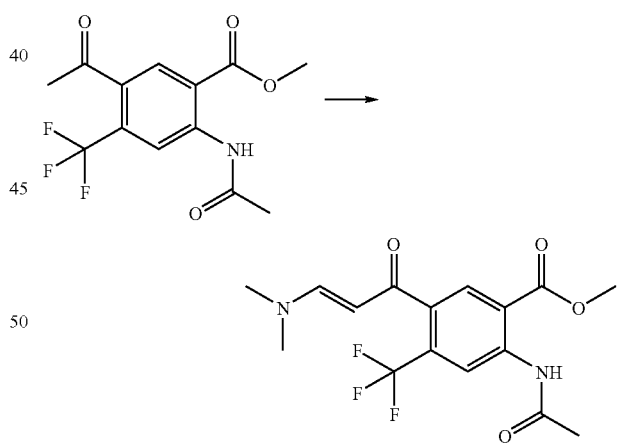

A mixture of 5-acetyl-2-acetylamino-4-trifluoromethyl-benzoic acid methyl ester (2.46 g, 8.1 mmol) and N,N dimethyl formamide dimethyl acetal (1.1 mL, 8.1 mmol) was stirred at 90° C. for 4 h. The mixture was diluted with AcOEt. The organic phase was washed with water, dried (Na$_2$SO$_4$) and concentrated in vacuo to afford a yellow paste. The crude product was purified by flash chromatography (silica gel, EtOAc/hexanes (50:50 to 100:0)) to provide the title compound as a beige paste (1.12 g, 39%). ES-MS: m/z 359.3 [M+H]$^+$, rt 4.77 min.

2-Acetylamino-5-[2-(2-methoxy-ethyl)-2H-pyrazol-3-yl]-4-trifluoromethyl-benzoic acid methyl ester

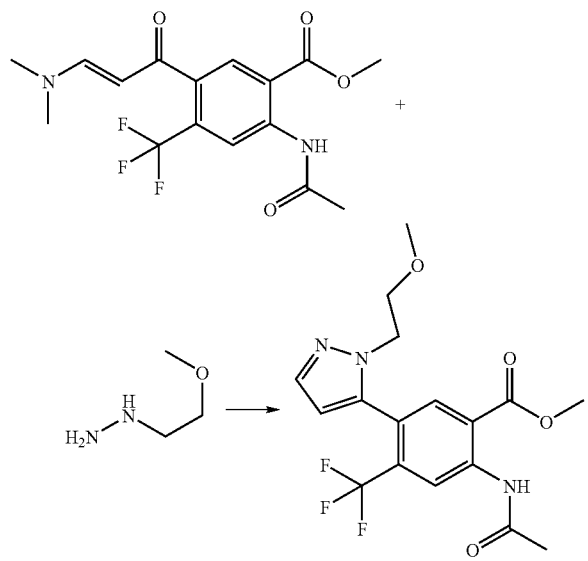

A mixture of 2-acetylamino-5-((E)-3-dimethylamino-acryloyl)-4-trifluoromethyl-benzoic acid methyl ester (600 mg, 1.67 mmol) and (2-methoxy-ethyl)-hydrazine (151 mg, 1.68 mmol) in toluene (10 mL) was stirred at 90° C. for 40 h. Four portions of (2-methoxy-ethyl)-hydrazine (one equiv each day) were added over 4 d and the mixture was kept at 90° C. The mixture was concentrated to dryness in vacuo. The crude product was purified by flash chromatography (silica gel, DCM/MeOH (100:0 to 60:40)) to provide the title compound as a yellow syrup (352 mg, 55%). ES-MS: m/z 386.3 [M+H]$^+$, rt 5.50 min.

2-Amino-5-[2-(2-methoxy-ethyl)-2H-pyrazol-3-yl]-4-trifluoromethyl-benzoic acid methyl ester

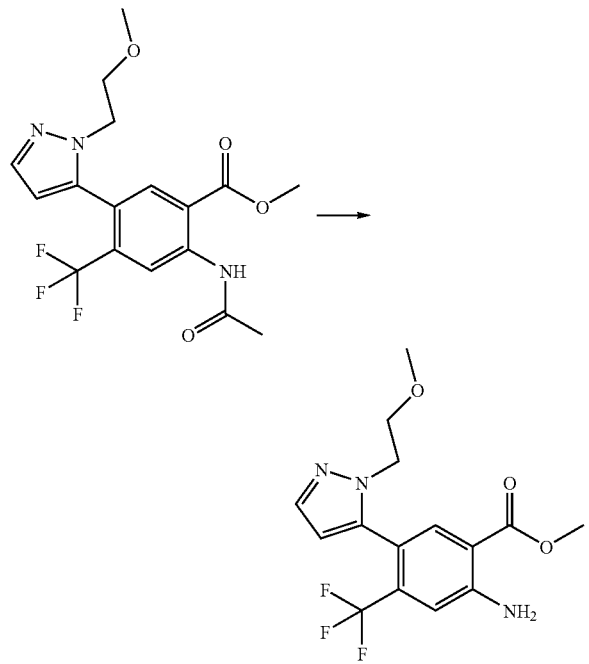

2-Acetylamino-5-[2-(2-methoxy-ethyl)-2H-pyrazol-3-yl]-4-trifluoromethyl-benzoic acid methyl ester (352 mg, 0.913 mmol) was treated with MeOH containing 10% of concd H$_2$SO$_4$ (10 mL) and the resultant solution was stirred at 70° C. for 2 h. The solvents were removed in vacuo and the residue was dissolved into water. The pH was adjusted to 10-11 by addition of 2N aq NaOH. The aqueous phase was extracted with AcOEt (2×). The organic phases were combined, dried (Na$_2$SO$_4$) and concentrated in vacuo to afford the title compound (238 mg, 76%). ES-MS: m/z 344.3 [M+H]$^+$, rt 5.52 min.

N-{6-[2-(2-Methoxy-ethyl)-2H-pyrazol-3-yl]-2,4-dioxo-7-trifluoromethyl-1,4-dihydro-2H-quinazolin-3-yl}-methanesulfonamide

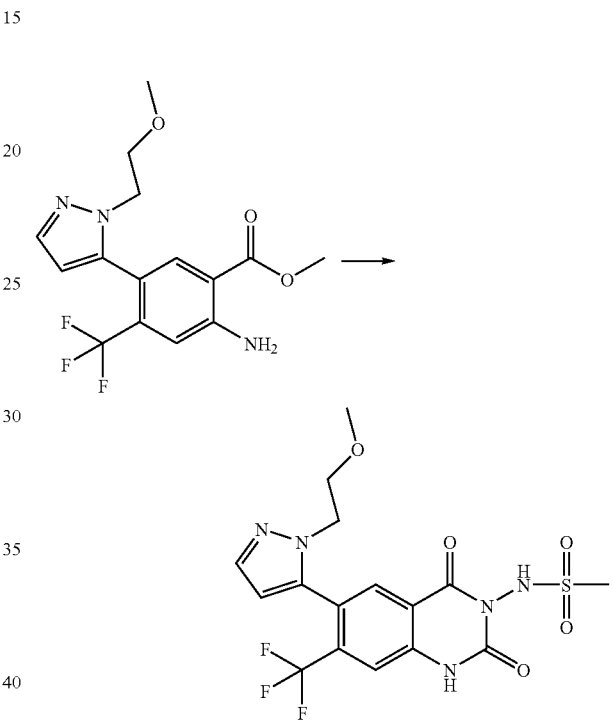

To a solution of 2-amino-5-[2-(2-methoxy-ethyl)-2H-pyrazol-3-yl]-4-trifluoromethyl-benzoic acid methyl ester (238 mg, 0.69 mmol) in DCM (15 mL) were added Et$_3$N (0.39 mL, 2.77 mmol) and then (CCl$_3$O)$_2$CO (168 mg, 0.55 mmol). The resulting mixture was stirred at r.t. for 3 h. The solvent was removed in vacuo and the residue was solubilised in THF. CH$_3$SO$_2$NHNH$_2$ (94 mg, 0.84 mmol) was added and the mixture was stirred at r.t. for 2 h. The solvent was removed in vacuo and water was added. The pH was adjusted to 2-3 by addition of 1N aq HCl. The aqueous phase was extracted with AcOEt (2×). The organic phases were combined, washed with brine, dried (Na$_2$SO$_4$) and concentrated in vacuo to afford a yellow syrup. The crude product was first purified by flash chromatography (silica gel, EtOAc/hexanes (50:50 to 100:0)). The fractions containing the expected product were concentrated. After precipitation in DCM/hexanes, the product was re-purified by flash chromatography (silica gel, DCM/MeOH (100:0 to 70:30)) to provide the title compound as a white powder (35 mg, 12%). ES-MS: m/z 448.3 [M+H]$^+$, rt 5.01 min. $^1$H-NMR (DMSO-d$_6$, 400 MHz) 12.06 (s, 1H), 10.40 (s, 1H), 8.00 (s, 1H), 7.63 (s, 1H), 7.54 (s, 1H), 6.29 (s, 1H), 3.94 (bs, 2H), 3.59 (bs, 2H), 3.15 (s, 3H), 3.09 (s, 3H).

Example 58

N-[6-(3-Methyl-3H-[1,2,3]triazol-4-yl)-2,4-dioxo-7-trifluoromethyl-1,4-dihydro-2H-quinazolin-3-yl]-methanesulfonamide 1-Methyl-1H-[1,2,3]triazole

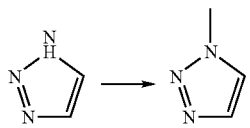

To a solution of NaOMe (3.91 g, 72.4 mmol) in MeOH (50 mL) was added 1,2,3-1H-triazole (5 g, 72.4 mmol). The mixture was then cooled to 0° C. and MeI (4.53 mL, 72.4 mmol) was added dropwise. The mixture was stirred allowed to warm up to r.t. and stirred at this temperature for 2 h. The solvent was removed in vacuo, the residue was treated with hot toluene (40 mL) and then filtered to afford a yellow paste. This paste was slurried in hot CHCl$_3$ and the solid was filtered off. The solid was washed with hot CHCl$_3$ (2×). The filtrates were combined, concentrated in vacuo and the residue distilled (112-116° C., water pump) to afford a mixture of starting material and final product. The distillate was dissolved in THF and NaH was added portionwise. The insoluble material was filtered off, washed with Et$_2$O and concentrated in vacuo to afford 1-methyl-1H-[1,2,3]triazole (1.33 g, 22%) as a yellow syrup.

1-Methyl-5-tributylstannanyl-1H-[1,2,3]triazole

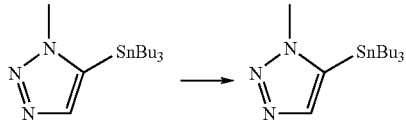

To a solution of 1-methyl-1H-[1,2,3]triazole (1.33 g, 16 mmol) in THF (20 mL) at −78° C., was added dropwise n-BuLi (11 mL, 1.6M, 18 mmol). The mixture was stirred at −78° C. for 2 h before addition of Bu$_3$SnCl (4.75 mL, 17.6 mmol). The mixture was stirred at this temperature for 1 h and at r.t. for 1 h. The mixture was concentrated in vacuo and hexanes was added. The insoluble material was removed by filtration and the filtrate was concentrated in vacuo to afford 1-methyl-5-tributylstannanyl-1H-[1,2,3]triazole (6.12 g, 82% yield) as a yellow syrup.

2-Amino-5-(3-methyl-3H-[1,2,3]triazol-4-yl)-4-trifluoromethyl-benzoic acid methyl ester

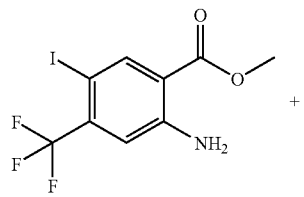

-continued

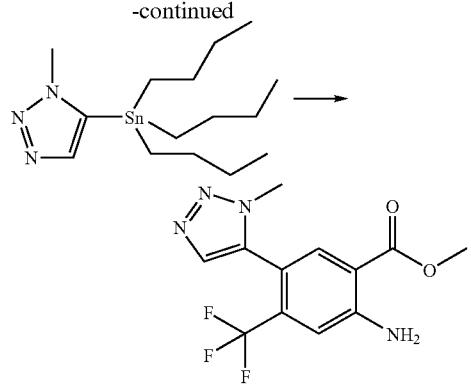

To a solution of 2-amino-4-trifluoromethyl-5-iodo-benzoic acid methyl ester (1 g, 2.90 mmol) in dioxane (20 mL) were added 1-methyl-5-tributylstannanyl-1H-[1,2,3]triazole (2.02 g, 4.34 mmol) and Pd(dppf)$_2$Cl$_2$ (237 mg, 0.29 mmol) and the resulting mixture was stirred at 100° C. for 24 h. A portion of catalyst (0.1 equiv) was added and the mixture was stirred at 100° C. for an additional 7 h. The solvent was removed in vacuo to afford a dark oil. The residue was purified by flash chromatography (silica gel, EtOAc/hexanes (0:1000 to 40:60)) to provide the title compound as an off-white solid (357 mg, 41% yield). ES-MS: m/z 301.2 [M+H]$^+$, rt 4.49 min.

N-[6-(3-Methyl-3H-[1,2,3]triazol-4-yl)-2,4-dioxo-7-trifluoromethyl-1,4-dihydro-2H-quinazolin-3-yl]-methanesulfonamide

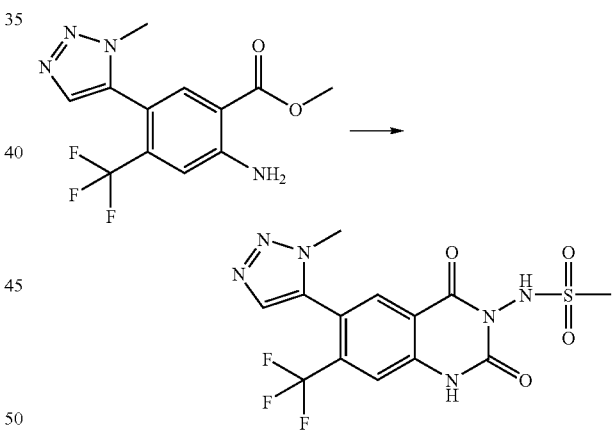

To a solution of 2-amino-5-(3-methyl-3H-[1,2,3]triazol-4-yl)-4-trifluoromethyl-benzoic acid methyl ester (357 mg, 1.19 mmol) in DCM (20 mL) were added Et$_3$N (0.67 mL, 4.76 mmol) and then (CCl$_3$O)$_2$CO (288 mg, 0.95 mmol). The resulting mixture was stirred at r.t. for 3 h. The solvent was removed in vacuo and the residue was solubilised in THF. CH$_3$SO$_2$NHNH$_2$ (170 mg, 1.54 mmol) was added and the mixture was stirred at r.t. for 2.5 h. Then, aq NaOH (1N, 1.6 mL) was added and the mixture was stirred for 30 min. The solvent was removed in vacuo and water was added. The pH was adjusted to 2-3 by addition of 1N aq HCl. The aqueous phase was extracted with AcOEt (2×). The organic phases were combined, washed with brine, dried (Na$_2$SO$_4$) and concentrated in vacuo to afford a yellow syrup. The yellow syrup was dissolved in DCM (2 mL). Hexanes (8 mL) was added and the resulting precipitate was filtered off, washed with hexanes and dried to afford the title compound as a grey powder (213 mg, 44%). ES-MS: m/z 405.3 [M+CH₃CN+H]⁺, rt 4.1 min. ¹H-NMR (DMSO-d₆, 400 MHz) 12.16 (s, 1H), 10.40 (s, 1H), 8.11 (s, 1H), 7.77 (s, 1H), 7.68 (s, 1H), 3.79 (s, 3H), 3.16 (s, 3H).

Example 59

N-[7-Fluoromethyl-6-(2-isopropyl-2H-pyrazol-3-yl)-2,4-dioxo-1,4-dihydro-2H-quinazolin-3-yl]-methanesulfonamide 2-Amino-4-hydroxymethyl-benzoic acid methyl ester

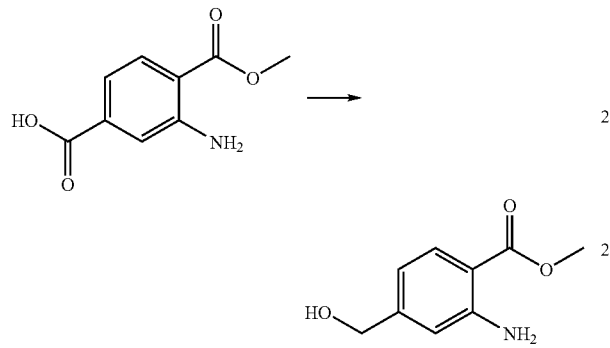

To a solution of 1-methyl 2-aminoterephthalate (10.0 g, 51.2 mmol) and NMM (5.75 mL, 1 equiv) in DME (90 mL) at −15° C. was added dropwise IBCl (6.7 mL, 1 equiv). The mixture was stirred at this temperature for 15 min. The salt was removed by filtration and the solution was cooled down to −15° C. A solution of NaBH₄ (3.06 g, 1.5 equiv) in water (30 mL) was added carefully dropwise. At the end of the addition, water (100 mL) was added and the mixture was stirred at r.t. for 15 min. Aq NaOH (2N, 50 mL) was added and the aqueous phase was extracted twice with AcOEt. The organic phase were combined and dried (Na₂SO₄). The solution was concentrated in vacuo to afford a white solid (8.0 g, 86%) (ES-MS: m/z 182.1 [M+H]⁺, rt 3.50 min).

2-Acetylamino-4-hydroxymethyl-benzoic acid methyl ester

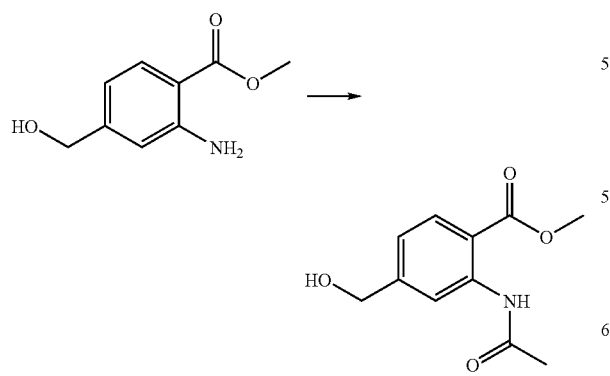

To a solution of 2-amino-4-hydroxymethyl-benzoic acid methyl ester (7.8 g, 43 mmol) in dioxane (150 mL) was added acetyl chloride (3.04 mL, 1 equiv) and the resulting mixture was stirred at 90° C. for 18 h. The solution was concentrated in vacuo and the resulting oil was sonicated in DCM/hexanes (2/8). The solid was filtered off, washed with hexanes and dried to afford a white solid (7.03 g, 73.2%) (ES-MS: m/z 224.2 [M+H]⁺, rt 3.75 min).

2-Acetylamino-4-methanesulfonyloxymethyl-benzoic acid methyl ester

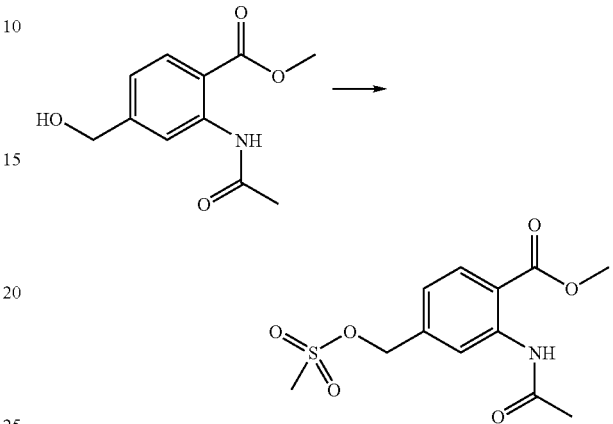

To a solution of 2-acetylamino-4-hydroxymethyl-benzoic acid methyl ester (4 g, 17.9 mmol) and Et₃N (7.5 mL, 3.0 equiv) in DCM (100 mL) at 0° C. was added MsCl (2.1 mL, 1.5 equiv) dropwise. At the end of the addition, the mixture was stirred 1 h at 0° C. The organic phase was washed with a saturated solution of NaHCO₃ and then dried (Na₂SO₄). The solution was concentrated in vacuo to afford the title compound as a brown paste (5.4 g, 100%) (ES-MS: m/z 302.2 [M+H]⁺, rt 4.58 min).

2-Acetylamino-4-fluoromethyl-benzoic acid methyl ester

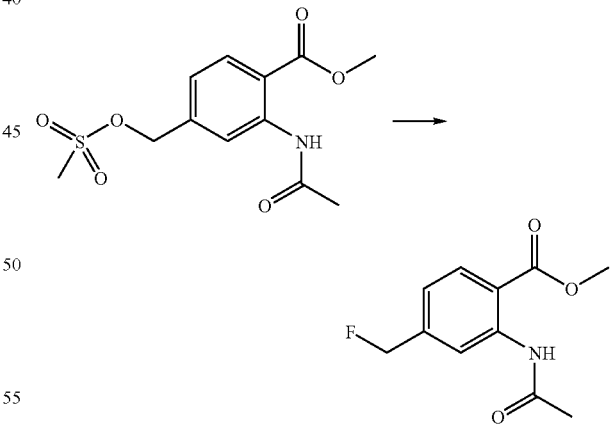

A solution of 2-acetylamino-4-methanesulfonyloxymethyl-benzoic acid methyl ester (5.2 g, 17.3 mmol) in CH₃CN (10 mL) was added over a period of 10 min to a pre-stirred mixture of potassium fluoride (2.01 g, 2 equiv) and 18-crown-6 (461 mg, 0.1 equiv) in CH₃CN (40 mL). The mixture was then stirred at 80° C. for 48 h. The mixture was cooled down and diluted with AcOEt. The organic phase was washed with aq HCl 1N, a saturated solution of NaHCO₃ and brine, dried (Na₂SO₄) and concentrated in vacuo to afford a brown residue (2.6 g). The crude product was purified by flash chromatography (silica gel, EtOAc/hexanes (0:100 to 40:60))

to provide a white solid (1.5 g, 39%) (ES-MS: m/z 267.2 [M+CH$_3$CN+H]$^+$, rt 4.86 min).

2-Amino-4-fluoromethyl-benzoic acid methyl ester

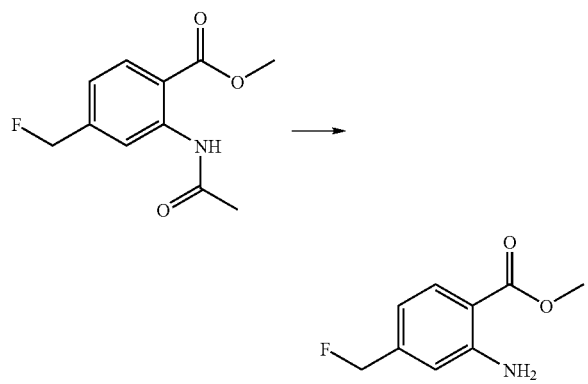

To a solution of 2-acetylamino-4-fluoromethyl-benzoic acid methyl ester (1.5 g, 6.66 equiv) in MeOH (50 mL) was added concd sulfuric acid (4 mL) and the mixture was refluxed for 1 h. The mixture was cooled down and concentrated in vacuo. Water was added and the pH was adjusted to 9-10 by addition of 2N NaOH. The aqueous phase was extracted with AcOEt. The organic phase were combined, washed with brine and dried (Na$_2$SO$_4$). The solution was concentrated in vacuo to afford the title compound as a yellow-orange oil (1.24 g, 100%) (ES-MS: m/z 184.1 [M+H]$^+$, rt 4.91 min).

2-Amino-4-fluoromethyl-5-iodo-benzoic acid methyl ester

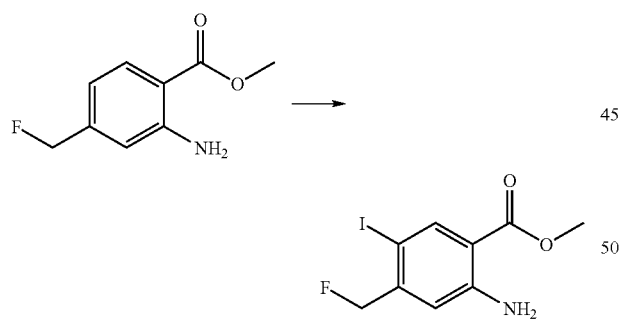

To a solution of 2-amino-4-fluoromethyl-benzoic acid methyl ester (1.24 g, 6.77 mmol) in EtOH (50 mL) were added silver sulfate (2.12 g, 1 equiv) and iodine (1.72 g, 1 equiv) and the resulting mixture was stirred at r.t. for 1 h. The mixture was filtered through a pad of celite and washed with EtOH. The solution was concentrated in vacuo and then diluted with AcOEt. The organic phase was washed with sat. aq NaHCO$_3$, 1M sodium thiosulfate solution and brine, dried (Na$_2$SO$_4$) and concentrated in vacuo to a afford a light solid (2.4 g). The crude product was purified by flash chromatography (silica gel, EtOAc/hexanes (0:100 to 20:80)) to provide an off-white solid (1.55 g, 74%) (ES-MS: m/z 351.2 [M+CH$_3$CN+H]$^+$, rt 5.81 min).

2-Amino-4-fluoromethyl-5-(2-isopropyl-2H-pyrazol-3-yl)-benzoic acid methyl ester

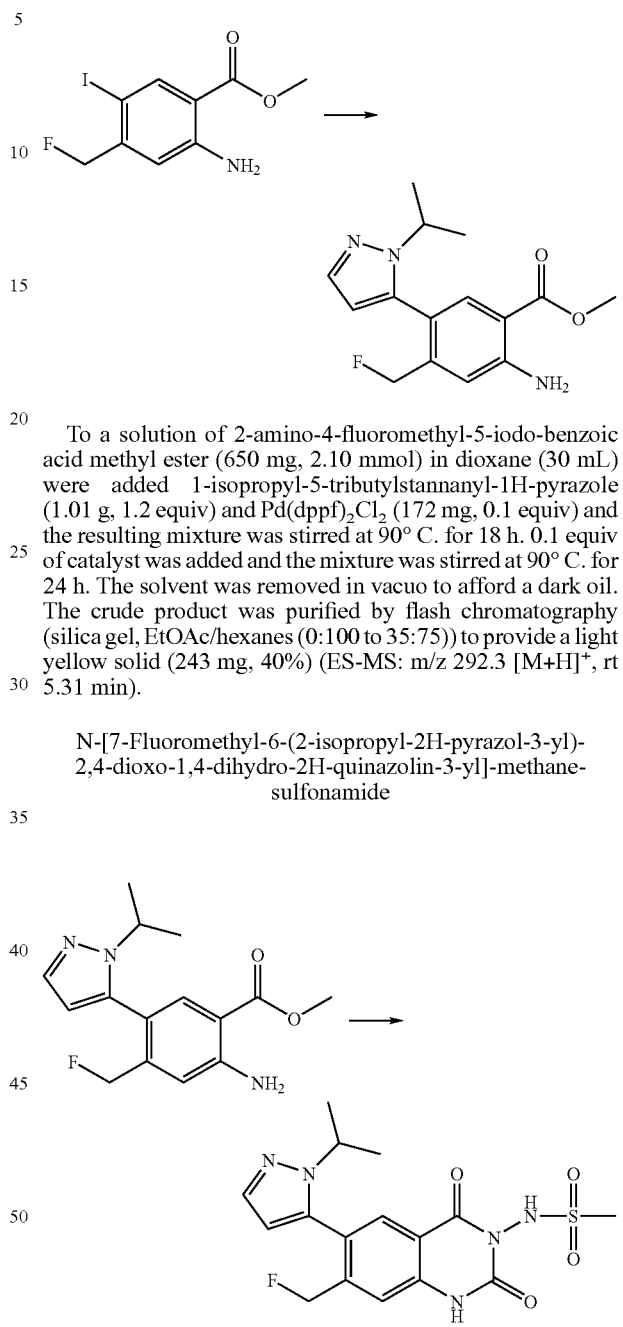

To a solution of 2-amino-4-fluoromethyl-5-iodo-benzoic acid methyl ester (650 mg, 2.10 mmol) in dioxane (30 mL) were added 1-isopropyl-5-tributylstannanyl-1H-pyrazole (1.01 g, 1.2 equiv) and Pd(dppf)$_2$Cl$_2$ (172 mg, 0.1 equiv) and the resulting mixture was stirred at 90° C. for 18 h. 0.1 equiv of catalyst was added and the mixture was stirred at 90° C. for 24 h. The solvent was removed in vacuo to afford a dark oil. The crude product was purified by flash chromatography (silica gel, EtOAc/hexanes (0:100 to 35:75)) to provide a light yellow solid (243 mg, 40%) (ES-MS: m/z 292.3 [M+H]$^+$, rt 5.31 min).

N-[7-Fluoromethyl-6-(2-isopropyl-2H-pyrazol-3-yl)-2,4-dioxo-1,4-dihydro-2H-quinazolin-3-yl]-methanesulfonamide To a solution of 2-amino-4-fluoromethyl-5-(2-isopropyl-2H-pyrazol-3-yl)-benzoic acid methyl ester (243 mg, 0.834 mmol) in DCM (15 mL) were added Et$_3$N (0.35 mL, 3 equiv) and then (CCl$_3$O)$_2$CO (177 mg, 0.7 equiv). The resulting mixture was stirred at r.t. for 1 h. The solvent was removed in vacuo and the crude solubilised in THF. CH$_3$SO$_2$NHNH$_2$ (101 mg, 1.1 equiv) was added and the mixture was stirred at r.t. for 1 h. Then, aq NaOH (1N, 0.92 mL) was added and the mixture was stirred for 30 min. The solvent was removed in vacuo and water was added. The pH was adjusted to 3-4 by addition of 1N aq HCl. The aqueous phase was extracted with AcOEt twice. The organic phases were combined, washed with brine, dried (Na$_2$SO$_4$) and concentrated in vacuo to afford a crude solid. This solid was dissolved into 10 mL of DCM and then 10 ml of hexanes was added. The mixture was sonicated for 1 min. The resulting solid was filtered off, washed with hexanes and high-vacuum dried to afford the title compound (227 mg, 69%) as an off-white solid. (ES-MS: m/z 396.4 [M+H]$^+$, rt 4.39 min). $^1$H-NMR (DMSO-d$_6$, 400 MHz) 11.07 (bs, 1H); 7.76 (d, 1H, J=1.07 Hz); 7.55 (d, 1H, J=1.58 Hz); 7.40 (s, 1H); 6.30 (d, 1H, J=1.77 Hz); 5.30 (d, 2H, J=46.55 Hz); 4.14 (m, 1H); 3.16 (s, 1H); 1.31 (d, 6H, J=6.51 Hz).

Example 60

N-[7-Difluoromethyl-6-(2-methyl-2H-pyrazol-3-yl)-2,4-dioxo-1,4-dihydro-2H-quinazolin-3-yl]-methane-sulfonamide 2-Acetylamino-4-formyl-benzoic acid methyl ester

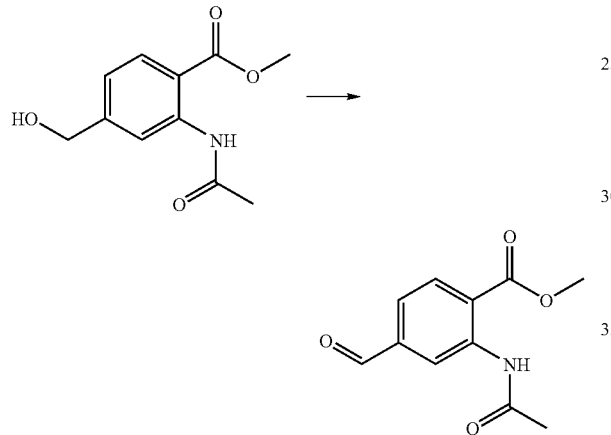

To a suspension of 2-acetylamino-4-hydroxymethyl-benzoic acid methyl ester (1.7 g, 7.62 mmol) in DCM (40 mL) was added MnO$_2$ (1.32 g, 2 equiv) and the resulting mixture was stirred at 50° C. for 18 h. MnO$_2$ (0.66 g, 1 equiv) was added and the mixture was stirred at 50° C. for 2 h. The mixture was cooled down, filtered through a pad of celite and washed with DCM. The solvent was removed in vacuo to afford a crude yellow solid. The residue was purified by flash chromatography (silica gel, EtOAc/hexanes (0:100 to 50:50)) to provide the title compound as a light yellow solid (1.15 g, 68%) (ES-MS: m/z 263.2 [M+CH$_3$CN+H]$^+$, rt 4.29 min).

2-Acetylamino-4-difluoromethyl-benzoic acid methyl ester

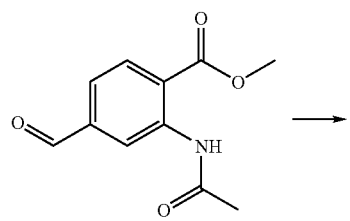

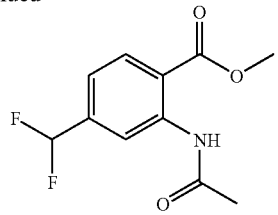

To a solution of 2-acetylamino-4-formyl-benzoic acid methyl ester (1.1 g, 4.97 mmol) in DCM (50 mL) was added deoxo-fluor (3.56 mL, 1.7 equiv) and the resulting solution was stirred at r.t. for 18 h. The mixture was poured into sat. aq NaHCO$_3$ (100 mL) and then stirred for 15 min. The organic phase was separated from the aqueous phase, dried (Na$_2$SO$_4$) and concentrated in vacuo to provide a crude orange oil (1.5 g). The residue was purified by flash chromatography (silica gel, EtOAc/hexanes (0:100 to 40:60)) to provide the title compound as a yellow solid (670 mg, 55%). ES-MS: m/z 285.3 [M+CH$_3$CN+H]$^+$, rt 5.03 min.

2-Amino-4-difluoromethyl-benzoic acid methyl ester

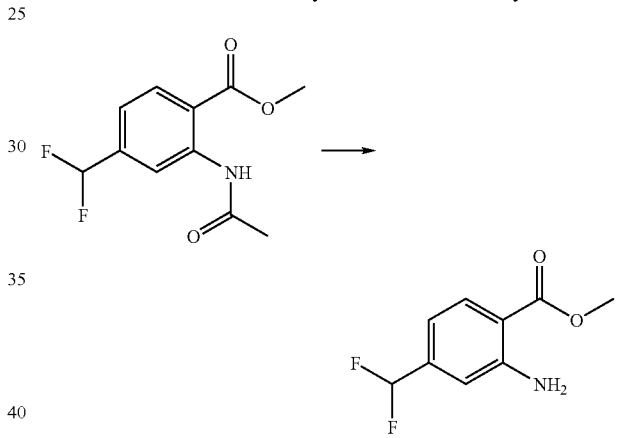

2-Acetylamino-4-difluoromethyl-benzoic acid methyl ester (3.3 g, 13.6 mmol) was dissolved in MeOH (100 mL) and concd H$_2$SO$_4$ (8 mL) was added. The resulting solution was refluxed for 1 h. The mixture was cooled down and concentrated in vacuo. Water was added and the pH was adjusted to 9-10 by addition of 2N NaOH. The aqueous phase was extracted with AcOEt (2×). The organic phases were combined, washed with brine and dried (Na$_2$SO$_4$). The solution was concentrated in vacuo to afford a yellow oil (2.6 g). The crude product was purified by flash chromatography (silica gel, EtOAc/hexanes (0:100 to 40:60)) to provide the title compound as a light yellow solid (1.98 g, 72.5% yield). ES-MS: m/z 243.2 [M+CH$_3$CN+H]$^+$, rt 5.20 min.

2-Amino-4-difluoromethyl-5-iodo-benzoic acid methyl ester

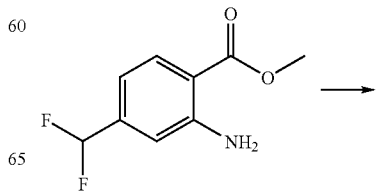

-continued

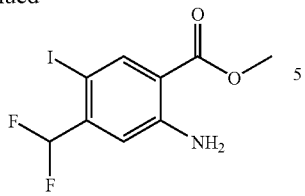

To a solution of 2-amino-4-difluoromethyl-benzoic acid methyl ester (1.98 g, 9.84 mmol) in EtOH (75 mL) were added Ag$_2$SO$_4$ (3.08 g, 1 equiv) and 12 (2.50 g, 1 equiv) and the resulting mixture was stirred at r.t. for 1 hour. The mixture was filtered through a pad of celite and washed with EtOH. The solution was concentrated in vacuo and then diluted with AcOEt. The organic phase was washed with sat. aq NaHCO$_3$, 1M aq Na$_2$S$_2$O$_3$ and brine and dried (Na$_2$SO$_4$). The solution was concentrated in vacuo to afford the title compound as an off-white solid (2.9 g, 90% yield). ES-MS: m/z 369.2 [M+CH$_3$CN+H]$^+$, rt 5.87 min.

2-Amino-4-difluoromethyl-5-(2-methyl-2H-pyrazol-3-yl)-benzoic acid methyl ester

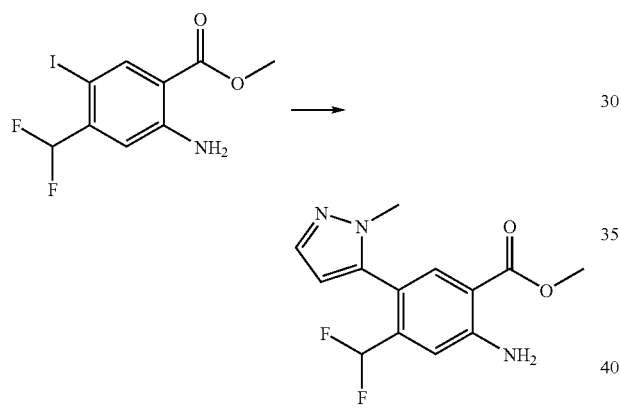

To a solution of 2-amino-4-difluoromethyl-5-iodo-benzoic acid methyl ester (750 mg, 2.29 mmol) in dioxane (30 mL) were added 1-methyl-5-tributylstannanyl-1H-pyrazole (1.28 g, 1.5 equiv) and Pd(PPh$_3$)$_2$Cl$_2$ (246 mg, 0.15 equiv) and the resulting mixture was stirred at 90° C. for 18 h. The solvent was removed in vacuo to afford a dark oil. The crude product was purified by flash chromatography (silica gel, EtOAc/hexanes (0:100 to 50:50)) to provide the title compound as a yellow oil (200 mg, 31%). ES-MS: m/z 282.3 [M+H]$^+$, rt 4.97 min.

N-[7-Difluoromethyl-6-(2-methyl-2H-pyrazol-3-yl)-2,4-dioxo-1,4-dihydro-2H-quinazolin-3-yl]-methanesulfonamide

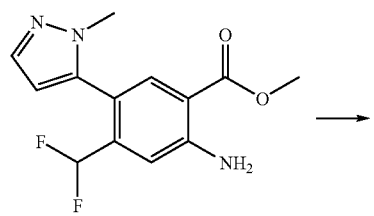

-continued

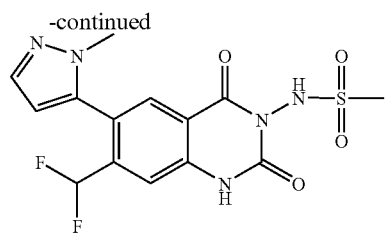

To a solution of 2-amino-4-difluoromethyl-5-(2-methyl-2H-pyrazol-3-yl)-benzoic acid methyl ester (200 mg, 0.71 mmol) in DCM (15 mL), was added (CCl$_3$O)$_2$CO (151 mg, 0.7 equiv). The resulting mixture was stirred at r.t. for 1 h. The solvent was removed in vacuo and the residue was solubilized in THF. CH$_3$SO$_2$NHNH$_2$ (86 mg, 1.1 equiv) was added and, after stirring at r.t. for 1 h, the mixture was treated with aq NaOH (1N, 0.78 mL) for 30 min. The solvent was removed in vacuo and water was added. The pH was adjusted to 3-4 by addition of 1N aq HCl. The aqueous phase was extracted with AcOEt (2×). The organic phases were combined, washed with brine, dried (Na2SO4) and concentrated in vacuo to afford a crude solid. This solid was triturated in 15 mL of DCM/hexanes (1/1). The resulting solid was filtered off, washed with hexanes and dried to afford the title compound as an off-white solid (150 mg, 55%). ES-MS: m/z 386.3 [M+H]$^+$, rt 4.16 min. $^1$H-NMR (DMSO-d$_6$, 400 MHz) 12.04 (s, 1H), 10.34 (s, 1H); 7.93 (s, 1H); 7.55 (s, 1H); 7.52 (s, 1H); 6.83 (t, 1H, J=54 Hz), 6.34 (s, 1H). 3.62 (s, 3H); 3.17 (s, 1H)

Example 61

N-[7-Difluoromethyl-6-(2-isopropyl-2H-pyrazol-3-yl)-2,4-dioxo-1,4-dihydro-2H-quinazolin-3-yl]-methanesulfonamide 2-Amino-4-difluoromethyl-5-(2-isopropyl-2H-pyrazol-3-yl)-benzoic acid methyl ester

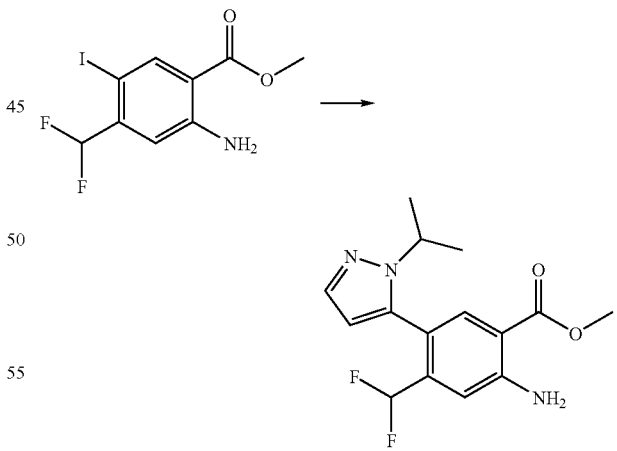

To a solution of 2-amino-4-difluoromethyl-5-iodo-benzoic acid methyl ester (750 mg, 2.29 mmol) in dioxane (30 mL) were added 1-isopropyl-5-tributylstannanyl-1H-pyrazole (1.1 g, 1.2 equiv) and Pd(dppf)$_2$Cl$_2$ (187 mg, 0.1 equiv) and the resulting mixture was stirred at 90° C. for 18 h. Another portion of catalyst (0.1 equiv) was added and the mixture was stirred at 90° C. for an additional 6 h. The solvent was removed in vacuo to afford a dark oil. The crude product was purified by flash chromatography (silica gel, EtOAc/hexanes (0:100 to 30:70)) to provide the title compound as an off-white solid (380 mg, 54%). ES-MS: m/z 310.3 [M+H]$^+$, rt 5.54 min.

N-[7-Difluoromethyl-6-(2-isopropyl-2H-pyrazol-3-yl)-2,4-dioxo-1,4-dihydro-2H-quinazolin-3-yl]-methanesulfonamide

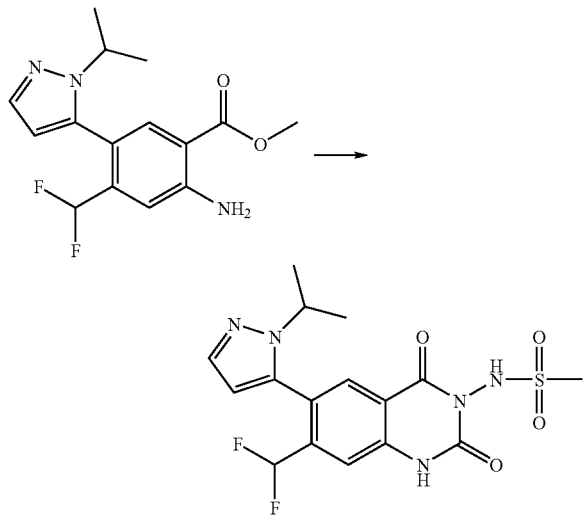

To a solution of 2-amino-4-difluoromethyl-5-(2-isopropyl-2H-pyrazol-3-yl)-benzoic acid methyl ester (380 mg, 1.23 mmol) in DCM (15 mL) were added Et$_3$N (0.52 mL, 3 equiv) and then (CCl$_3$O)$_2$CO (261 mg, 0.7 equiv). The resulting mixture was stirred at r.t. for 1 h. The solvent was removed in vacuo and the residue was solubilized in THF. CH$_3$SO$_2$NHNH$_2$ (149 mg, 1.1 equiv) was added and the mixture was stirred at r.t. for 1 h. Then, aq NaOH (1N, 1.4 mL) was added and the mixture was stirred at r.t. for 30 min. The solvent was removed in vacuo and water was added. The pH was adjusted to pH 3-4 by addition of 1N aq HCl. The aqueous phase was extracted with AcOEt (2×). The organic phases were combined, washed with brine, dried (Na$_2$SO$_4$) and concentrated in vacuo to afford a crude solid. This solid was dissolved in DCM (10 mL) and hexanes (10 mL) was added. The mixture was sonicated for 1 min. The resulting solid was filtered off, washed with hexanes and dried to afford the title compound as an off-white solid (305 mg, 60%). ES-MS: m/z 414.4 [M+H]$^+$, rt 4.52 min. $^1$H-NMR (DMSO-d$_6$, 400 MHz) 11.23 (bs, 1H); 7.83 (s, 1H); 7.57 (d, 1H, J=1.64 Hz); 7.55 (s, 1H); 6.80 (t, 1H, J=54.1 Hz); 6.32 (d, 1H, J=1.71 Hz); 4.12 (m, 1H); 3.16 (s, 1H); 1.31 (d, 6H, J=6.38 Hz).

Example 62

N-[7-ethyl-6-(2-methyl-2H-pyrazol-3-yl)-2,4-dioxo-1,4-dihydro-2H-quinazolin-3-yl]-methanesulfonamide 4-Bromo-2-nitro-benzoic acid methyl ester

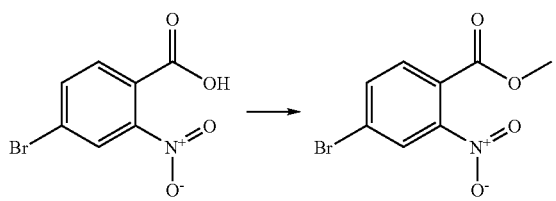

To a solution of 4-bromo-2-nitrobenzoic acid (25.3 g, 103 mmol) in DMF (200 mL) at 0° C. were added DBU (79.1 mL, 514.8 mmol) and MeI (32.2 mL, 515 mmol). The reaction mixture was stirred for 15 min at this temperature and for 72 h at r.t. The mixture was poured into water and extracted with EtOAc (2×). The combined organic layers were washed with water (2×), dried (Na$_2$SO$_4$) and the solvent was removed in vacuo. The residue was purified by flash chromatography (silica gel, 7:3 hexanes:EtOAc) to provide the title compound (26.24 g, 98%) as a yellow oil.

2-Nitro-4-vinyl-benzoic acid methyl ester

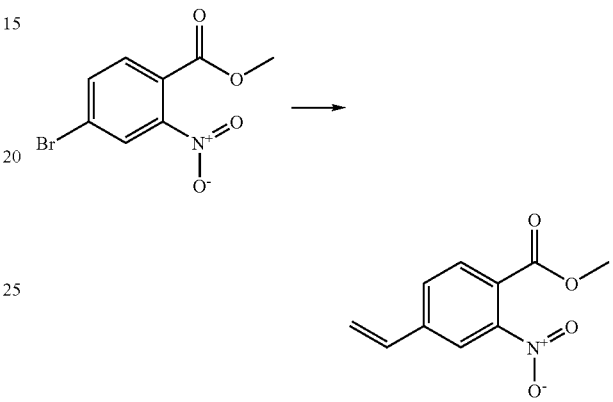

To a solution of 4-bromo-2-nitro-benzoic acid methyl ester (1 g, 3.85 mmol) in dioxane (5 mL) were added tributylvinyltin (1.7 mL, 5.76 mmol) and Pd(Ph$_3$P)$_2$Cl$_2$ (275.4 mg, 0.385 mmol). The reaction mixture was stirred at 80° C. for 18 h, was cooled to r.t. and was diluted with EtOAc. After removal of the precipitate by filtration, the solution was concentrated in vacuo. The residue was purified by flash chromatography (silica gel, hexanes 1:1 hexanes:EtOAc) to provide the title compound (820 mg, 100%, 97% purity by HPLC) as a yellow oil. ESI-MS: m/z 208.2 [M+H]$^+$, rt 5.14 min.

2-Amino-4-ethyl-benzoic acid methyl ester

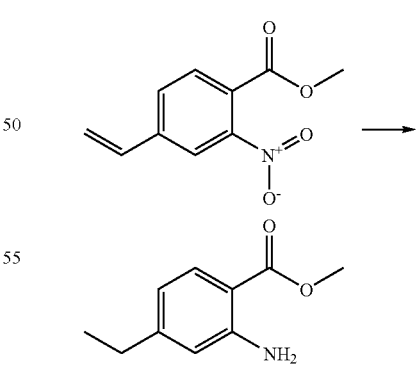

A solution of 2-nitro-4-vinyl-benzoic acid methyl ester (820 mg, 3.96 mmol) in MeOH (15 mL) was shaken under H$_2$ (0.1 bar) in the presence of Pd/C (10%, 0.2 g) at 50° C. for 5 h. After cooling to r.t., the reaction mixture was filtered and the solvent was removed in vacuo to provide the title product (680 mg, 96%) which was used in the next step without further purification. ESI-MS: m/z 180.1 [M+H]$^+$, rt 5.13 min

2-Amino-4-ethyl-5-iodo-benzoic acid methyl ester

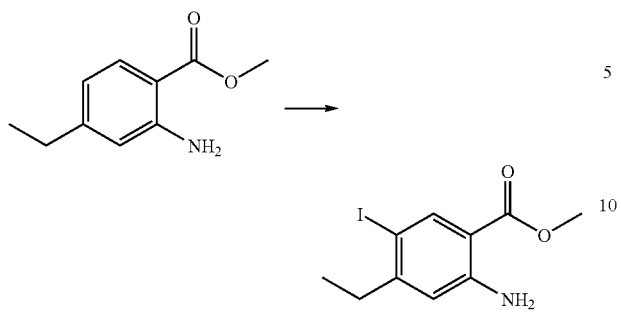

To a solution of 2-amino-4-ethyl-benzoic acid methyl ester (500 mg, 2.79 mmol) in EtOH (2 mL) were added $Ag_2SO_4$ (868.15 mg, 2.79 mmol) and 12 (708.1 mg, 2.79 mmol) and the resultant mixture was stirred at r.t. for 3 h. The reaction mixture was filtered and the solvent was removed in vacuo. The residue was dissolved in EtOAc and the organic phase was washed with 1M $Na_2S_2O_3$ and sat. aq $NaHCO_3$. The solvent was removed in vacuo and the orange oil was purified by flash chromatography (silica gel, hexanes→4:1 hexanes: EtOAc) to provide the title compound (620 mg, 73%) as an orange solid. ESI-MS: m/z 306.2 $[M+H]^+$, rt 6.03 min

2-Amino-4-ethyl-5-(2-methyl-2H-pyrazol-3-yl)-benzoic acid methyl ester

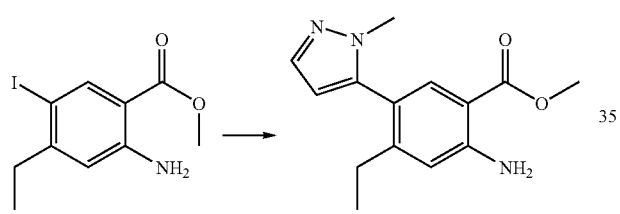

The 1-methyl-5-tributylstannanyl-1H-pyrazole required for the coupling reaction was prepared according to the procedure described above.

2-Amino-5-iodo-4-ethyl-benzoic acid methyl ester (280 mg, 0.92 mmol) and 1-methyl-5-tributylstannanyl-1H-pyrazole (409 mg, 1.2 equiv) were weighed in air and added to a flame-dried flask. [1,1'-bis(diphenylphosphino)-ferrocene] dichloropalladium (75 mg, 0.1 equiv) was added and the flask was closed by a septum. Dioxane (1 mL) was added and the mixture was stirred at 100° C. for 18 h (TLC control). The mixture was dissolved with EtOAc, filtered and evaporated to dryness. The crude product was purified by flash chromatography (hexanes to EtOAc/hexanes (4:6)) to yield 2-amino-4-ethyl-5-(2-methyl-2H-pyrazol-3-yl)-benzoic acid methyl ester (163 mg, 68% yield) as a yellow solid. ESI-MS: m/z 260.3 $[M+H]^+$, rt 6.37 min.

2-(4-Chloro-phenoxycarbonylamino)-4-ethyl-5-(2-methyl-2H-pyrazol-3-yl)-benzoic acid methyl ester

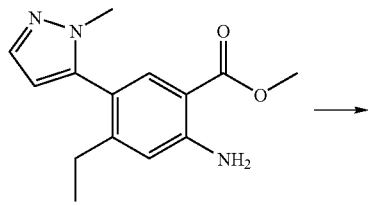

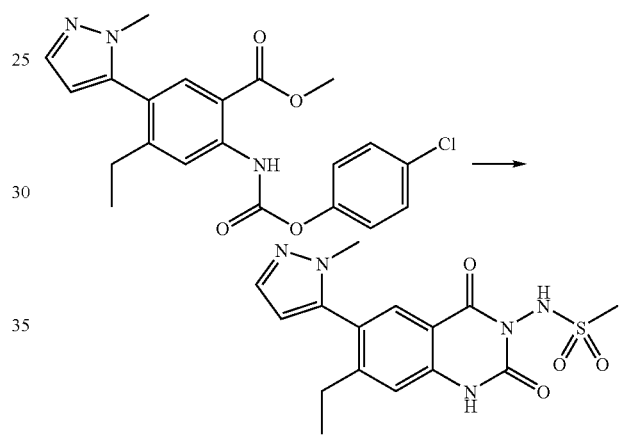

4-Chlorophenyl-chloroformate (86 μL, 1.1 equiv) was added to a solution of 2-amino-4-ethyl-5-(2-methyl-2H-pyrazol-3-yl)-benzoic acid methyl ester (145 mg, 0.56 mmol) in dioxane (1.5 mL). The mixture was stirred at 80° C. for 2 h (TLC control). The mixture was evaporated to dryness. The obtained yellow solid was used in the next step without further purification. (rt 6.81 min).

N-[7-Ethyl-6-(2-methyl-2H-pyrazol-3-yl)-2,4-dioxo-1,4-dihydro-2H-quinazolin-3-yl]-methanesulfonamide Methanesulfonyl hydrazide (77 mg, 1.1 equiv) and i-$Pr_2$NEt (217 μL, 2 equiv) were added to a solution of 2-(4-chloro-phenoxycarbonylamino)-4-isopropyl-5-(2-methyl-2H-pyrazol-3-yl)-benzoic acid methyl ester (262 mg, 0.63 mmol) in dioxane (1 mL). The mixture was stirred at 80° C. for 16 h (TLC control). The mixture was evaporated to dryness. The crude product was purified by flash chromatography (MeOH/DCM (1:9)) to provide N-[7-ethyl-6-(2-methyl-2H-pyrazol-3-yl)-2,4-dioxo-1,4-dihydro-2H-quinazolin-3-yl]-methanesulfonamide (172 mg, 74% yield) as a white solid. ESI-MS: m/z 364.4 $[M+H]^+$, rt 4.54 min).

The following products were synthesized by analogous procedures.

Example 63

N-[7-ethyl-6-(2-ethyl-2H-pyrazol-3-yl)-2,4-dioxo-1,4-dihydro-2H-quinazolin-3-yl]-methanesulfonamide

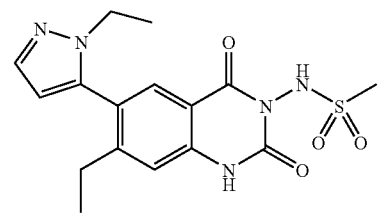

ESI-MS: m/z 378.4 $[M+H]^+$, rt 4.06 min.

Example 64

N-[7-ethyl-6-(2-isopropyl-2H-pyrazol-3-yl)-2,4-dioxo-1,4-dihydro-2H-quinazolin-3-yl]-methanesulfonamide

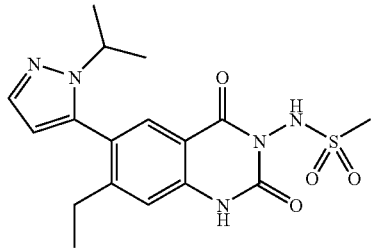

(ESI-MS: m/z 392.4 [M+H]$^+$, rt 4.19 min).

Example 65

N-{7-Isopropyl-6-[2-(2-methoxy-ethyl)-2H-pyrazol-3-yl]-2,4-dioxo-1,4-dihydro-2H-quinazolin-3-yl}-methanesulfonamide

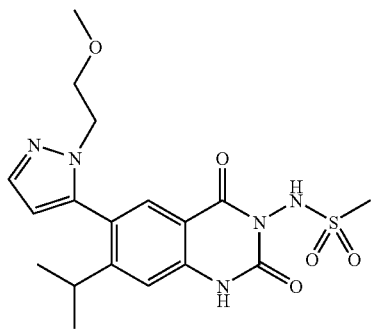

ESI-MS: m/z 422.4 [M+H]$^+$, rt 4.83 min.

Example 66

N-[7-Isopropyl-6-(2-isopropyl-2H-pyrazol-3-yl)-2,4-dioxo-1,4-dihydro-2H-quinazolin-3-yl]-methanesulfonamide

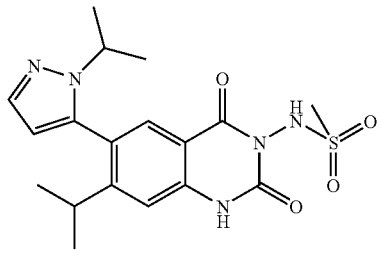

ESI-MS: m/z 406.4 [M+H]$^+$, rt 4.68 min.

Example 67

N-[2,4-Dioxo-6-(2H-pyrazol-3-yl)-7-trifluoromethyl-1,4-dihydro-2H-quinazolin-3-yl]-methanesulfonamide

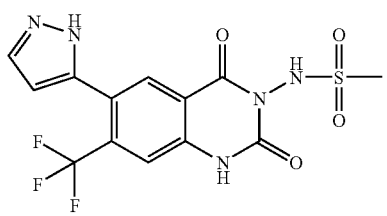

ESI-MS: m/z 431.3 [M+H+CH$_3$CN]$^+$, rt 4.01 min.

Example 68

N-[6-(1-Methyl-1H-imidazol-2-yl)-2,4-dioxo-7-trifluoromethyl-1,4-dihydro-2H-quinazolin-3-yl]-methanesulfonamide

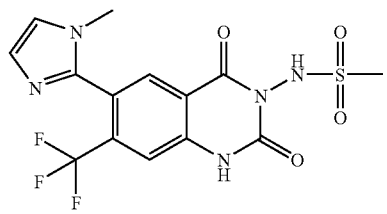

ESI-MS: m/z 404.3 [M+H]$^+$, rt 2.85 min.

Example 69

N-(6-Methanesulfonylmethyl-2,4-dioxo-7-trifluoromethyl-1,4-dihydro-2H-quinazolin-3-yl)-methanesulfonamide

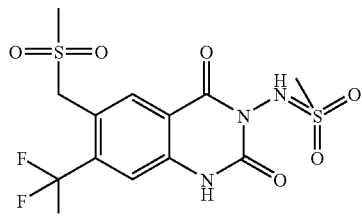

ESI-MS: m/z 416.2 [M+H]$^+$, rt 3.63 min.

Example 70

N-[7-Fluoromethyl-6-(2-methyl-2H-pyrazol-3-yl)-2,4-dioxo-1,4-dihydro-2H-quinazolin-3-yl]-methanesulfonamide

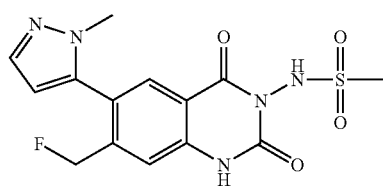

ESI-MS: m/z 368.3 [M+H]$^+$, rt 3.73 min.

Example 71

N-[7-(1,1-difluoro-ethyl)-6-(2-isopropyl-2H-pyrazol-3-yl)-2,4-dioxo-1,4-dihydro-2H-quinazolin-3-yl]-methanesulfonamide 4-Bromo-2-nitro-benzoic acid methyl ester

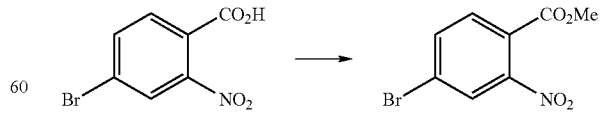

To solution of 4-bromo-2-nitro-benzoic acid (9 g, 36.58 mmol) in dimethylformamide (36 mL) cooled to 0° C. were added 1,8-diazabicyclo[5.4.0]und-7-ene (28.09 mL, 182.9 mmol) and MeI (11.4 mL, 182.5 mmol). The reaction mixture was stirred at 0° C. for 15 min and at r.t. for 48 h. The mixture was poured into water and extracted with EtOAc (2×). The combined organic phases were washed with water (2×), dried (Na$_2$SO$_4$) and concentrated to dryness. The crude product was purified by flash chromatography (hexanes to EtOAc/hexanes (4:6)) to give 4-bromo-2-nitro-benzoic acid methyl ester (8.62 g, 33.147 mmol, 90%). $^1$H-NMR (CDCl$_3$, 400 MHz) 8.02 (s, 1H), 7.81 (dd, J=2.3, 10.5 Hz 1H), 7.66 (d, J=8.2 Hz, 1H), 3.92 (s, 3H).

4-(1-ethoxy-vinyl)-benzoic acid methyl ester

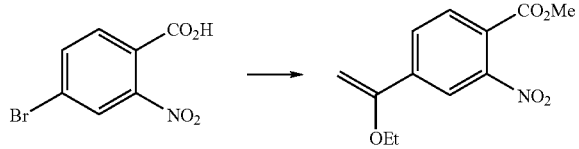

A solution of 4-bromo-2-nitro-benzoic acid methyl ester (10 g, 38.5 mmol) tetrakis-(triphenylphosphine)-palladium (4.44 g, 3.84 mmol), and tributyl-(ethoxyvinyl)-tin (21.5 g, 57.8 mmol) in dioxane (125 mL) was heated to 140° C. for 19 h. The mixture was allowed to cool to r.t., and then water and EtOAc were added. The aqueous phase was extracted with EtOAc (3×). The combined organic phases were dried (Na$_2$SO$_4$) and concentrated to dryness. The crude product was purified by flash chromatography (hexanes to EtOAc/hexanes (4:6) to give 4-(1-ethoxy-vinyl)-benzoic acid methyl ester (7.63 g, 30.4 mmol, 79%) as a brown solid. ES-MS: m/z 252 [M+H]$^+$, rt 6.04 min 4-Acetyl-2-nitro-benzoic acid methyl ester

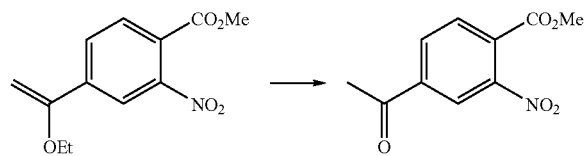

A solution of 4-(1-ethoxy-vinyl)-benzoic acid methyl ester (7.63 g, 30.4 mmol) in THF (100 mL) was treated with aq HCl (1N, 43 mL) and the mixture was stirred at r.t. for 1 h. The mixture was then poured into EtOAc and washed with water (2×). The organic phase was dried (Na$_2$SO$_4$), filtered and concentrated in vacuo. The crude product was purified by flash chromatography (EtOAc/hexanes (1:9 to 1:1) to give 4-acetyl-2-nitro-benzoic acid methyl ester (6.37 g, 28.5 mmol, 94%). rt 4.79 min. $^1$H-NMR (CDCl$_3$, 400 MHz) 8.50 (d, J=1.6 Hz, 1H), 8.28 (dd, J=1.6, 9.8 Hz 1H), 7.87 (d, J=8.2 Hz, 1H), 3.99 (s, 3H), 2.73 (s, 3H).

4-(1,1-Difluoro-ethyl)-2-nitro-benzoic acid methyl ester

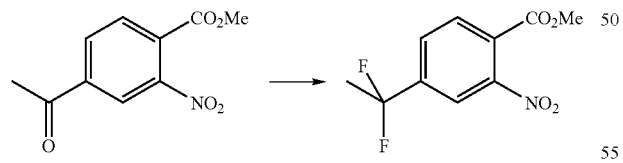

To a solution of 4-acetyl-2-nitro-benzoic acid methyl ester (1.0 g, 4.48 mmol) in DCM (100 mL) was added deoxofluor (2.83 mL, 6.7 mmol). The reaction mixture was stirred at r.t. for 48 h and another portion of deoxofluor (0.95 mL, 2.23 mmol) was added. The reaction mixture was stirred at r.t. for 48 h. Sat. aq NaHCO$_3$ was added and the solution was stirred at r.t. for 15 min. The aqueous phase was extracted with DCM (3×) and the combined organic phases were dried (Na$_2$SO$_4$), filtered and concentrated in vacuo. The crude product was purified by flash chromatography (hexanes to EtOAc/hexanes (1:1) to give 4-(1,1-difluoro-ethyl)-2-nitro-benzoic acid methyl ester (0.627 g, 2.56 mmol, 57%). $^1$H-NMR (CDCl$_3$, 400 MHz) 8.02 (s, 1H), 7.79 (s, 2H), 3.92 (s, 3H), 1.95 (t, J=18.5 Hz, 3H).

2-Amino-4-(1,1-difluoro-ethyl)-benzoic acid methyl ester

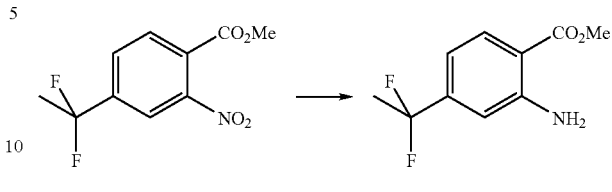

A solution of 4-(1,1-difluoro-ethyl)-2-nitro-benzoic acid methyl ester (1.61 g, 6.57 mmol) in MeOH (40 mL) was treated with Nickel-raney in EtOH (400 mL) and the mixture was stirred at r.t. for 5 h under H$_2$ (0.1 bar). The mixture was then filtered and concentrated in vacuo to give 2-amino-4-(1,1-difluoro-ethyl)-benzoic acid methyl ester (1.30 g, 6.05 mmol, 92%) as a yellow oil. ESI-MS: m/z 216 [M+H]$^+$, rt 6.30 min.

2-amino-4-(1,1-difluoro-ethyl)-5-iodo-benzoic acid methyl ester

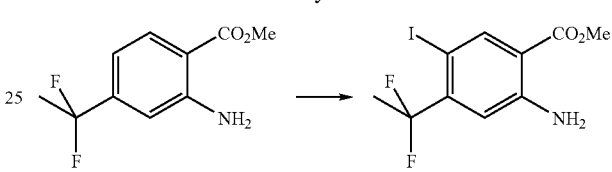

A mixture of 2-amino-4-(1,1-difluoro-ethyl)-benzoic acid methyl ester (1.3 g, 6.04 mmol), I2 (1.53 g, 6.03 mmol) and Ag$_2$SO$_4$ (1.89 g, 6.03 mmol) in EtOH (40 mL) was stirred for 1 h at r.t. The suspension was then filtered and the filtrate diluted with EtOAc and washed once with a 10% aqueous Na$_2$SO$_3$. The organic layer was dried (Na$_2$SO$_4$), filtered and concentrated in vacuo to give 2-amino-4-(1,1-difluoro-ethyl)-5-iodo-benzoic acid methyl ester (1.98 g, 5.8 mmol, 96%) as a brown solid, ESI-MS: m/z 383 [M+CH$_3$CN+H]$^+$. rt 6.71 min 2-Amino-4-(1,1-difluoro-ethyl)-5-(2-isopropyl-2H-pyrazol-3-yl)-benzoic acid methyl ester

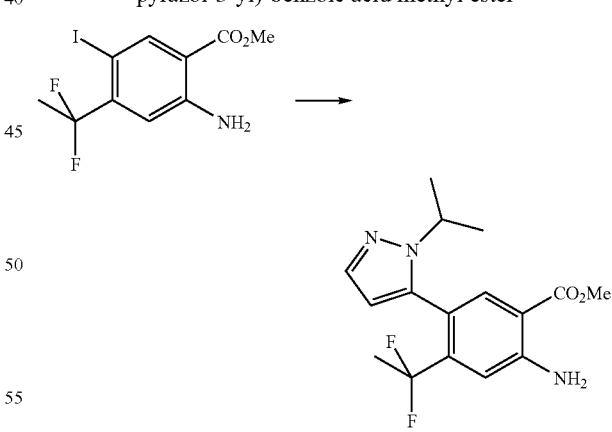

To a solution of 2-amino-4-(1,1-difluoro-ethyl)-5-iodo-benzoic acid methyl ester (0.809 g, 2.37 mmol) in dioxane (10 mL) were added 1-isopropyl-5-tributylstannanyl-1H-pyrazole (1.14 g, 2.84 mmol) and Pd(PPh$_3$)$_2$Cl$_2$ (170 mg, 0.237 mmol) and the resulting mixture was stirred at 90° C. for 72 h. The solvent was removed in vacuo to afford a dark oil. The crude product was purified by flash chromatography (silica gel, EtOAc/hexanes (0:10 to 3:7)) to give 2-amino-4-(1,1-difluoro-ethyl)-5-(2-isopropyl-2H-pyrazol-3-yl)-benzoic acid methyl ester (141 mg, 0.436 mmol, 18%) ES-MS: m/z 324 [M+H]$^+$, rt 6.39 min.

153

N-[7-(1,1-difluoro-ethyl)-6-(2-isopropyl-2H-pyrazol-3-yl)-2,4-dioxo-1,4-dihydro-2H-quinazolin-3-yl]-methanesulfonamide

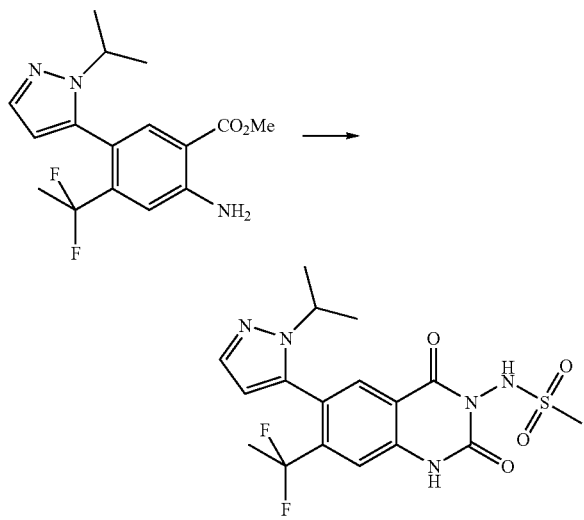

To a solution of 2-amino-4-(1,1-difluoro-ethyl)-5-(2-isopropyl-2H-pyrazol-3-yl)-benzoic acid methyl ester (141 mg, 0.436 mmol) in DCM (10 mL) were added Et₃N (0.244 mL, 1.74 mmol) and then (CCl₃O)₂CO (106 mg, 0.349 mmol). The resulting mixture was stirred at r.t. for 3 h. The solvent was removed in vacuo and the crude solubilised in THF (5 mL). CH₃SO₂NHNH₂ (44.8 mg, 0.399 mmol) was added and the mixture was stirred at r.t. for 2 h. Aq NaOH (1N, 0.4 mL, 0.4 mmol) was then added. After stirring the mixture at r.t. for 1 h, another portion of aq NaOH (1N, 0.4 mL, 0.4 mmol) was added and stirring was continued for 12 h. The solvent was removed in vacuo and water was added. The pH was adjusted to 3-4 by addition of 2N HCl. The aqueous phase was extracted with EtOAc (2×). The organic phases were combined, washed with brine, dried (Na₂SO₄) and concentrated in vacuo to afford a crude solid. The residue was purified by flash chromatography (silica gel, EtOAc/hexanes (1:1 to 10:0)) to give N-[7-(1,1-difluoro-ethyl)-6-(2-isopropyl-2H-pyrazol-3-yl)-2,4-dioxo-1,4-dihydro-2H-quinazolin-3-yl]-methanesulfonamide as a yellow solid (52 mg, 0.122 mmol, 39%). ES-MS: m/z 428.4 [M+H]⁺, rt 5.94 min. ¹H-NMR (CDCl₃, 300 MHz) 10.15 (s, 1H); 7.99 (s, 1H); 7.90 (br s, 1H); 7.58 (d, J=1.7 Hz, 1H); 7.54 (s, 2H); 6.17 (d, J=1.8 Hz, 1H); 4.02 (m, 1H); 3.33 (s, 1H); 1.71 (t, J=18.7 Hz, 3H), 1.41 (br d, 6H).

Example 72

N-[7-(1,1-difluoro-ethyl)-6-(2-methyl-2H-pyrazol-3-yl)-2,4-dioxo-1,4-dihydro-2H-quinazolin-3-yl]-methanesulfonamide 2-Amino-4-(1,1-difluoro-ethyl)-5-(2-methyl-2H-pyrazol-3-yl)-benzoic acid methyl ester

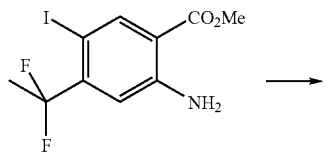

-continued

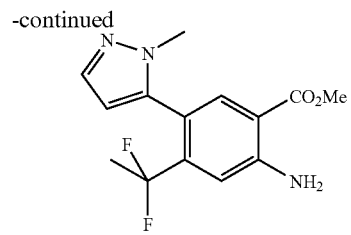

To a solution of 2-amino-4-(1,1-difluoro-ethyl)-5-iodo-benzoic acid methyl ester (0.80 g, 2.35 mmol) in dioxane (10 mL) were added 1-methyl-5-tributylstannanyl-1H-pyrazole (1.05 g, 2.81 mmol) and Pd(PPh₃)₂Cl₂ (168 mg, 0.235 mmol) and the resulting mixture was stirred at 90° C. for 72 h. The solvent was removed in vacuo to afford a dark oil. The crude product was purified by flash chromatography (silica gel, EtOAc/hexanes (0:10 to 3:7)) to give 2-amino-4-(1,1-difluoro-ethyl)-5-(2-methyl-2H-pyrazol-3-yl)-benzoic acid methyl ester (430 mg, 1.46 mmol, 62%). ES-MS: m/z 296 [M+H]⁺, rt 6.05 min.

N-[7-(1,1-difluoro-ethyl)-6-(2-methyl-2H-pyrazol-3-yl)-2,4-dioxo-1,4-dihydro-2H-quinazolin-3-yl]-methanesulfonamide

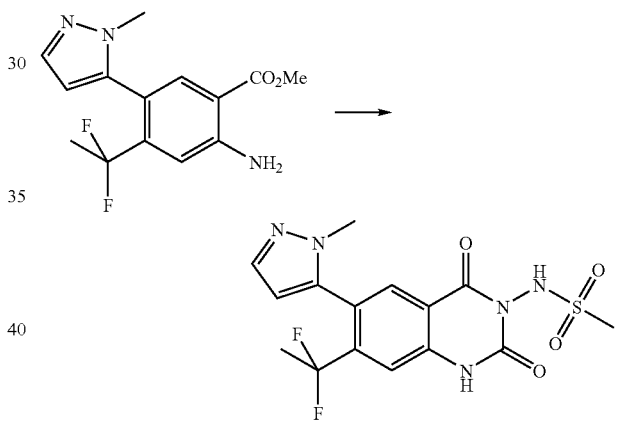

To a solution of 2-amino-4-(1,1-difluoro-ethyl)-5-(2-methyl-2H-pyrazol-3-yl)-benzoic acid methyl ester (430 mg, 1.43 mmol) in DCM (33 mL) were added Et₃N (0.820 mL, 5.82 mmol) and then (CCl₃O)₂CO (353 mg, 1.16 mmol). The resulting mixture was stirred at r.t. for 3 h. The solvent was removed in vacuo and the residue was solubilised in THF (33 mL). CH₃SO₂NHNH₂ (213 mg, 1.90 mmol) was added and the mixture was stirred at r.t for 2 h. Aq NaOH (1N, 1.9 mL, 1.9 mmol) was then added and the mixture was stirred at r.t. for 1 h. The solvent was removed in vacuo and water was added. The pH was adjusted to 3-4 by addition of 2N aq HCl. The aqueous phase was extracted with EtOAc (2×). The organic phases were combined, washed with brine, dried (Na₂SO₄) and concentrated in vacuo to afford a crude solid. The crude product was purified by flash chromatography (silica gel, EtOAc/hexanes to EtOAc/MeOH (1:1 to 8:2)) to give N-[7-(1,1-difluoro-ethyl)-6-(2-methyl-2H-pyrazol-3-yl)-2,4-dioxo-1,4-dihydro-2H-quinazolin-3-yl]-methanesulfonamide as a yellow solid (470 mg, 1.18 mmol, 80%) ES-MS: m/z 400.4 [M+H]⁺, rt 5.52 min. ¹H-NMR (CDCl₃, 300 MHz) 9.23 (br s, 1H); 8.06 (s, 1H); 7.90 (br s, 1H); 7.55 (d, J=2.05 Hz, 1H); 7.48 (s, 2H); 7.45 (s, 1H); 6.26 (d, J=1.8 Hz, 1H); 3.64 (s, 3H); 3.36 (s, 1H); 1.70 (t, J=18.7 Hz, 3H).

Example 73

N-[7-(1-fluoro-ethyl)-6-(2-isopropyl-2H-pyrazol-3-yl)-2,4-dioxo-1,4-dihydro-2H-quinazolin-3-yl]-methanesulfonamide 4-(1-hydroxy-ethyl)-2-nitro-benzoic acid methyl ester

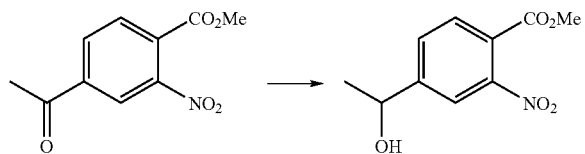

To a solution of 4-acetyl-2-nitro-benzoic acid methyl ester (1 g, 4.48 mmol) in MeOH (5 mL) was added NaBH$_4$. The reaction mixture was stirred at r.t. for 24 h (TLC control). To the reaction mixture was added water until the appearance of a white turbid solution and the reaction was stirred for 15 min at r.t. MeOH was removed under reduced pressure. The aqueous phase was extracted with EtOAc three times. The combined organic phases were dried (Na$_2$SO$_4$) and concentrated in vacuo to afford 4-(1-hydroxy-ethyl)-2-nitro-benzoic acid methyl ester (0.742 g, 73%) as a brown oil which was used in the next step without further purification. rt 4.74 min.

4-(1-Fluoro-ethyl)-2-nitro-benzoic acid methyl ester

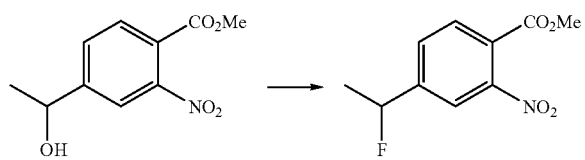

To a solution of 4-(1-hydroxy-ethyl)-2-nitro-benzoic acid methyl ester (1.09 g, 4.84 mmol) in DCM (15 mL) cooled at −50° C. was added dropwise a solution of DAST (0.734 mL, 5.32 mmol) in DCM (2 mL). The reaction was stirred at −50° C. for 2 h. Sat. aq NaHCO$_3$ was added to reaction mixture and the solution was stirred at r.t. for 1 h. The aqueous phase was extracted with DCM (3×) and the combined organic phases were dried (Na$_2$SO$_4$) and concentrated in vacuo. The crude residue was purified by flash chromatography (silica gel, hexanes to EtOAc/hexanes (4:6)) to give 4-(1-fluoro-ethyl)-2-nitro-benzoic acid methyl ester (0.60 g, 2.64 mmol, 56%). $^1$H-NMR (CDCl$_3$, 300 MHz) 7.85 (s, 1H); 7.75 (d, J=7.9 Hz, 1H); 7.7.61 (d, J=7.3 Hz, 1H); 5.60-5.82 (qd, J=6.45, 47.2 Hz, 1H); 3.92 (s, 3H); 1.70 (dd, J=6.4, 23.7 Hz, 3H).

N-[7-(1-fluoro-ethyl)-6-(2-isopropyl-2H-pyrazol-3-yl)-2,4-dioxo-1,4-dihydro-2H-quinazolin-3-yl]-methanesulfonamide 2-Amino-4-(1-fluoro-ethyl)-benzoic acid methyl ester

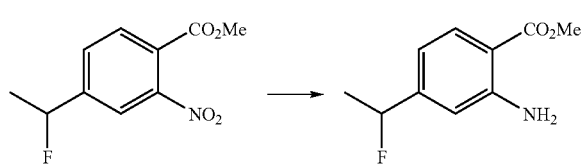

A solution of 4-(1-fluoro-ethyl)-2-nitro-benzoic acid methyl ester (0.6 g, 2.64 mmol) in MeOH (15 mL) was treated with Nickel-raney in EtOH (254 mL) and the mixture was stirred at r.t. for 3 h under H$_2$ (0.1 bar). The mixture was then filtered and concentrated in vacuo to give 2-amino-4-(1-fluoro-ethyl)-benzoic acid methyl ester (334 g, 1.69 mmol, 93%) as a yellow oil. ESI-MS: m/z 198 [M+H]$^+$, rt 4.86 min.

2-Amino-4-(1-fluoro-ethyl)-5-iodo-benzoic acid methyl ester

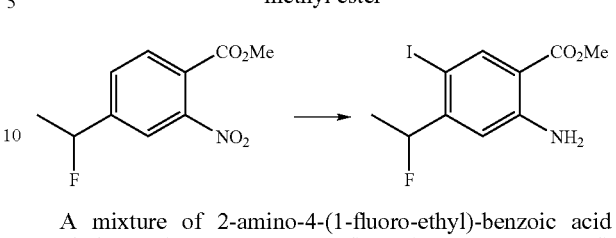

A mixture of 2-amino-4-(1-fluoro-ethyl)-benzoic acid methyl ester (0.334 g, 1.69 mmol), 12 (0.430 g, 1.69 mmol) and Ag$_2$SO$_4$ (0.533 g, 1.69 mmol) in EtOH (15 mL) was stirred for 2 h at r.t. The suspension was then filtered and the filtrate diluted with EtOAc and washed once with a 10% aq Na$_2$SO$_4$. The organic layer was dried (Na$_2$SO$_4$), filtered and concentrated in vacuo to give 2-amino-4-(1,1-Difluoro-ethyl)-5-iodo-benzoic acid methyl ester (0.561 g, 1.69 mmol, 100%) which was used in the next step without further purification. ESI-MS: m/z 365 [M+CH$_3$CN+H]$^+$. rt 6.57 min 2-Amino-4-(1-fluoro-ethyl)-5-(2-isopropyl-2H-pyrazol-3-yl)-benzoic acid methyl ester

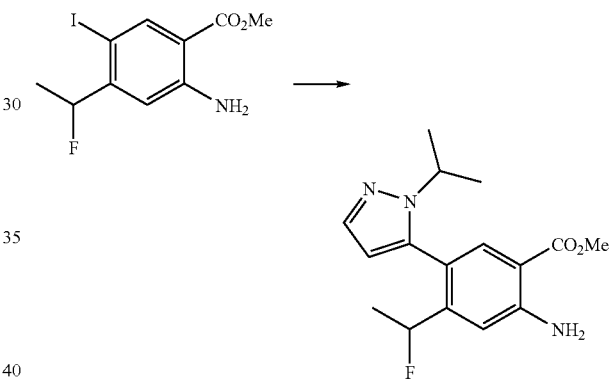

To a solution of 2-amino-4-(1-fluoro-ethyl)-5-iodo-benzoic acid methyl ester (0.561 g, 1.74 mmol) in dioxane (5 mL) were added 1-isopropyl-5-tributylstannanyl-1H-pyrazole (0.84 g, 2.08 mmol) and Pd(PPh$_3$)$_2$Cl$_2$ (142 mg, 0.174 mmol) and the resulting mixture was stirred at 90° C. for 24 h. The solvent was removed in vacuo to afford a dark oil. The crude product was purified by flash chromatography (silica gel, EtOAc/hexanes (0:10 to 3:7)) to give 2-amino-4-(1-fluoro-ethyl)-5-(2-isopropyl-2H-pyrazol-3-yl)-benzoic acid methyl ester (90 mg, 0.287 mmol, 16%) ES-MS: m/z 306 [M+H]$^+$, rt 6.47 min.

N-[7-(1-fluoro-ethyl)-6-(2-isopropyl-2H-pyrazol-3-yl)-2,4-dioxo-1,4-dihydro-2H-quinazolin-3-yl]-methanesulfonamide

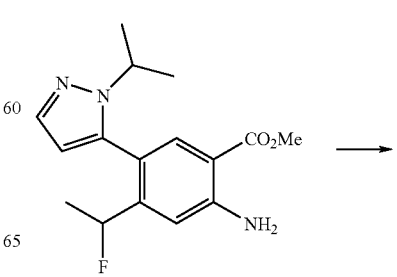

-continued

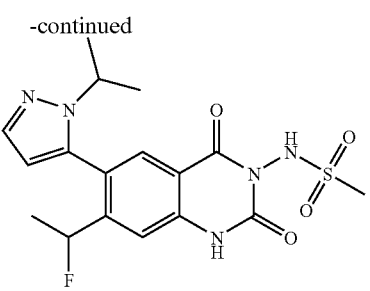

To a solution of 2-amino-4-(1-fluoro-ethyl)-5-(2-isopropyl-2H-pyrazol-3-yl)-benzoic acid methyl ester (90 mg, 0.295 mmol) in DCM (7 mL) were added Et$_3$N (0.165 mL, 1.18 mmol) and then (CCl$_3$O)$_2$CO (71.4 mg, 0.236 mmol). The resulting mixture was stirred at r.t. for 3 h. The solvent was removed in vacuo and the residue was solubilised in THF (5 mL). CH$_3$SO$_2$NHNH$_2$ (44.1 mg, 0.392 mmol) was added, the mixture was stirred at r.t. for 2 h. Aq NaOH (1N, 0.39 mL, 0.4 mmol) was then added and stirring was pursued for 1 h prior to the addition of an additional portion of aq NaOH (1N, 0.4 mL, 0.4 mmol). After stirring for 48 h, the solvent was removed in vacuo and water was added. The pH was adjusted to 3-4 by addition of 2N HCl. The aqueous phase was extracted with EtOAc (2×). The organic phases were combined, washed with brine, dried (Na$_2$SO$_4$) and concentrated in vacuo to afford a crude solid. The crude product was purified by flash chromatography (silica gel, EtOAc/hexanes (3:7 to 7:3)) to provide after trituration in DCM/hexanes (2/8) and filtration N-[7-(1-fluoro-ethyl)-6-(2-isopropyl-2H-pyrazol-3-yl)-2,4-dioxo-1,4-dihydro-2H-quinazolin-3-yl]-methanesulfonamide as a white solid (19 mg, 0.047 mmol, 15%). ES-MS: m/z 410 [M+H]$^+$, rt 6.05 min. $^1$H-NMR (DMSO-d$_6$, 400 MHz) 10.6 (bs, 2H); 7.73 (s, 1H); 7.54 (s, 1H); 7.44 (s, 1H); 6.27 (s, 1H); 5.45 (qd, J=6.6, 47.5 Hz 1H); 4.12 (m, 1H); 3.15 (s, 1H); 1.44 (dd, J=5.6, 24.6 Hz, 3H); 1.41 (dd, J=6.6, 12.9 Hz, 6H).

Example 74

N-[7-(1-fluoro-ethyl)-6-(2-methyl-2H-pyrazol-3-yl)-2,4-dioxo-1,4-dihydro-2H-quinazolin-3-yl]-methanesulfonamide 2-Amino-4-(1-fluoro-ethyl)-5-(2-methyl-2H-pyrazol-3-yl)-benzoic acid methyl ester

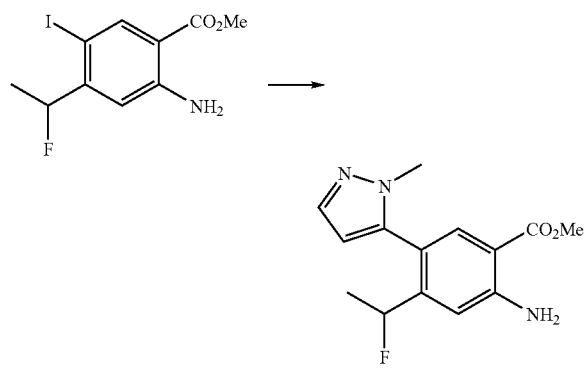

To a solution of 2-amino-4-(1-fluoro-ethyl)-5-iodo-benzoic acid methyl ester (0.339 g, 1.05 mmol) in dioxane (5 mL) were added 1-methyl-5-tributylstannanyl-1H-pyrazole (0.842 g, 2.14 mmol) and Pd(PPh$_3$)$_2$Cl$_2$ (75.1 mg, 0.105 mmol) and the resulting mixture was stirred at 90° C. for 24 h. The solvent was removed in vacuo to afford a dark oil. The crude product was purified by flash chromatography (silica gel, EtOAc/hexanes (0:10 to 4:6)) to give 2-amino-4-(1-fluoro-ethyl)-5-(2-methyl-2H-pyrazol-3-yl)-benzoic acid methyl ester (280 mg, 0.982 mmol, 93%). ES-MS: m/z 278 [M+H]$^+$, rt 4.66 min.

N-[7-(1-fluoro-ethyl)-6-(2-methyl-2H-pyrazol-3-yl)-2,4-dioxo-1,4-dihydro-2H-quinazolin-3-yl]-methanesulfonamide

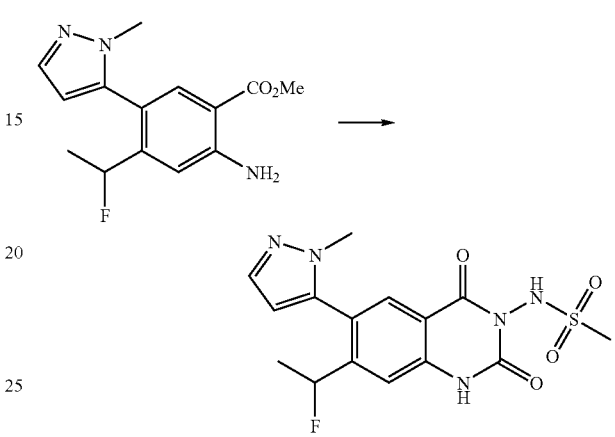

To a solution of 2-amino-4-(1-fluoro-ethyl)-5-(2-methyl-2H-pyrazol-3-yl)-benzoic acid methyl ester (280 mg, 1.01 mmol) in DCM (20 mL) were added Et$_3$N (0.565 mL, 4.04 mmol) and then (CCl$_3$O)$_2$CO (245 mg, 0.808 mmol). The resulting mixture was stirred at r.t. for 3 h. The solvent was removed in vacuo and the residue solubilised in THF (20 mL). CH$_3$SO$_2$NHNH$_2$ (152 mg, 1.35 mmol) was added and, after stirring at r.t for 3 h, a second portion of CH$_3$SO$_2$NHNH$_2$ was added (117 mg) and the reaction was allowed to proceed for 1 h. Aq NaOH (1N, 1.4 mL, 1.4 mmol) was then added and the mixture was stirred for 19 h. The solvent was removed in vacuo and water was added. The pH was adjusted to 3-4 by addition of 2N aq HCl. The aqueous phase was extracted with EtOAc (2×). The organic phases were combined, washed with brine, dried (Na$_2$SO$_4$) and concentrated in vacuo to afford a crude solid. The crude product was purified by flash chromatography (silica gel, EtOAc/hexanes (3:7 to 10:)) to give N-[7-(1-fluoro-ethyl)-6-(2-methyl-2H-pyrazol-3-yl)-2,4-dioxo-1,4-dihydro-2H-quinazolin-3-yl]-methanesulfonamide (150 mg, 0.383 mmol, 36%) as a light yellow solid. ES-MS: m/z 382 [M+H]$^+$. $^1$H-NMR (CDCl$_3$, 400 MHz) 10.5 (s, 1H); 8.02 (s, 1H); 7.61 (d, J=1.6 Hz, 1H); 7.53 (s, 1H); 6.27 (d, J=1.95 Hz, 1H); 5.44-5.45 (qd, J=6.3, 46.9 Hz, 1H); 3.72 (s, 3H); 3.33 (s, 1H); 1.40-1.48 (dd, J=6.3, 24.2 Hz, 3H).

HPLC Method Used for the Following Examples, Unless Otherwise Noted:

HPLC analyses carried out on an Agilent 1100 series (quaternary pump, DAD, autosampler, column thermostat) coupled with a UV/visible diode array: range from 190 to 400 nm with 2 nm step increment. Column: Nucleosil C18HD 4×70 mm 3 um; Flow: 1.0 mL/min; Temperature: 35.0° C.; Injection volume: 5.0 uL. Solvent A: 0.05% TFA in water; Solvent B: 0.05% TFA in CH$_3$CN. Method N_20_100: 20%→100% (6 min), 100% (1.5 min), 100%→20% (0.5 min).

Example 75

N-(2,4-Dioxo-6-pyridazin-4-yl-7-trifluoromethyl-1,4-dihydro-2H-quinazolin-3-yl)-methanesulfonamide 2-Amino-5-ethynyl-4-trifluoromethyl-benzoic acid methyl ester

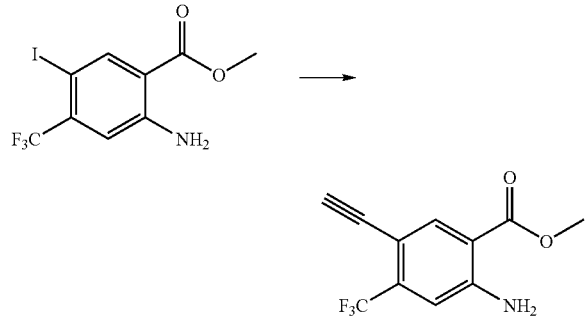

To a solution of 2-amino-5-iodo-4-trifluoromethyl-benzoic acid methyl ester (1.5 g, 4.35 mmol) in dioxane (80 mL) were added tributyl(ethynyl)tin (1.4 mL, 4.78 mmol) and (Ph₃P)₄Pd (251.2 mg, 0.217 mmol) and the mixture was heated to 120° C. for 1.5 h. After cooling to r.t., the solvent was removed in vacuo and the residue was purified by two successive flash chromatographies (150 g silica gel, hexanes→DCM:hexanes (3:7 to 1:1) and then (50 g silica gel, hexanes→EtOAc:hexanes (1:9)) to provide the title compound (730 mg, 69%) as a beige-orange solid. API-ES: m/z 244 [M+H]⁺, rt 5.14 min.

2-Amino-5-pyridazin-4-yl-4-trifluoromethyl-benzoic acid methyl ester

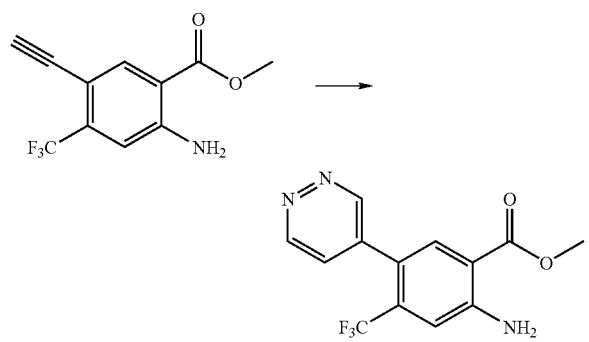

A solution of 2-amino-5-ethynyl-4-trifluoromethyl-benzoic acid methyl ester (150 mg, 0.62 mmol) and tetrazine (55.7 mg, 0.68 mmol) in 1,2-dichloroethane (3 mL) in a sealed tube was heated in the microwave at 130° C. for 40 min and at 120° C. for 40 min. After cooling to r.t., the solvent was removed in vacuo. The residue was purified by flash chromatography (10 g silica gel, hexanes→EtOAc:hexanes (2:3)) to provide 2-amino-5-pyridazin-4-yl-4-trifluoromethyl-benzoic acid methyl ester (74 mg, 40%) as a solid. API-ES: m/z 298 [M+H]⁺, rt 3.54 min.

Tetrazine was synthesized according to a procedure described in J. Heterocycl. Chem. 1987, 24, 545-548.

N-(2,4-Dioxo-6-pyridazin-4-yl-7-trifluoromethyl-1,4-dihydro-2H-quinazolin-3-yl)-methanesulfonamide

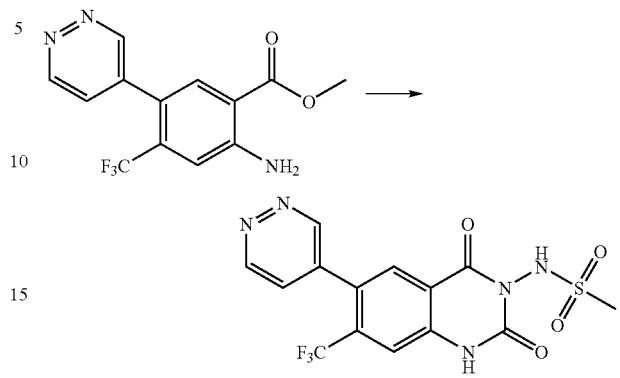

A solution containing 2-amino-5-pyridazin-4-yl-4-trifluoromethyl-benzoic acid methyl ester (65.5 mg, 0.22 mmol) and 4-chlorophenyl chloroformate (34 µL, 0.24 mmol) in dioxane (3 mL) was heated at 80° C. for 1.5 h. After allowing the reaction mixture to cool down to r.t., CH₃SO₂NHNH₂ (48.5 mg, 0.44 mmol) and i-Pr₂NEt (38.5 µL, 0.22 mmol) were added. The mixture was heated to 80° C. for 1 h and, after cooling to r.t., the solvent was removed in vacuo. The residue was dissolved in DCM and the product was precipitated by addition of Et₂O. Filtration and drying provided the title product (34.4 mg, 39%) as a white solid. API-ES: m/z 402 [M+H]⁺, rt 2.02 min.

Example 76

N-(7-Isopropyl-2,4-dioxo-6-pyridazin-4-yl-1,4-dihydro-2H-quinazolin-3-yl)-methanesulfonamide 2-Amino-5-ethynyl-4-isopropyl-benzoic acid methyl ester

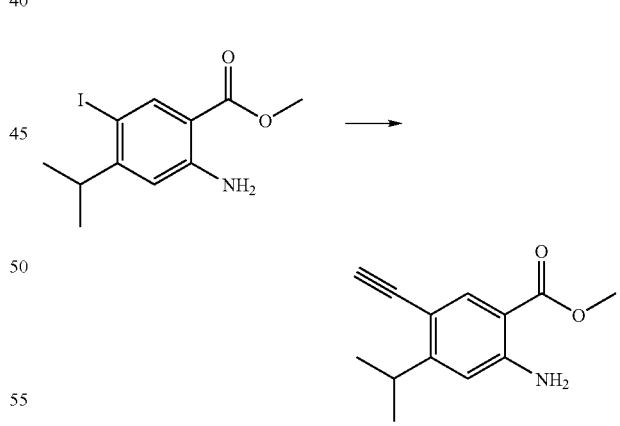

A solution of 2-amino-5-iodo-4-isopropyl-benzoic acid methyl ester (1.5 g, 4.7 mmol), Bu₃SnCCH (1.5 mL, 5.17 mmol) and (Ph₃P)₄Pd (271.6 mg, 0.235 mmol) in dioxane (80 mL) was heated at 120° C. for 1.5 h. The solvent was removed in vacuo. The residue was purified by two successive flash chromatographies (160 g silica gel, hexanes→EtOAc:hexanes (3:7 to 1:1), then (50 g silica gel, hexanes→EtOAc:hexanes (1:9)) to provide 2-amino-5-ethynyl-4-isopropyl-benzoic acid methyl ester (738 mg, 72%) as a yellowish oil. API-ES: m/z 218 [M+H]⁺, rt 5.45 min.

2-Amino-4-isopropyl-5-pyridazin-4-yl-benzoic acid methyl ester

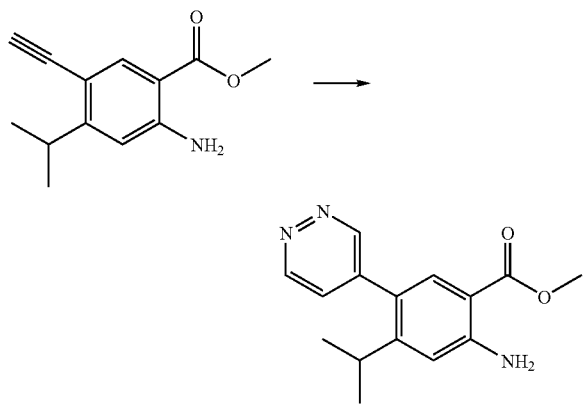

A solution of 2-amino-5-ethynyl-4-isopropyl-benzoic acid methyl ester (718 mg, 3.3 mmol) and tetrazine (406.8 mg, 5.0 mmol) in 1,2-dichloroethane (15 mL) in a sealed tube was heated in the microwave at 130° C. for 45 min. The reaction mixture was then concentrated in vacuo and the residue was purified by flash chromatography (50 g silica gel, hexanes→EtOAc:hexanes (1:1)) to provide the title compound (236 mg, 26%). API-ES: m/z 272 [M+H]$^+$, rt 3.38 min.

N-(7-Isopropyl-2,4-dioxo-6-pyridazin-4-yl-1,4-dihydro-2H-quinazolin-3-yl)-methanesulfonamide

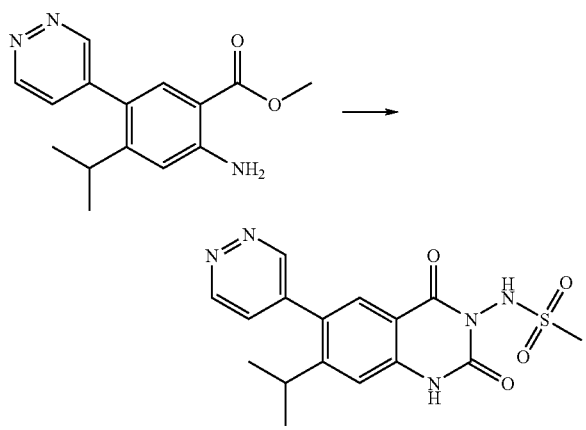

A solution of 2-amino-4-isopropyl-5-pyridazin-4-yl-benzoic acid methyl ester (220 mg, 0.81 mmol) and 4-chlorophenyl chloroformate (170 µL, 1.22 mmol) in dioxane (10 mL) was stirred at r.t. for 10 min and at 80° C. for 30 min. After cooling to r.t., CH$_3$SO$_2$NHNH$_2$ (178.6 mg, 1.6 mmol) and i-Pr$_2$NEt (425 µL, 2.43 mmol) were added. The mixture was heated at 80° C. for 1.5 h, cooled to r.t., and the solvent was removed in vacuo. The residue was purified by flash chromatography (100 g silica gel, DCM→MeOH in DCM (2.5% to 5%)). The fractions containing the product were combined and concentrated in vacuo and the residue was further purified by trituration in MeOH-Et$_2$O. After filtration and drying, the title compound (156 mg, 51%) was isolated as a white powder. API-ES: m/z 376 [M+H]$^+$, rt 2.12 min.

Example 77

N-(2,4-Dioxo-6-pyrazin-2-yl-7-trifluoromethyl-1,4-dihydro-2H-quinazolin-3-yl)-methanesulfonamide

2-Amino-5-pyrazin-2-yl-4-trifluoromethyl-benzoic acid methyl ester

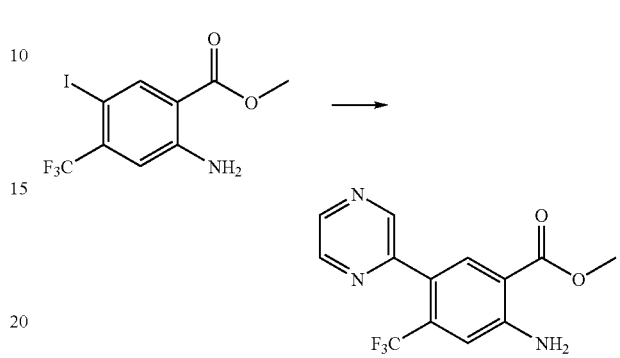

A solution containing 2-amino-5-iodo-4-trifluoromethyl-benzoic acid methyl ester (750 mg, 2.17 mmol), 2-tributylstannylpyrazine (1.0 g, 2.7 mmol) and (Ph$_3$P)$_4$Pd (125.6 mg, 0.109 mmol) in dioxane (40 mL) was heated at 120° C. for 17 h. LiCl (276.4 mg, 6.5 mmol) was added and the reaction mixture was refluxed for 1.5 h prior to the addition of di-t-butyl-p-cresol (188 mg, 0.85 mmol) and another portion of (Ph$_3$P)$_4$Pd (251.2 mg, 0.22 mmol). Heating was continued for 16 h, for a total reaction time of 36 h. After cooling to r.t., the solvent was removed in vacuo and the residue was purified by flash chromatography (200 g silica gel, hexanes→EtOAc:hexanes (3:7 to 1:1)). The fractions containing the product were combined and concentrated in vacuo. The resultant oil was further purified by partitioning between CH$_3$CN and hexanes. The acetonitrile layer was concentrated in vacuo to furnish the title compound (248 mg, 38%) as a solid. API-ES: m/z 298 [M+H]$^+$, rt 4.18 min.

N-(2,4-Dioxo-6-pyrazin-2-yl-7-trifluoromethyl-1,4-dihydro-2H-quinazolin-3-yl)-methanesulfonamide

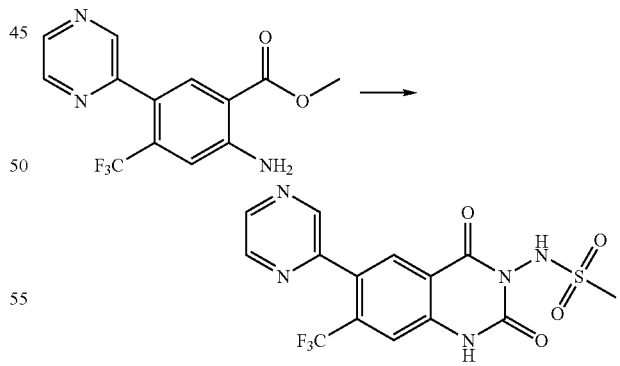

A solution of 2-amino-5-pyrazin-2-yl-4-trifluoromethyl-benzoic acid methyl ester (235 mg, 0.79 mmol) and 4-chlorophenyl chloroformate (133 µL, 0.95 mmol) in dioxane (8 mL) was stirred at 80° C. for 105 min. After cooling to r.t., CH$_3$SO$_2$NHNH$_2$ (130.6 mg, 1.19 mmol) and i-Pr$_2$NEt (276 µL, 1.58 mmol) were added. The mixture was heated to 80° C. for 45 min, cooled to r.t., and the solvent was removed in vacuo. The residue was purified by flash chromatography (50 g silica gel, DCM→MeOH in DCM (2% to 5%)) to provide the title compound (241.5 mg, 76%) as a white powder. API-ES: m/z 402 [M+H]+, rt 2.69 min.

Example 78

N-(2,4-Dioxo-6-pyrimidin-5-yl-7-trifluoromethyl-1,4-dihydro-2H-quinazolin-3-yl)-methanesulfonamide 2-Amino-5-pyrimidin-5-yl-4-trifluoromethyl-benzoic acid methyl ester

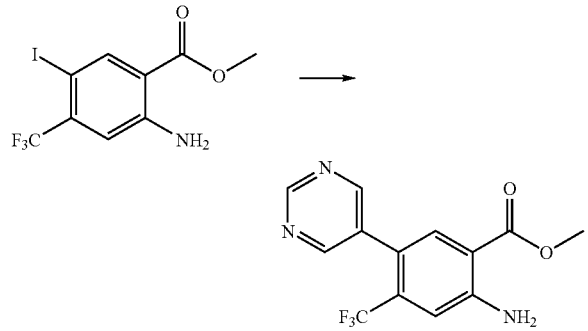

To a solution of 2-amino-5-iodo-4-trifluoromethyl-benzoic acid methyl ester (1.5 g, 4.35 mmol) in DME (50 mL) were added pyrimidine-5-boronic acid (538.7 mg, 4.35 mmol), Pd(dppf)Cl$_2$.CH$_2$Cl$_2$ (355 mg, 0.43 mmol), Cs$_2$CO$_3$ (2.8 g, 8.7 mmol) and the resultant mixture was stirred at reflux temperature for 36 h. The solvent was removed in vacuo and the residue was purified by flash chromatography (120 g silica gel, hexanes→EtOAc/hexanes (3:7 to 1:1)) to furnish the title product (528 mg, 41%) as a beige solid. API-ES: m/z 298 [M+H]+, rt 4.06 min.

N-(2,4-Dioxo-6-pyrimidin-5-yl-7-trifluoromethyl-1,4-dihydro-2H-quinazolin-3-yl)-methanesulfonamide

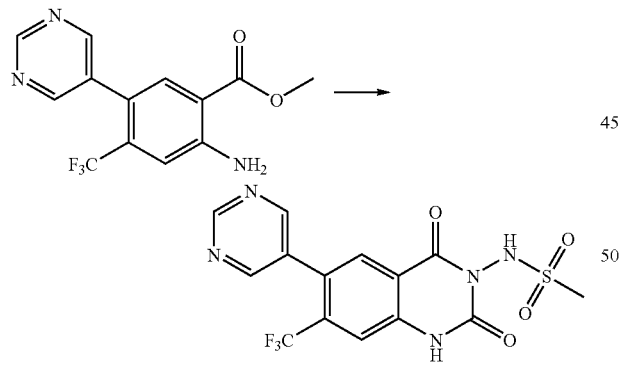

A solution of 2-amino-5-pyrimidin-5-yl-4-trifluoromethyl-benzoic acid methyl ester (518 mg, 1.74 mmol) and 4-chlorophenyl chloroformate (244 µL, 1.74 mmol) in dioxane (8 mL) was stirred at 80° C. for 2 h. After cooling to r.t., CH$_3$SO$_2$NHNH$_2$ (230.4 mg, 2.1 mmol) and i-Pr$_2$NEt (609 µL, 3.49 mmol) were added. The mixture was heated to 80° C. for 4 h and, cooled to r.t., and the solvent was removed in vacuo. The residue was purified by flash chromatography (120 g silica gel, DCM→MeOH in DCM (2% to 5%)). The product was sonicated in MeOH/Et$_2$O to furnish the title compound (252 mg, 36%) as a beige powder. API-ES: m/z 402 [M+H]+, rt 2.52 min.

Example 79

N-(2,4-Dioxo-6-pyridazin-3-yl-7-trifluoromethyl-1,4-dihydro-2H-quinazolin-3-yl)-methanesulfonamide 2-Acetylamino-5-[1-(ethoxycarbonyl-hydrazono)-ethyl]-4-trifluoromethyl-benzoic acid methyl ester

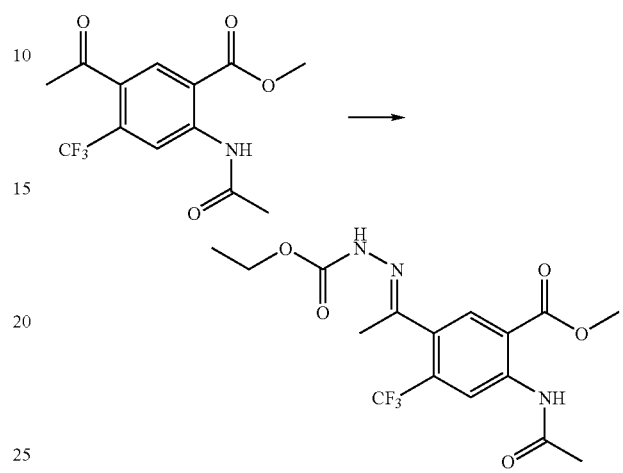

In a round bottom flask fitted with a Dean-Stark, a solution of 5-acetyl-2-acetylamino-4-trifluoromethyl-benzoic acid methyl ester (2.384 g, 7.86 mmol) in toluene (16 mL) was treated with ethylcarbazate (2.61 g, 25 mmol) followed by p-toluenesulfonamide (103 mg, 0.60 mmol). The reaction was stirred at 150° C. for 40 h. The solvent was removed by distillation and the residue was purified by flash column chromatography (silica gel, 1:1 EtOAc/hexanes) to give the title compound (1.24 g, 40%). API-ES: m/z 390.1 [M+H]+, rt 4.14 min, 4.20 min: mixture of cis and trans.

3-(4-Acetylamino-5-methoxycarbonyl-2-trifluoromethyl-phenyl)-4-chloro-6-ethoxy-5,6-dihydro-4H-pyridazine-1-carboxylic acid ethyl ester

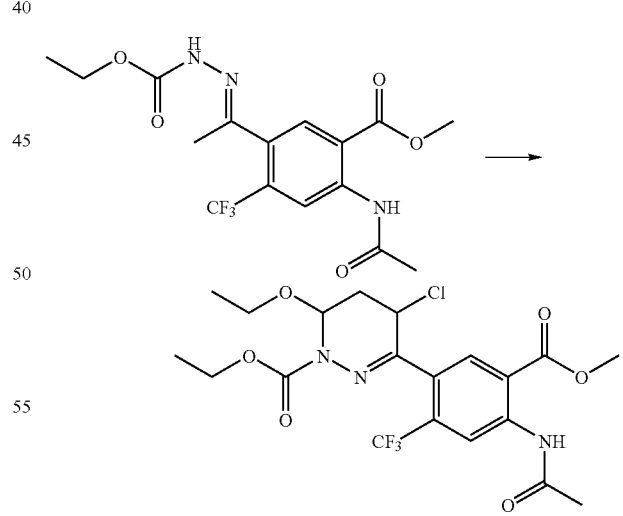

To a solution of 2-acetylamino-5-[1-(ethoxycarbonyl-hydrazono)-ethyl]-4-trifluoromethyl-benzoic acid methyl ester (1.1 g, 2.83 mmol) in CCl$_4$ (18 mL) was added N-chlorosuccinimide (770 mg, 5.65 mmol). The reaction vessel was flushed with argon and the reaction mixture was heated to 110° C. for 38 h. After cooling to r.t., the mixture was filtered and the filtrate was concentrated in vacuo to provide the intermediate 2-acetylamino-5-[2,2-dichloro-1-(ethoxycarbonyl-hydrazono)-ethyl]-4-trifluoromethyl-benzoic acid methyl ester which was used directly in the next step. (API-ES: m/z 455.9 [M−H]⁻, rt 5.04 min).

A solution of the crude residue in DCM (10 mL) was added dropwise under argon to a solution of ethyl vinyl ether (1.35 mL, 14.1 mmol) and i-Pr₂NEt (1.2 mL, 7.0 mmol) in DCM (10 mL). The reaction mixture was heated to 65° C. for 4 h. After cooling to r.t., the mixture was diluted with EtOAc and washed with H₂O. The organic phase was dried (MgSO₄), and the solvent was removed in vacuo. The residue was purified by flash chromatography (silica gel, 1:4 EtOAc/hexanes) to give the title product (401 mg, 29%). API-ES: m/z 494.1 [M+H]⁺, rt 5.39 min.

2-Amino-5-pyridazin-3-yl-4-trifluoromethyl-benzoic acid

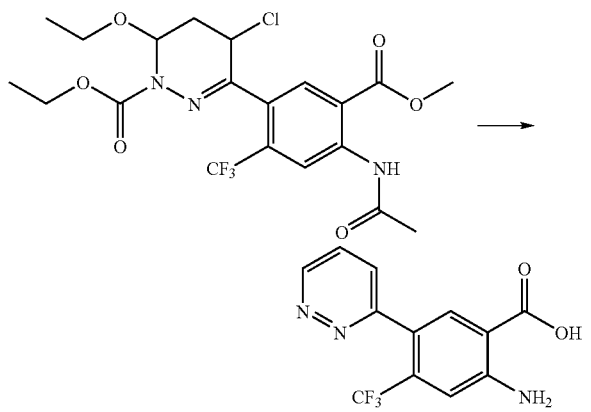

A solution of 3-(4-acetylamino-5-methoxycarbonyl-2-trifluoromethyl-phenyl)-4-chloro-6-ethoxy-5,6-dihydro-4H-pyridazine-1-carboxylic acid ethyl ester (400 mg, 0.81 mmol) in EtOH (20 mL) containing KOH (227 mg, 4.05 mmol) was heated to 110° C. for 18 h. Water (2 mL) was added and the reaction was heated to 110° C. for 8 h. The solution was poured onto ice/water/2 N aq HCl (2.5 mL) then extracted with EtOAc. The organic phase was washed with brine, dried (MgSO₄) and the solvent was removed in vacuo to give the title compound (170 mg, 74%). API-ES: m/z 284.0 [M+H]⁺, rt 2.78 min.

2-Amino-5-pyridazin-3-yl-4-trifluoromethyl-benzoic acid methyl ester

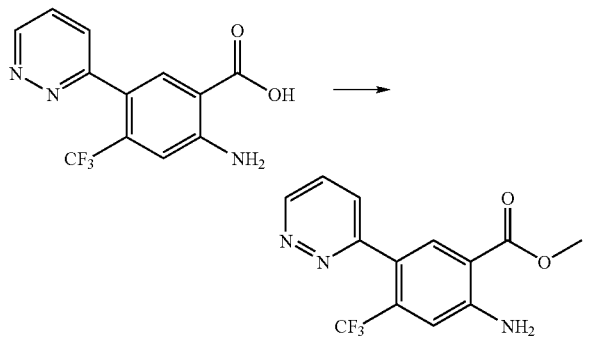

2-Amino-5-pyridazin-3-yl-4-trifluoromethyl-benzoic acid (165 mg, 0.583 mmol) was dissolved in MeOH (15 mL). Concd H₂SO₄ (360 μL) was added and solution was heated to 110° C. for 11.5 h. The solution was concentrated in vacuo and the residue was dissolved in water (2 mL). The aqueous layer was neutralized with aq NaOH (2 N) and extracted with DCM. The organic phase was washed with brine, dried (Na₂SO₄), and concentrated in vacuo. The residue was purified by flash chromatography (silica gel, EtOAc/hexanes (1:4 to 1:1)) to give the title compound (79 mg, 46%). API-ES: m/z 298.1 [M+H]⁺, rt 3.48 min N-(2,4-Dioxo-6-pyridazin-3-yl-7-trifluoromethyl-1, 4-dihydro-2H-quinazolin-3-yl)-methanesulfonamide

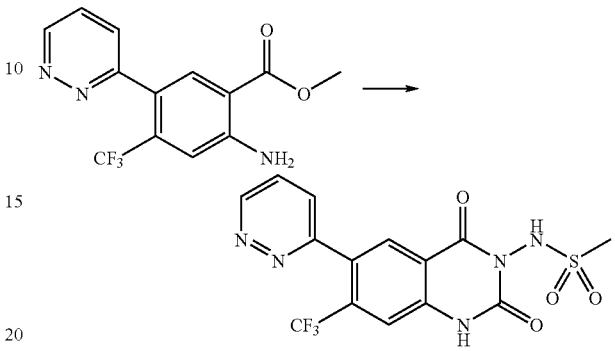

To a solution of 2-amino-5-pyridazin-3-yl-4-trifluoromethyl-benzoic acid methyl ester (79 mg, 0.266 mmol) in dioxane (4 mL) under argon was added 4-chlorophenyl chloroformate (44.6 μL, 0.319 mmol). The solution was stirred at 85° C. for 30 min and cooled to r.t. CH₃SO₂NHNH₂ (58.5 mg, 0.531 mmol) and i-Pr₂NEt (46.4 μL, 0.266 mmol) were added and the reaction mixture was heated back to 85° C. for 3 h. The mixture was concentrated in vacuo and the residue was purified by two consecutive flash chromatographies (silica gel, DCM 5% MeOH in DCM) then (silica gel, 7:3 EtOAc/hexanes). The product was suspended in a minimum amount of EtOAc, sonicated then taken into hexanes. The solid was collected by vacuum filtration to furnish the title compound (13 mg, 12%) as a white solid. API-ES: m/z 402.0 [M+H]⁺, rt 3.36 min, Method N_05_100: 5%→100% (6 min), 100% (1.5 min), 100%→5% (0.5 min)

Example 80

N-(6-Oxazol-5-yl-2,4-dioxo-7-trifluoromethyl-1,4-dihydro-2H-quinazolin-3-yl)-methanesulfonamide 2-Amino-5-oxazol-5-yl-4-trifluoromethyl-benzoic acid methyl ester

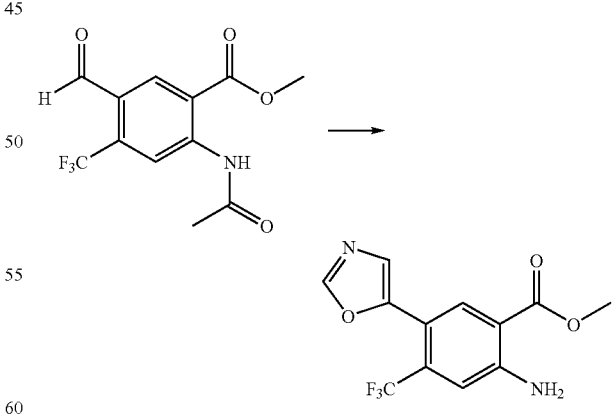

2-Acetylamino-5-formyl-4-trifluoromethyl-benzoic acid methyl ester (880 mg, 3.043 mmol) in MeOH (10 mL) was treated with potassium carbonate (463 mg, 3.35 mmol) and toluene-4-sulfonyl methylisocyanide (594 mg, 3.04 mmol) and the mixture was refluxed for 5 h. The reaction mixture was cooled to r.t., concentrated in vacuo and the residue was purified by flash chromatography (100 g silica gel, DCM) to give the title product (248 mg, 28%) as a yellow powder. API-ES: m/z 287.1 [M+H]$^+$, rt 4.40 min.

N-(6-Oxazol-5-yl-2,4-dioxo-7-trifluoromethyl-1,4-dihydro-2H-quinazolin-3-yl)-methanesulfonamide

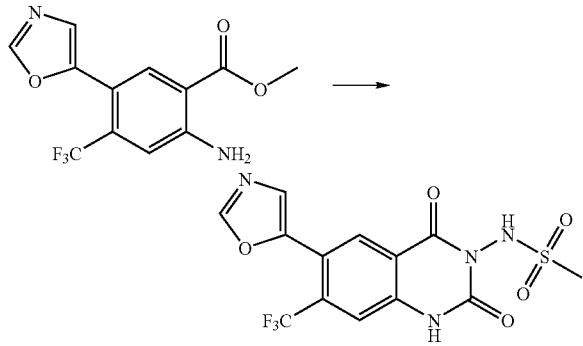

A mixture of 2-amino-5-oxazol-5-yl-4-trifluoromethyl-benzoic acid methyl ester (248 mg, 0.866 mmol) and 4-chlorophenyl chloroformate (121 µL, 0.886 mmol) in dioxane (4 mL) was heated to 80° C. for 1 h. The reaction mixture was concentrated in vacuo. The crude residue was dissolved in dioxane (4 mL) and treated with $CH_3SO_2NHNH_2$ (191 mg, 1.732 mmol) and i-$Pr_2NEt$ (454 µL, 2.60 mmol). After heating at 80° C. for 1 h, the reaction mixture was concentrated in vacuo. The residue was purified by two successive flash chromatographies (70 g of silica gel, 2% MeOH in DCM), then (20 g silica gel, DCM→MeOH in DCM (1% to 3%)) to give the title compound (65 mg) as an off-white powder. This solid was further purified by sonication in DCM to provide 24 mg of pure product. The filtrate was concentrated in vacuo and sonicated in $Et_2O$ to give a further 27.8 mg of title product, for a total of 51.8 mg (15%) of the title compound as an off-white powder. API-ES: m/z 408.0 [M+$NH_4$]$^+$, rt 2.89 min.

Example 81

N-(7-Isopropyl-2,4-dioxo-6-pyrimidin-5-yl-1,4-dihydro-2H-quinazolin-3-yl)-methanesulfonamide This compound was synthesized by an analogous manner.

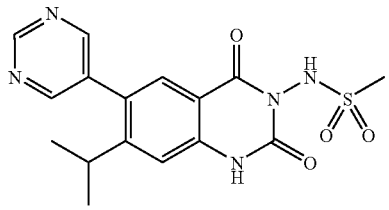

API-ES: m/z 393.1 [M+$NH_4$]$^+$, m/z 374.0 [M−H]$^-$, rt 2.51 min.

Biological Assays

AMPA-Receptor Binding

This can be demonstrated in standard tests, e.g. the [$^3$H] CNQX binding test (Honoré et al. Biochem. Pharmacol. 1989, 38: 3207-3212). This test is performed as follows:

Brain membranes: The animals are decapitated, the brain removed and homogenized in 10 volumes of ice-cold 10% sucrose with a glass/Teflon homogenizer at positions 5 for 30 sec. The membranes are centrifuged at 1000×g for 10 min, and the supernatant centrifuged at 20,000×g for 15 min. The resulting pellet is resuspended in 10 volumes of cold water with a tissue homogenizer (Brinkman Polytron) at position 5 for 15 sec and the suspension centrifuged at 8000×g for 10 min. The supernatant including the buffy layer is centrifuged at 40,000×g for 20 min, the pellet resuspended in 5 volumes of water and the suspension frozen (20-30 min in dry ice/MeOH) and thawed (water-bath at 37° C.) twice. The suspension is centrifuged at 40,000×g for 20 min, the pellet resuspended in 50 mM HEPES/KOH, pH 7.5, and centrifuged at 40,000×g for 10 min. The final pellet is resuspended with a glass/Teflon homogenizer in 5 volumes of HEPES/KOH buffer; 2 mL aliquots are frozen and stored in liquid nitrogen.

Pretreatment of membranes: Membranes are thawed at 35° C. and once washed with 50 mM HEPES/KOH by centrifugation at 39,000×g for 10 min. The final pellet is resuspended with a glass/Teflon homogenizer in the same buffer.

Radioligand binding assay: It is performed using 96-well microtiterplates in a volume of 0.3 mL of 50 mM HEPES/KOH, pH 7.2, 100 µg membrane protein, 5 nM [$^3$H]-CNQX (NEN) and the compound to be tested. Incubation is performed at 4° C. for 40 min and the reaction is terminated by centrifugation (Sigma 4K10) at 3700×g for 30 min. The pellet is washed once with cold buffer and then dissolved in 0.02 mL of the tissue solubilizer Soluene for 20 min. Two hundred µL of the scintillation fluid Microscint 20 (Packard) are added and the radioactivity is counted in a Packard Topcount scintillation counter at an efficiency of 40-45%. Nonspecific binding is defined by 10 µM CNQX. Assays are performed in triplicate.

For example, in this assay the compound of Example 4 has an $IC_{50}$ better than 1 µM.

Functional Test for AMPA-Receptor Activity

For the determination of functional agonism or antagonism at the AMPA-receptor, experiments can be performed on Xenopus oocytes as previously described in detail (Urwyler et al., Mol. Pharmacol. 2001, 60, 963-971). Briefly, two electrode voltage clamp recordings are performed from Xenopus laevis oocytes expressing GluR3 AMPA receptors. Plasmids for the rat GluR3-(flop) (Hollmann et al., Science 1991, 252, 851-853) are linearized and transcribed into capped cRNA using an in vitro RNA synthesis kit (Ambion, Texas) with T7 Polymerase. Stock solutions are kept in 70% EtOH. Before use, cRNA is precipitated and resuspended in DEPC-treated water. Oocytes are injected with RNA coding the rat GluR3-(flop) AMPA receptor. For recordings, oocytes are placed in a perfusion chamber with continuous gravity flow of frog Ringer's solution. For recordings from oocytes expressing rGluR3-(flop) receptors frog, Ringer's solution containing $Mg^{2+}$ (81 mM NaCl; 2.5 mM KCl; 1 mM $CaCl_2$; 1 mM $MgCl_2$, 2.5 mM $NaHCO_3$, 5 mM HEPES, pH 7.4) is used. Test compounds are washed in with gravity.

For example, in this assay the compound of Example 4 is an antagonist at the rGluR3 AMPA receptor with an $IC_{50}$-value better than 3 µM.

Audiogenic Seizures Model

For example the compounds of the invention have pronounced anticonvulsive properties which are determined in vivo, for example in mice, by reference to their pronounced protective action with respect to convulsions triggered by sound, electric shock or metrazole.

Sound induced seizures were elicited in DBA/2 mice (Collins R L in: Experimental models of epilepsy, eds Pupura, Penry Tower, Woodbury Walter; Raven Press, New York, 1972). For testing, 20-day-old animals are placed in a sound attenuated chamber. Following a 60 s habituation period the animals are stimulated using band limited noise (14-20 kHz, 118 dB SPL) lasting for maximally 60 s. DBA/2 mice respond with a sequence of wild running, clonic seizures, tonic seizures, and respiratory arrest to the acoustic stimulus. For data analysis the occurrence as well as the duration of the different behavioural phases are measured. The ED50 values for the different behavioural phases are calculated. ED50 values following systemic drug applications (intraperitoneal, subcutaneous, oral) range between 0.5 mg/kg and 100 mg/kg.

In addition, the compounds of the invention show pronounced effects in the well established electric shock mouse model or the mouse model for metrazole-induced convulsions according to Schmutz et al, *Naunyn-Schmiedeberg's Arch Pharmacol* 1990, 342, 61-66. ED50 values range between 1 mg/kg and 200 mg/kg.

The antischizophrenic activity of the compounds of the invention can be demonstrated, e.g. in the amphetamine-induced hyperlocomotion test. Blockade of amphetamine-induced hyperlocomotion is well known as screening paradigm for antischizophrenic activity.

We claim:

1. A compound selected from the group consisting of:

N-[7-Trifluoromethyl-6-(2-methyl-2H-pyrazol-3-yl)-2,4-dioxo-1,4-dihydro-2H-quinazolin-3-yl]-methanesulfonamide;

N-[6-(1-Methyl-1H-[1,2,3]triazol-4-yl)-2,4-dioxo-7-trifluoromethyl-1,4-dihydro-2H-quinazolin-3-yl]-methanesulfonamide;

N-[6-(5-Methyl-2H-pyrazol-3-yl)-2,4-dioxo-7-trifluoromethyl-1,4-dihydro-2H-quinazolin-3-yl]-methanesulfonamide;

N-[6-(2,5-Dimethyl-2H-pyrazol-3-yl)-2,4-dioxo-7-trifluoromethyl-1,4-dihydro-2H-quinazolin-3-yl]-methanesulfonamide;

N-[6-(1-methyl-1H-pyrazol-4-yl)-2,4-dioxo-7-trifluoromethyl-1,4-dihydro-2H-quinazolin-3-yl]-methanesulfonamide;

N-[6-(1-Methyl-1H-pyrrol-2-yl)-2,4-dioxo-7-trifluoromethyl-1,4-dihydro-2H-quinazolin-3-yl]-methanesulfonamide;

N-[2,4-Dioxo-6-(tetrahydro-furan-3-yl)-7-trifluoromethyl-1,4-dihydro-2H-quinazolin-3-yl]-methanesulfonamide;

N-(2,4-Dioxo-6-pyrrol-1-ylmethyl-7-trifluoromethyl-1,4-dihydro-2H-quinazolin-3-yl)-methanesulfonamide;

N-[6-(2-Methyl-pyrrol-1-ylmethyl)-2,4-dioxo-7-trifluoromethyl-1,4-dihydro-2H-quinazolin-3-yl]-methanesulfonamide;

N-[7-Isopropyl-6-(2-methyl-2H-pyrazol-3-yl)-2,4-dioxo-1,4-dihydro-2H-quinazolin-3-yl]-methanesulfonamide;

N-[7-Isopropyl-2,4-dioxo-6-(2H-pyrazol-3-yl)-1,4-dihydro-2H-quinazolin-3-yl]-methanesulfonamide;

N-[7-Isopropyl-2,4-dioxo-6-(1H-pyrazol-4-yl)-1,4-dihydro-2H-quinazolin-3-yl]-methanesulfonamide;

N-[7-Isopropyl-6-(1-methyl-1H-pyrazol-4-yl)-2,4-dioxo-1,4-dihydro-2H-quinazolin-3-yl]-methanesulfonamide;

N-(2,4-Dioxo-6-pyridin-4-yl-7-trifluoromethyl-1,4-dihydro-2H-quinazolin-3-yl)-methanesulfonamide;

N-(2,4-Dioxo-6-pyridin-3-yl-7-trifluoromethyl-1,4-dihydro-2H-quinazolin-3-yl)-methanesulfonamide;

N-[6-(6-Methoxy-pyridin-3-yl)-2,4-dioxo-7-trifluoromethyl-1,4-dihydro-2H-quinazolin-3-yl]-methanesulfonamide;

and pharmaceutically acceptable salts thereof.

2. N-[7-Trifluoromethyl-6-(2-methyl-2H-pyrazol-3-yl)-2,4-dioxo-1,4-dihydro-2H-quinazolin-3-yl]-methanesulfonamide, or a pharmaceutically acceptable salt thereof.

3. N-[2,4-Dioxo-6-(tetrahydro-furan-3-yl)-7-trifluoromethyl-1,4-dihydro-2H-quinazolin-3-yl]-methanesulfonamide, or a pharmaceutically acceptable salt thereof.

4. N-[7-Isopropyl-6-(2-methyl-2H-pyrazol-3-yl)-2,4-dioxo-1,4-dihydro-2H-quinazolin-3-yl]-methanesulfonamide, or a pharmaceutically acceptable salt thereof.

5. A pharmaceutical composition comprising a compound according to any one of claims 1 to 4.

* * * * *